US009359381B2

(12) United States Patent
Ahmed et al.

(10) Patent No.: US 9,359,381 B2
(45) Date of Patent: Jun. 7, 2016

(54) TRICYCLIC COMPOUNDS FOR INHIBITING THE CFTR CHANNEL

(71) Applicants: Mahbub Ahmed, London (GB); Alexander Ashall-Kelly, London (GB); Louisa Gueritz, London (GB); Jeffrey McKenna, Horsham (GB); Joseph McKenna, London (GB); Simon Mutton, London (GB); Rakesh Parmar, London (GB); Jon Shepherd, London (GB); Paul Wright, London (GB)

(72) Inventors: Mahbub Ahmed, London (GB); Alexander Ashall-Kelly, London (GB); Louisa Gueritz, London (GB); Jeffrey McKenna, Horsham (GB); Joseph McKenna, London (GB); Simon Mutton, London (GB); Rakesh Parmar, London (GB); Jon Shepherd, London (GB); Paul Wright, London (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/653,084

(22) PCT Filed: Dec. 17, 2013

(86) PCT No.: PCT/IB2013/061043
§ 371 (c)(1),
(2) Date: Jun. 17, 2015

(87) PCT Pub. No.: WO2014/097148
PCT Pub. Date: Jun. 26, 2014

(65) Prior Publication Data
US 2015/0336986 A1 Nov. 26, 2015

Related U.S. Application Data

(60) Provisional application No. 61/739,335, filed on Dec. 19, 2012, provisional application No. 61/906,141, filed on Nov. 19, 2013.

(51) Int. Cl.
| A61K 31/519 | (2006.01) |
| A61K 31/542 | (2006.01) |
| A61K 31/5025 | (2006.01) |
| A61K 31/551 | (2006.01) |
| C07D 471/14 | (2006.01) |
| C07D 487/14 | (2006.01) |
| C07D 513/14 | (2006.01) |
| C07D 513/00 | (2006.01) |
| A61K 31/55 | (2006.01) |
| A61K 45/06 | (2006.01) |
| C07D 487/22 | (2006.01) |
| C07D 487/04 | (2006.01) |
| C07D 495/14 | (2006.01) |

(52) U.S. Cl.
CPC ............ *C07D 513/14* (2013.01); *A61K 31/519* (2013.01); *A61K 31/542* (2013.01); *A61K 31/55* (2013.01); *A61K 45/06* (2013.01); *C07D 471/14* (2013.01); *C07D 487/04* (2013.01); *C07D 487/14* (2013.01); *C07D 487/22* (2013.01); *C07D 495/14* (2013.01); *C07D 513/00* (2013.01)

(58) Field of Classification Search
CPC .............. A61K 31/519; A61K 31/542; A61K 31/5025; A61K 31/551; C07D 471/14; C07D 487/14; C07D 513/14
USPC .................. 514/214.02, 220, 224.5, 248, 267; 540/561, 578; 544/34, 234, 250
See application file for complete search history.

(56) References Cited

U.S. PATENT DOCUMENTS

| 2009/0163545 A1 | 6/2009 | Goldfarb et al. |
| 2014/0171412 A1 | 6/2014 | Mahbub et al. |
| 2014/0171417 A1 | 6/2014 | Mahbub et al. |

FOREIGN PATENT DOCUMENTS

| JP | 2002-255967 A | 9/2002 |
| WO | 01-14386 A1 | 3/2001 |
| WO | 2008/073365 A1 | 6/2008 |
| WO | 2011/019737 A1 | 2/2011 |
| WO | 2012/166658 A1 | 12/2012 |

OTHER PUBLICATIONS

Carosati et al., Ligand-based virtual screening and ADME-tox guided approach to identify triazolo-quinoxalines as folate cycle inhibitors. Bioorg Med Chem. Nov. 15, 2010;18(22):7773-85. Epub Oct. 1, 2010.
Lee et al., Development of improved inhibitors of wall teichoic acid biosynthesis with potent activity against *Staphylococcus aureus*. Bioorg Med Chem Lett. Mar. 1, 2010;20(5):1767-70. Epub Jan. 20, 2010.

(Continued)

*Primary Examiner* — Brenda Coleman
(74) *Attorney, Agent, or Firm* — Jing Sun

(57) ABSTRACT

The present invention provides a compound of formula I or a pharmaceutically acceptable salt thereof; and its therapeutic uses. The present invention further provides a combination of pharmacologically active agents and a pharmaceutical composition.

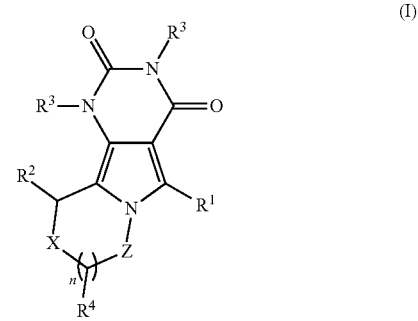

(I)

23 Claims, No Drawings

(56) References Cited

OTHER PUBLICATIONS

Snyder et al., Absolute Configuration and Biological Properties of Enantiomers of CFTR Inhibitor BPO-27. ACS Med Chem Lett. May 9, 2013;4(5):456-459.

Snyder et al., Potent, metabolically stable benzopyrimido-pyrrolo-oxazine-dione (BPO) CFTR inhibitors for polycystic kidney disease. J Med Chem. Aug. 11, 2011;54(15):5468-77. Epub Jul. 12, 2011.

Tanifum et al., Novel pyridopyrimidine derivatives as inhibitors of stable toxin a (STa) induced cGMP synthesis. Bioorg Med Chem Lett. Jun. 1, 2009;19(11):3067-71. Epub Apr. 12, 2009.

Toropov et al., QSAR models for inhibitors of physiological impact of *Escherichia coli* that leads to diarrhea. Biochem Biophys Res Commun. Mar. 8, 2013;432(2):214-25. Epub Feb. 10, 2013.

Tradtrantip et al., Nanomolar potency pyrimido-pyrrolo-quinoxalinedione CFTR inhibitor reduces cyst size in a polycystic kidney disease model. J Med Chem. Oct. 22, 2009;52(20):6447-55.

Tsupak et al., [3,4] Annulated pyrroles 1. Polynuclear heterocyclic systems based on pyrrolo[3,4 d]pyrimidine 2,4 dione. Russian Chemical Bulletin. 2006;55(12):2265-70.

Tsupak et al., Pyrrolopyrimidines. 5*. Reaction of 6-Amino-1,3-Dimethylpyrrolo[ 3,4-d]Pyrimidine-2,4(1H,3H)—Diones With 1,3-Diketones. Chemistry of Heterocyclic Compounds. 2003;39(7):953-9.

Wetzel et al., A scaffold-tree-merging strategy for prospective bioactivity annotation of gamma-pyrones. Angew Chem Int Ed Engl. May 10, 2010;49(21):3666-70.

International Search Report and Written Opinion for International Application No. PCT/IB2013/061043 mailed Mar. 11, 2014. 8 pages.

TRICYCLIC COMPOUNDS FOR INHIBITING THE CFTR CHANNEL

FIELD OF THE INVENTION

The invention provides tricyclic compounds, the use thereof for inhibiting the CFTR channel and methods of treating disease using same.

BACKGROUND OF THE INVENTION

The cystic fibrosis transmembrane conductance regulator protein (CFTR) is a cAMP-activated chloride channel which is expressed in epithelial cells in mammalian airways, intestine, pancreas, and testis (Sheppard et al., *Physiol. Rev.* 79:S23-45 (1999); Gadsby et al., *Nature* 40:477-83 (2006)). The CFTR chloride channel is known to be associated with a number of diseases and conditions, including cystic fibrosis (CF), polycystic kidney disease and secretory diarrhea.

Diarrheal disease remains an area of high unmet medical need, resulting in approximately 2 million deaths in 2002, of which more than 95% were children under the age of 5 years. Infectious secretory diarrhea, the result of poor sanitation and close living conditions, is responsible for most acute episodes and there is a defined need for an adjunct therapy to be used in combination with existing oral rehydration and antibiotic therapies.

CFTR inhibitors are discussed by Thiagarajah and Verkman in Clinical Pharmacology and Therapeutics (2012): 92, 3, 287-290.

SUMMARY OF THE INVENTION

There is a need to provide new CFTR inhibitors that are good drug candidates. In particular, compounds of the invention should bind potently to the cystic fibrosis transmembrane conductance regulator protein whilst showing little affinity for other receptors and show functional activity as CFTR inhibitors. They should be well absorbed from the gastrointestinal tract, be metabolically stable and possess favourable pharmacokinetic properties. Furthermore, the ideal drug candidate will exist in a physical form that is stable, non-hygroscopic and easily formulated.

The compounds of the invention are high affinity inhibitors of the CFTR channel and are therefore potentially useful in the treatment of a wide range of disorders, particularly polycystic kidney disease and diarrhea (including infectious secretory diarrhea, travellers diarrhea, diarrhea associated with HIV and diarrhea predominant irritable bowel syndrome (IBS)).

The treatment of polycystic kidney disease and diarrhea is a contemplated use. All forms of polycystic kidney disease and diarrhea are potentially treatable with the compounds of the present invention including infectious secretory diarrhea, travellers diarrhea, diarrhea associated with HIV and diarrhea predominant irritable bowel syndrome (IBS).

The invention therefore provides, as Embodiment 1, a compound of the formula (I) or a pharmaceutically acceptable salt thereof:

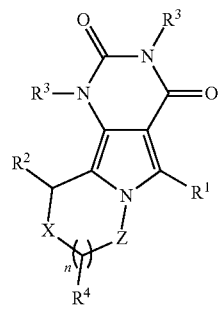

wherein $R^1$ represents phenyl, $(C_4-C_7)$cycloalkenyl or $Het^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1-C_4)$alkyl, halo, halo$(C_1-C_4)$alkyl, cyano, hydroxy$(C_1-C_4)$alkyl, $(C_1-C_4)$alkoxy, halo$(C_1-C_4)$alkoxy, $(C_1-C_4)$alkoxy$(C_1-C_4)$alkyl, $R^6OC(O)$—, or $R^6OC(O)(C_1-C_4)$alkyl-;

$R^{a1}$ represents $(C_1-C_4)$alkyl, hydroxy$(C_1-C_4)$alkyl, $(C_1-C_4)$alkoxy$(C_1-C_4)$alkyl, $(C_1-C_4)$alkylamino$(C_1-C_4)$alkyl-, di[$(C_1-C_4)$alkyl]amino$(C_1-C_4)$alkyl-, aryl$(C_1-C_4)$alkyl or $R^6OC(O)(C_1-C_4)$alkyl-;

$R^2$ represents $(C_1-C_6)$alkyl, $(C_3-C_7)$cycloalkyl, $(C_4-C_7)$cycloalkenyl, phenyl, furanyl, thiazolyl or thienyl, which $R^2$ may be unsubstituted or substituted on from one to three carbon atoms with substituents $R^b$;

each $R^b$ independently represents $(C_1-C_4)$alkyl, halo, halo$(C_1-C_4)$alkyl, cyano, $(C_1-C_4)$alkylamino$(C_1-C_4)$alkyl-, di[$(C_1-C_4)$alkyl]amino$(C_1-C_4)$alkyl-, $(R^6)_2NC(O)(C_1-C_4)$alkyl- or $R^6OC(O)(C_1-C_4)$alkyl-;

X represents S, Z represents $CHR^{4a}$ and n represents 1; or
X represents $CHR^{4b}$, Z represents $NR^5$ and n represents 1 or 2; or
X represents $CHR^{4b}$, Z represents $CHR^{4a}$ and n represents 0, 1 or 2; or
X represents $C(=CH_2)$, $CF_2$ or $C(CH_3)_2$, Z represents $CHR^{4a}$ and n represents 0 or 1;

each $R^3$ independently represents methyl or ethyl;

when X represents S, $R^4$ represents hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, phenyl, $Het^1(C_1-C_4)$alkyl-, $Het^2(C_1-C_4)$alkyl-, $(C_1-C_4)$alkylS(O)$_2$NH$(C_1-C_4)$alkyl-, or $R^7C(O)NH(C_1-C_4)$alkyl-;

when X represents $CHR^{4b}$, each $R^4$ independently represents hydrogen, hydroxy, $(C_1-C_4)$alkyl, $(C_1-C_4)$alkoxy, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, amino, $(C_1-C_4)$alkylamino-, di[$(C_1-C_4)$alkyl]amino-, phenyl, $Het^1(C_1-C_4)$alkyl-, $Het^2(C_1-C_4)$alkyl-, $(C_1-C_4)$alkylS(O)$_2$NH$(C_1-C_4)$alkyl-, or $R^7C(O)NH(C_1-C_4)$alkyl-;

$R^{4a}$ represents hydrogen, $(C_1-C_4)$alkyl, hydroxy$(C_1-C_4)$alkyl, halo$(C_1-C_4)$alkyl, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, $Het^1(C_1-C_4)$alkyl-, $Het^2(C_1-C_4)$alkyl-, or $R^6OC(O)$—;

$R^{4b}$ represents hydrogen or methyl;
$R^5$ represents hydrogen or $(C_1-C_4)$alkyl;
$R^6$ represents hydrogen or $(C_1-C_4)$alkyl;

$R^7$ represents $(C_1-C_2)$alkyl, $(C_1-C_2)$alkoxy, $(C_1-C_2)$alkoxy$(C_1-C_2)$alkyl or phenyl;

Het$^1$ represents a 5- or 6-membered heteroaryl ring comprising a) one oxygen or sulphur atom and optionally one or two nitrogen atoms; or b) from one to four nitrogen atoms; and Het$^2$ represents a 4- to 7-membered heterocyclic ring comprising a) 1 or 2 heteroatoms selected from N, O and S; or b) —C(O)— and 1 or 2 heteroatoms selected from N and O.

In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof and one or more therapeutically active agent.

In another embodiment, the invention provides a method of modulating CFTR activity in a subject, wherein the method comprises administering to the subject a therapeutically effective amount of a compound according to the definition of formula (I), or a pharmaceutically acceptable salt thereof, or subformulae thereof.

In another embodiment, the invention provides a method of treating a disorder or disease selected from polycystic kidney disease and diarrhea, comprising administering to the subject a therapeutically effective amount of a compound according to the definition of formula (I), or a pharmaceutically acceptable salt thereof, or subformulae thereof.

DETAILED DESCRIPTION

The invention therefore provides a compound of the formula (I) as described hereinabove as Embodiment 1.

Unless specified otherwise, the term "compounds of the present invention" refers to compounds of formula (I) and formula (Ia), salts of the compound, hydrates or solvates of the compounds, as well as all stereoisomers (including diastereoisomers and enantiomers), tautomers and isotopically labeled compounds (including deuterium substitutions). Compounds of the present invention further comprise polymorphs of compounds of formula I and formula (Ia) and salts thereof.

For purposes of interpreting this specification, the following definitions will apply and whenever appropriate, terms used in the singular will also include the plural and vice versa.

As used herein, the term "$C_{1-6}$alkyl" refers to a fully saturated branched or unbranched hydrocarbon moiety having 1 to 6 carbon atoms. The terms "$C_{1-4}$alkyl" and "$C_{1-2}$alkyl" are to be construed accordingly. Representative examples of $C_{1-6}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, and n-heptyl.

As used herein, the term "halo$C_{1-6}$alkyl" refers to a $C_{1-6}$alkyl group as defined herein, wherein at least one of the hydrogen atoms is replaced by a halo atom. The halo$C_{1-6}$alkyl group can be monohalo$C_{1-6}$alkyl, dihalo$C_{1-6}$alkyl or polyhalo$C_{1-6}$alkyl including perhalo$C_{1-6}$alkyl. A monohalo$C_{1-6}$alkyl can have one iodo, bromo, chloro or fluoro within the alkyl group. Dihalo$C_{1-6}$alkyl and polyhalo$C_{1-6}$alkyl groups can have two or more of the same halo atoms or a combination of different halo groups within the alkyl. Typically the polyhalo$C_{1-6}$alkyl group contains up to 12, or 10, or 8, or 6, or 4, or 3, or 2 halo groups.

Non-limiting examples of halo$C_{1-6}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-6}$alkyl group refers to an $C_{1-6}$alkyl group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-6}$alkoxy" refers to $C_{1-6}$alkyl-O—, wherein $C_{1-6}$alkyl is defined herein above. Representative examples of $C_{1-1}$alkoxy include, but are not limited to, methoxy, ethoxy, propoxy, 2-propoxy, butoxy, tert-butoxy, pentyloxy, and hexyloxy.

As used herein, the term "Het$^2$" or "heterocyclic ring" refers to a saturated or unsaturated non-aromatic ring or ring system, which is a 4-, 5-, 6-, or 7-membered monocyclic ring comprising a) 1 or 2 heteroatoms selected from N, O and S; or b) —C(O)— and 1 or 2 heteroatoms selected from N and O. The heterocyclic group can be attached via a heteroatom or a carbon atom. Examples of heterocyclic rings include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, pyrrolidinonyl, oxazolidinonyl, and thiomorpholine.

The term "$C_{3-7}$cycloalkyl" refers to a fully saturated or unsaturated monocyclic hydrocarbon group of 3-7 carbon atoms. Exemplary monocyclic hydrocarbon groups include, but are not limited to, cyclopropyl, cyclobutyl, cyclopentyl, cyclopentenyl, cyclohexyl and cyclohexenyl.

As used herein, the term "Het$^1$" or "heteroaryl ring" refers to an aromatic ring system, which is a 5- or 6-membered monocyclic ring comprising a) one oxygen or sulphur atom and optionally one or two nitrogen atoms; or b) from one to four nitrogen atoms. Typical Heteroaryl rings include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), and 4- or 5-(1,2,3-triazolyl), tetrazolyl, pyrimidinyl and pyridinyl.

As used herein, the term "halogen" or "halo" refers to fluoro, chloro, bromo, and iodo.

Embodiment 2. A compound of the formula (I) or a pharmaceutically acceptable salt thereof:

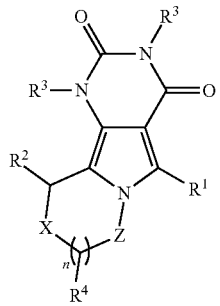

wherein $R^1$ represents phenyl, $(C_4-C_7)$cycloalkenyl or $Het^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1-C_4)$alkyl, halo, halo$(C_1-C_4)$alkyl, cyano, hydroxy$(C_1-C_4)$alkyl, $(C_1-C_4)$alkoxy, halo$(C_1-C_4)$alkoxy, $(C_1-C_4)$alkoxy$(C_1-C_4)$alkyl, $R^6OC(O)$—, or $R^6OC(O)(C_1-C_4)$alkyl-;

$R^{a1}$ represents $(C_1-C_4)$alkyl, hydroxy$(C_1-C_4)$alkyl, $(C_1-C_4)$alkoxy$(C_1-C_4)$alkyl, $(C_1-C_4)$alkylamino$(C_1-C_4)$alkyl-, di[$(C_1-C_4)$alkyl]amino$(C_1-C_4)$alkyl-, aryl$(C_1-C_4)$alkyl or $R^6OC(O)(C_1-C_4)$alkyl-;

$R^2$ represents $(C_1-C_6)$alkyl, $(C_3-C_7)$cycloalkyl, $(C_4-C_7)$cycloalkenyl, phenyl, furanyl, thiazolyl or thienyl, which $R^2$ may be unsubstituted or substituted on from one to three carbon atoms with substituents $R^b$;

each $R^b$ independently represents $(C_1-C_4)$alkyl, halo, halo$(C_1-C_4)$alkyl, cyano, $(C_1-C_4)$alkylamino$(C_1-C_4)$alkyl-, di[$(C_1-C_4)$alkyl]amino$(C_1-C_4)$alkyl-, $(R^6)_2NC(O)(C_1-C_4)$alkyl- or $R^6OC(O)(C_1-C_4)$alkyl-;

X represents S, Z represents $CHR^{4a}$ and n represents 1; or

X represents $CHR^{4b}$, Z represents $NR^5$ and n represents 1; or

X represents $CHR^{4b}$, Z represents $CHR^{4a}$ and n represents 0 or 1;

each $R^3$ independently represents methyl or ethyl;

when X represents S, $R^4$ represents hydrogen, $(C_1-C_4)$alkyl, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, or phenyl; or when X represents $CHR^{4b}$, $R^4$ represents hydrogen, hydroxy, $(C_1-C_4)$alkyl, $(C_1-C_4)$alkoxy, halo$(C_1-C_4)$alkyl, hydroxy$(C_1-C_4)$alkyl, $(C_1-C_4)$alkoxy$(C_1-C_4)$alkyl-, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, amino, $(C_1-C_4)$alkylamino-, di[$(C_1-C_4)$alkyl]amino- or phenyl;

$R^{4a}$ represents hydrogen, $(C_1-C_4)$alkyl, halo$(C_1-C_4)$alkyl, amino$(C_1-C_4)$alkyl-, $(C_1-C_4)$alkylamino$(C_1-C_4)$alkyl-, di[$(C_1-C_4)$alkyl]amino$(C_1-C_4)$alkyl-, $Het^2(C_1-C_4)$alkyl-, or $R^6OC(O)$—;

$R^{4b}$ represents hydrogen or methyl;

$R^5$ represents hydrogen or $(C_1-C_4)$alkyl;

$R^6$ represents hydrogen or $(C_1-C_4)$alkyl;

$Het^1$ represents a 5- or 6-membered heteroaryl ring comprising a) one oxygen or sulphur atom and optionally one or two nitrogen atoms; or b) from one to four nitrogen atoms; and $Het^2$ represents a 4- to 7-membered heterocyclic ring comprising 1 or 2 heteroatoms selected from N, O and S.

Embodiment 3. A compound according to Embodiment 1 or Embodiment 2, wherein $R^1$ represents phenyl, cyclohexenyl, thiazolyl, pyrazolyl, thienyl, pyrimidin-2-yl or pyridine-2-yl and wherein $R^1$ may be unsubstituted or substituted on one or two carbon atoms by substituents $R^a$, and may further be substituted on a nitrogen atom with a substituent $R^{a1}$.

Embodiment 4. A compound according to any preceding Embodiment, wherein $R^1$ represents thiazol-2-yl, thiazol-4-yl, thien-2-yl or pyrazol-4-yl, which $R^1$ group may be unsubstituted or substituted on one or two carbon atoms by substituents $R^a$, and may further be substituted on a nitrogen atom with a substituent $R^{a1}$ Embodiment 5. A compound according to any preceding Embodiment, wherein $R^1$ represents phenyl, which may be unsubstituted or substituted by 1 or 2 substituents $R^a$.

Embodiment 6. A compound according to Embodiment 5, wherein the $R^a$ substituents are in the 3-position, 2- and 3-positions, 3- and 4-positions, 3- and 5-positions or 3- and 6-positions.

Embodiment 7. A compound according to any preceding Embodiment, wherein each $R^a$ independently represents $(C_1-C_4)$alkyl, halo, halo$(C_1-C_4)$alkyl, hydroxy$(C_1-C_4)$alkyl, cyano, $(C_1-C_4)$alkoxy, $R^6OC(O)$—, or $R^6OC(O)(C_1-C_4)$alkyl-.

Embodiment 8. A compound according to any preceding Embodiment, wherein $R^2$ represents phenyl, furanyl, thiazolyl, or thienyl, which $R^2$ may be unsubstituted or substituted on from one to three carbon atoms with substituents $R^b$.

Embodiment 9. A compound according to any preceding Embodiment, wherein each $R^b$ independently represents $(C_1-C_2)$alkyl, halo, halo$(C_1-C_2)$alkyl, or cyano.

Embodiment 10. A compound according to any preceding Embodiment, wherein each $R^b$ independently represents methyl, ethyl, bromo, chloro, fluoro, trifluoromethyl, or cyano.

Embodiment 11. A compound according to any preceding Embodiment, wherein each $R^3$ represents methyl.

Embodiment 12. A compound according to any preceding Embodiment, wherein $R^4$ represents hydrogen, methyl, phenyl or $HOCH_2$—.

Embodiment 13. A compound according to any preceding Embodiment, wherein Z represents —$CHR^{4a}$ and $R^{4a}$ represents hydrogen or methyl.

Embodiment 14. A compound according to any preceding Embodiment, wherein:

X represents S, Z represents $CHR^{4a}$ and n represents 1; or

X represents $CHR^{4b}$, Z represents $CHR^{4a}$ and n represents 1.

Embodiment 15. A compound according to any one of Embodiments 1 to 13, wherein Z represents $NR^5$ and $R^5$ represents hydrogen.

Embodiment 16. A compound according to any preceding Embodiment, wherein $R^6$ represents hydrogen, methyl or ethyl.

Embodiment 17. A compound according to any preceding Embodiment, wherein the compound is of formula (Ia):

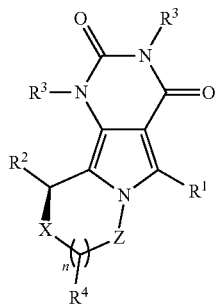

(Ia)

Embodiment 18. A compound according to any preceding Embodiment, wherein the compound of formula (I) is racemic or has the stereochemistry as shown in formula (Ia).

Embodiment 19. A compound of formula (I) or formula (Ia), which is selected from the list consisting of:

Example 1.1

1,3-Dimethyl-10-(5-methylfuran-2-yl)-5-phenyl-7,8-dihydro-1H-pyrimido[4',5':3,4]pyrrolo[2,1-c][1,4]thiazine-2,4 (3H,10H)-dione;

Example 1.4

1,3-Dimethyl-10-(4-methylthiazol-2-yl)-5-phenyl-7,8-dihydro-1H-pyrimido[4',5':3,4]pyrrolo[2,1-c][1,4]thiazine-2,4 (3H,10H)-dione;

Example 1.5

10-(5-Chlorofuran-2-yl)-1,3-dimethyl-5-phenyl-7,8-dihydro-1H-pyrimido[4',5':3,4]pyrrolo[2,1-c][1,4]thiazine-2,4 (3H,10H)-dione;

Example 1.6

10-(3-Chlorophenyl)-1,3-dimethyl-5-phenyl-7,8-dihydro-1H-pyrimido[4',5':3,4]pyrrolo[2,1-c][1,4]thiazine-2,4 (3H,10H)-dione;

Example 1.7

1,3-Dimethyl-5-phenyl-10-(m-tolyl)-7,8-dihydro-1H-pyrimido[4',5':3,4]pyrrolo[2,1-c][1,4]thiazine-2,4(3H,10H)-dione;

Example 1.8

10-(5-Chlorofuran-2-yl)-1,3-dimethyl-5-(m-tolyl)-7,8-dihydro-1H-pyrimido[4',5':3,4]pyrrolo[2,1-c][1,4]thiazine-2,4 (3H,10H)-dione;

Example 1.9

1,3-Dimethyl-10-(4-methylthiazol-2-yl)-5-(m-tolyl)-7,8-dihydro-1H-pyrimido[4',5':3,4]pyrrolo[2,1-c][1,4]thiazine-2,4(3H,10H)-dione;

Example 1.10

1,3-Dimethyl-10-(5-methylthiophen-2-yl)-5-phenyl-7,8-dihydro-1H-pyrimido[4',5':3,4]pyrrolo[2,1-c][1,4]thiazine-2,4(3H,10H)-dione Example 1.11

1,3-Dimethyl-10-(4-methylthiophen-2-yl)-5-phenyl-7,8-dihydro-1H-pyrimido[4',5':3,4]pyrrolo[2,1-c][1,4]thiazine-2,4(3H,10H)-dione Example 1.1.1

10-(5-chlorofuran-2-yl)-1,3-dimethyl-5-phenyl-7,8-dihydro-1H-pyrimido[4',5':3,4]pyrrolo[2,1-c][1,4]thiazine-2,4 (3H,10H)-dione;

Example 1.1.2

1,3-Dimethyl-10-(4-methylthiazol-2-yl)-5-phenyl-7,8-dihydro-1H-pyrimido[4',5':3,4]pyrrolo[2,1-c][1,4]thiazine-2,4 (3H,10H)-dione;

Example 1.1.3

1,3-Dimethyl-10-(5-methylfuran-2-yl)-5-phenyl-7,8-dihydro-1H-pyrimido[4',5':3,4]pyrrolo[2,1-c][1,4]thiazine-2,4 (3H,10H)-dione;

Example 1.1.4

10-(3-Chlorophenyl)-1,3-dimethyl-5-phenyl-7,8-dihydro-1H-pyrimido[4',5':3,4]pyrrolo[2,1-c][1,4]thiazine-2,4 (3H,10H)-dione;

Example 1.1.5

10-(5-Chlorofuran-2-yl)-1,3-dimethyl-5-(m-tolyl)-7,8-dihydro-1H-pyrimido[4',5':3,4]pyrrolo[2,1-c][1,4]thiazine-2,4 (3H,10H)-dione;

Example 2.0

7-((dimethylamino)methyl)-1,3-dimethyl-10-(5-methylfuran-2-yl)-5-phenyl-7,8-dihydro-1H-pyrimido[4',5':3,4] pyrrolo[2,1-c][1,4]thiazine-2,4(3H,10H)-dione;

Example 3.0

10-(5-chlorofuran-2-yl)-1,3,8-trimethyl-5-phenyl-7,8-dihydro-1H-pyrimido[4',5':3,4]pyrrolo[2,1-c][1,4]thiazine-2,4 (3H,10H)-dione;

Example 3.3

1,3,8-trimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione;

Example 3.4

3-(10-(5-Chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

Example 3.7

10-(5-Chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 3.8

10-(5-Chlorofuran-2-yl)-5-(cyclohex-1-en-1-yl)-1,3-dimethyl-7,8-dihydro-1H-pyrimido[4',5':3,4]pyrrolo[2,1-c][1,4]thiazine-2,4(3H,10H)-dione;

Example 3.9

10-(5-Chlorofuran-2-yl)-5-(3,5-difluorophenyl)-1,3-dimethyl-7,8-dihydro-1H-pyrimido[4',5':3,4]pyrrolo[2,1-c][1,4]thiazine-2,4(3H,10H)-dione;

Example 3.1.1

10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 3.1.2

10-(5-chlorofuran-2-yl)-5-(cyclohex-1-en-1-yl)-1,3-dimethyl-7,8-dihydro-1H-pyrimido[4',5':3,4]pyrrolo[2,1-c][1,4]thiazine-2,4(3H,10H)-dione;

Example 4.1

10-(5-Chlorofuran-2-yl)-1,3-diethyl-5-phenyl-7,8-dihydro-1H-pyrimido[4',5':3,4]pyrrolo[2,1-c][1,4]thiazine-2,4(3H,10H)-dione;

Example 5

3-Chloro-5-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

Example 6.1

10-(2,3-Difluorophenyl)-1,3-dimethyl-5-phenyl-7,8,9,10-tetrahydropyrimido[4,5-a]indolizine-2,4(1H,3H)-dione;

Example 6.2

1,3-Dimethyl-10-(5-methylfuran-2-yl)-5-phenyl-7,8,9,10-tetrahydropyrimido[4,5-a]indolizine-2,4(1H,3H)-dione;

Example 6.5

1,3-Dimethyl-10-(4-methylthiazol-2-yl)-5-phenyl-7,8,9,10-tetrahydropyrimido[4,5-a]indolizine-2,4(1H,3H)-dione;

Example 7.1

5-(3-Fluorophenyl)-1,3-dimethyl-10-(5-methylfuran-2-yl)-7,8,9,10-tetrahydro pyrimido[4,5-a]indolizine-2,4(1H,3H)-dione;

Example 7.4

5-(3-fluorophenyl)-1,3,9-trimethyl-10-(5-methylfuran-2-yl)-7,8,9,10-tetrahydropyrimido[4,5-a]indolizine-2,4(1H,3H)-dione;

Example 7.5

5-(3-fluorophenyl)-1,3,8-trimethyl-10-(5-methylfuran-2-yl)-7,8,9,10-tetrahydropyrimido[4,5-a]indolizine-2,4(1H,3H)-dione;

Example 7.6

5-(3-fluorophenyl)-1,3,9-trimethyl-10-(4-methylthiazol-2-yl)-7,8,9,10-tetrahydropyrimido[4,5-a]indolizine-2,4(1H,3H)-dione;

Example 8.1

1,3-Dimethyl-10-(4-methylthiazol-2-yl)-5-m-tolyl-7,8,9,10-tetrahydropyrimido[4,5-a]indolizine-2,4(1H,3H)-dione;

Example 8.3

5-(3-Chlorophenyl)-10-(4-chlorothiazol-2-yl)-1,3-dimethyl-7,8,9,10-tetrahydropyrimido[4,5-a]indolizine-2,4(1H,3H)-dione;

Example 9.0

3-(1,3-Dimethyl-10-(4-methylthiazol-2-yl)-2,4-dioxo-1,2,3,4,7,8,9,10-octahydro pyrimido[4,5-a]indolizin-5-yl)benzonitrile;

Example 9.2

3-(1,3-Dimethyl-2,4-dioxo-5-phenyl-1,2,3,4,7,8,9,10-octahydropyrimido[4,5-a]indolizin-10-yl)benzonitrile;
1,3-Dimethyl-10-(4-methylthiazol-2-yl)-5-phenyl-7,8,9,10-tetrahydropyrimido[4',5':3,4]pyrrolo[1,2-b]pyridazine-2,4(1H,3H)-dione;

Example 10.2

5-(3-Chlorophenyl)-1,3-dimethyl-10-(4-methylthiazol-2-yl)-7,8,9,10-tetrahydropyrimido[4',5':3,4]pyrrolo[1,2-b]pyridazine-2,4(1H,3H)-dione;

Example 11

1,3-dimethyl-9-(5-methylfuran-2-yl)-5-phenyl-8,9-dihydro-1H-pyrimido[4,5-a]pyrrolizine-2,4(3H,7H)-dione;

Example 12.0

10-(5-chlorofuran-2-yl)-8-(hydroxymethyl)-1,3-dimethyl-5-phenyl-7,8-dihydro-1H-pyrimido[4',5':3,4]pyrrolo[2,1-c][1,4]thiazine-2,4(3H,10H)-dione;

Example 12.1

10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione;

Example 12.2

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

Example 12.3

3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile

Example 12.4

10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione;

Example 13

3-(10-(4-Chlorothiazol-2-yl)-1,3-dimethyl-2,4-dioxo-1,2,3,4,7,8,9,10-octahydropyrimido[4,5-a]indolizin-5-yl)benzonitrile;

Example 13.1

10-(4-Chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione;

Example 13.2

1,3-Dimethyl-5,10-bis(4-methylthiazol-2-yl)-7,8,9,10-tetrahydropyrimido[4,5-a]indolizine-2,4(1H,3H)-dione;

Example 13.3

10-(4-Chlorothiazol-2-yl)-1,3-dimethyl-5-(4-methylthiazol-2-yl)-7,8,9,10-tetrahydropyrimido[4,5-a]indolizine-2,4(1H,3H)-dione;

Example 13.4

10-(4-Chlorothiazol-2-yl)-1,3-dimethyl-5-(2-methylthiazol-4-yl)-7,8,9,10-tetrahydropyrimido[4,5-a]indolizine-2,4(1H,3H)-dione;

Example 14

10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione;

Example 15

10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 15.1

10-(4-Chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 15.2

10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione;

Example 15.3

5-(3-Methoxyphenyl)-1,3-dimethyl-10-(4-methylthiazol-2-yl)-7,8-dihydro-1H-pyrimido[4',5':3,4]pyrrolo[2,1-c][1,4]thiazine-2,4(3H,10H)-dione;

Example 15.4

10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione;

Example 15.5

10-(2-Chlorothiazol-4-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 15.6

10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 15.7

10-(5-Chlorofuran-2-yl)-1,3-dimethyl-5-(1-methyl-1H-imidazol-4-yl)-7,8-dihydro-1H-pyrimido[4',5':3,4]pyrrolo[2,1-c][1,4]thiazine-2,4(3H,10H)-dione;

Example 15.8

10-(5-Chlorofuran-2-yl)-1,3-dimethyl-5-(1-methyl-1H-pyrazol-4-yl)-7,8-dihydro-1H-pyrimido[4',5':3,4]pyrrolo[2,1-c][1,4]thiazine-2,4(3H,10H)-dione;

Example 15.9

10-(5-Chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione;

Example 15.10

10-(5-Chlorofuran-2-yl)-1,3-dimethyl-5-(4-methyloxazol-2-yl)-7,8-dihydro-1H-pyrimido[4',5':3,4]pyrrolo[2,1-c][1,4]thiazine-2,4(3H,10H)-dione;

Example 15.11

10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 15.12

10-(5-chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione;

Example 15.13

10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione;

Example 15.14

10-(5-chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione;

Example 15:15

10-(5-chlorofuran-2-yl)-5-(4-(1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 15:16

10-(4-chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 16

9-(4-Chlorothiazol-2-yl)-1,3-dimethyl-5-phenyl-8,9-dihydro-1H-pyrimido[4,5-a]pyrrolizine-2,4(3H,7H)-dione;

Example 16.1

1,3-Dimethyl-9-(4-methylthiazol-2-yl)-5-phenyl-8,9-dihydro-1H-pyrimido[4,5-a]pyrrolizine-2,4(3H,7H)-dione;

Example 17

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 17.1

10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 17.2

10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione;

Example 18

9,9-Difluoro-5-(3-fluorophenyl)-1,3-dimethyl-10-(5-methylfuran-2-yl)-7,8,9,10-tetrahydropyrimido[4,5-a]indolizine-2,4(1H,3H)-dione;

Example 19

8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 20

3-(9-(4-Chlorothiazol-2-yl)-1,3-dimethyl-2,4-dioxo-2,3,4,7,8,9-hexahydro-1H-pyrimido[4,5-a]pyrrolizin-5-yl)benzonitrile;

Example 20.1

9-(4-Chlorothiazol-2-yl)-1,3-dimethyl-5-(4-methylthiazol-2-yl)-8,9-dihydro-1H-pyrimido[4,5-a]pyrrolizine-2,4(3H,7H)-dione;

Example 20.2

9-(4-Chlorothiazol-2-yl)-5-(3-fluorophenyl)-1,3-dimethyl-8,9-dihydro-1H-pyrimido[4,5-a]pyrrolizine-2,4(3H,7H)-dione;

Example 21

9-(4-Chlorothiazol-2-yl)-1,3,8,8-tetramethyl-5-phenyl-8,9-dihydro-1H-pyrimido[4,5-a]pyrrolizine-2,4(3H,7H)-dione;

Example 21.1

9-(4-Chlorothiazol-2-yl)-5-(3-fluorophenyl)-1,3,8,8-tetramethyl-8,9-dihydro-1H-pyrimido[4,5-a]pyrrolizine-2,4(3H,7H)-dione;

Example 21.2

9-(4-Chlorothiazol-2-yl)-1,3,8,8-tetramethyl-5-phenyl-8,9-dihydro-1H-pyrimido[4,5-a]pyrrolizine-2,4(3H,7H)-dione;

Example 21.3

3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile;

Example 21.4

5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione;

Example 21.5

1,3,8,8-Tetramethyl-9-(4-methylthiazol-2-yl)-5-phenyl-8,9-dihydro-1H-pyrimido[4,5-a]pyrrolizine-2,4(3H,7H)-dione;

Example 21.6

9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione;

Example 21.7

5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione;

Example 21.8

3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile;

Example 21.9

1,3,8,8-Tetramethyl-9-(4-methylthiazol-2-yl)-5-phenyl-8,9-dihydro-1H-pyrimido[4,5-a]pyrrolizine-2,4(3H,7H)-dione;

Example 22

10-(4-Chlorothiazol-2-yl)-1,3-dimethyl-5-(1-methyl-1H-pyrazol-3-yl)-7,8,9,10-tetrahydropyrimido[4,5-a]indolizine-2,4(1H,3H)-dione;

Example 23

10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione;

Example 23.1

3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile;

Example 24

7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione;

Example 25

2-(10-(5-Chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylic acid;

Example 26

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8)methyl)methanesulfonamide;

Example 26.1

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide;

Example 26.2

Methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate;

Example 26.3

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide;

Example 26.4

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide;

Example 27

9-(4-Chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione;

Example 27.1

9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione;

Example 27.2

7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione;

Example 27.3

3-(9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile;

Example 28

8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 29

9-(4-Chlorothiazol-2-yl)-5-(3-fluorophenyl)-1,3-dimethyl-8-methylene-8,9-dihydro-1H-pyrimido[4,5-a]pyrrolizine-2,4(3H,7H)-dione;

Example 30

10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione;

Example 30.1

10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione;

Example 31

3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile;

Example 32

11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione;

Example 33

1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione;

Example 34

11-(4-Chlorothiazol-2-yl)-1,3-dimethyl-5-phenyl-8,9,10,11-tetrahydro-1H-pyrimido[4',5':3,4]pyrrolo[1,2-a]azepine-2,4(3H,7H)-dione;

and the pharmaceutically acceptable salts thereof.

Embodiment 20. A compound of formula (I) or formula (Ia), which is selected from the list consisting of:

Example 13a (R)-3-(10-(4-chlorothiazol-2-yl)-1,3-dimethyl-2,4-dioxo-1,2,3,4,7,8,9,10-octahydropyrimido[4,5-a]indolizin-5-yl)benzonitrile;

Example 13.2a 10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione;

Example 13.3a 10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione;

Example 13.1a 10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione;

Example 15

10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 15.11

10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 17

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 17.1

10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

Example 23a 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione;

Example 23.1a 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile;

Example 28a 8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

and the pharmaceutically acceptable salts thereof.

Embodiment 21. A compound of formula (I) or formula (Ia), which is selected from the list consisting of:

Example 13a (R)-3-(10-(4-chlorothiazol-2-yl)-1,3-dimethyl-2,4-dioxo-1,2,3,4,7,8,9,10-octahydropyrimido[4,5-a]indolizin-5-yl)benzonitrile;

Example 13.1a 10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione;

Example 13.2a 10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione;

Example 13.3a 10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione;

Example 15

10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

Example 17

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

Example 23a 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione;

Example 23.1a 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile;

and the pharmaceutically acceptable salts thereof.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides as Embodiment 22, a compound of formula (I), or a pharmaceutically acceptable salt thereof, according to any one of embodiments 1 to 21, in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/di hydrogen phosphate, polygalacturonate, propionate, sebacate, stearate, succinate, sulfosalicylate, sulfate, tartrate, tosylate trifenatate, trifluoroacetate or xinafoate salt form.

Embodiment 23. A compound of formula (I), or a pharmaceutically acceptable salt thereof, according to any one of Embodiments 1 to 21, which is in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by CFTR or (ii) associated with CFTR activity, or (iii) characterized by activity (normal or abnormal) of CFTR or (2) reduce or inhibit the activity of CFTR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CFTR; or at least partially reducing or inhibiting the expression of CFTR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra.

Compounds of formula (I), wherein X is S, Z is $CH_2$, n is 1, $R^4$ is H, and $R^1$, $R^2$ and $R^3$ are as defined hereinabove, may be prepared according to Scheme 1.

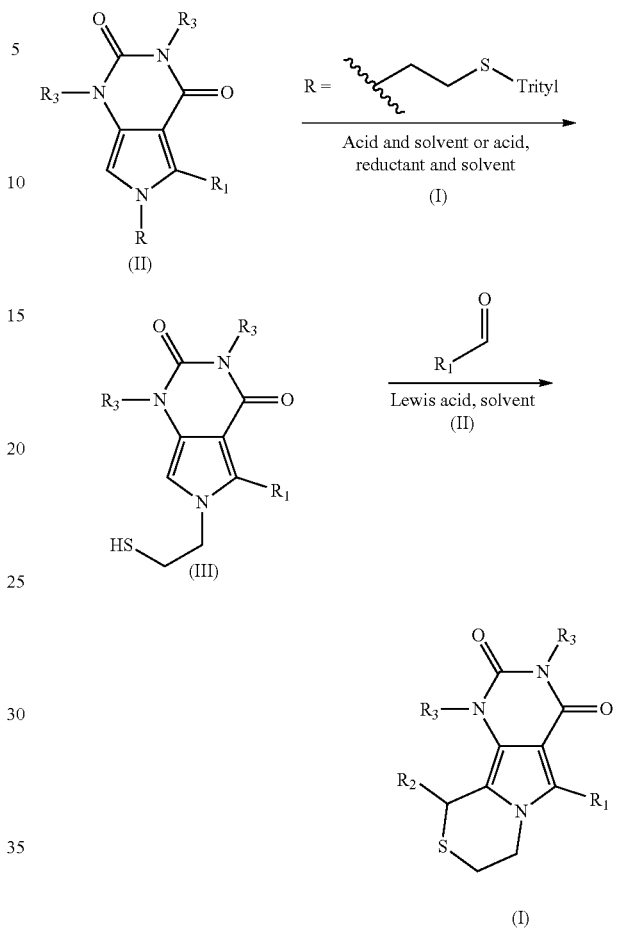

Step 1(i) An intermediate of formula (III) may be prepared from an intermediate of formula (II) by removal of the trityl moiety in the presence of a suitable acid, such as HCl, or acid and reducing agent, such as trifluoroacetic acid and triethylsilane.

Step 1(ii) A compound of formula (I) may be prepared from an intermediate of formula (III) by reaction with a suitable aldehyde in the presence of a Lewis acid, such as bismuth triflate.

Intermediates of formula (II) may be prepared according to Scheme 2.

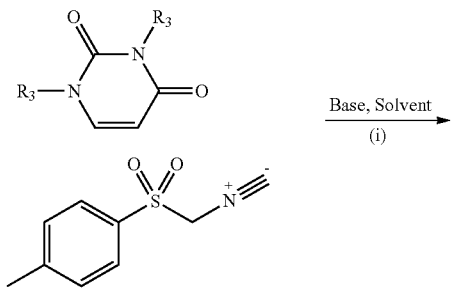

wherein R represents

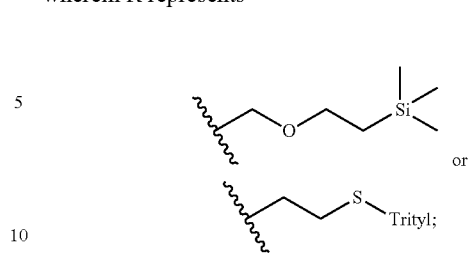

$R^a$ represents methyl or i-propyl; E represents I and $G^1$ represents boronic acid or boronate ester; or E represents $B(OH)_2$ and $G^1$ represents Cl, Br, I or OTf Step 2(i) An intermediate of formula (IV) may be prepared by reaction of a suitable pyrimidine-2,4(1H,3H)-dione with 1-(isocyanomethyl)sulfonyl)-4-methylbenzene in the presence of a suitable base, such as sodium hydride in DMSO/THF or potassium t-butoxide in 5-methyl-tetrahydrofuran.

Step 2(ii) An intermediate of formula (V) may be prepared by N-alkylation of an intermediate of formula (IV) with a compound R—Cl.

Step 2(iii) An intermediate of formula (VI) may be prepared from an intermediate of formula (V) by reaction with a suitable electrophile, such as $I_2$ or $B(OR^a)_3$, in the presence of a suitable base, such as LDA or BuLi. The skilled person will recognize that the C5-lithiated species may either be preformed or formed in-situ in the presence of the appropriate electrophile.

Step 2(iv) An intermediate of formula (II) may be prepared from an intermediate of formula (VI) via a Suzuki cross-coupling reaction with a compound of formula $R^1$-$G^1$, in the presence of a suitable palladium catalyst, such as tetrakis-(triphenylphosphine)palladium (0) or 1,1"bis(di-t-butylphosphino)ferrocene palladium dichloride (Johnson Matthey PD-118).

Compounds of formula (I) wherein Z is $CR^{4a}$, n is 1, and X, $R^1$, $R^2$, $R^3$ and $R^4$ are as defined hereinabove, may be prepared according to Scheme 3.

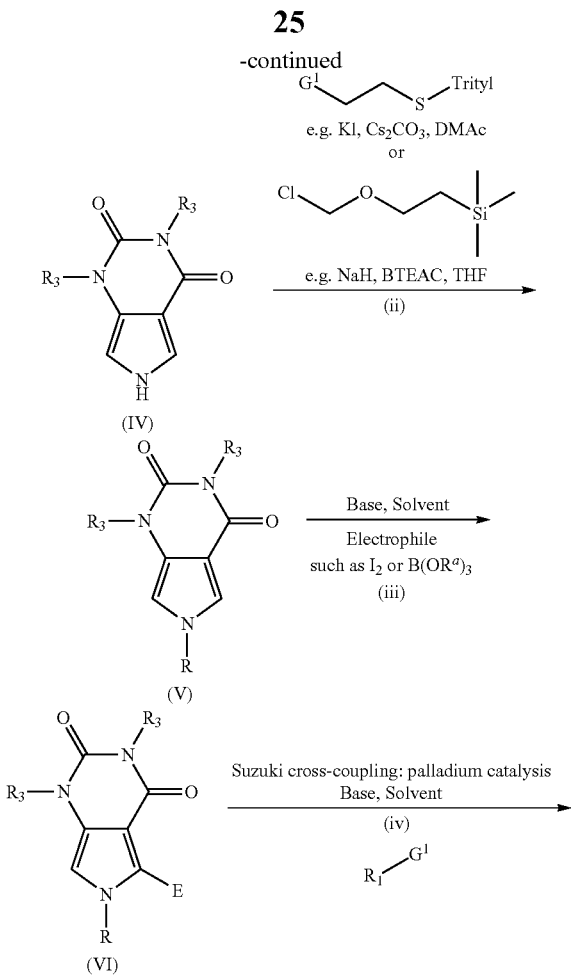

Scheme 3

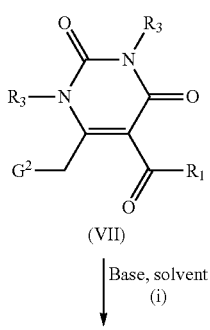

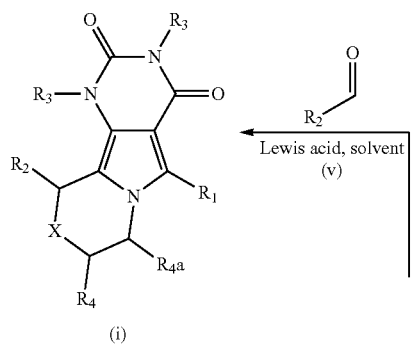

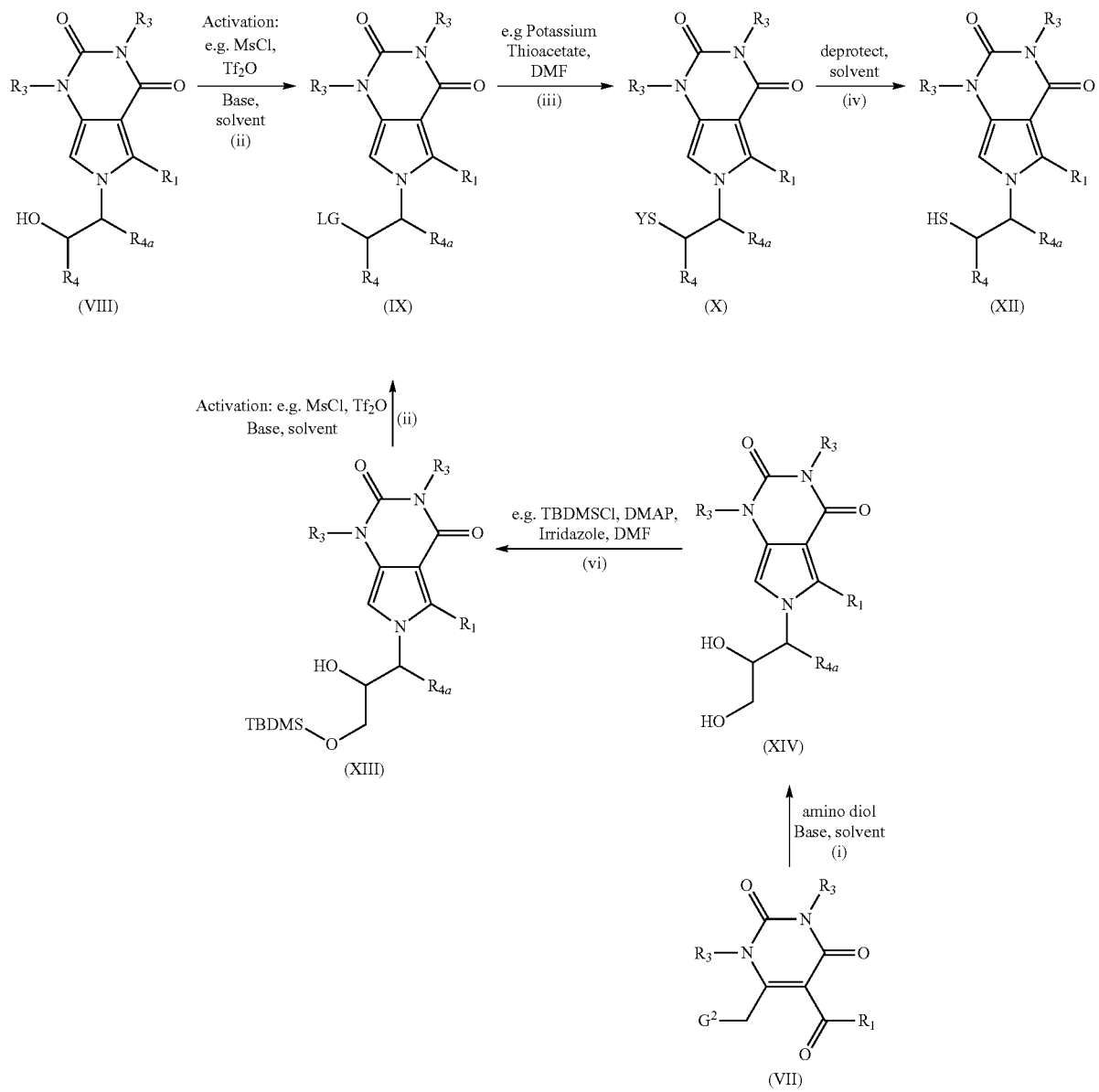

wherein LG represents a suitable leaving group such as mesylate or triflate; $G^2$ represents halide, preferably bromide; and Y represents trityl or acetyl.

Step 3(i) An intermediate of formula (VIII) may be prepared by reaction of an intermediate of formula (VII) with the required amino alcohol in the presence of a suitable base, such as triethylamine in ethanol.

Step 3(ii) An intermediate of formula (IX), may be prepared from an intermediate of formula (VIII) by reaction with a suitable agent, such as mesyl chloride, mesyl anhydride or triflic anhydride, optionally in the presence of a suitable catalyst such as DMAP. Alternatively, where $R^4$ in the compound of formula (I) is —$CH_2OH$, an intermediate of formula (IX) may be prepared from an intermediate of formula (VII) according to the process described in Steps 3(i), 3(vi) and 3(ii), using the required amino diol and a suitable protecting group for the primary hydroxy group, such as TBDMS, followed by reaction of the secondary alcohol as described in Step 3(ii).

Step 3(iii) Direct displacement of the activated secondary alcohol (IX) to provide an intermediate of formula (X) can be achieved by reaction with a suitable sulphur based nucleophile, such as potassium thioacetate or the sodium salt of triphenylmethyl mercaptan.

Step 3(iv) When Y is acetyl, deprotection of intermediate (X), can be achieved using $NaBH_4$ in ethanol. When Y is trityl, intermediate (X) may be deprotected using the conditions described in Step 1(i).

Step 3(v) Cyclisation to provide a compound of formula (I) can be achieved by a process analogous to that described in Step 1(ii).

Intermediates of formula (VII) may be prepared according to Scheme 4.

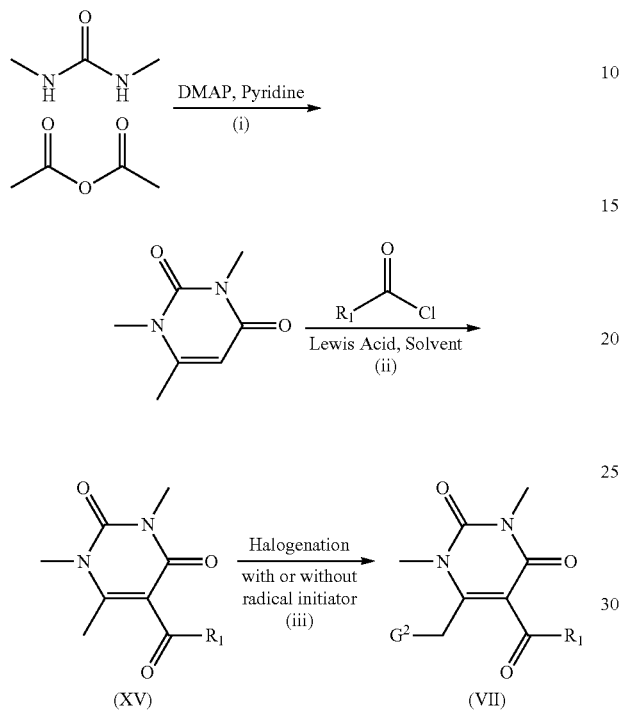

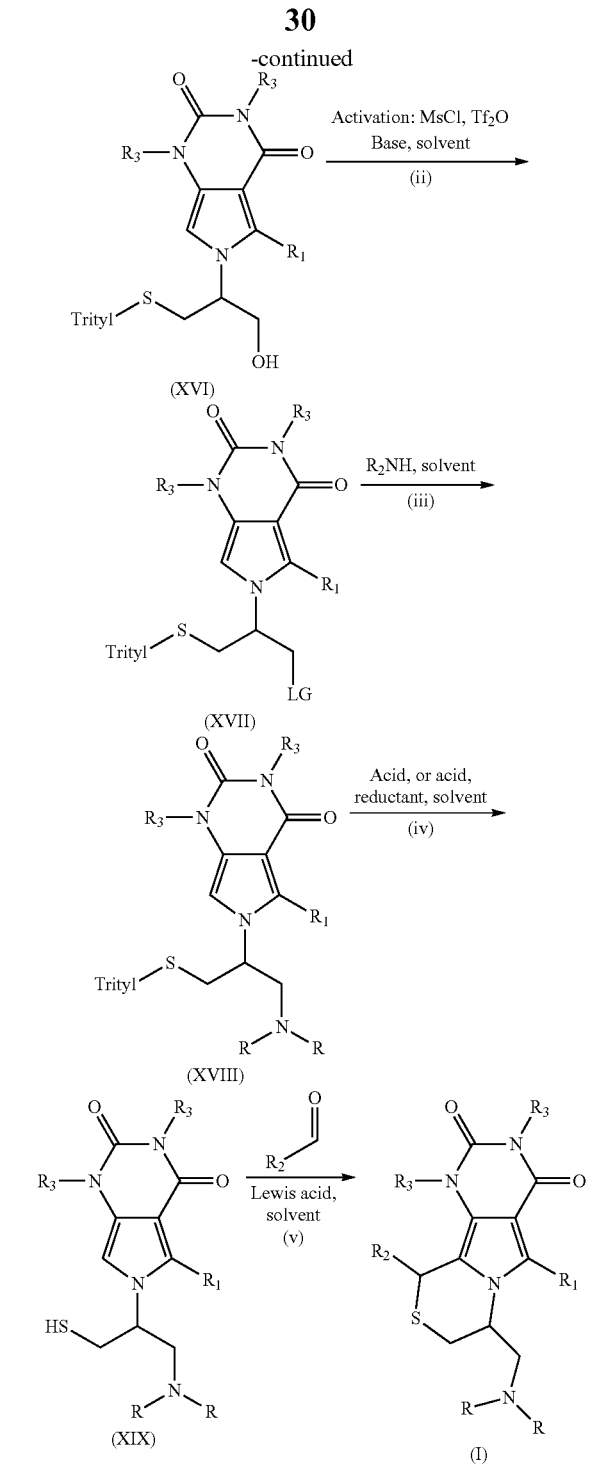

Steps 4(i) and (ii) Intermediates of formula (XV) may be prepared in a two-step process by reaction of acetic anhydride and dimethyl urea, followed by a Friedel-Crafts acylation using the required acyl chloride in the presence of a suitable Lewis acid, such as zinc chloride or aluminium trichloride.

Step 4(iii) An intermediate of formula (VII) may be prepared by halogenation of an intermediate of formula (XV) in the presence or absence of a radical initiator. Suitably, bromine in chloroform may be used.

Compounds of formula (I), wherein X is S, Z is $CR^{4a}$, $R^{4a}$ is amino-$CH_2$—, $(C_1-C_4)$alkylamino-$CH_2$— or di[$(C_1-C_4)$alkyl]amino-$CH_2$—, n is 1, $R^4$ is H, and $R^1$, $R^2$ and $R^3$ are as defined hereinabove, may be prepared according to Scheme 5.

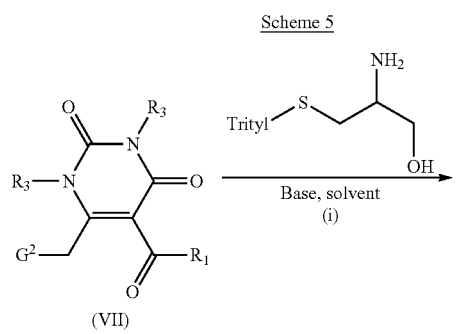

wherein each R is independently selected from H and $(C_1-C_4)$alkyl; and LG represents a suitable leaving group such as mesylate or triflate.

Step 5(i) and (ii) An intermediate of formula (XVII) may be prepared from an intermediate of formula (VII) via processes analogous to those described in step 3(i) followed by step 3(ii).

Step 5(iii) An intermediate of formula (XVII) may be converted to the corresponding secondary amine of formula (XVIII) by displacement of the leaving group with a suitable nucleophile, $R_2NH$.

Steps 5(iv) and (v) A compound of formula (I) may be prepared from an intermediate of formula (XVIII) via processes analogous to those described in Step 1(i) followed by Step 1(ii).
Compounds of formula (I), wherein X is CH$_2$, Z is NH, n is 1, R$^4$ is H and R$^1$, R$^2$ and R$^3$ are as defined hereinabove, may be prepared according to Scheme 6.
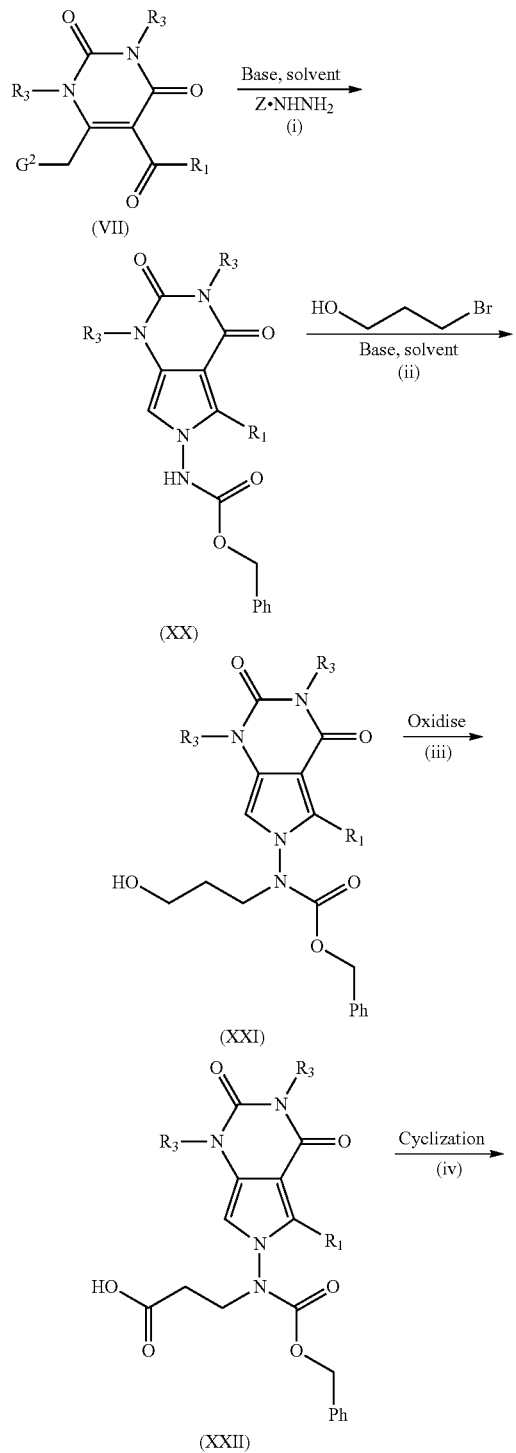
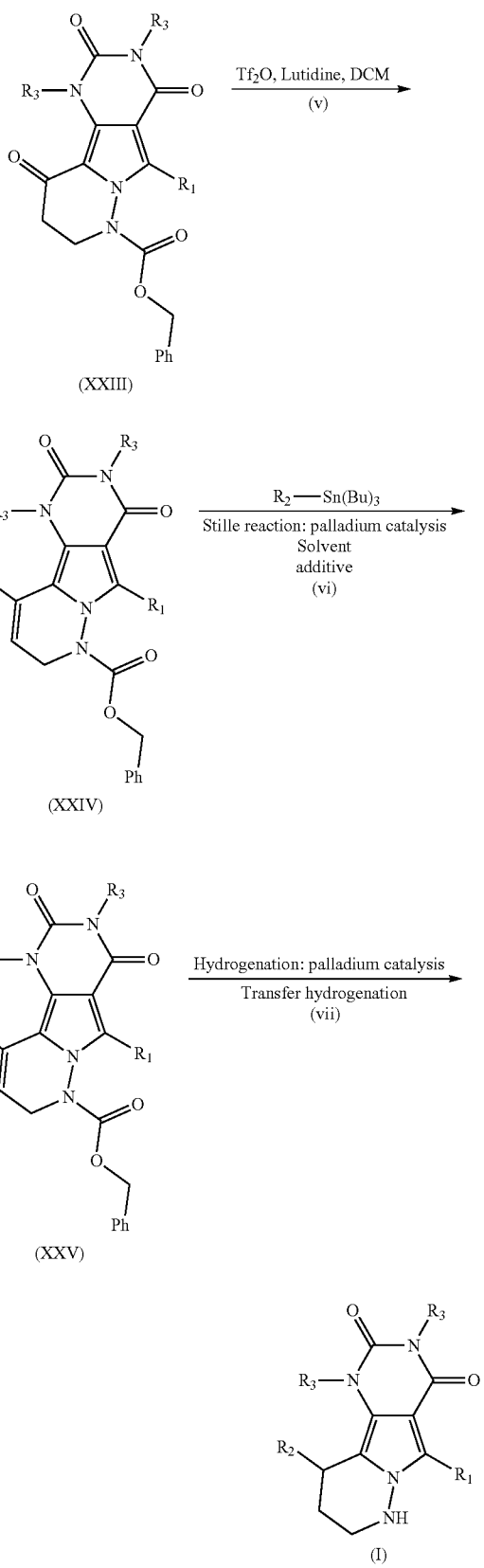
wherein ZNHNH$_2$ is benzyl carbazate.

Step 6(i) An intermediate of formula (XX) may be prepared by reaction of an intermediate of formula (VII) with benzyl carbazate using conditions analogous to those described in step 3(i)

Step 6(ii) An intermediate of formula (XXI) may be prepared by N-alkylation of an intermediate of formula (XX) with 3-bromopropan-1-ol in the presence of a suitable base, such as potassium carbonate.

Step 6(vii) A compound of formula (I) may be prepared from an intermediate of formula (XXV) by transfer hydrogenation, using ammonium formate in the presence of palladium on carbon in a suitable solvent such as ethanol.

Compounds of formula (I), wherein X and Z are $CH_2$, n is 1, $R^4$ is H, and $R^1$, $R^2$ and $R^3$ are as defined hereinabove, may be prepared according to Scheme 7. When $R^2$ is 2-furyl, a compound of formula (I) may be prepared according to steps 7(iv) and 7(v)

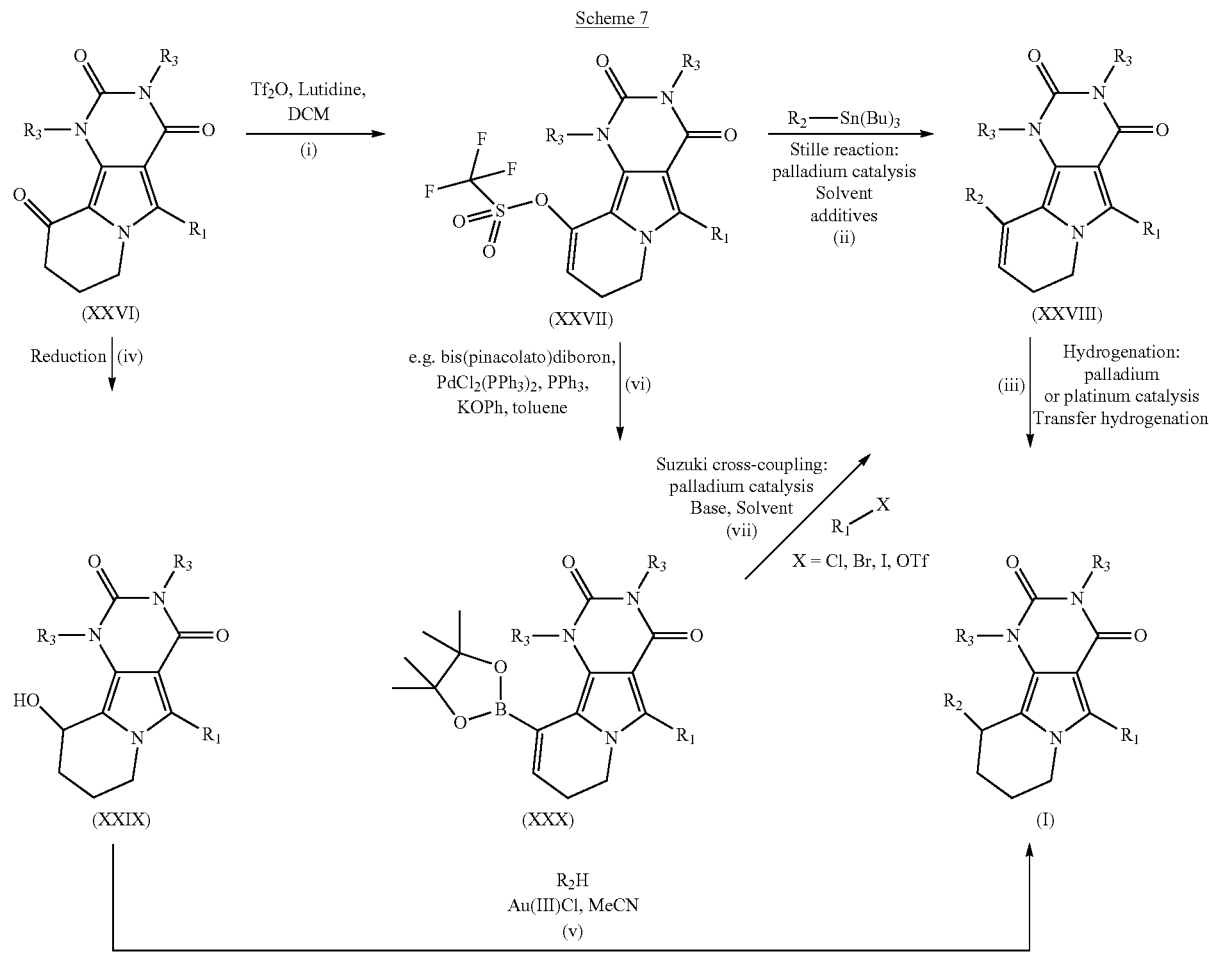

Scheme 7

Step 6(iii) Oxidation of the alcohol intermediate of formula (XXI) to provide the corresponding acid intermediate of formula (XXII) can suitably be achieved using TPAP/NMO conditions Step 6(iv) An intermediate of formula (XXIII) may be prepared by cyclization of (XXII), suitably using polyphosphoric acid (PPA).

Step 6(v) An enol-triflate of formula (XXIV) may be prepared by reaction of an intermediate of formula (XXIII) with triflic anhydride in the presence of a base, such as lutidine.

Step 6(vi) An intermediate of (XXV) may be prepared by reaction of an enol-triflate of formula (XXIV) with a suitable stannane, such as $R^2$-tributyl tin in the presence of a suitable palladium catalyst such as [1,1'-bis(diphenylphosphino)ferrocene]dichloropalladium(II) and suitable additives such as LiCl and CuI.

Steps 7(i), (ii) and (iii) may be carried out in an analogous fashion to the reactions described in Steps 6(v), (vi) and (vii). Step 7(iii) may alternatively be carried out using hydrogenation under palladium or platinum catalysis conditions, such as palladium on carbon or platinum on carbon in ethanol.

Step 7(iv) An intermediate of formula (XXIX) may be prepared by reduction of a compound of formula (XXVI) using a suitable reducing agent such as $NaBH_4$ in a suitable solvent such as methanol.

Step 7(v) When $R^2$ is a 2-furyl moiety, a compound of formula (I) may be prepared directly from an intermediate of formula (XXIX) by gold(III) catalysis.

Step 7(vi) An intermediate of formula (XXX) may be prepared by reaction of an intermediate of formula (XXVII) with a suitable boron species, such as bis(pinacolato)diboron, in the presence of a suitable palladium catalyst, such as $PdCl_2(PPh_3)_2$, and KOPh.

Step 7(vii) An intermediate of formula (XXVIII) may alternatively be prepared from an intermediate of formula (XXX) by a Suzuki cross-coupling reaction in an analogous fashion to the reaction described in Step 2(iv).

An intermediate of formula (XXVI) may be prepared according to Scheme 8.

Step 8(iv) An intermediate of formula (XXVI) may be prepared by cyclisation of an intermediate of formula (XXXIII) under conditions analogous to those described in Step 6(iv), or by using propane phosphonic acid anhydride (T3P®) in ethyl acetate or DMF.

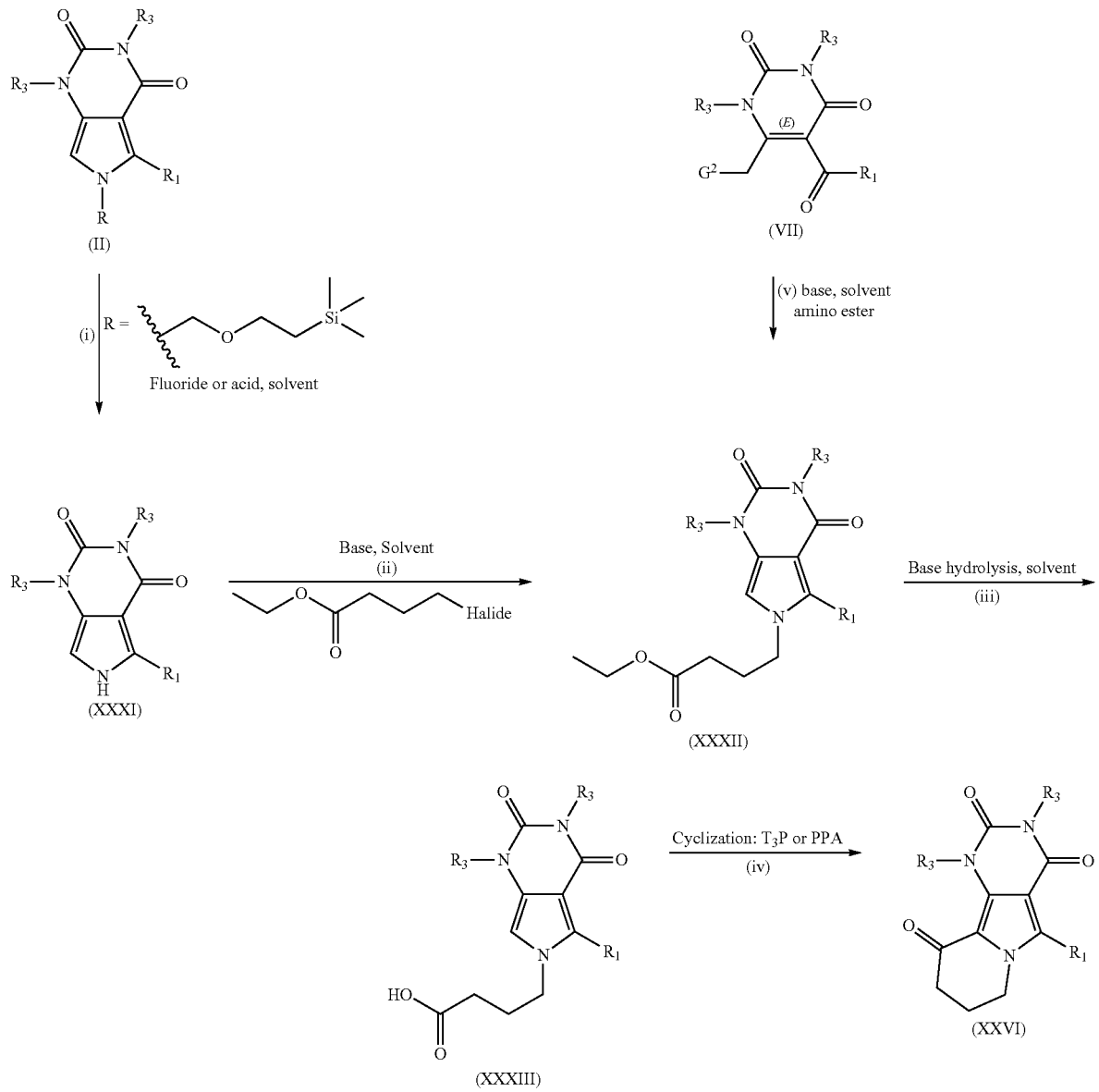

Scheme 8

Step 8(i) An intermediate of formula (XXXI) may be prepared by fluoride- or acid-catalysed deprotection of an intermediate of formula (II), such as TBAF in THF.

Step 8(ii) N-alkylation of an intermediate of formula (XXXI) to give an intermediate of formula (XXXII) may be carried out under conditions analogous to those described in Step 2(ii), such as caesium carbonate in DMF.

Step 8(iii) Ester hydrolysis of an intermediate of formula (XXXII) to give an intermediate of formula (XXXIII) may be carried out using a suitable base, such as LiOH in THF/H$_2$O.

Step 8(v) Alternatively, an intermediate of formula (XXXII) may be prepared from an intermediate of formula (VII) using the required amino ester in the presence of a suitable base, such as triethylamine, in a suitable solvent such as ethanol.

Compounds of formula (I), wherein X and Z are CH$_2$, n is 0, and R$^1$, R$^2$ and R$^3$ are as defined hereinabove, may also be prepared according to Schemes 7 and 8, using the corresponding ω-amino ester.

Alternatively, an intermediate of formula (XXVIII), may be prepared according to Scheme 9.

Scheme 9

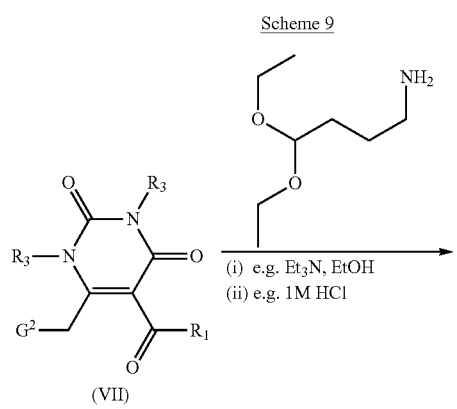

(VII)

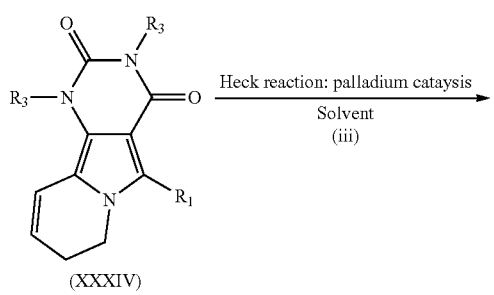

(XXXIV)

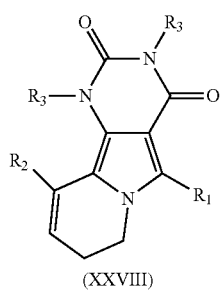

(XXVIII)

Step 9(i) and (ii) An intermediate of formula (XXXIV) may be prepared by reaction of an intermediate of formula (VII) with an amino acetal followed by acid catalyzed cyclisation, suitably using HCl.

Step 9(iii) An intermediate of formula (XXVIII) may be prepared from an intermediate of formula (XXXIV) using a Heck reaction under palladium catalysis, suitably using palladium acetate in the presence of tri-tert-butylphosphine tetrafluorohydroborate in dimethylacetamide (DMA).

Intermediates of formula (XIV) may also be prepared according to scheme 10.

Scheme 10

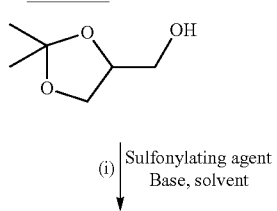

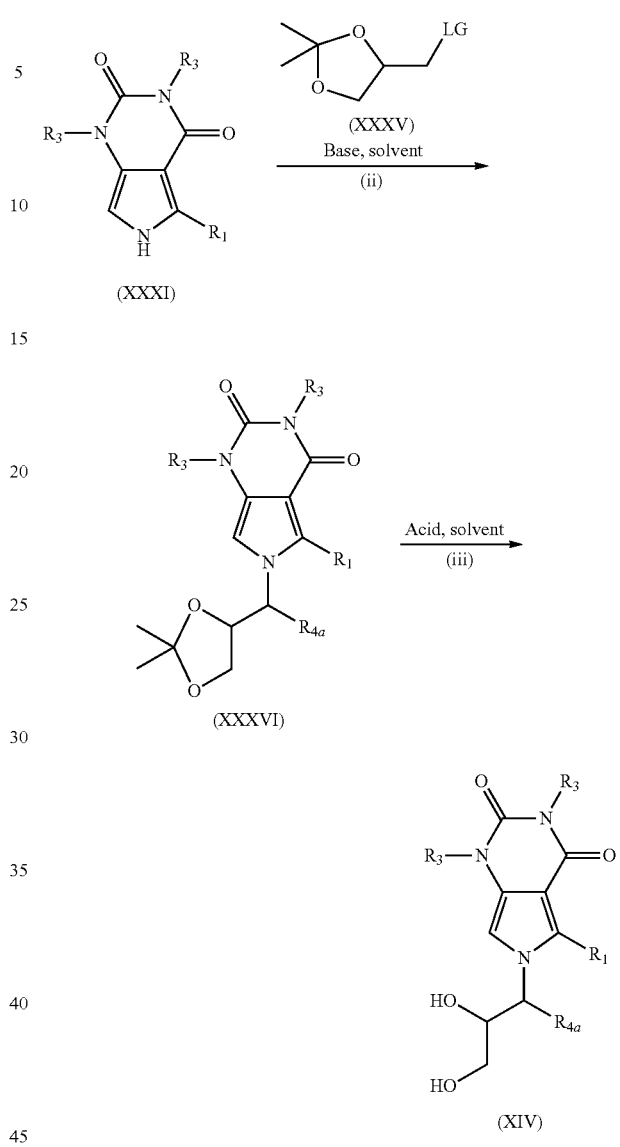

wherein LG is a leaving group such as mesylate or triflate, preferably triflate.

Step 10(i) An intermediate of formula (XXXV) may be prepared by treatment of the appropriate commercially available alcohol by treatment with an appropriate sulfonylating agent in the presence of a suitable base, such as trifluoromethanesulfonic anhydride in the presence of 2,6-lutidine.

Step 10(ii) An intermediate of formula (XXXVI) may be prepared from an intermediate of formula (XXXI) by treatment with intermediate (XXXV) and a suitable base, such as sodium hydride in DMF.

Step 10(iii) An intermediate of formula (XIV) may be prepared from an intermediate of formula (XXXVI) by treatment with an appropriate acid, such as HCl in diethyl ether.

Further compounds of formula (I) wherein Z is $CR^{4a}$, n is 1, and X, $R^1$, $R^2$, $R^3$ and $R^4$ are as defined hereinabove, may be prepared by derivatisation of another compound of formula (I) where $R^4$ is $CH_2OH$ according to Scheme 11.

Scheme 11

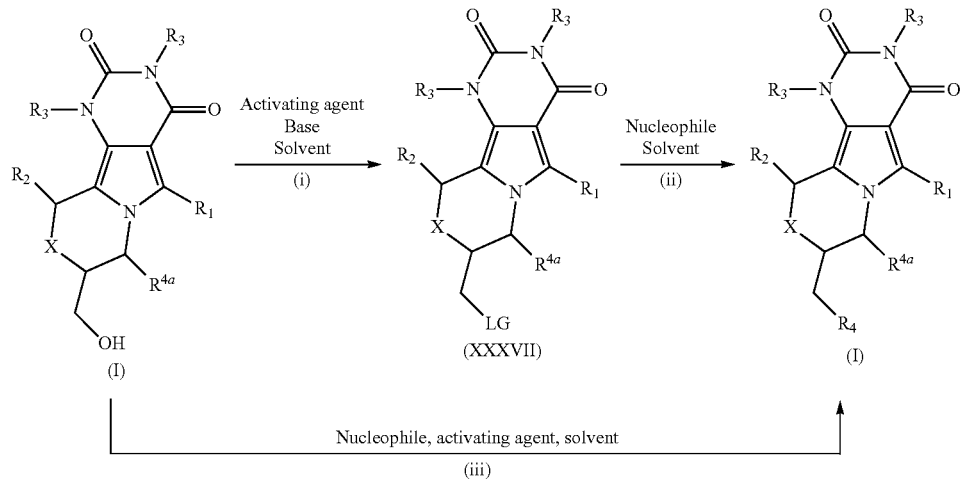

wherein LG represents a suitable leaving group such as mesylate or triflate.

Step 11(i) An intermediate of formula (XXXVII) may be prepared by reaction of a compound of formula (I) in the manner described in Step 3(ii).

Step 11(ii) A compound of formula (I) may be prepared by reaction of an intermediate of formula (XXXVII) by treatment with a nucleophile and application of heat in a suitable solvent, such as dimethylamine in THF.

Step 11(iii) Compounds of formula (I) may also be prepared directly by direct treatment of another compound of formula (I) with an appropriate nucleophile in the presence of a sulfonic anhydride in a suitable solvent, such as sodium imidazolide in the presence of triflic anhydride in DCM.

Compounds of formula (I), wherein X is $CF_2$ and Z is $CH_2$, n is 1, $R^4$ is H, and $R^1$, $R^2$ and $R^3$ are as defined hereinabove, may be prepared according to Scheme 12.

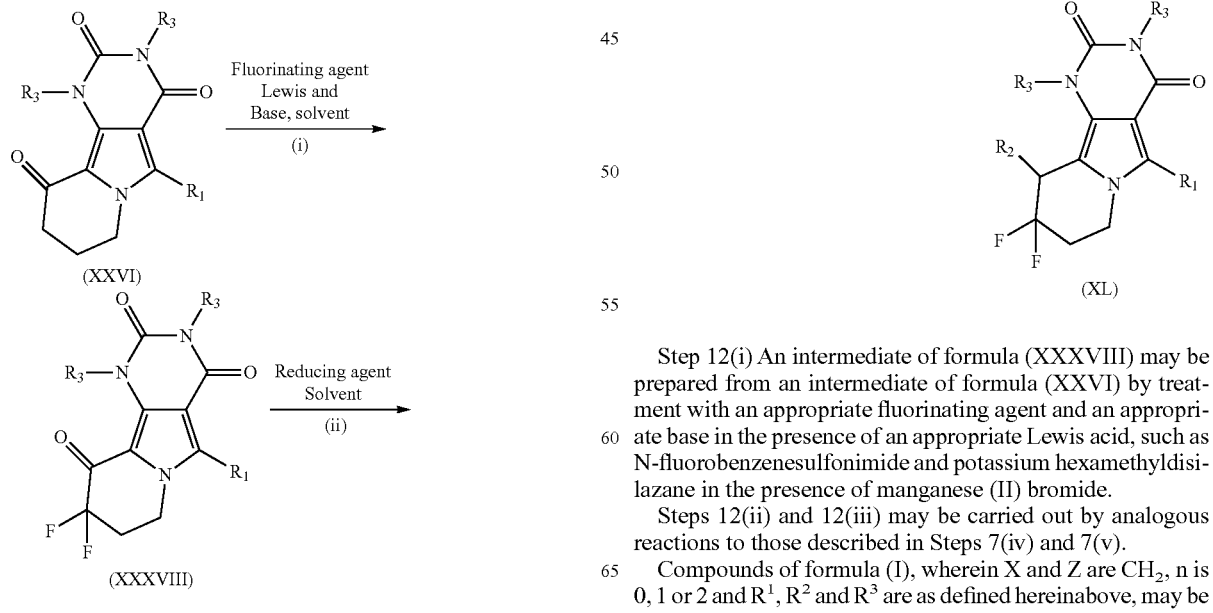

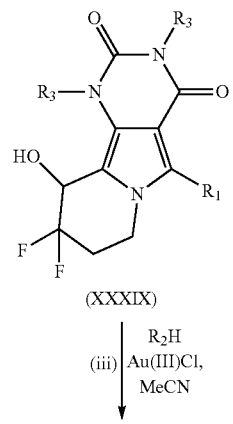

Step 12(i) An intermediate of formula (XXXVIII) may be prepared from an intermediate of formula (XXVI) by treatment with an appropriate fluorinating agent and an appropriate base in the presence of an appropriate Lewis acid, such as N-fluorobenzenesulfonimide and potassium hexamethyldisilazane in the presence of manganese (II) bromide.

Steps 12(ii) and 12(iii) may be carried out by analogous reactions to those described in Steps 7(iv) and 7(v).

Compounds of formula (I), wherein X and Z are $CH_2$, n is 0, 1 or 2 and $R^1$, $R^2$ and $R^3$ are as defined hereinabove, may be prepared according to Scheme 13.

Scheme 13
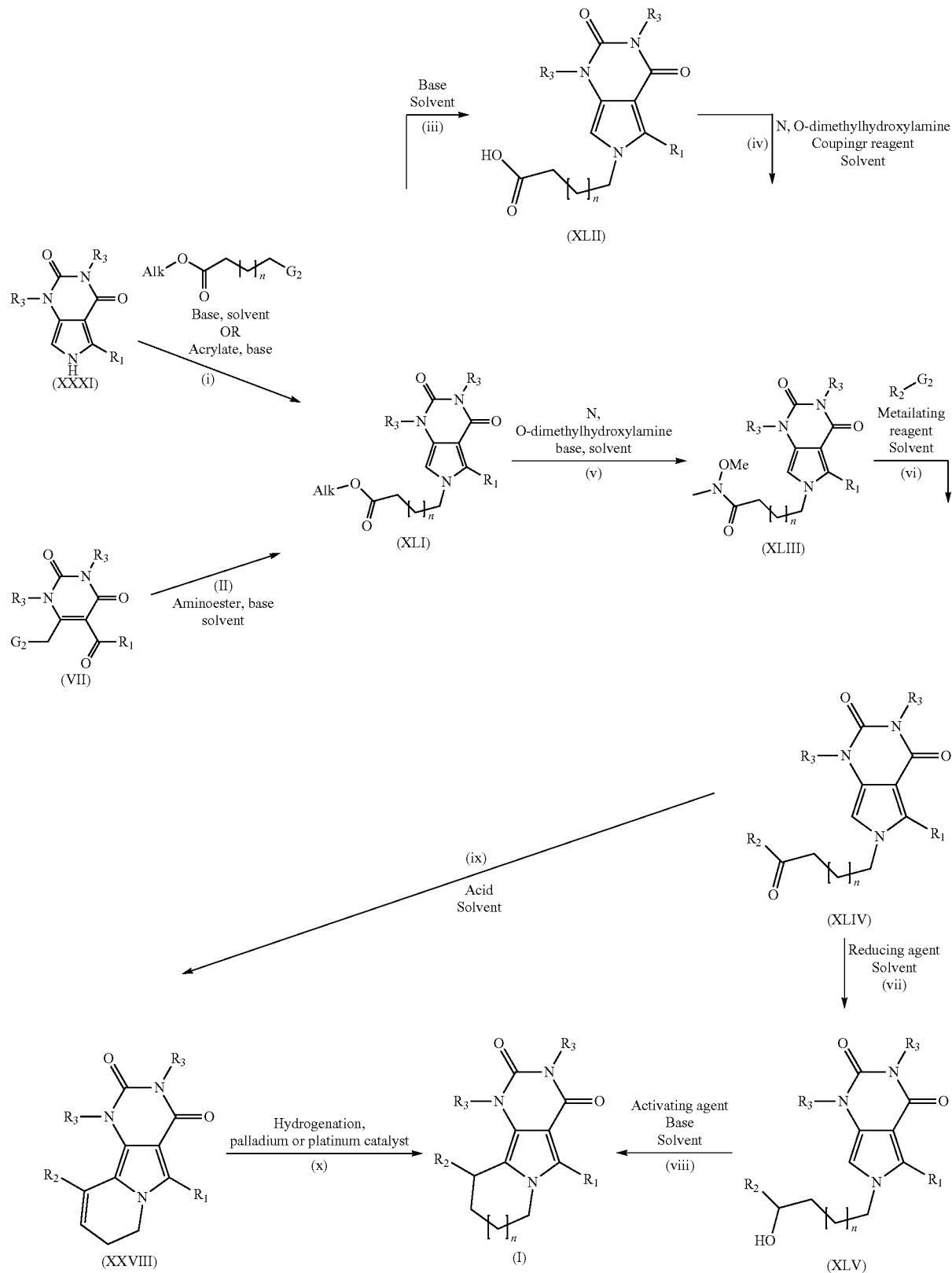

wherein $G_2$ represents halide, preferably bromide or iodide, and Alk represents methyl or ethyl.

Step 13(i) For n=1 or 2, N-alkylation of an intermediate of formula (XXXI) with a commercially available halide to give an intermediate of formula (XLI) may be carried out under conditions analogous to those described in Step 2(ii), such as cesium carbonate in DMF. Alternatively, for n=0, N-alkylation of an intermediate of formula (XXXI) to give an intermediate of formula (XLI) may be carried out by treatment by treatment with a suitable acrylate ester and a suitable base, such as methyl acrylate and DBU.

Step 13(ii) Alternatively, an intermediate of formula (XLI) may be prepared from an intermediate of formula (VII) using the required commercially available amino ester in the presence of a suitable base in a suitable solvent, such as triethylamine in ethanol.

Step 13(iii) Ester hydrolysis of an intermediate of formula (XLI) may be carried out to give an intermediate of formula (XLII) by use of an appropriate base, such as lithium hydroxide.

Step 13(iv) An intermediate of formula (XLIII) may be prepared from an intermediate of formula (XLII) by treatment with N,O-dimethylhydroxylamine and an appropriate coupling reagent in the presence of a suitable base, such as T3P in EtOAc or DMF in the presence of DIPEA.

Step 13(v) Alternatively, an intermediate of formula (XLIII) may be directly prepared from an intermediate of formula (XLI) by treatment with N,O-dimethylhydroxylamine and a suitable base, such as isopropylmagnesium bromide in THF.

Step 13(vi) An intermediate of formula (XLIV) may be prepared from an intermediate of formula (XLIII) by reaction with an appropriate halo compound $R_2$-$G_2$ in the presence of an appropriate metallating reagent, such as isopropylmagnesium chloride-lithium chloride complex.

Step 13(vii) An intermediate of formula (XLV) may be prepared from an intermediate of formula (XLIV) by treatment with an appropriate reducing agent, such as sodium borohydride-lithium chloride in methanol.

Step 13(viii) A compound of formula (I) may be prepared from an intermediate of formula (XLV) by treatment with an appropriate activating agent and an appropriate base, such as triflic anhydride in the presence of triethylamine.

Alternatively, compounds of formula (I) may be prepared from and intermediate of formula (XLIV) by Steps 13(ix) and 13(x).

Step 13(ix) An intermediate of formula (XXVIII) may be prepared by treatment of an intermediate of formula (XLIV) by treatment with an appropriate acid, such as triflic acid.

Step 13(x) may be carried out using hydrogenation under palladium or platinum catalysis conditions, such as palladium on carbon or platinum on carbon in ethanol, analogously to Step 7(ii).

Compounds of formula (I), wherein Z is $CHR^{4s}$, n is 0, and $R^1$, $R^2$ and $R^3$ are as defined hereinabove, may be prepared according to Scheme 14.

Scheme 14

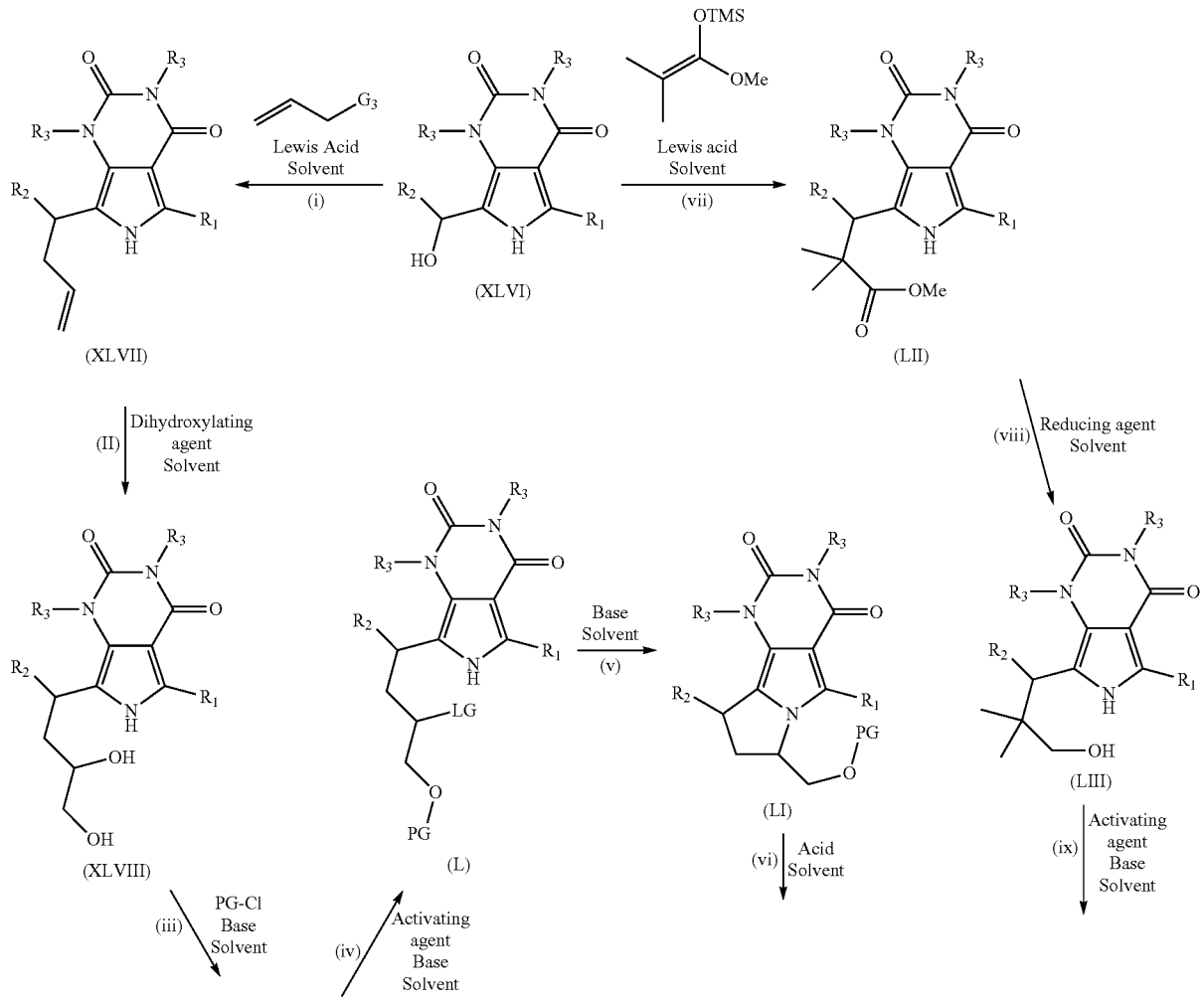

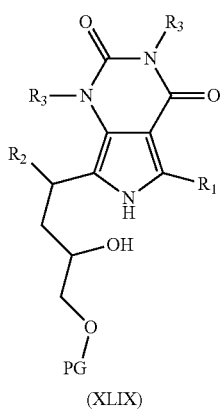

(XLIX)

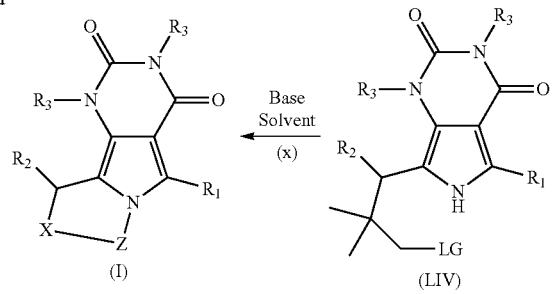

wherein $G_3$ represents an appropriate metal or metalloid residue, such as trialkylstannyl, PG represents an appropriate protecting group, such as trialkylsilyl, and LG represents a leaving group, such as mesylate.

Where $X=CH_2$ and $Z=CHCH_2OH$, compounds of formula (I) may be prepared according to Steps 14(i)-14(vi). Where $X=CMe_2$ and $Z=CH_2$, compounds of formula (I) may be prepared according to Steps 14(vii)-14(x).

Step 14(i) An intermediate of formula (XLVII) may be prepared from an intermediate of formula (XLVI) by treatment with an appropriate allylating agent in the presence of an appropriate lewis acid, such as tri-n-butylallylstannane in the presence of boron trifluoride in THF.

Step 14(ii) An intermediate of formula (XLVIII) may be prepared from an intermediate of formula (XLVII) by treatment with an appropriate dihydroxylating reagent in an appropriate solvent, such as osmium tetroxide and N-methylmorpholine oxide in acetonitrile/water.

Step 14(iii) An intermediate of formula (XLIX) may be prepared from an intermediate of formula (XLVIII) by O-protection with a compound PG-Cl in the presence of a suitable base, such as tertbutyldimethylsillylchloride in the presence of imidazole.

Step 14(iv) An intermediate of formula (L) may be prepared from an intermediate of formula (XLIX) by an analogous reaction to Step 3(ii).

Step 14(v) An intermediate of formula (LI) may be prepared from an intermediate of formula (L) by treatment with a suitable base in a suitable solvent, such as sodium hydride in THF.

Step 14(vi) A compound of formula (I) may be prepared from an intermediate of formula (LI) by removal of the protecting group in the presence of a suitable acid, such as TFA in methanol/water mixtures.

Step 14(vii) An intermediate of formula (LII) may be prepared from an intermediate of formula (XLVI) by treatment with the commercially available silyl ketene acetal in the presence of a suitable lewis acid, such as boron trifluoride.

Step 14(viii) An intermediate of formula (LIII) may be prepared from an intermediate of formula (LII) by treatment with an appropriate reducing agent in an appropriate solvent, such as sodium borohydride-lithium chloride in methanol.

Step 14(ix) An intermediate of formula (LIV) may be prepared from an intermediate of formula (LIII) by an analogous reaction to Step 3(ii)

Step 14(x) A compound of formula (I) may be prepared from an intermediate of formula (LIV) by an analogous reaction to Step 14(v).

Intermediates of formula (XLVI) may be prepared according to Scheme 15.

Scheme 15

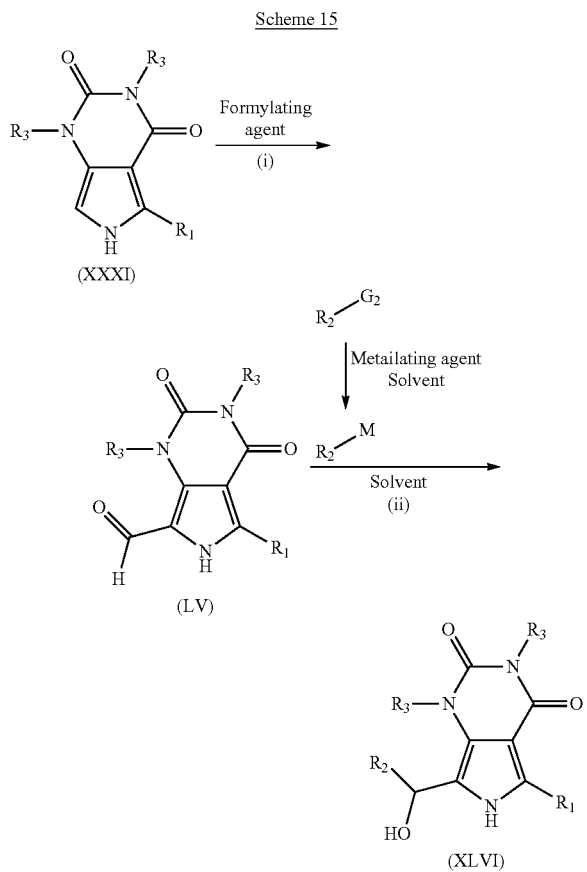

wherein $G_2$ represents halide, preferably bromide or iodide, and M represents a metal residue, preferably magnesium halide.

Step 15(i) An intermediate of formula (LV) may be prepared from an intermediate of formula (XXXI) by reaction with a suitable formylating agent, such as $POCl_3$ in DMF Step 15(ii) An intermediate of formula (XLVI) may be prepared from an intermediate of formula (LV) by treatment with an organometallic compound $R^2$-M, which itself may by prepared directly prior to use by treatment of a compound $R^2$-$G_2$ with a metallating agent, such as isopropylmagnesium chloride-lithium chloride.

Compounds of formula (I), wherein X is C=$CH_2$, Z is $CHR^{4s}$, n is 0, and $R^1$, $R^2$, $R^3$ and $R^{4a}$ are as defined hereinabove, may be prepared according to Scheme 16.

and an appropriate Lewis acid, such as dimethyl malonate in the presence of sodium hexamethyldisilazane and boron trifluoride.

Steps 16(ii), 16(iii) and 16(iv) may be carried out in by reactions analogous to Steps 15(viii), 3(ii) and 14(v) respectively.

Compounds of formula (I), wherein X is S and Z is $CH_2$, n is 1, $R^1$, $R^2$, $R^3$, $R^4$, $R^a$ and $Het^2$ are as defined hereinabove and W is C=O or $SO_2$, may be prepared according to Scheme 17.

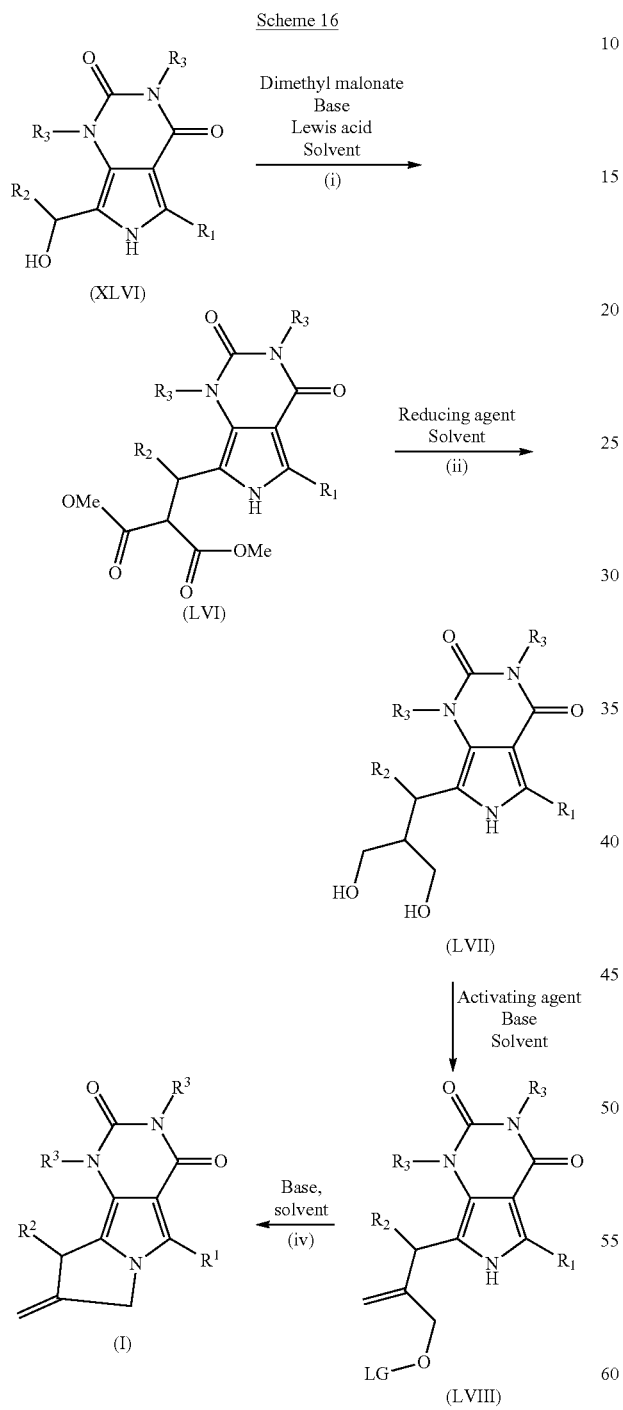

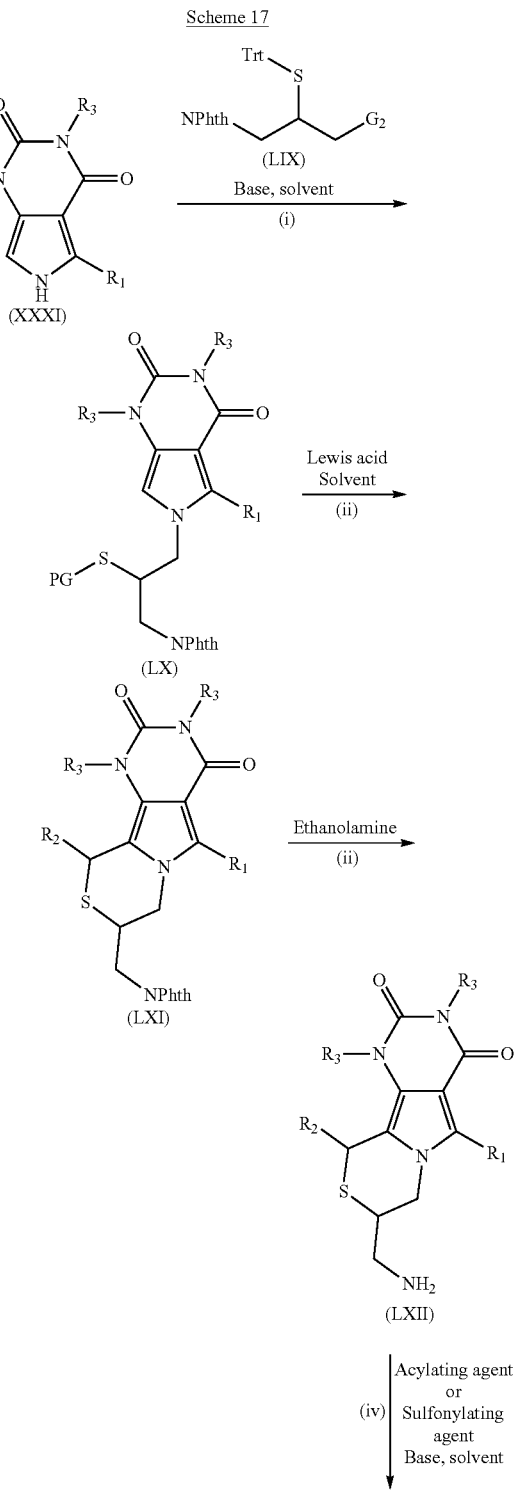

wherein LG is a leaving group such as mesylate.

Step 16(i) An intermediate of formula (LVI) may be prepared from an intermediate of formula (XLVI) by treatment with dimethyl malonate in the presence of an appropriate base

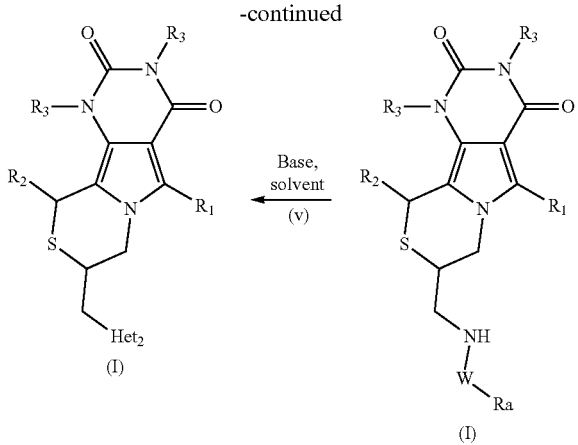

wherein $G_2$ is halide, preferably bromide

Step 17(i) An intermediate of formula (LX) may be prepared by treatment of an intermediate of formula (XXXI) with an intermediate of formula (LIX) and a suitable base in a suitable solvent, such as cesium carbonate in DMF.

Step 17(ii) An intermediate of formula (LXI) may be prepared from an intermediate of of formula (LX) by reactions analogous to Steps 1(i) and 1(ii).

Step 17(iii) Deprotection of the Phth protecting group may be carried out by using ethanolamine and the application of heat to give an intermediate of formula (LXII).

Step 17(iv) Compounds of formula (I) may be prepared by treatment of an intermediate of formula (LXII) with suitable acylating agent or sulfonylating agent in the presence of a suitable base in a suitable solvent, such as acetyl chloride or methanesulfonyl chloride in the presence of DIPEA in DCM.

Step 17(v) Further compounds of formula (I) may be prepared from an appropriate compound of formula (I) where $R^a$ is halo($C_1$-$C_4$)alkyl or ($C_1$-$C_4$)alkoxy by treatment with an appropriate base in an appropriate solvent, such as sodium hydride in THF.

An intermediate of formula (LIX) may be prepared according to Scheme 18.

Scheme 18

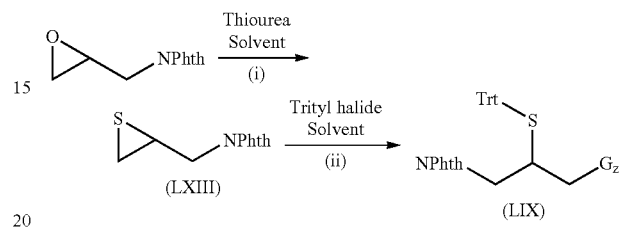

wherein $G_2$ is halide, preferably bromide

Step 18(i) An intermediate of formula (LXIII) may be prepared from the commercially available epoxide by treatment with thiourea in an appropriate solvent, such as methanol.

Step 18(ii) An intermediate of formula (LIX) may be prepared from an intermediate of formula (LXIII) by treatment with an appropriate trityl halide in an appropriate solvent, such a trityl bromide in DCM.

Compounds of formula (I), wherein X is $CHR^{4b}$ and Z is $CHR^{4a}$, n is 1, $R^1$, $R^2$ and $R^3$ are as defined hereinabove, may be prepared according to Scheme 19.

Scheme 19

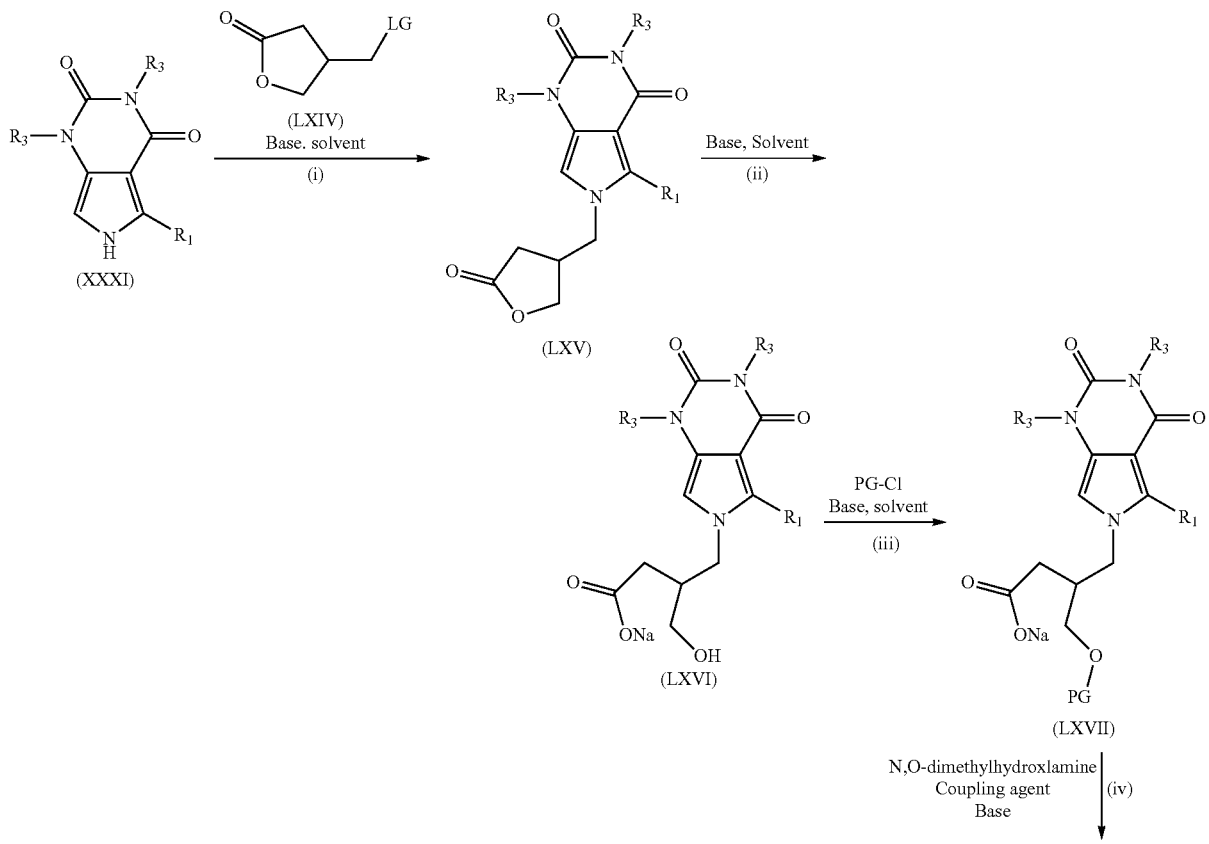

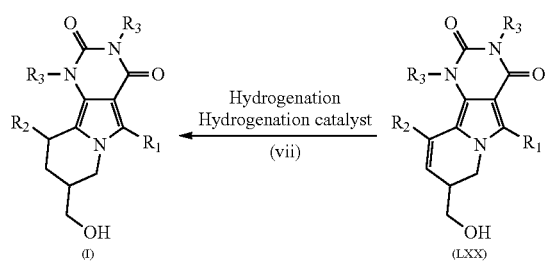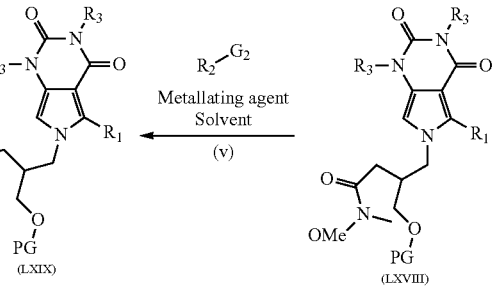

wherein LG is a leaving group such as mesylate or triflate, preferably triflate, $G_2$ is a halide, preferably bromide or iodide and PG is a protecting group such as trialkylsilyl.

Step 19(i) An intermediate of formula (LXV) may be prepared from an intermediate of formula (XXXI) and an intermediate of formula (LXIV) by treatment with a suitable base in a suitable solvent, such as potassium tert-butoxide in THF.

Step 19(ii) An intermediate of formula (LXVI) may be prepared from an intermediate of formula (LXV) by base-mediated hydrolysis with a suitable base, such as sodium hydroxide.

Step 19(iii), Step 19(iv) and 19(v) may be carried out by analogous reactions to Steps 14(iii), 13(iv) and 13(vi) respectively.

Step 19(vi) An intermediate of formula (LXX) may be prepared from an intermediate of formula (LXIX) by treatment with a suitable acid in a suitable solvent, such as pyridinium hydrochloride in methanol and water.

Step 19(vii) may be carried out by an analogous reaction to Step 7(iii).

Scheme 20

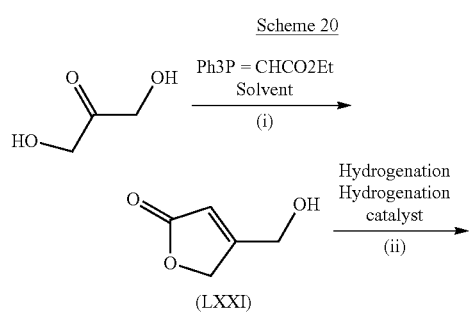

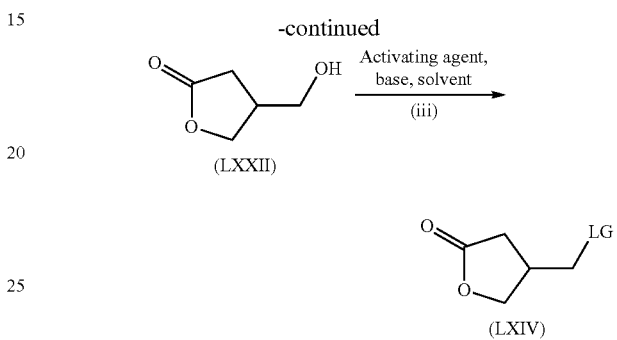

wherein LG is a leaving group such as mesylate or triflate, preferably triflate.

Step 20(i) An intermediate of formula (LXXI) may be prepared from the commerically available dihydroxyacetone by treatment with (carbethoxymethylene)triphenylphosphorane in a suitable solvent, such as DCM Step 20(ii) An intermediate of formula (LXXII) may be prepared from an intermediate of formula (LXXI) by hydrogenation over a suitable catalyst, such as palladium on charcoal in 2-methyltetrahydrofuran Step 20(iii) An intermediate of formula (LXIV) may be prepared from an intermediate of formula (LXXII) by treatment with a suitable activating agent in the presence of a suitable base, such as trifluoromethanesulfonic anhydride in the presence of 2,6-lutidine Compounds of formula (I), wherein X is $CH_2$ and Z is $CHR^{4a}$, n is 1, $R^1$, $R^2$, $R^3$ and $Het^2$ are as defined hereinabove, may be prepared according to Scheme 21.

Scheme 21

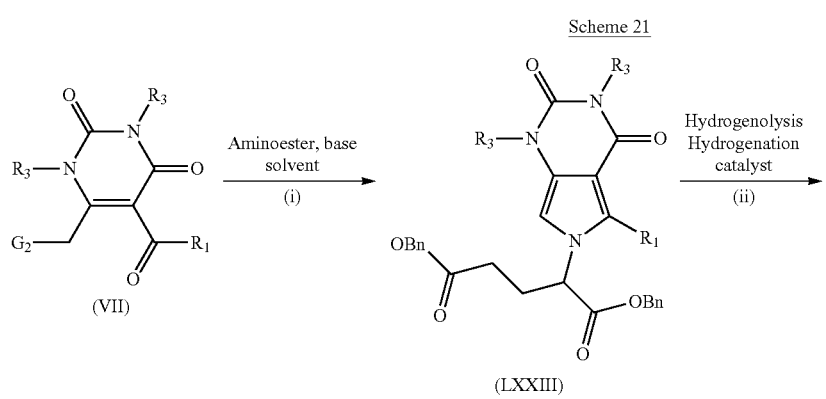

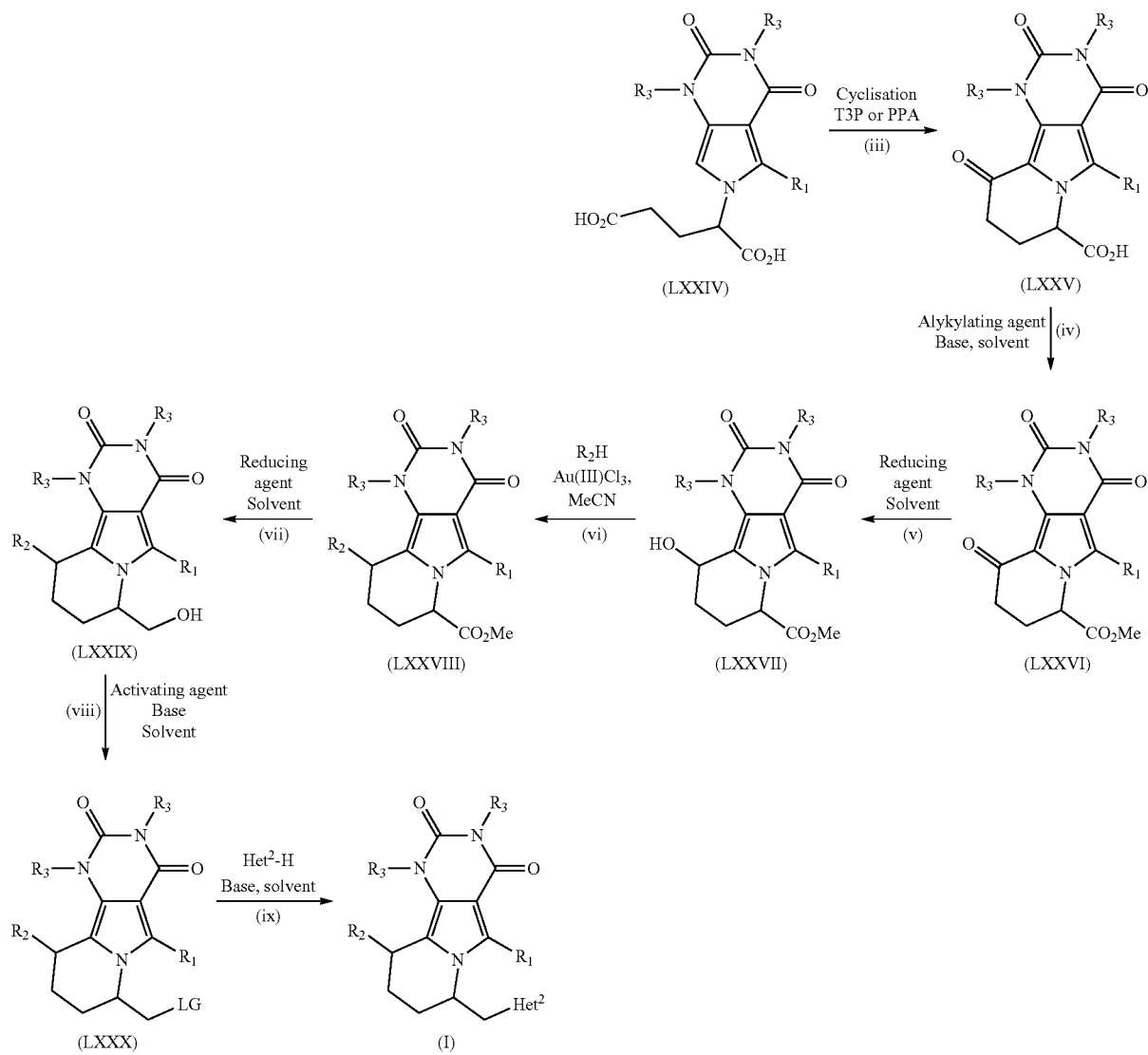

wherein LG is a leaving group such as mesylate.

Steps 21(v) and 21(vi) may be carried out in a similar manner to Steps 7(iv) and 7(v).

Step 21(i) An intermediate of formula (LXXIII) may be prepared from an intermediate of formula (VII) in a similar manner to Step 3(i) using the appropriate commercially available aminodiester.

Step 21(ii) An intermediate of formula (LXXIV) may be prepared from an intermediate of formula (LXXIII) by hydrogenolysis under palladium catalysis conditions, such as palladium on carbon in ethanol.

Step 21(iii) An intermediate of formula (LXXV) may be prepared from an intermediate of formula (LXXIV) by an analogous reaction to Step 8(iv).

Step 21(iv) An intermediate of formula (LXXVI) may be prepared from an intermediate of formula (LXXV) by treatment with an appropriate alkylating agent in the presence of a suitable base with the application of heat in a suitable solvent, such as dimethyl sulfate in the presence of potassium carbonate in wet acetone.

Steps 21(v) and 21(vi) may be carried out by analogous reactions to those described in Steps 7(iv) and 7(v).

Step 21(vii) An intermediate of formula (LXXIX) may be prepared from an intermediate of formula (LXXVIII) by treatment with a suitable reducing agent, such as lithium aluminium hydride in THF.

Step 21(viii) An intermediate of formula (LXXX) may be prepared from an intermediate of formula (LXXIX) by treatment with an appropriate activating agent in the presence of a suitable base, such as methansulfonyl chloride in the presence of triethylamine.

Step 21(ix) A compound of formula (I) may be prepared from an intermediate of formula (LXXX) by treatment with an appropriate heterocycle $Het^2$-H in the presence of a suitable base, such as potassium carbonate in DMF.

Compounds of formula (I), wherein X is $CH_2$ or CHMe, Z is $CH_2$, n is 1, $R^4$ is H or Me, and $R^1$, $R^2$ and $R^3$ are as defined hereinabove, may be prepared according to Scheme 22. When $R^2$ is 2-furyl, compounds of formula (I) may be prepared according to steps 7(iv) and 7(v)

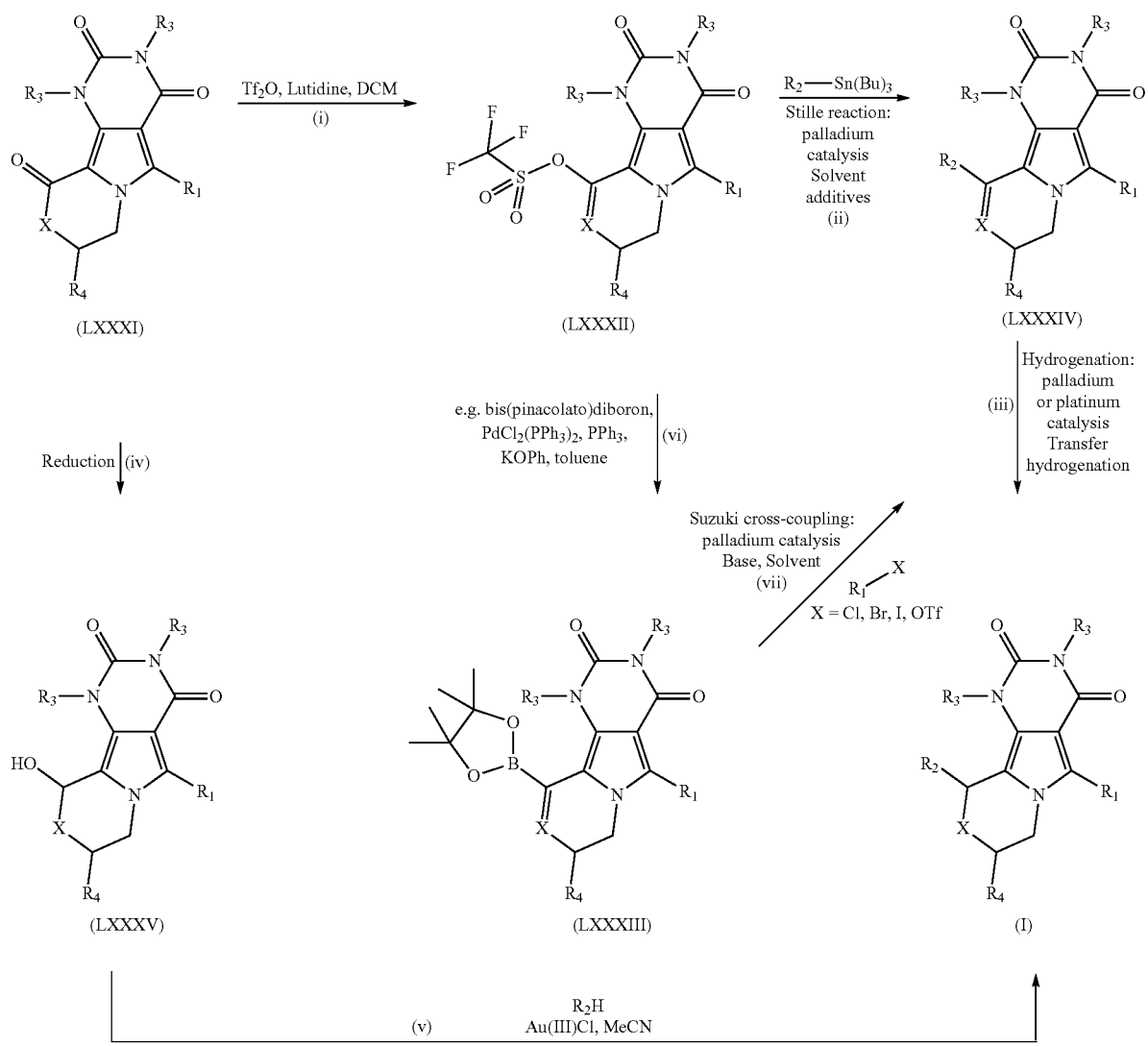

Steps 22(i) to 22(vii) may be carried out by analogous reactions to those detailed in appropriate Intermediate (LXXXVII) in Step 8(ii). Intermediates of formula (LXXXVII) may be prepared according to Scheme 23.

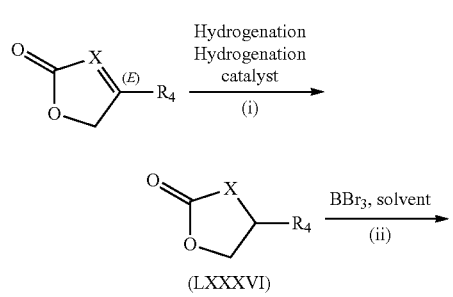

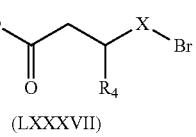

wherein X is $CH_2$ or CHMe and $R^4$ is H or Me.

Step 23(i) An intermediate of formula (LXXXVI) may be prepared from a commercially available lactone using hydrogenation under palladium catalysis conditions, such as palladium on carbon or platinum on carbon in ethyl acetate.

Step 23(ii) An intermediate of formula (LXXXVII) may be prepared from an intermediate of formula (LXXXVI) by treatment with boron tribromide in DCM.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The CFTR chloride channel is known to be associated with a number of diseases and conditions, including cystic fibrosis (CF) (Quinton, *Physiol. Rev.* 79:S3-S22 (1999); Boucher, *Eur. Respir. J* 23:146-58 (2004)), polycystic kidney disease (O'Sullivan et al., *Am. J Kidney Dis.* 32:976-983 (1998); Sullivan et al., *Physiol. Rev.* 78:1165-91 (1998); Strong et al., *J Clin. Invest.* 93:347-54 (1994); Mall et al., *Gastroenterology* 126:32-41 (2004); Hanaoka et al., *Am. J Physiol.* 270: C389-C399 (1996); Kunzelmann et al., *Physiol. Rev.* 82:245-289 (2002); Davidow et al., *Kidney Int.* 50:208-18 (1996); Li et al., *Kidney Int.* 66:1926-38 (2004); Al-Awqati, *J Clin. Invest.* 110:1599-1601 (2002); Thiagarajah et al., *Curr. Opin. Pharmacol.* 3:594-99 (2003)) and secretory diarrhea (Clarke et al., *Science* 257:1125-28 (1992); Gabriel et al., *Science* 266:107-109 (1994); Kunzelmann and Mall, *Physiol. Rev.*

82:245-89 (2002); Field, M. *J Clin. Invest.* 111:931-43 (2003); and Thiagarajah et al., *Gastroenterology* 126:511-519 (2003)).

The compounds of formula (I) in free form or in salt form, exhibit valuable pharmacological properties, e.g. CFTR modulating properties, e.g. as indicated in in vitro and in vivo tests as provided in the next sections, and are therefore indicated for therapy or for use as research chemicals, e.g. as tool compounds. The compounds of formula (I) and (Ia) may be useful in vivo in the development of models of cystic fibrosis.

Compounds of the invention may be useful in the treatment of an indication selected from polycystic kidney disease and diarrhea, including infectious secretory diarrhea, travellers diarrhea, diarrhea associated with HIV and diarrhea predominant irritable bowel syndrome (IBS).

Thus, as a further embodiment, the present invention provides the use of a compound of formula (I) or (Ia) in therapy. In a further embodiment, the therapy is selected from a disease which may be treated by inhibition of CFTR. In another embodiment, the disease is selected from the afore-mentioned list, suitably polycystic kidney disease and diarrhea, more suitably polycystic kidney disease, infectious secretory diarrhea, travellers diarrhea, diarrhea associated with HIV and diarrhea predominant irritable bowel syndrome (IBS).

In another embodiment, the invention provides a method of treating a disease which is treated by inhibition of CFTR comprising administration of a therapeutically acceptable amount of a compound of formula (I) or (Ia) In a further embodiment, the disease is selected from the afore-mentioned list, suitably polycystic kidney disease and diarrhea, more suitably polycystic kidney disease, infectious secretory diarrhea, travellers diarrhea, diarrhea associated with HIV and diarrhea predominant irritable bowel syndrome (IBS). Thus, as a further embodiment, the present invention provides the use of a compound of formula (I) or (Ia) for the manufacture of a medicament. In a further embodiment, the medicament is for treatment of a disease which may be treated by inhibition of CFTR. In another embodiment, the disease is selected from the afore-mentioned list, suitably polycystic kidney disease and diarrhea, more suitably polycystic kidney disease, infectious secretory diarrhea, travellers diarrhea, diarrhea associated with HIV and diarrhea predominant irritable bowel syndrome (IBS).

Embodiment 24. A compound according to any one of previous Embodiments 1 to 21, or a pharmaceutically acceptable salt thereof, for use in the treatment of polycystic kidney disease and diarrhea, more suitably polycystic kidney disease, infectious secretory diarrhea, travellers diarrhea, diarrhea associated with HIV and diarrhea predominant irritable bowel syndrome (IBS).

The pharmaceutical composition or combination of the present invention can be in unit dosage of about 1-2000 mg of active ingredient(s) for a subject of about 50-70 kg, or about 1-1000 mg or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following methods.

IonWorks Quattro Assay:

CFTR activity can be quantified by electrophysiology methods, using the whole-cell configuration of the patch clamp technique (Hamill O, Marty A, Neher E, Sakmann B and Sigworth F. 'Improved patch-clamp techniques for high resolution current recording from cells and cell-free membrane patches.' Pflugers Archive 1981 391: 85-100). This assay directly measures the currents associated with chloride flow through CFTR channels whilst either maintaining or adjusting the transmembrane voltage. This assay can use either single glass micropipettes or parallel planar arrays to measure CFTR activity from native or recombinant cell systems. Currents measured using parallel planar arrays can be quantified using an appropriately equipped instrument such as the IonWorks Quattro (Molecular Devices Corporation, Sunnyvale, Calif.). The Quattro system can measure CFTR currents from either a single cell per recording well (HT configuration) or alternatively from a population of 64 cells per well (Population Patch Clamp PPC) (Finkel A, Wittel A, Yang N, Handran S, Hughes J, Costantin J. 'Population patch clamp improves data consistency and success rates in the measurement of ionic currents.' J Biomol Screen. 2006 August; 11(5):488-96).

Cell Culture:

Chinese hamster ovary (CHO) cells stably expressing WT-CFTR channels were used for the IonWorks Quattro experiments. Cells were maintained at 37° C. in 5% v/v $CO_2$ at 100% humidity in MEM alpha medium supplemented with 10% (v/v) FCS, 100 U/mL Penicillin/Streptomycin, and 100 µg/L methotrexate. For experiments, cells were grown in 225 cm² tissue culture flasks until almost confluent. Cells were removed from the flask using trypsin-EDTA and resuspended in extracellular recording solution for immediate experimentation.

CFTR Inhibitor Assay:

Cells, at a density of 1.5-2 million per mL, were placed on the Quattro system, added to the planar patch plate and seals allowed to establish for 5-10 mins. After assessing seal resistances (typically >50 MO), whole-cell access was obtained by perforation with 100 µg/mL amphotericin B. Baseline currents were measured by a pre-compound scan obtained by application of a voltage ramp from −100 to +100 mV. CFTR was activated by the addition of 10 µM forskolin to each of the 384 wells of the patch plate. After 5 min incubation the post-compound 1 currents were measured, again by application of a voltage ramp from −100 to +100 mV. Test compounds, diluted from 10 mM stocks in DMSO in extracellular solution were then added to the patch plate and were incubated for a further 10 min. The post-compound 2 currents were measured by the application of the same voltage ramp from −100 to +100 mV. The inhibition of CFTR was determined from the difference in current between the forskolin addition (post-compound 1) and the test compound (post-compound 2). This was determined at both −100 mV and +100 mV which represents the inward and outward current respectively.

Solutions:

Extracellular solution (ECS): 145 mM NaCl, 4 mM CsCl, 5 mM D-glucose, 10 mM TES, 1 mM CaCl$_2$, 1 mM MgCl$_2$, pH 7.4 NaOH Intracellular solution (ICS): 113 mM L-Aspartic acid, 113 mM CsOH, 27 mM CsCl, 1 mM NaCl, 1 mM MgCl$_2$, 1 mM EGTA, 10 mM TES. pH 7.2 with CsOH. Filter sterilized before use.

Using the Ion Works Quattro assay (as described in this application) compounds of the invention exhibit CFTR inhibitory efficacy in accordance with Table A:

TABLE A

Inhibitory Activity of Compounds of Formula (I)

| Example Number | CFTR IC50 (µM) Inward current |
|---|---|
| 1.2 | 0.79 |
| 1.3 | >30 |
| 1.1.1 | 0.63 |
| 1.6 | 11.13 |
| 1.10 | 8.08 |
| 2.1 | 0.41 |
| 3.1.1 | 0.41 |
| 3.1.2 | 1.51 |
| 3.5 | 0.16 |
| 4.2 | 1.67 |
| 6.1 | 27.63 |
| 6.3 | 2.24 |
| 6.4 | >30 |
| 7.5b | 2.18 |
| 8.2 | 0.29 |
| 9.1 | 0.29 |
| 9.2 | 9.30 |
| 10.0 | 2.15 |
| 10.2 | 0.70 |
| 11.0 | 9.14 |
| 12.1b | 0.18 |
| 12.b | 0.54 |
| 12.a | 0.20 |
| 13.1a | 0.10 |
| 13.2a | 0.05 |
| 13a | 0.07 |
| 13.3a | 0.09 |
| 14a | 0.31 |
| 15 | 0.10 |
| 15.7 | 5.50 |
| 15.8 | 3.93 |
| 15.9 | 1.90 |
| 15.10 | 1.18 |
| 15.11 | 0.13 |
| 15.12 | 9.27 |
| 15.13 | 0.62 |
| 17 | 0.10 |
| 17.1 | 0.23 |
| 17.2 | 0.24 |
| 18 | 0.48 |
| 19 | 5.38 |
| 20a | 0.27 |
| 21a | 0.33 |
| 21.8 | 1.39 |
| 22 | 0.47 |
| 23a | 0.05 |
| 23.1a | 0.10 |
| 24 | 1.74 |
| 25 | 4.84 |
| 26a | 0.15 |
| 26.1a | 0.23 |
| 26.3a | 0.45 |
| 27a | 0.15 |
| 28a | 0.11 |
| 29 | 0.44 |
| 30a | 0.16 |
| 30.1a | 0.25 |
| 31 | 1.45 |

The compounds of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by CFTR. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I).

In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or (Ia) for treating a disease or condition mediated by CFTR, wherein the medicament is prepared for administration with another therapeutic agent. The invention also provides the use of another therapeutic agent for treating a disease or condition mediated by CFTR, wherein the medicament is administered with a compound of formula (I).

The invention also provides a compound of formula (I) or (Ia) for use in a method of treating a disease or condition mediated by CFTR, wherein the compound of formula (I) or (Ia) is prepared for administration with another therapeutic agent. The invention also provides another therapeutic agent for use in a method of treating a disease or condition mediated by CFTR, wherein the other therapeutic agent is prepared for administration with a compound of formula (I) or (Ia). The invention also provides a compound of formula (I) or (Ia) for use in a method of treating a disease or condition mediated by CFTR, wherein the compound of formula (I) or (Ia) is administered with another therapeutic agent. The invention also provides another therapeutic agent for use in a method of treating a disease or condition mediated by CFTR, wherein the other therapeutic agent is administered with a compound of formula (I) or (Ia).

The invention also provides the use of a compound of formula (I) for treating a disease or condition mediated by CFTR, wherein the patient has previously (e.g. within 24 hours) been treated with another therapeutic agent. The invention also provides the use of another therapeutic agent for treating a disease or condition mediated by CFTR, wherein the patient has previously (e.g. within 24 hours) been treated with a compound of formula (I).

In one embodiment, the invention provides a combination comprising a therapeutically effective amount of a compound of formula (I) or (Ia) according to any preceding Embodiment, or a pharmaceutically acceptable salt thereof, and one or more therapeutically active co-agent is selected from an anti-diarrheal agent, including an oral rehydration agent; an antibiotic; and an antimotility agent such as loperamide.

Specific individual combinations which may provide particular treatment benefits include a combination of a compound of formula (I) or (Ia) according to any preceding Embodiment, or a pharmaceutically acceptable salt thereof, and loperamide.

EXAMPLES

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer, or Micromass Platform Mass Spectrometer or Thermo LTQ Mass Spectrometer; a Waters Acquity UPLC system with SQD Mass Spectrometer, a Waters FractionLynx HPLC system with 3100 Mass Spectrometer, a Waters UPC2 system with TQD Mass Spectrometer or a Waters Prep100 SFC-MS system with SQD2 Mass Spectrometer. [M+H]+ refers to protonated molecular ion of the chemical species.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

ABBREVIATIONS

BOC tertiary butyl carboxy
br broad
CBA weak cation exchange (e.g Isolute® CBA columns from Biotage)
d doublet
d.e. or de diastereomeric excess
degC ° C.
dd doublet of doublets
ddd doublet of doublet of doublets
DBU 1,8-Diazabicyclo[5.4.0]undec-7-ene
DCM dichloromethane
DIPEA diisopropylethylamine
DMA dimethyl acetamide
DMAP 4-dimethylaminopyridine
DMF N,N-dimethylformamide
DMSO dimethylsulfoxide
e.e. or ee enantiomeric excess
EtOAc ethyl acetate
EtOH ethanol
h hour(s)
HCl hydrochloric acid
HPLC high pressure liquid chromatography
IR infra-red
KOtBu potassium t-butoxide
LCMS liquid chromatography and mass spectrometry
LDA lithium diisopropylamide
MeOH methanol
2-Me-THF 2-methyltetrahydrofuran
MS mass spectrometry
m multiplet
mult multiplet
min minutes
mL or ml milliliter(s)
m/z mass to charge ratio
NaOH sodium hydroxide
NBS N-bromosuccinimide
NMR nuclear magnetic resonance
Pd-118 1,1"bis(di-t-butylphosphino)ferrocene palladium dichloride
ppm parts per million
PS polymer supported
RT room temperature
Rt retention time
s singlet
SCX-2 strong cation exchange (e.g. Isolute® SCX-2 columns from Biotage)
SEM-Cl (2-(chloromethoxy)ethyl)trimethylsilane
SFC Supercritical fluid chromotography
t triplet
T3P® 2,4,6-Tripropyl-1,3,5,2,4,6-trioxatriphosphorinane-2,4,6-trioxide solution
TBAF Tetrabutylammonium fluoride solution
TBS-Cl tert-Butyldimethylsilyl chloride
TEA triethylamine
TFA trifluoroacetic acid
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:
2minLC_v003

| Column | Waters BEH C18 50 × 2.1 mm, 1.7 µm |
|---|---|
| Column Temperature | 50° C. |
| Eluents | A: H₂O, B: acetonitrile, both containing 0.1% TFA |
| Flow Rate | 0.8 mL/min |
| Gradient | 0.20 min 5% B; 5% to 95% B in 1.30 min, 0.25 min 95% B |

10minLC_v003

| Column | Waters BEH C18 50 × 2.1 mm, 1.7 µm |
|---|---|
| Column Temperature | 50° C. |
| Eluents | A: H₂O, B: acetonitrile, both containing 0.1% TFA |
| Flow Rate | 0.8 mL/min |
| Gradient | 0.20 min 5% B; 5% to 95% B in 7.80 min, 1.00 min 95% B |

2minLowpH:
  Column: Waters Acquity CSH 1.7 µm, 2.1×50 mm
  Temperature: 50° C.
  Mobile Phase: A: Water+0.1% Formic Acid B: Acetonitrile+0.1% Formic Acid
  Flow rate: 1.0 mL/min
  Gradient: 0.0 min 5% B, 0.2-1.3 min 5-98% B, 1.3-1.55 min 98% B, 1.55-1.6 min 98-5% B
2minLowpHv01:
  Column: Waters Acquity CSH 1.7 µm, 2.1×50 mm
  Temperature: 50° C.
  Mobile Phase: A: Water+0.1% Formic Acid B: Acetonitrile+0.1% Formic Acid
  Flow rate: 1.0 mL/min
  Gradient: 0.0 min 5% B, 0.2-1.55 min 5-98% B, 1.55-1.75 min 98% B, 1.75-1.8 min 98-5% B
2minLowpHv02:
  Column: Waters Acquity CSH 1.7 µm, 2.1×50 mm
  Temperature: 50° C.
  Mobile Phase: A: Water+0.1% TFA B: Acetonitrile+0.1% TFA
  Flow rate: 1.0 mL/min
  Gradient: 0.0 min 5% B, 0.2-1.55 min 5-98% B, 1.55-1.75 min 98% B, 1.75-1.8 min 98-5% B
2minLowpHv03:
  Column: Waters Acquity CSH 1.7 µm, 2.1×50 mm
  Temperature: 50° C.
  Mobile Phase: A: Water+0.1% Formic Acid B: Acetonitrile+0.1% Formic Acid
  Flow rate: 1.0 mL/min
  Gradient: 0.0 min 5% B, 0.2-1.8 min 5-98% B, 1.8-2.1 min 98% B, 2.1-2.3 min 98% B
2minLowpHv04:
  Column: Waters Acquity CSH C18 50×2.1 mm
  Temperature: 50° C.
  Mobile Phase: A: Water+0.1% TFA B: Acetonitrile+0.1% TFA
  Flow rate: 1.0 mL/min
  Gradient: 0.0 min 5% B, 0.2-1.8 min 5-98% B, 1.8-2.1 min 98% B Preparation of Final Compounds Unless otherwise indicated, the chemical name refers to the racemic compound or to the diastereomeric mixture. The term 'Enantiomer 1' refers to the more active of the separated enantiomers and does not indicate the relative position of the eluted peak within the chromatogram (where separation is achieved by SFC under the specified conditions). The term 'Diastereomer 1' refers to the more active of the separated diastereomers and does not indicate the relative position of the eluted peak within the chromatogram (where separation is achieved by SFC under the specified conditions).

Example 1.1

1,3-Dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione

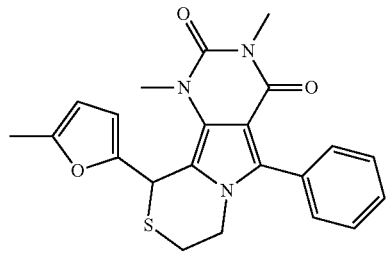 [SMILES: Cc1ccc(C2SCCn3c(-c4ccccc4)c4c(=O)n(C)c(=O)n(C)c4c32)o1]

To 6-(2-mercapto-ethyl)-1,3-dimethyl-5-phenyl-1,6-dihydro-pyrrolo[3,4-d]pyrimidine-2,4-dione (Intermediate A) (207 mg, 0.656 mmol) and bismuth triflate (43.1 mg, 0.066 mmol) in toluene (5 ml) was added 5-methylfuran-2-carbaldehyde (commercial) (0.065 ml, 0.656 mmol) the mixture heated to 100° C. for 1 hour. The reaction mixture was cooled to RT and the solvent was removed under reduced pressure. The residue was partitioned between EtOAc (20 mL) and water (20 mL) and the phases separated. The aqueous phase was extracted with EtOAc (2×20 ml) the combined organic phases were dried over magnesium sulfate and the solvent removed under vacuum. Purification by chromatography on silica, eluting with 0-50% EtOAc/hexane gave the title compound.

1H NMR (400 MHz, DMSO-d6) δ 7.45 (5H, s), 6.03 (1H, s), 5.99 (1H, dd), 5.88 (1H, d), 4.18-4.11 (1H, m), 4.02-3.97 (1H, m), 3.42 (3H, s), 3.11 (3H, s), 3.03-2.89 (2H, m), 2.25 (3H, s).

LC-MS: Rt=1.11 mins; MS m/z 408.4 [M+H]⁺ Method 2minLowpH

Chiral separation of the racemate by Supercritical Fluid Chromatography was carried out using the following conditions to afford the compounds listed hereinafter:
  Mobile Phase: 50% MeOH/50% CO2
  Column: Chiralcel OJ-H, 250×10 mm, 5 um
  Detection: UV@220 nm
  Flow rate: 10 mL/min
  Injection volume: 200 µl
  Examples 1.2 and 1.3 are enantiomers.

Example 1.2

Enantiomer 1 of 1,3-Dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione:
  SFC retention time=5.09 min.
  1H NMR (400 MHz, DMSO-d6) δ 7.45 (5H, s), 6.03 (1H, s), 5.99 (1H, dd), 5.88 (1H, d), 4.18-4.11 (1H, m), 4.02-3.97 (1H, m), 3.42 (3H, s), 3.11 (3H, s), 3.03-2.89 (2H, m), 2.25 (3H, s).

LC-MS: Rt=1.11 mins; MS m/z 408.4 [M+H]⁺ Method 2minLowpH
Chiral purity 99% ee

Example 1.3

Enantiomer 2 of 1,3-Dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione:
SFC retention time=6.82 min.
1H NMR (400 MHz, DMSO-d6) δ 7.45 (5H, s), 6.03 (1H, s), 5.99 (1H, dd), 5.88 (1H, d), 4.18-4.11 (1H, m), 4.02-3.97 (1H, m), 3.42 (3H, s), 3.11 (3H, s), 3.03-2.89 (2H, m), 2.25 (3H, s).

LC-MS: Rt=1.11 mins; MS m/z 408.4 [M+H]⁺ Method 2minLowpH
Chiral purity 99% ee

The compounds of the following tabulated examples (Table 1) were prepared by a similar method to that of Example 1.1 from the appropriate thiol (preparation described hereinafter) and commercially available aldehyde.

TABLE 1

| Ex | Structure | Name | LC-MS NMR |
|---|---|---|---|
| 1.4 | 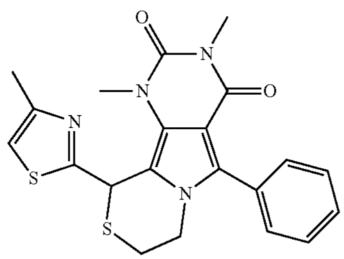 [SMILES: Cc1csc(C2SCCn3c(-c4ccccc4)c4c(=O)n(C)c(=O)n(C)c4c32)n1] | 1,3-Dimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione | LC-MS: Rt 1.03 mins; 425.4 [M + H]+; 2 min Low pH 1H NMR (400 MHz, CDCl3) δ 7.54-7.43 (m, 5H), 6.86 (d, 1H), 6.02 (s, 1H), 4.21 (dd, 1H), 4.20 (dd, 1H), 3.64 (s, 3H), 3.36 (s, 3H), 3.21 (ddd, 1H), 2.90 (ddd, 1H), 2.46 (d, 3H) |
| 1.5 | 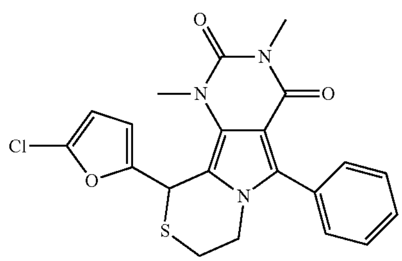 [SMILES: Cn1c(=O)c2c(-c3ccccc3)n3c(c2n(C)c1=O)C(c1ccc(Cl)o1)SCC3] | 10-(5-Chlorofuran-2-yl)-1,3-dimethyl-5-phenyl-7,8-dihydro-1H-pyrimido[4',5':3,4]pyrrolo[2,1-c][1,4]thiazine-2,4(3H,10H)-dione | LC-MS: Rt 1.13 mins; 428 [M + H]+; 2 min Low pH; 1H NMR: (400 MHz, CDCl3) δ 7.53-7.46 (3H, m), 7.44-7.41 (2H, m), 6.10 (1H, d), 5.94 (1H, dd), 5.73 (1H, s), 4.24-4.17 (1H, m), 4.16-4.08 (1H, m), 3.59 (3H, s), 3.35 (3H, s), 3.11-3.04 (1H, m), 2.87-2.80 (1H, m). |
| 1.6 | 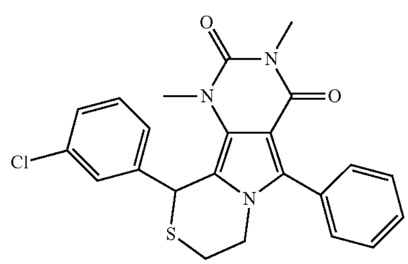 [SMILES: Cn1c(=O)c2c(-c3ccccc3)n3c(c2n(C)c1=O)C(c1cccc(Cl)c1)SCC3] | 10-(3-Chlorophenyl)-1,3-dimethyl-5-phenyl-7,8-dihydro-1H-pyrimido[4',5':3,4]pyrrolo[2,1-c][1,4]thiazine-2,4(3H,10H)-dione | LC-MS: Rt 1.12 mins; 438 [M + H]+; 2 min Low pH; 1H NMR: (400 MHz, CDCl3) δ 7.54-7.44 (5H, m), 7.28 (2H, m), 7.17 (1H, s), 6.99 (1H, d), 5.73 (1H, s), 4.17-4.06 (2H, m), 3.46 (3H, s), 3.35 (3H, s), 2.98-2.90 (1H, m), 2.80-2.73 (1H, m) |
| 1.7 | 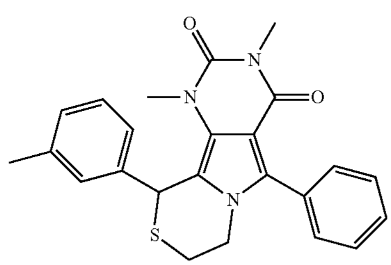 [SMILES: Cc1cccc(C2SCCn3c(-c4ccccc4)c4c(=O)n(C)c(=O)n(C)c4c32)c1] | 1,3-Dimethyl-5-phenyl-10-(m-tolyl)-7,8-dihydro-1H-pyrimido[4',5':3,4]pyrrolo[2,1-c][1,4]thiazine-2,4(3H,10H)-dione | LC-MS: Rt 1.16 mins; 418.5 [M + H]+; 2 min Low pH 1H NMR: (400 MHz, CDCl3) δ 7.49 (5H, m), 7.22 (1H, t), 7.09 (1H, d), 6.99 (1H, s), 6.86 (1H, d), 5.75 (1H, 8), 4.12 (2H, m), 3.46 (3H, s), 3.35 (3H, s), 2.98 (1H, m), 2.75 (1H, m), 2.37 (3H, s). |

TABLE 1-continued

| Ex | Structure | Name | LC-MS NMR |
|---|---|---|---|
| 1.8 | 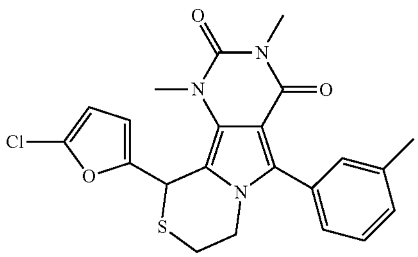 [SMILES: Cc1cccc(-c2c3c(=O)n(C)c(=O)n(C)c3c3n2CCSC3c2ccc(Cl)o2)c1] | 10-(5-Chlorofuran-2-yl)-1,3-dimethyl-5-(m-tolyl)-7,8-dihydro-1H-pyrimido[4',5':3,4]pyrrolo[2,1-c][1,4]thiazine-2,4(3H,10H)-dione | LC-MS: Rt 1.14 mins; 442.4 [M + H]+; 2 min Low pH; 1H NMR: (400 MHz, DMSO-d6) δ 7.35 (1H, q), 7.29-7.22 (3H, m), 6.41 (1H, d), 6.13 (1H, s), 6.11 (1H, dd), 4.13-4.07 (1H, m), 3.99-3.92 (1H, m), 3.44 (3H, s), 3.13 (3H, s), 2.96-2.92 (2H, m), 2.36 (3H, s). |
| 1.9 | 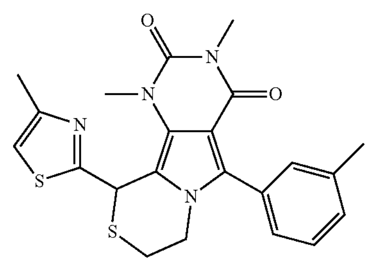 [SMILES: Cc1cccc(-c2c3c(=O)n(C)c(=O)n(C)c3c3n2CCSC3c2nc(C)cs2)c1] | 1,3-Dimethyl-10-(4-methylthiazol-2-yl)-5-(m-tolyl)-7,8-dihydro-1H-pyrimido[4',5':3,4]pyrrolo[2,1-c][1,4]thiazine-2,4(3H,10H)-dione | LC-MS; Rt 1.09 mins; 439.4 [M + H]+; 2 min Low pH; 1H NMR (400 MHz, DMSO-d6) δ 7.36 (1H, t), 7.29-7.19 (4H, m), 6.36 (1H, s), 4.11-3.99 (1H, m), 3.52 (3H, s), 3.18 (3H, s), 3.11 (1H, m), 3.02 (1H, m), 2.35 (3H, s), 2.30 (3H, s) |
| 1.10 | 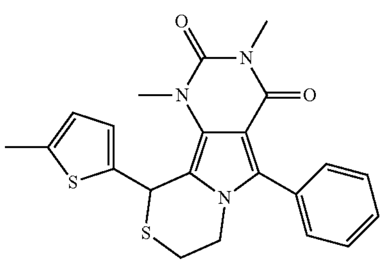 | 1,3-Dimethyl-10-(5-methylthiophen-2-yl)-5-phenyl-7,8-dihydro-1H-pyrimido[4',5':3,4]pyrrolo[2,1-c][1,4]thiazine-2,4(3H,10H)-dione | LC-MS Rt 1.18 mins [M + H]+ 424.2 (Method 2 min Low pH) 1H NMR (400 MHz, CDCl3) δ 7.47 (5H, mult), 6.86 (1H, s), 6.50 (1H, s), 5.87 (1H, s), 4.11 (2H, mult), 3.62 (3H, s), 3.37 (3H, s), 3.16 (1H, mult), 2.87 (1H, mult), 2.21 (3H, s). |
| 1.11 | 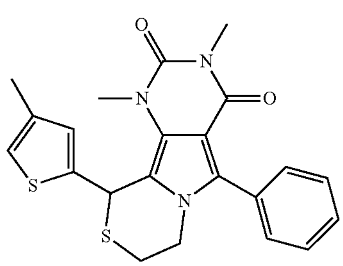 [SMILES: Cc1csc(C2SCCn3c(-c4ccccc4)c4c(=O)n(C)c(=O)n(C)c4c32)n1] | 1,3-Dimethyl-10-(4-methylthiophen-2-yl)-5-phenyl-7,8-dihydro-1H-pyrimido[4',5':3,4]pyrrolo[2,1-c][1,4]thiazine-2,4(3H,10H)-dione | LC-MS Rt 1.30 mins [M + H]+ 424.3 (Method 2 min Low pH v01) 1H NMR (400 MHz, CDCl3) δ 7.47 (5H, mult), 6.86 (1H, s), 6.51 (1H, s), 5.87 (1H, s), 4.11 (2H, mult), 3.62 (3H, s), 3.37 (3H, s), 3.16 (1H, mult), 2.87 (1H, mult), 2.21 (3H, s) |

The compounds of the following tabulated Examples (Table 1.1) were prepared by SFC chromatographic resolution of the appropriate racemate.

TABLE 1.1

| Ex | Structure Name | LC-MS NMR SFC (Method; Rt (min); Chiral purity) |
|---|---|---|
| 1.1.1 | (R)-10-(5-chlorofuran-2-yl)-1,3-dimethyl-5-phenyl-7,8-dihydro-1H-pyrimido[4',5':3,4]pyrrolo[2,1-c][1,4]thiazine-2,4(3H,10H)-dione (see X-ray data below table) | LC-MS: Rt 1.14 mins; 428 [M + H]+; 2 min Low pH; 1H NMR: (400 MHz, DMSO-d6) δ 7.47 (5H, s), 6.41(1H, d), 6.14 (1H, s), 6.13 (1H, s), 4.14-4.07 (1H, m), 4.02-3.95 (1H, m), 3.45 (3H, s), 3.14 (3H, s), 2.97-2.93 (2H, m). SFC: Co-SolventIPA + 0.1% DEA Instrument Method OJ50IPA_DEA Column CHIRALCEL OJ-H 250 × 10 mm, 5 mic Rt 5.32 min; >99.9% ee |
| 1.1.2 | Enantiomer 1 of 1,3-Dimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione | LC-MS: Rt 1.04 mins; 425.2 [M + H]+; 2 min Low pH; 1H NMR: (400 MHz, DMSO-d6) δ 7.47 (5H, m), 7.25 (1H, s), 6.39 (1H, s), 4.15-4.08 (1H, m), 4.09-3.99 (1H, m), 3.53 (3H, s), 3.15 (3H, s), 3.13-3.08 (1H, m), 3.04-2.99 (1H, m), 2.31 (3H, s). SFC: Column: Chiralcel OJ-H 250 × 10 mm, 5 um Mobile phase: 50% methanol + 0.1% DEA/50% CO2 Flow: 10 ml/min Detection: UV @ 220 nm Rt 4.99 min; >99% ee |
| 1.1.3 | Enantiomer 1 of 1,3-Dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione | LC-MS: Rt 1.12 min; 408.2 [M + H]+; 2 min Low pH; 1H NMR: (400 MHz, DMSO-d6) δ 7.42 (5H, s), 6.05 (1H, s), 5.98 (1H, d), 5.86 (1H, d), 5.16-4.10 (1H, m), 4.02-3.94 (1H, m), 3.44 (3H, s), 3.13 (3H, s), 3.01-2.87 (2H, m), 2.26 (3H, s). SFC: Column: Chiralcel OJ-H 250 × 10 mm, 5 um Mobile phase: 50% methanol/50% CO2 Flow: 10 ml/min Detection: UV @ 220 nm Column temp: 35 deg C. Berger Minigram system 2 Rt 5.09 min; >99.9% ee |

TABLE 1.1-continued

| Ex | Structure Name | LC-MS NMR SFC (Method; Rt (min); Chiral purity) |
|---|---|---|
| 1.1.4 | Enantiomer 1 of 10-(3-Chlorophenyl)-1,3-dimethyl-5-phenyl-7,8-dihydro-1H-pyrimido[4',5':3,4]pyrrolo[2,1-c][1,4]thiazine-2,4(3H,10H)-dione | LC-MS: Rt 1.19 mins; 438.2 [M + H]+; 2 min Low pH; 1H NMR: (400 MHz, DMSO-d6) δ 7.52-7.45 (5H, m), 7.39-7.30 (3H, m), 7.00 (1H, d), 6.17 (1H, s), 4.15 (1H, dt), 3.98-3.90 (1H, m), 3.30 (3H, s), 3.12 (3H, s), 2.91-2.75 (2H, m) SFC: Column: Chiralcel OD-H 250 × 10 mm, 5 um @ 35 deg C. Mobile phase: 50% Isopropanol/50% CO2 Flow: 10 ml/min Detection: UV @ 220 nm System: Berger Minigram SFC1 Rt 7.88 min; >99.9% ee |
| 1.1.5 | Enantiomer 1 of 10-(5-Chlorofuran-2-yl)-1,3-dimethyl-5-(m-tolyl)-7,8-dihydro-1H-pyrimido[4',5':3,4]pyrrolo[2,1-c][1,4]thiazine-2,4(3H,10H)-dione | LC-MS: Rt 1.19 mins; 442.4 [M + H]+; 2 min Low pH; 1H NMR: (400 MHz, DMSO-d6) δ 7.35 (1H, q), 7.29-7.22 (3H, m), 6.41 (1H, d), 6.13 (1H, s), 6.11 (1H, dd), 4.13-4.07 (1H, m), 3.99-3.92 (1H, m), 3.44 (3H, s), 3.13 (3H, s), 2.96-2.92 (2H, m), 2.36 (3H, s). SFC: Column: Chiralcel OD-H 250 × 10 mm, 5 um Mobile phase: 40% methanol + 0.1% DEA/60% CO2 Flow: 10 ml/min Detection: UV @ 220 nm Rt 7.34min; >99.9% ee |

Example 1.1.1

X-ray Crystallography

Absolute stereochemistry of (R)-10-(5-chlorofuran-2-yl)-1,3-dimethyl-5-phenyl-7,8-dihydro-1H-pyrimido[4',5':3,4]pyrrolo[2,1-c][1,4]thiazine-2,4(3H,10H)-dione was confirmed by X-ray crystallography:

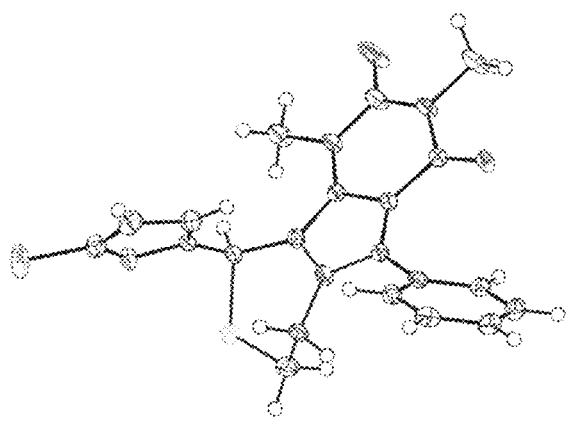

TABLE 1

| Crystal data and structure refinement | | |
|---|---|---|
| Empirical formula | C21H18ClN3O3S | |
| Formula weight | 427.89 | |
| Temperature | 100(2) K | |
| Wavelength | 1.54178 Å | |
| Crystal system | Orthorhombic | |
| Space group | P212121 | |
| Unit cell dimensions | a = 7.1030(10) Å | α = 90° |
| | b = 11.330(2) Å | β = 90° |
| | c = 23.851(4) Å | γ = 90° |
| Volume | 1919.5(5) Å$^3$ | |
| Z | 4 | |
| Density (calculated) | 1.481 g/cm$^3$ | |
| Absorption coefficient | 3.030 mm$^{-1}$ | |
| F(000) | 888 | |
| Crystal size | 0.31 × 0.14 × 0.03 mm$^3$ | |
| Theta range for data collection | 3.71 to 68.36° | |
| Index ranges | −8 <= h <= 8, −13 <= k <= 13, −28 <= l <= 28 | |
| Reflections collected | 40374 | |
| Independent reflections | 3517 [R(int) = 0.0389] | |
| Completeness to theta = 68.36° | 99.9% | |
| Absorption correction | Semi-empirical from equivalents | |
| Max. and min. transmission | 0.9146 and 0.4535 | |
| Refinement method | Full-matrix least-squares on F$^2$ | |

TABLE 1-continued

Crystal data and structure refinement

| | |
|---|---|
| Data/restraints/parameters | 3517/68/273 |
| Goodness-of-fit on $F^2$ | 1.040 |
| Final R indices [I > 2sigma(I)] | R1 = 0.0240, wR2 = 0.0635 |
| R indices (all data) | R1 = 0.0243, wR2 = 0.0637 |
| Absolute structure parameter | 0.010(10) |
| Largest diff. peak and hole | 0.190 and −0.225 e · Å$^{-3}$ |

Example 2.0

7-((dimethylamino)methyl)-1,3-dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione

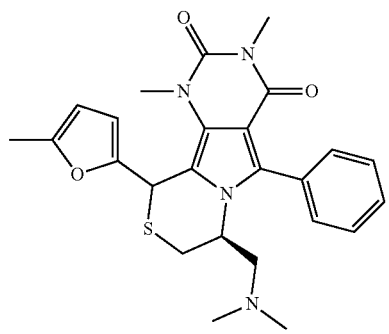 [SMILES: Cc1ccc(C2SC[C@H](CN(C)C)n3c(-c4ccccc4)c4c(=O)n(C)c(=O)n(C)c4c32)o1]

(S)-6-(1-(dimethylamino)-3-mercaptopropan-2-yl)-1,3-dimethyl-5-phenyl-1H-pyrrolo[3,4-d]pyrimidine-2,4(3H,6H)-dione (Intermediate B) (370 mg, 0.993 mmol), 5-methylfurfural (0.109 mL, 1.093 mmol) and bismuth triflate (65.2 mg, 0.099 mmol) were combined in toluene (15 mL) and the mixture was heated at 100° C. for 1 hour 40 mins. The reaction mixture was cooled to room temperature and evaporated under vacuum. The residue was partitioned between DCM and sat. NaHCO₃(aq) and the phases were separated.

The organic phase was passed through a hydrophobic frit and evaporated under vacuum. Purification by chromatography on silica, eluting with 10-50% EtOAc/hexane afforded a diastereomeric mixture of 7-((dimethylamino)methyl)-1,3-dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione (Example 2.0).

The diastereoisomers were separated under the following conditions to afford the compound listed hereinafter:
Mobile Phase: 20% (MeOH+0.1% DEA)/80% CO₂
Column: Chiralcel OJ-H 250 mm×10 mm×5 μm
Detection: UV@220 nm
Flow rate: 10 mL/min Example 2.1

Diastereomer 1 of 7-((dimethylamino)methyl)-1,3-dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione SFC Retention Time=8.42 min (second eluted peak)
LC-MS: Rt 0.75 mins; MS 465.6 m/z [M+H] Method 2minLowpHv01

1H NMR (400 MHz, CDCl3) δ 7.64-7.33 (5H, mult), 5.96-5.83 (3H, mult), 4.58 (1H, dddd), 3.55 (3H, s), 3.34 (3H, s), 3.18 (1H, dd), 3.13 (1H, dd), 2.77 (1H, mult), 2.32 (3H, s), 2.22 (1H, dd), 1.89 (6H, s).

Example 3.0

(8S)-10-(5-chlorofuran-2-yl)-1,3,8-tri methyl-5-phenyl-7,8-dihydro-1H-pyrimido[4',5':3,4]pyrrolo[2,1-c][1,4]thiazine-2,4(3H,10H)-dione

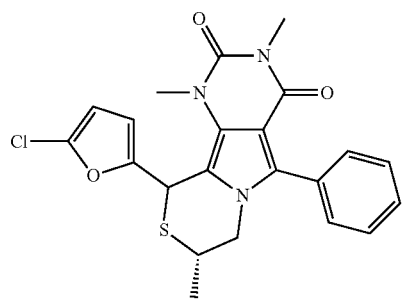 [SMILES: C[C@H]1Cn2c(-c3ccccc3)c3c(=O)n(C)c(=O)n(C)c3c2C(c2ccc(Cl)o2)S1]

(S)-6-(2-Mercaptopropyl)-1,3-dimethyl-5-phenyl-1H-pyrrolo[3,4-d]pyrimidine-2,4(3H,6H)-dione (Intermediate E) (200 mg 0.61 mmol) was added to a microwave vial (0.5-2 mL) equipped with a stirrer bar. To the vial was added toluene (2 ml) followed by bismuth triflate (38 mg, 0.061 mmol) and 5-chlorofuran-2-carbaldehyde (87 mg, 0.67 mmol). The reaction mixture was heated to 100° C. in a microwave reactor for 15 min and then reduced in vacuo. The resulting residue was partitioned between EtOAc and water and the layers were separated. The aqueous was extracted with EtOAc and the combined organic extracts were dried (MgSO₄), filtered and concentrated in vacuo to yield an oil. The brown oil was dissolved in smallest minimal volume of DCM and purified by chromatography on silica eluting with 0-40% EtOAc in iso-hexane to afford a diasteromeric mixture of (8S)-10-(5-chlorofuran-2-yl)-1,3,8-trimethyl-5-phenyl-7,8-dihydro-1H-pyrimido[4',5':3,4]pyrrolo[2,1-c][1,4]thiazine-2,4(3H,10H)-dione as a pale yellow white solid. LCMS Rt 1.32 mins; MS m/z 442 [M+H]+; (Method 2minLowpHv01).

The diastereoisomers were separated under the following conditions to afford the compounds listed hereinafter:
Mobile phase: 50% Isopropanol/50% CO2
Column: Chiralpak IB, 250×10 mm, 5 um
Flow: 10 ml/min Example 3.1

Diastereoisomer 1 of (8S)-10-(5-chlorofuran-2-yl)-1,3,8-trimethyl-5-phenyl-7,8-dihydro-1H-pyrimido[4',5':3,4]pyrrolo[2,1-c][1,4]thiazine-2,4(3H,10H)-dione SFC retention time=2.45 min
1H NMR (400 MHz, CD₂Cl₂) δ 7.53-7.49 (3H, m); 7.44-7.41 (2H, m); 6.13 (1H, d); 5.93 (1H, dd); 5.76 (1H, s with splitting); 4.19 (1H, dd); 3.74 (1H, dd); 3.54 (3H, s); 3.37-3.29 (1H, m); 3.28 (3H, s); 1.17 (3H, d).
LC-MS Rt 1.31 mins; MS m/z 442 [M+H]+ (Method 2min-LowpHv01)
>99% de

Example 3.2

Diastereoisomer 2 of (8S)-10-(5-chlorofuran-2-yl)-1,3,8-trimethyl-5-phenyl-7,8-dihydro-1H-pyrimido[4',5':3,4]pyrrolo[2,1-c][1,4]thiazine-2,4(3H,10H)-dione
SFC retention time 4.35 min

Example 3.3

(8S)-1,3,8-trimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione

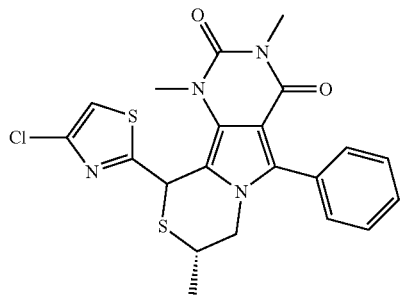 [SMILES: C[C@H]1Cn2c(-c3ccccc3)c3c(=O)n(C)c(=O)n(C)c3c2C(c2nc(Cl)cs2)S1]

The diastereoisomeric mixture was prepared analogously to Example 3.0 from (S)-6-(2-mercaptopropyl)-1,3-dimethyl-5-phenyl-1H-pyrrolo[3,4-d]pyrimidine-2,4(3H,6H)-dione (Intermediate E) and the appropriate aldehyde.
LCMS: Rt 1.19/1.22 mins; MS m/z 439 [M+H]+; Method 2minLowpHv01 The diastereoisomers were separated under the following conditions to afford the title compound;
Sample 110 mg in 3 ml EtOH+1.5 ml THF
Column: Chiralpak IB, 250×10 mm, 5 um
Mobile phase: 35% Methanol/65% CO₂
Flow: 10 ml/min

Example 3.3a

Diastereoisomer 1 of (8S)-1,3,8-trimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione
>99% de
SFC Retention Time: Rt 3.71
LC-MS: Rt 1.18 mins; MS 439 m/z [M+H] Method 2min-LowpHv01
1H NMR (400 MHz, CDCl₃) δ 7.53-7.41 (5H, m); 6.84 (1H, s); 6.02 (1H, s); 4.22 (1H, dd) 3.79 (1H, dd); 3.60 (3H, s); 3.51-3.42 (1H, m); 3.35 (3H, s); 2.45 (3H, s); 1.17 (3H, d).

Example 3.4

3-(10-(5-Chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile

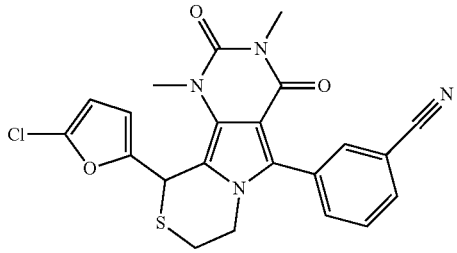 [SMILES: Cn1c(=O)c2c(-c3cccc(C#N)c3)n3c(c2n(C)c1=O)C(c1ccc(Cl)o1)SCC3]

A suspension comprising 3-(6-(2-mercaptoethyl)-1,3-dimethyl-2,4-dioxo-2,3,4,6-tetrahydro-1H-pyrrolo[3,4-d]pyrimidin-5-yl)benzonitrile (Intermediate G) (150 mg, 0.441 mmol), 5-chlorofuran-2-carbaldehyde (57.5 mg, 0.441 mmol) and bismuth triflate (28.9 mg, 0.044 mmol) in toluene (5 ml) was heated to 100° C. for 10 min using microwave radiation. After cooling to RT, the reaction mixture was diluted with EtOAc (25 ml) and washed with water. The layers were separated and the aqueous extracted with EtOAc (3×20 ml). The combined organics were dried over MgSO₄, filtered and concentrated to yield a brown oil. Purification was carried out by chromatography on silica eluting with 0-45% EtOAc in iso-hexane. The relevant fraction were combined and concentrated in vacuo to yield a pale yellow oil. Diethyl ether (5 ml) was added to the oil to give a white solid. The solid was isolated by suction filtration to afford the title compound.
LCMS: Rt 1.22 in, [M+H]+ 453.4. Method 2minLowpHv01.
1H NMR: (400 MHz, CDCl3) δ 7.77 (1H, d), 7.72 (2H, m), 7.64 (1H, t), 6.13 (1H, d), 5.98 (1H, dd), 5.74 (1H, s), 4.19 (1H, m), 4.11 (1H, m), 3.60 (3H, s), 3.36 (3H, s), 3.13 (1H, m), 2.87 (1H, m).

Chiral separation of the racemate by Supercritical Fluid Chromatography was carried out using the following conditions to afford the compounds listed hereinafter:
Mobile Phase: 35% MeOH/65% CO₂
Column: Chirapak AD-H, 250×10 mm, 5 um
Detection: UV@220 nm
Flow rate: 10 mL/min
Examples 3.5 and 3.6 are enantiomers.

Example 3.5

Enantiomer 1 of 3-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile
SFC retention time=4.12 min.
1H NMR (400 MHz, CDCl3) δ 7.78 (1H, d), 7.72 (2H, mult), 7.64 (1H, t), 6.13 (1H, d), 5.98 (1H, d), 5.73 (1H, s), 4.23-4.06 (2H, mult), 3.60 (3H, s), 3.36 (3H, s), 3.13 (1H, mult), 2.87 (1H, mult).

Example 3.6

Enantiomer 2 of 3-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile
SFC retention time=4.88 min.
1H NMR: (400 MHz, CDCl3) δ 7.78 (1H, d), 7.72 (2H, mult), 7.64 (1H, t), 6.13 (1H, d), 5.98 (1H, d), 5.74 (1H, s), 4.24-4.07 (2H, mult), 3.60 (3H, s), 3.36 (3H, s), 3.13 (1H, mult), 2.87 (1H, mult).

The compounds of the following tabulated examples (Table 3) were prepared analogously to Example 3.4 by replacing Intermediate G with the appropriate starting compound (prepared by a similar Method to Intermediate G from Intermediate F and the appropriate halo compound in step 1) and the commercially available aldehyde:

TABLE 3

| Ex | Structure | Name | LCMS NMR |
|---|---|---|---|
| 3.7 | 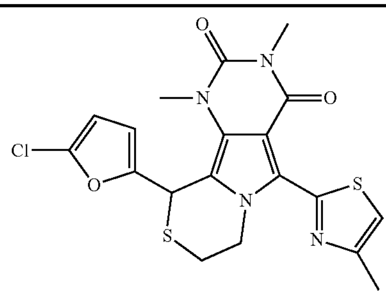 | 10-(5-Chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione | LC-MS: Rt 1.26 mins; 449.4 [M + H]+; 2 min Low pH v01; 1H NMR: (400 MHz, CDCl3) δ 7.22 (1H, s), 7.61 (2H, d), 5.73 (1H, s), 4.79 (1H, m), 4.54 (1H, m), 3.60 (3H, s), 3.41 (3H, s), 3.23 (1H, m), 2.94 (1H, m), 2.60 (3H, s). |
| 3.8 | 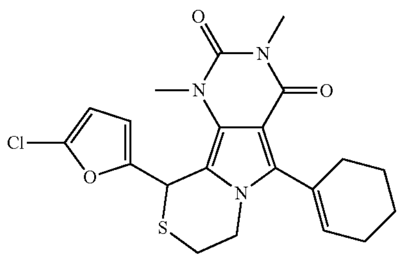 [SMILES: Cn1c(=O)c2c(C3=CCCCC3)n3c(c2n(C)c1=O)C(c1ccc(Cl)o1)SCC3] | 10-(5-Chlorofuran-2-yl)-5-(cyclohex-1-en-1-yl)-1,3-dimethyl-7,8-dihydro-1H-pyrimido[4',5':3,4]pyrrolo[2,1-c][1,4]thiazine-2,4(3H,10H)-dione | LC-MS: Rt 1.35 mins; 432.5/434.5 [M + H]+; 2 min Low pH v01 1H NMR: (400 MHz, CDCl3) δ 6.06(1H, d), 5.86-5.78 (2H, m), 5.64 (1H, s), 4.30 (1H, m), 4.15 (1H, m), 3.52 (3H, s), 3.38 (3H, s), 3.10 (1H, m), 2.85 (1H, dt), 2.74-2.07 (4H, m), 1.91-1.79 (2H, m), 1.78-1.66 (2H, m). |
| 3.9 | 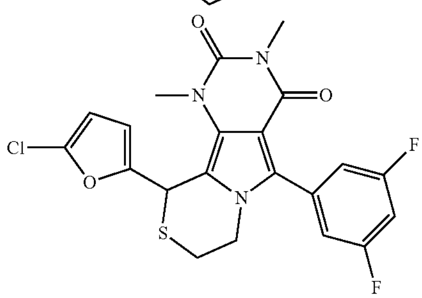 | 10-(5-Chlorofuran-2-yl)-5-(3,5-difluorophenyl)-1,3-dimethyl-7,8-dihydro-1H-pyrimido[4',5':3,4]pyrrolo[2,1-c][1,4]thiazine-2,4(3H,10H)-dione | LC-MS: Rt 1.33 mins; 464.5/466.5[M + H]+; 2 min Low pH v01 1H NMR: (400 MHz, CDCl3) δ 7.01-6.90 (3H, m), 6.11 (1H, m), 5.94 (1H, dd), 5.71 (1H, s), 4.19 (1H, m), 4.10 (1H, m), 3.58 (3H, s), 3.35 (3H, s), 3.10 (1H, ddd), 2.85 (1H, ddd). |

The compounds of the following tabulated examples (Table 3.1) were prepared analogously to Example 3.4 by replacing (Intermediate G) with the appropriate starting compound (prepared by a similar Method to Intermediate G from Intermediate F and the appropriate halo compound in step 1) and the commercially available aldehyde. The resulting racemates were separated by SFC chromatographic resolution to yield single enantiomers.

TABLE 3.1

| Ex | Structure Name | LCMS NMR SFC |
|---|---|---|
| 3.1.1 | Enantiomer 1 of 10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione | LC-MS: Rt 1.23 mins 449.4 [M + H]+; 2 min Low pH v01 1H NMR: (400 MHz, CDCl3) δ 7.14 (1H, s), 6.11 (1H, mult), 6.01 (1H, mult), 5.73 (1H, s), 4.66 (2H, mult), 3.59 (3H, s), 3.41 (3H, s), 3.15 (1H, mult), 2.92 (1H, mult), 2.54 (3H, s). SFC: Column: Chiralpak IB 250 × 10 mm, 5 um @ 35 deg C. Mobile phase: 40% Methanol/60% CO2 Flow: 10 ml/min Detection: UV @ 220 nm Rt: 5.98 min >99% ee |

TABLE 3.1-continued

| Ex | Structure Name | LCMS NMR SFC |
|---|---|---|
| 3.1.2 | 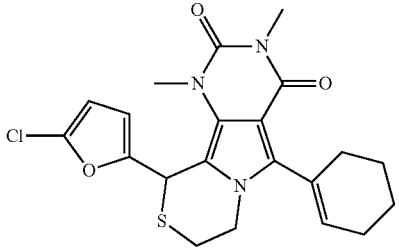 [SMILES: Cn1c(=O)c2c(C3=CCCCC3)n3c(c2n(C)c1=O)C(c1ccc(Cl)o1)SCC3]

Enantiomer 1 of 10-(5-chlorofuran-2-yl)-5-(cyclohex-1-en-1-yl)-1,3-dimethyl-7,8-dihydro-1H-pyrimido[4',5':3,4]pyrrolo[2,1-c][1,4]thiazine-2,4(3H,10H)-dione | LC-MS: Rt 1.35 mins; 432.5/434.5 [M + H]+; 2 min Low pH v01
1H NMR: (400 MHz, CDCl3) δ 6.06 (1H, d), 5.86-5.78 (2H, m), 5.64 (1H, s), 4.30 (1H, m), 4.15 (1H, m), 3.52 (3H, s), 3.38 (3H, s), 3.10 (1H, m), 2.85 (1H, dt), 2.74-2.07 (4H, m), 1.91-1.79 (2H, m), 1.78-1.66 (2H, m).
SFC: Column: Chiralpak IB 250 × 10 mm, 5 um @ 35 deg C.
Mobile phase: 25% Methanol/75% CO2
Flow: 10 ml/min
Detection: UV @ 220 nm
Rt: 5.10 min
>99% ee |

Example 4.1

10-(5-Chlorofuran-2-yl)-1,3-diethyl-5-phenyl-7,8-dihydro-1H-pyrimido[4',5':3,4]pyrrolo[2,1-c][1,4]thiazine-2,4(3H,10H)-dione

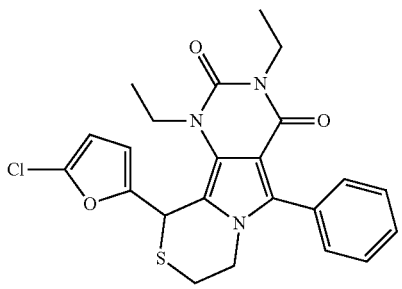 [SMILES: CCn1c(=O)c2c(-c3ccccc3)n3c(c2n(CC)c1=O)C(c1ccc(Cl)o1)SCC3]

1,3-Diethyl-6-(2-mercaptoethyl)-5-phenyl-1H-pyrrolo[3,4-d]pyrimidine-2,4(3H,6H)-dione (Intermediate H) (329 mg, 0.958 mmol), 5-chlorofurfual (138 mg, 1.054 mmol) and bismuth triflate (62.9 mg, 0.096 mmol) were combined in toluene (Volume: 10 mL) and the mixture heated at 95° C. for 15 mins. The reaction mixture was cooled to room temp. and evaporated under vacuum. The residue was partitioned between DCM and sat. NaHCO3(aq) and the phases separated. The organic phase was passed through a hydrophobic frit and evaporated onto silica. The silica was deposited onto a 10 g silica cartridge and the system gradient-eluted from 10-60% EtOAc/hexane. Product eluted at 20-30% EtOAc/hexane, fractions were combined and evaporated. The residue was triturated with Et2O/hexane and the precipitate collected by filtration to yield the title compound as a white solid.

1H NMR (400 MHz, CDCl3) δ 7.54-7.41 (5H, m), 6.10 (1H, d), 5.93 (1H, dd), 5.48 (1H, s), 4.39 (1H, ddd), 4.17 (2H, m), 4.02 (2H, q), 3.60 (1H, ddd), 3.08 (1H, ddd), 2.84 (1H, ddd), 1.35 (3H, t), 1.21 (3H, t).

LC-MS Rt 1.37 mins; MS 456.4 m/z [M+H] (Method 2minLowpHv01)

Chiral separation of the racemate by Supercritical Fluid Chromatography was carried out using the following conditions to afford the compounds listed hereinafter:

Mobile Phase: 45% MeOH/55% CO2
Column: SFC Chiralcel OJ-H 250×10 mm, 5 μm diameter@35° C.
Detection: UV@220 nm
Flow rate: 10 mL/min Example 4.2

Enantiomer 1 of 10-(5-Chlorofuran-2-yl)-1,3-diethyl-5-phenyl-7,8-dihydro-1H-pyrimido[4',5':3,4]pyrrolo[2,1-c][1,4]thiazine-2,4(3H,10H)-dione
SFC retention time=5.00 mins.
LC-MS: Rt 1.41 mins; MS 456.2 m/z [M+H] Method 2minLowpHv01
1H NMR (400 MHz, CDCl3) δ 7.54-7.41 (5H, m), 6.10 (1H, d), 5.93 (1H, dd), 5.48 (1H, s), 4.39 (1H, ddd), 4.17 (2H, m), 4.02 (2H, q), 3.60 (1H, ddd), 3.08 (1H, ddd), 2.84 (1H, ddd), 1.35 (3H, t), 1.21 (3H, t).
Enantiomer 2 of 10-(5-Chlorofuran-2-yl)-1,3-diethyl-5-phenyl-7,8-dihydro-1H-pyrimido[4',5':3,4]pyrrolo[2,1-c][1,4]thiazine-2,4(3H,10H)-dione
SFC retention time=6.88 mins was also isolated.

Example 5

3-Chloro-5-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile

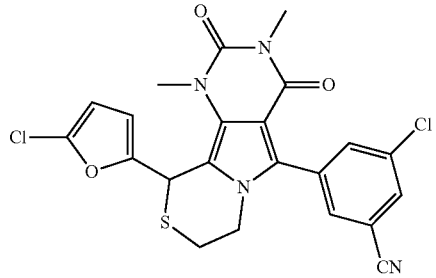 [SMILES: Cn1c(=O)c2c(-c3cc(Cl)cc(C#N)c3)n3c(c2n(C)c1=O)C(c1ccc(Cl)o1)SCC3]

3-Chloro-5-(1,3-dimethyl-2,4-dioxo-6-(2-(tritylthio)ethyl)-2,3,4,6-tetrahydro-1H-pyrrolo[3,4-d]pyrimidin-5-yl)benzonitrile (Intermediate GA) (146 mg, 0.237 mmol), 5-chlorofuran-2-carbaldehyde (34.0 mg, 0.260 mmol) and bismuth (III) triflate (31.0 mg, 0.047 mmol) were suspended in toluene (Volume: 2.5 ml). The reaction was then heated to 100° C. under microwave irradiation for 3 hr. The reaction mixture was suspended in MeOH (50 mL) and adsorbed onto silica. The residue was purified via ISCO SiO2 12 g Redisep Rf column eluting with 20% EtOAc/hexane. Fractions were combined and evaporated to afford a pale yellow gum. The gum was dissolved in Et$_2$O (30 mL) and iso-hexane (30 mL) was added to afford a suspension. The solvent was evaporated to afford the title compound as a pale yellow solid.

LC-MS Rt 1.32 mins; MS m/z 487.1/489.1/491.1[M+H]+; (Method 2minLowpHv01)

1H NMR (400 MHz, CDCl3) δ 7.74 (1H, s), 7.68 (1H, s), 7.63 (1H, s), 6.13 (1H, d), 5.98 (1H, d), 5.72 (1H, s), 4.19 (1H, dt), 4.10 (1H, m), 3.60 (3H, s), 3.36 (3H, s), 3.13 (1H, ddd), 2.87 (1H, dt).

Example 6.1

10-(2,3-Difluorophenyl)-1,3-dimethyl-5-phenyl-7,8,9,10-tetrahydropyrimido[4,5-a]indolizine-2,4(1H,3H)-dione

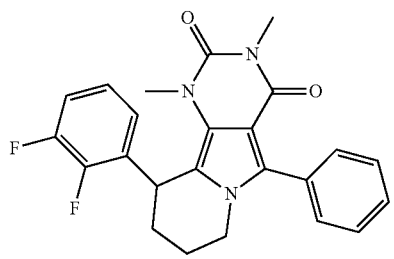 [SMILES: Cn1c(=O)c2c(-c3ccccc3)n3c(c2n(C)c1=O)C(c1cccc(F)c1F)CCC3]

Step 1: 10-(2,3-Difluorophenyl)-1,3-dimethyl-5-phenyl-7,8-dihydropyrimido[4,5-a]indolizine-2,4(1H,3H)-dione 1,3-Dimethyl-5-phenyl-7,8-dihydropyrimido[4,5-a]indolizine-2,4(1H,3H)-dione (Intermediate I) (180 mg, 0.586 mmol), 1-bromo-2,3-difluorobenzene (commercially available) (0.085 mL, 0.761 mmol) and N-cyclohexyl-N-methyl-cyclohexanamine (commercially available) (0.251 mL, 1.171 mmol) were combined in DMA (2.5 mL) and the mixture sparged with nitrogen for 30 min. [1,1'-Bis(di-tert-butylphosphino)ferrocene]dichloropalladium(II) (commercially available) (38.2 mg, 0.059 mmol) was then added and the mixture heated at 110° C. for 1 hour under microwave irradiation. After cooling to room temperature, the mixture was heated at 110° C. for a further 6 hours. Further portions of 1-bromo-2,3-difluorobenzene (0.085 mL, 0.761 mmol) and [1,1'-Bis(di-tert-butylphosphino)ferrocene]dichloropalladium(II) (38.2 mg, 0.059 mmol) were added, and the mixture heated at 110° C. for a further 5 h. Further [1,1'-Bis(di-tert-butylphosphino)ferrocene]dichloropalladium(II) (38.2 mg, 0.059 mmol) and 1-bromo-2,3-difluorobenzene (0.085 mL, 0.761 mmol) were added and the mixture heated 110° C. for a further 6 hours. Further [1,1'-Bis(di-tert-butylphosphino)ferrocene]dichloropalladium(II) (38.2 mg, 0.059 mmol) was added and the mixture heated at 110° C. for a further 6 h. The reaction mixture was diluted with EtOAc and washed with water and brine. The organic phase was dried over sodium sulphate and evaporated under reduced pressure. Purification by chromatography on silica, eluting with 15% EtOAc in iso-hexane afforded the title compound, which was used without further purification.

Step 2: 10-(2,3-Difluorophenyl)-1,3-dimethyl-5-phenyl-7,8,9,10-tetrahydropyrimido[4,5-a]indolizine-2,4(1H,3H)-dione 10-(2,3-Difluorophenyl)-1,3-dimethyl-5-phenyl-7,8-dihydropyrimido[4,5-a]indolizine-2,4(1H,3H)-dione (step 1,) (40 mg, 0.095 mmol), 10% wt. palladium on activated carbon (10 mg, 9.54 μmol) and ammonium formate (30.1 mg, 0.477 mmol) were suspended in EtOH (5 mL) and the mixture stirred at 50° C. for 19 hours, adding extra 10% wt. palladium on activated carbon (10 mg, 9.54 μmol) after 17 hours. The reaction mixture was cooled to RT and filtered through a Celite® (filter material) cartridge (10 g), rinsing the residues with MeOH. The filtrates were evaporated under reduced pressure. The residue was partitioned between DCM and water and the phases separated. The organic phase was passed through a hydrophobic frit and evaporated under reduced pressure to afford the title product as a pale yellow oil.

1H NMR (400 MHz, CDCl$_3$) δ 7.45-7.34 (m, 5H), 7.01 (m, 1H), 6.91 (m, 1H), 6.33 (t, 1H), 5.08 (dd, 1H), 4.02 (ddd, 1H), 3.70 (m, 1H), 3.24 (s, 3H), 3.21 (s, 3H), 2.22 (m, 1H), 2.05 (ddd, 1H), 1.73 (m, 2H);

LC-MS Rt 1.29 min [M+H]+ 422 (Method 2min-LC_v003).

Example 6.2

1,3-Dimethyl-10-(5-methylfuran-2-yl)-5-phenyl-7,8,9,10-tetrahydropyrimido[4,5-a]indolizine-2,4(1H,3H)-dione

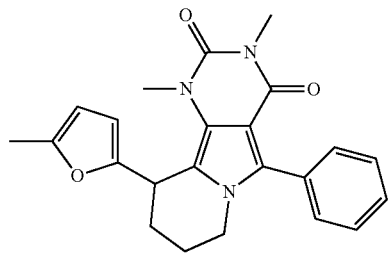 [SMILES: Cc1ccc(C2CCCn3c(-c4ccccc4)c4c(=O)n(C)c(=O)n(C)c4c32)o1]

Step 1: 1,3-Dimethyl-10-(5-methylfuran-2-yl)-5-phenyl-7,8-dihydropyrimido[4,5-a]indolizine-2,4(1H,3H)-dione 1,3-dimethyl-5-phenyl-7,8-dihydropyrimido[4,5-a]indolizine-2,4(1H,3H)-dione (Intermediate I), 2-bromo-5-methylfuran (commercially available) (390 mg, 2.421 mmol), palladium acetate (commercially available) (36.2 mg, 0.161 mmol), tri-tert-butylphosphine tetrafluorohydroborate (commercially available) (94 mg, 0.323 mmol) and N-cyclohexyl-N-methylcyclohexylamine (commercially available) (0.691 mL, 3.23 mmol) were combined in dimethyl acetamide (4 mL) and the mixture sparged with nitrogen for 30 min. The mixture was then heated at 120° C. for 15 h under microwave irradiation. The reaction mixture was diluted with water and extracted with EtOAc. The combined organic phases were washed with brine, dried over sodium sulphate and evaporated under reduced pressure. Purification by chromatography on silica, eluting with 20% EtOAc in iso-hexane, afforded 1,3-dimethyl-10-(5-methylfuran-2-yl)-5-phenyl-7, 8-dihydropyrimido[4,5-a]indolizine-2,4(1H,3H)-dione as a yellow solid which was used without further purification.

Step 2: 1,3-Dimethyl-10-(5-methylfuran-2-yl)-5-phenyl-7,8,9,10-tetrahydropyrimido[4,5-a]indolizine-2,4(1H,3H)-dione 1,3-Dimethyl-10-(5-methylfuran-2-yl)-5-phenyl-7,8-dihydropyrimido[4,5-a]indolizine-2,4(1H,3H)-dione (step 1) (411 mg, 1.061 mmol), 10% wt. palladium on activated carbon (113 mg, 0.106 mmol) and ammonium formate (669 mg, 10.61 mmol) were suspended in EtOH (30 mL) and the mixture stirred at 50° C. for 1 h. A further portion of 10% wt. palladium on activated carbon (113 mg, 0.106 mmol) was added and heating continued at 50° C. for a further 1 hour. The reaction mixture was cooled to RT and filtered through a Celite® (filter material) cartridge (10 g), rinsing the residue with MeOH. The filtrates were evaporated under reduced pressure. The residue was taken up in a small volume of MeOH and solids precipitated by addition of diethyl ether. The salts were removed by filtration and rinsing with diethyl ether. The solvent was evaporated and the residue was purified by chromatography on silica, eluting with 20% EtOAc in iso-hexane. Precipitation from EtOAc/iso-hexane afforded the title compound as a white solid.

1H NMR (400 MHz, CDCl3) δ 7.51-7.41 (m, 5H), 5.84 (d, 1H), 5.63 (d, 1H), 4.77 (m, 1H), 4.03 (dt, 1H), 3.72 (td, 1H), 3.48 (s, 3H), 3.35 (s, 3H), 2.39 (m, 1H), 2.29 (s, 3H), 2.08 (m, 1H), 1.96-1.76 (m, 2H);

LC-MS Rt=1.17 min [M+H]+ 390.5 (Method 2min-LowpH).

Chiral separation of the racemate by Supercritical Fluid Chromatography was carried out using the following conditions to afford the compounds listed hereinafter:

Mobile Phase: 40% MeOH/60% CO2
Column: Chiralpak AS-H, 250×10 mm, 5 um
Detection: UV@220 nm
Flow rate: 10 mL/min
Injection volume: 200 μl
Examples 6.3 and 6.4 are enantiomers.

Example 6.3

(R)-1,3-Dimethyl-10-(5-methylfuran-2-yl)-5-phenyl-7,8,9,10-tetrahydropyrimido[4,5-a]indolizine-2,4(1H,3H)-dione:
SFC retention time=8.35 min.
1H NMR (400 MHz, CDCl3) δ 7.51-7.41 (m, 5H), 5.84 (d, 1H), 5.63 (d, 1H), 4.77 (m, 1H), 4.03 (st, 1H), 3.72 (td, 1H), 3.48 (s, 3H), 3.35 (s, 3H), 2.39 (m, 1H), 2.29 (s, 3H), 2.08 (m, 1H), 1.96-1.76 (m, 2H);
LC-MS Rt=1.17 min MS m/z 390.5 [M+H] (Method 2min-LowpH).
Chiral purity 99% ee Example 6.4

(S)-1,3-Dimethyl-10-(5-methylfuran-2-yl)-5-phenyl-7,8,9,10-tetrahydropyrimido[4,5-a]indolizine-2,4(1H,3H)-dione:
SFC retention time=7.12 min.
1H NMR (400 MHz, CDCl3) δ 7.51-7.41 (m, 5H), 5.84 (d, 1H), 5.63 (d, 1H), 4.77 (m, 1H), 4.03 (st, 1H), 3.72 (td, 1H), 3.48 (s, 3H), 3.35 (s, 3H), 2.39 (m, 1H), 2.29 (s, 3H), 2.08 (m, 1H), 1.96-1.76 (m, 2H);

LC-MS Rt=1.17 min MS m/z 390.5 [M+H] (Method 2min-LowpH).

Chiral purity>99% ee

X-ray Crystallography

The absolute stereochemistry of the enantiomers was confirmed by X-ray crystallography of (S)-1,3-Dimethyl-10-(5-methylfuran-2-yl)-5-phenyl-7,8,9,10-tetrahydropyrimido[4,5-a]indolizine-2,4(1H,3H)-dione.

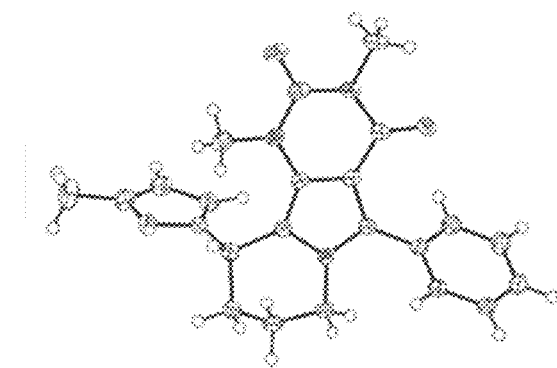

TABLE 1

| Crystal data and structure refinement | | |
|---|---|---|
| Empirical formula | C23H23N3O3 | |
| Formula weight | 389.44 | |
| Temperature | 100(2) K | |
| Wavelength | 1.54178 Å | |
| Crystal system | Orthorhombic | |
| Space group | P212121 | |
| Unit cell dimensions | a = 6.391(2) Å | α = 90°. |
| | b = 7.731(2) Å | β = 90°. |
| | c = 40.480(11) Å | γ = 90°. |
| Volume | 2000.1(10) Å$^3$ | |
| Z | 4 | |
| Density (calculated) | 1.293 Mg/m$^3$ | |
| Absorption coefficient | 0.703 mm$^{-1}$ | |
| F(000) | 824 | |
| Crystal size | 0.30 × 0.14 × 0.07 mm$^3$ | |
| Theta range for data collection | 2.18 to 68.18°. | |
| Index ranges | −7 <= h <= 7, −9 <= k <= 9, | |
| | −48 <= l <= 48 | |
| Reflections collected | 39930 | |
| Independent reflections | 3651 [R(int) = 0.0412] | |
| Completeness to theta = 68.18° | 100.0% | |
| Absorption correction | Semi-empirical from equivalents | |
| Max. and min. transmission | 0.9525 and 0.8169 | |
| Refinement method | Full-matrix least-squares on F$^2$ | |
| Data/restraints/parameters | 3651/0/265 | |
| Goodness-of-fit on F$^2$ | 1.111 | |
| Final R indices [I > 2sigma(I)] | R1 = 0.0295, wR2 = 0.0753 | |
| R indices (all data) | R1 = 0.0297, wR2 = 0.0754 | |
| Absolute structure parameter | 0.05(17) | |
| Largest diff. peak and hole | 0.188 and −0.175 e · Å$^{-3}$ | |

Example 6.5

1,3-Dimethyl-10-(4-methylthiazol-2-yl)-5-phenyl-7,8,9,10-tetrahydropyrimido[4,5-a]indolizine-2,4(1H,3H)-dione

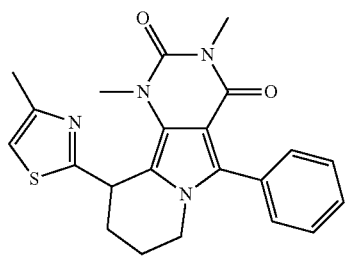 [SMILES: Cc1csc(C2CCCn3c(-c4ccccc4)c4c(=O)n(C)c(=O)n(C)c4c32)n1]

Step 1: 1,3-Dimethyl-10-(4-methylthiazol-2-yl)-5-phenyl-7,8-dihydropyrimido[4,5-a]indolizine-2,4(1H,3H)-dione 4-Methyl-2-tributylstannanyl-thiazole (Intermediate J) (491 mg, 1.265 mmol) was added to a suspension of trifluoromethanesulfonic acid 2,4-dimethyl-1,3-dioxo-9-phenyl-1,2,3,4,7,8-hexahydro-2,4,8a-triaza-fluoren-5-yl ester (Intermediate K) (480 mg, 1.054 mmol), lithium chloride (4.47 mg, 0.105 mmol), copper(I) iodide (20.07 mg, 0.105 mmol) and $PdCl_2(dppf)$ (77 mg, 0.105 mmol) in THF (12 ml) and the mixture heated at reflux under nitrogen for 2 h. Further 4-methyl-2-tributylstannanyl-thiazole (Intermediate J) (491 mg, 1.265 mmol) was added and the mixture continued at reflux for 2 h, then further 4-methyl-2-tributylstannanyl-thiazole (Intermediate J) (491 mg, 1.265 mmol) was added and the mixture stirred at reflux for 1 h. The mixture was cooled to RT, diluted with EtOAc and washed with dilute aqueous $NH_4OH$, water and brine. The organic phase was dried over sodium sulphate and evaporated under reduced pressure. The residue was triturated with $MeOH/Et_2O$ and the precipitate collected by filtration. The precipitate was purified by chromatography on silica, eluting with 50% EtOAc in hexane. Trituration with $Et_2O$ and collection by filtration afforded 1,3-dimethyl-10-(4-methylthiazol-2-yl)-5-phenyl-7,8-dihydropyrimido[4,5-a]indolizine-2,4(1H,3H)-dione as a pale yellow solid Step 2: 1,3-Dimethyl-10-(4-methylthiazol-2-yl)-5-phenyl-7,8,9,10-tetrahydropyrimido[4,5-a]indolizine-2,4(1H,3H)-dione 1,3-Dimethyl-10-(4-methylthiazol-2-yl)-5-phenyl-7,8-dihydropyrimido[4,5-a]indolizine-2,4(1H,3H)-dione (from Step 1) (174 mg, 0.430 mmol), Pd/C (commercially available) (45.8 mg, 0.043 mmol) and ammonium formate (271 mg, 4.30 mmol) were combined in EtOH (8 ml) and the mixture heated at 60° C. for 2 days. Further portions of Pd/C (45.8 mg, 0.043 mmol) and ammonium formate (271 mg, 4.30 mmol) were added as required to ensure completion of the reaction. The reaction mixture was cooled to RT and filtered through a Celite® (filter material) cartridge (10 g), rinsing the residue with MeOH. The filtrates were evaporated under reduced pressure. The residue was partitioned between DCM and water and the phases separated. The organic phase was passed through a hydrophobic frit and evaporated under vacuum. The residue was purified by chromatography on silica, eluting from 50% EtOAc in hexane to 80% EtOAc in hexane.

Precipitation from $Et_2O$/hexane afforded the title compound as a white solid.

1H NMR (400 MHz, CDCl3) δ 7.52-7.45 (m, 5H), 6.78 (d, 1H), 5.14 (dd, 1H), 4.10 (ddd, 1H), 3.75 (ddd, 1H), 3.42 (s, 3H), 3.36 (s, 3H), 2.59 (m, 1H), 2.48 (d, 3H), 2.32 (m, 1H), 1.88 (m, 2H).

LC-MS Rt 1.03 min [M+H]$^+$ 407.5 (Method 2minLowpH)

Chiral separation of the racemate by Supercritical Fluid Chromatography was carried out using the following conditions to afford the compounds listed hereinafter:

Mobile Phase: 50% IPA+0.1% DEA/50% $CO_2$
Column: Chiralpak ID, 250×10 mm, 5 um
Detection: UV@220 nm
Flow rate: 10 mL/min
Injection volume: 200 µl
Examples 6.6 and 6.7 are enantiomers.

Example 6.6

(R)-1,3-Dimethyl-10-(4-methylthiazol-2-yl)-5-phenyl-7,8,9,10-tetrahydropyrimido[4,5-a]indolizine-2,4(1H,3H)-dione:

SFC retention time=8.21 min.

1H NMR (400 MHz, CDCl$_3$) δ 7.52-7.45 (m, 5H), 6.78 (d, 1H), 5.14 (dd, 1H), 4.10 (ddd, 1H), 3.75 (ddd, 1H), 3.42 (s, 3H), 3.36 (s, 3H), 2.59 (m, 1H), 2.48 (d, 3H), 2.32 (m, 1H), 1.88 (m, 2H);

LC-MS Rt=1.03 min MS m/z 407.5 [M+H] (Method 2minLowpH).

Chiral purity>99% ee

Example 6.7

(S)-1,3-Dimethyl-10-(4-methylthiazol-2-yl)-5-phenyl-7,8,9,10-tetrahydropyrimido[4,5-a]indolizine-2,4(1H,3H)-dione SFC retention time=4.75 min was also isolated.

Chiral purity>99% ee

Example 7.1

5-(3-Fluorophenyl)-1,3-dimethyl-10-(5-methylfuran-2-yl)-7,8,9,10-tetrahydro pyrimido[4,5-a]indolizine-2,4(1H,3H)-dione

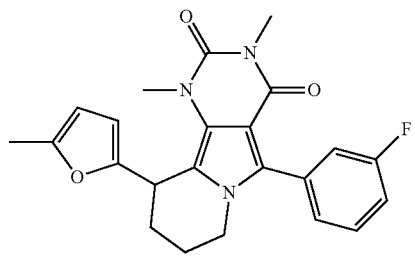 [SMILES: Cc1ccc(C2CCCn3c(-c4cccc(F)c4)c4c(=O)n(C)c(=O)n(C)c4c32)o1]

To a stirred suspension of 2-methylfuran (31.1 mg, 0.379 mmol) and 5-(3-fluorophenyl)-10-hydroxy-1,3-dimethyl-7,8,9,10-tetrahydropyrimido[4,5-a]indolizine-2,4(1H,3H)-dione (Intermediate L) (100 mg, 0.291 mmol) in MeCN (2912 µL) was added gold (III) chloride (8.83 mg, 0.029 mmol) at ambient temperature. Upon addition the white suspension formed a dark brown solution. The reaction was left for 30 mins. The reaction mixture was concentrated in-vacuo, then diluted with DCM (10 mL) and water (10 mL). The biphasic solution was passed through a phase-separator, then concentrated in-vacuo to afford a brown oil. The residue was purified using the Agilent Prep. System (50-98%, low pH) to the title compound as an off-white solid.

LCMS Rt 1.33 mins; MS m/z 408.6 [M+H]+; Method 2minlowpHv01.

Examples 7.2 and 7.3 are enantiomers.

Chiral separation of the racemate by Supercritical Fluid Chromatography was carried out using the following conditions to afford the compounds listed hereinafter:

Mobile Phase: 30% MeOH/70% $CO_2$

Column: 2× Chiralpak ID coupled 250×10 mm, 5 um@35 degC

Detection: UV@220 nm

Flow rate: 10 mL/min

Example 7.2

Enantiomer 1 of 5-(3-fluorophenyl)-1,3-dimethyl-10-(5-methylfuran-2-yl)-7,8,9,10-tetrahydropyrimido[4,5-a]indolizine-2,4(1H,3H)-dione SFC retention time=14.40 mins:

1H NMR (400 MHz, CDCl3) δ 7.43 (1H, q), 7.26-7.22 (1H, m), 7.19-7.11 (2H, m), 5.85 (1H, d), 5.63 (1H, d), 4.77 (1H, t), 4.06-3.99 (1H, m), 3.77-3.69 (1H, m), 3.48 (3H, s), 3.37 (3H, s), 2.44-2.37 (1H, m), 2.30 (3H, s), 2.13-2.04 (1H, m), 1.95-1.79 (2H, m).

LCMS Rt 1.30 mins; MS m/z 408.4 [M+H]+; (Method) 2minlowpHV01.

>99% ee

Example 7.3

Enantiomer 2 of 5-(3-fluorophenyl)-1,3-dimethyl-10-(5-methylfuran-2-yl)-7,8,9,10-tetrahydropyrimido[4,5-a]indolizine-2,4(1H,3H)-dione SFC retention time=13.07 mins was also isolated:

>99% ee

The following listed examples were prepared in a similar manner to Example 7, replacing 5-(3-fluorophenyl)-10-hydroxy-1,3-dimethyl-7,8,9,10-tetrahydropyrimido[4,5-a]indolizine-2,4(1H,3H)-dione (Intermediate L) with the appropriate starting material (either Intermediate La or Intermediate Lb). The mixtures of diastereomers were resolved by SFC chromatographic resolution under the listed conditions to afford the title compounds.

Example 7.4

(9R,10R)-5-(3-fluorophenyl)-1,3,9-trimethyl-10-(5-methylfuran-2-yl)-7,8,9,10-tetrahydropyrimido[4,5-a]indolizine-2,4(1H,3H)-dione or (9R,10S)-5-(3-fluorophenyl)-1,3,9-trimethyl-10-(5-methylfuran-2-yl)-7,8,9,10-tetrahydro pyrimido[4,5-a]indolizine-2,4(1H,3H)-dione or (9S,10R)-5-(3-fluorophenyl)-1,3,9-trimethyl-10-(5-methylfuran-2-yl)-7,8,9,10-tetrahydropyrimido[4,5-a]indolizine-2,4(1H,3H)-dione or (9S,10S)-5-(3-fluorophenyl)-1,3,9-trimethyl-10-(5-methylfuran-2-yl)-7,8,9,10-tetrahydropyrimido[4,5-a]indolizine-2,4(1H,3H)-dione

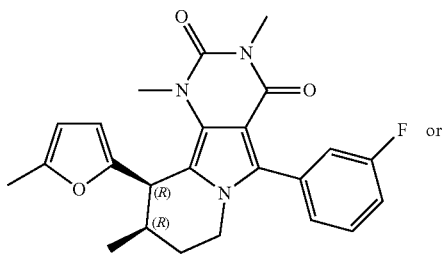

(9R,10R)-5-(3-fluorophenyl)-1,3,9-trimethyl-10-(5-methylfuran-2-yl)-7,8,9,10-tetrahydropyrimido[4,5-a]indolizine-2,4(1H,3H)-dione

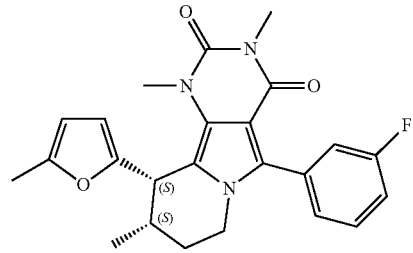

(9S,10S)-5-(3-fluorophenyl)-1,3,9-trimethyl-10-(5-methylfuran-2-yl)-7,8,9,10-tetrahydropyrimido[4,5-a]indolizine-2,4(1H,3H)-dione

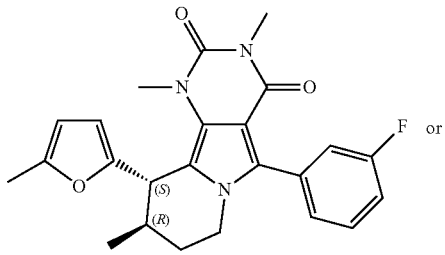

(9R,10S)-5-(3-fluorophenyl)-1,3,9-trimethyl-10-(5-methylfuran-2-yl)-7,8,9,10-tetrahydropyrimido[4,5-a]indolizine-2,4(1H,3H)-dione

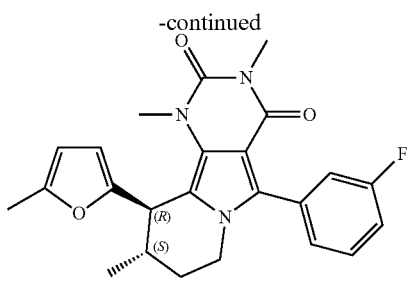

(9S,10R)-5-(3-fluorophenyl)-1,3,9-trimethyl-10-(5-methylfuran-2-yl)-7,8,9,10-tetrahydropyrimido[4,5-a]indolizine-2,4(1H,3H)-dione Separation Conditions:
Column: Chiralcel OD-H 250×10 mm, 5 um@35 degC
Mobile phase: 25% Isopropanol/75% CO2
Flow: 10 ml/min
Detection: UV@220 nm
Diastereomer 1 of 5-(3-fluorophenyl)-1,3,9-trimethyl-10-(5-methylfuran-2-yl)-7,8,9,10-tetrahydropyrimido[4,5-a]indolizine-2,4(1H,3H)-dione,
Rt=4.49 mins
1H NMR (400 MHz, CDCl3) δ 7.45 (1H, mult), 7.26 (1H, mult), 7.20-7.12 (2H, mult), 5.85 (1H, d), 5.61 (1H, d), 4.38 (1H, mult), 3.96-3.81 (2H, mult), 3.45 (3H, s), 3.35 (3H, s), 2.54 (1H, mult), 2.29 (3H, s), 2.06 (1H, mult), 1.64-1.58 (1H, mult), 1.26 (3H, d).
LC-MS Rt 1.34 mins [M+H]+ 422.2 (Method 2minLow-pHv01).

Example 7.5a and 7.5b (8R,10R)-5-(3-Fluorophenyl)-1,3,8-trimethyl-10-(5-methylfuran-2-yl)-7,8,9,10-tetrahydropyrimido[4,5-a]indolizine-2,4(1H,3H)-dione or (8S,10R)-5-(3-fluorophenyl)-1,3,8-trimethyl-10-(5-methylfuran-2-yl)-7,8,9,10-tetrahydro pyrimido[4,5-a]indolizine-2,4(1H,3H)-dione or (8R,10S)-5-(3-fluorophenyl)-1,3,8-trimethyl-10-(5-methylfuran-2-yl)-7,8,9,10-tetrahydropyrimido[4,5-a]indolizine-2,4(1H,3H)-dione or (8S,10S)-5-(3-fluorophenyl)-1,3,8-trimethyl-O-(5-methylfuran-2-yl)-7,8,9,10-tetrahydropyrimido[4,5-a]indolizine-2,4(1H,3H)-dione

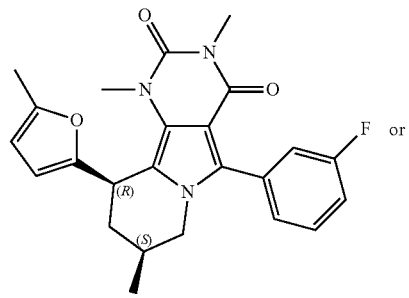

(8S,10R)-5-(3-fluorophenyl)-1,3,8-trimethyl-10-(5-methylfuran-2-yl)-7,8,9,10-tetrahydropyrimido[4,5-a]indolizine-2,4(1H,3H)-dione

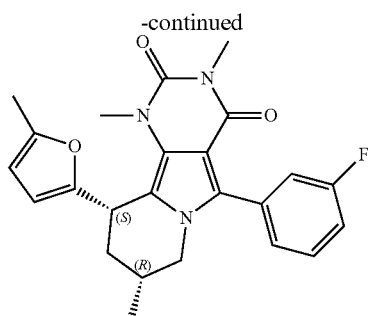

(8R,10S)-5-(3-fluorophenyl)-1,3,8-trimethyl-10-(5-methylfuran-2-yl)-7,8,9,10-tetrahydropyrimido[4,5-a]indolizine-2,4(1H,3H)-dione

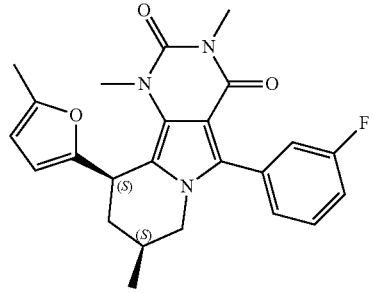

(8R,10R)-5-(3-fluorophenyl)-1,3,8-trimethyl-10-(5-methylfuran-2-yl)-7,8,9,10-tetrahydropyrimido[4,5-a]indolizine-2,4(1H,3H)-dione (8S,10S)-5-(3-fluorophenyl)-1,3,8-trimethyl-10-(5-methylfuran-2-yl)-7,8,9,10-tetrahydropyrimido[4,5-a]indolizine-2,4(1H,3H)-dione Separation Conditions:
Column: 2 coupled Chiralcel OD-H 250×10 mm, 5 um@35 degC
Mobile phase: 15% Methanol/85% CO2
Flow: 10 ml/min
Detection: UV@220 nm Example 7.5a Diastereomer 1 of 5-(3-fluorophenyl)-1,3,8-trimethyl-10-(5-methylfuran-2-yl)-7,8,9,10-tetrahydropyrimido[4,5-a]indolizine-2,4(1H,3H)-dione,
Rt=11.80 mins
1H NMR (400 MHz, CDCl3) δ 7.45 (1H, m), 7.23 (1H, d), 7.15 (2H, m), 5.83 (1H, dd), 5.58 (1H, dd), 4.76 (1H, d), 3.95 (1H, dd), 3.46 (3H, s), 3.35 (3H, s), 3.27 (1H, br t), 2.34 (1H, d), 2.29 (3H, s), 2.06 (1H, m), 1.79 (1H, td), 1.00 (3H, d).
LC-MS Rt 1.35 mins [M+H]+ 422.3 (Method 2minLow-pHv01)

Example 7.5b

Diastereomer 2 of 5-(3-fluorophenyl)-1,3,8-trimethyl-10-(5-methylfuran-2-yl)-7,8,9,10-tetrahydropyrimido[4,5-a]indolizine-2,4(1H,3H)-dione, Rt=13.82 mins 1H NMR (400 MHz, CDCl3) δ 7.45 (1H, m), 7.20 (1H, d), 7.15 (2H, m), 5.87 (1H, dd), 5.72 (1H, dd), 4.68 (1H, t), 3.83 (1H, dq), 3.47 (1H, br t), 3.35 (3H, s), 3.33 (3H, s), 2.52 (1H, m), 2.29 (3H, s), 2.01 (1H, m), 1.68 (1H, m), 1.03 (3H, d)

LC-MS Rt 1.34 mins [M+H]+ 422.4 (Method 2minLowpHv01)

Example 7.6

(9R,10R)-5-(3-Fluorophenyl)-1,3,9-trimethyl-10-(4-methylthiazol-2-yl)-7,8,9,10-tetrahydropyrimido[4,5-a]indolizine-2,4(1H,3H)-dione or (9S,10R)-5-(3-fluorophenyl)-1,3,9-trimethyl-10-(4-methylthiazol-2-yl)-7,8,9,10-tetrahydro pyrimido[4,5-a]indolizine-2,4(1H,3H)-dione or (9R,10S)-5-(3-fluorophenyl)-1,3,9-trimethyl-10-(4-methylthiazol-2-yl)-7,8,9,10-tetrahydropyrimido[4,5-a]indolizine-2,4(1H,3H)-dione or (9S,10S)-5-(3-fluorophenyl)-1,3,9-trimethyl-10-(4-methylthiazol-2-yl)-7,8,9,10-tetrahydropyrimido[4,5-a]indolizine-2,4(1H,3H)-dione

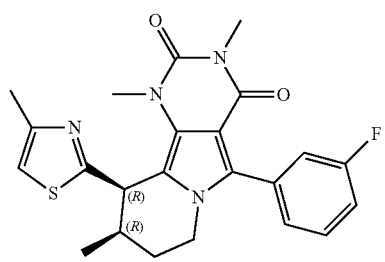

(9R,10R)-5-(3-fluorophenyl)-1,3,9-trimethyl-10-(4-methylthiazol-2-yl)-7,8,9,10-tetrahydropyrimido[4,5-a]indolizine-2,4(1H,3H)-dione

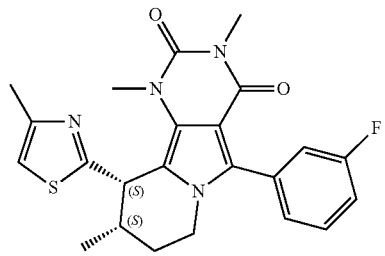

(9S,10S)-5-(3-fluorophenyl)-1,3,9-trimethyl-10-(4-methylthiazol-2-yl)-7,8,9,10-tetrahydropyrimido[4,5-a]indolizine-2,4(1H,3H)-dione -continued

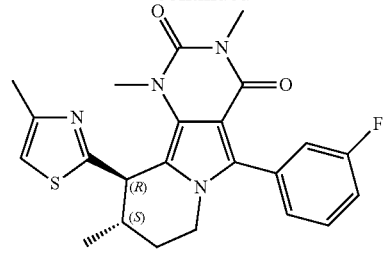

(9S,10R)-5-(3-fluorophenyl)-1,3,9-trimethyl-10-(4-methylthiazol-2-yl)-7,8,9,10-tetrahydropyrimido[4,5-a]indolizine-2,4(1H,3H)-dione

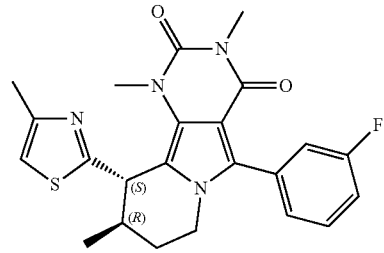

(9R,10S)-5-(3-fluorophenyl)-1,3,9-trimethyl-10-(4-methylthiazol-2-yl)-7,8,9,10-tetrahydropyrimido[4,5-a]indolizine-2,4(1H,3H)-dione Separation Conditions:
Column: Chiralpak AD 250×10 mm, 5 um@35.2° C.
Mobile phase: 25% Methanol/75% CO2
Flow: 10 ml/min
Detection: UV@220 nm Diastereomer 1 of 5-(3-fluorophenyl)-1,3,9-trimethyl-10-(4-methylthiazol-2-yl)-7,8,9,10-tetrahydropyrimido[4,5-a]indolizine-2,4(1H,3H)-dione Rt=4.22 mins 1H NMR (400 MHz, CDCl3) δ 7.47 (1H, mult), 7.26 (1H, d), 7.21-7.14 (2H, mult), 6.82 (1H, s), 5.09 (1H, d), 4.19 (1H, dd), 3.79 (1H, td), 3.47 (3H, s), 3.31 (3H, s), 2.49-2.40 (4H, mult), 2.06 (1H, mult), 1.75 (1H, mult), 1.09 (3H, d).

LC-MS Rt 1.22 mins [M+H]+ 439.6 (Method 2minLowpHv01)

Example 8.1

1,3-Dimethyl-10-(4-methylthiazol-2-yl)-5-m-tolyl-7,8,9,10-tetrahydropyrimido[4,5-a]indolizine-2,4(1H,3H)-dione

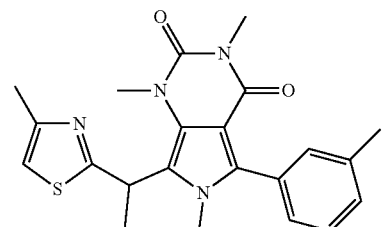

1,3-Dimethyl-10-(4-methylthiazol-2-yl)-5-m-tolyl-7,8-dihydropyrimido[4,5-a]indolizine-2,4(1H,3H)-dione (Intermediate M) (100 mg, 0.24 mmol) was dissolved in ethyl acetate (20 mL) and the resulting solution was hydrogenated using the H-Cube® (10% platinum on carbon CatCart®), at atmospheric pressure of hydrogen and 20° C., for 6.5 hours. The solvent was removed under vacuum. The crude material was purified by chromatography on silica, eluting with 1-2% MeOH/DCM to obtain a gum. Diethyl ether was added and removed under vacuum to give the title compound as a solid.

$^1$H NMR (400 MHz, CDCl3) δ 7.39 (1H, t), 7.30-7.23 (3H, mult), 6.88 (1H, s), 5.33 (1H, mult), 4.07 (1H, mult), 3.72 (1H, mult), 3.40 (3H, s), 3.34 (3H, s), 2.69 (1H, mult), 2.56 (3H, s), 2.45-2.36 (4H, mult), 1.92-1.82 (2H, mult);

LC-MS Rt=1.20 min [M+H]$^+$ 421.5 (Method 2minLowpHv01).

Chiral separation of the racemate by Supercritical Fluid Chromatography was carried out using the following conditions to afford the compounds listed hereinafter:
Mobile Phase: 25% IPA/75% CO$_2$
Column: Chiralpak IB 250×10 mm, 5 μM
Detection: UV@220 nM
Flow rate: 10 mL/min
Injection volume: 50 μL Example 8.2

Enantiomer 1 of 1,3-dimethyl-10-(4-methylthiazol-2-yl)-5-m-tolyl-7,8,9,10-tetrahydropyrimido[4,5-a]indolizine-2,4(1H,3H)-dione:
First eluted peak Rt=5.15 min
$^1$H NMR (400 MHz, CDCl3) δ 7.38 (1H, t), 7.27-7.22 (3H, mult), 6.76 (1H, s), 5.10 (1H, dd), 4.06 (1H, mult), 3.71 (1H, mult), 3.41 (3H, s), 3.35 (3H, s), 2.56 (1H, mult), 2.47 (3H, s), 2.43 (3H, s), 2.30 (1H, mult), 1.96-1.80 (2H, mult);
LC-MS Rt=1.19 min [M+H]$^+$ 421.2 (Method 2minLowpHv01);
Chiral purity>99.9% ee.

Example 8.3

Enantiomer 1 of 5-(3-Chlorophenyl)-10-(4-chlorothiazol-2-yl)-1,3-dimethyl-7,8,9,10-tetrahydropyrimido[4,5-a]indolizine-2,4(1H,3H)-dione

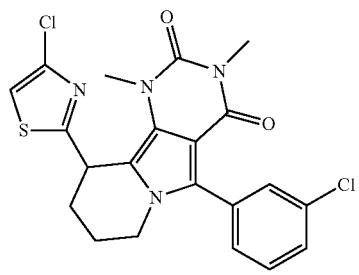 [SMILES: Cn1c(=O)c2c(-c3cccc(Cl)c3)n3c(c2n(C)c1=O)C(c1nc(Cl)cs1)CCC3]

The title compound was prepared analogously to Example 8.1. The racemate was separated by SFC chromatographic resolution under the following conditions:
Chiralpak AD 250×10 mm
Co-Solvent IPA 35%
Total Flow 10 ml/min
Column Temp. 34.9° C.
SFC Retention time=5.03 min
LC-MS Rt 1.28 mins; m/z 461.4 [M+H]$^+$; Method 2minlowpHV01.
1H NMR (400 MHz, CDCl3) δ 7.47-7.41 (3H, m), 7.40-7.34 (1H, m), 7.02 (1H, s), 5.13 (1H, t), 4.11-4.04 (1H, m), 3.80-3.73 (1H, m), 3.41 (3H, s), 3.36 (3H, s), 2.68-2.61 (1H, m), 2.35-2.26 (1H, m), 1.95-1.80 (2H, m).

Example 9.0

3-(1,3-Dimethyl-10-(4-methylthiazol-2-yl)-2,4-dioxo-1,2,3,4,7,8,9,10-octahydro pyrimido[4,5-a]indolizin-5-yl)benzonitrile

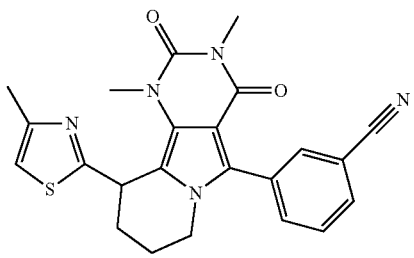 [SMILES: Cc1csc(C2CCCn3c(-c4cccc(C#N)c4)c4c(=O)n(C)c(=O)n(C)c4c32)n1]

Step 1: 1,3-Dimethyl-6-((2-(trimethylsilyl)ethoxy)methyl)-1H-pyrrolo[3,4-d]pyrimidine-2,4(3H,6H)-dione Sodium hydride (60% in mineral oil, 335 mg, 8.4 mmol) was added to an ice cooled partial suspension of 1,3-dimethyl-1H-pyrrolo[3,4-d]pyrimidine-2,4(3H,6H)-dione (Intermediate F step 2) (1.00 g, 5.6 mmol), SEM-Cl (1.485 mL, 8.4 mmol) and benzyl triethylammonium chloride (76 mg, 0.34 mmol) in THF (15 mL). The mixture was allowed to reach room temperature slowly and was stirred for 18 hours. The reaction mixture was quenched cautiously with sat ammonium chloride solution (80 mL, added dropwise), then was extracted with ethyl acetate (3×40 mL). The combined organic layers were washed with water (1×40 mL), brine (1×40 mL) then dried with magnesium sulfate and the solvent was removed under vacuum. The residue was triturated with iso-hexane and was dried under vacuum at 50° C.

1H NMR (400 MHz, CDCl3) b 7.38 (1H, s), 6.47 (1H, s), 5.26 (2H, s), 3.48 (2H, t), 3.41 (3H, s), 3.40 (3H, s), 0.93 (2H, t), 0.00 (9H, s).
LC-MS Rt 1.15 mins; MS m/z 310.4 [M+H]+; (Method 2minLowpHv01)

Step 2: 1,3-Dimethyl-2,4-dioxo-6-((2-(trimethylsilyl)ethoxy)methyl)-2,3,4,6-tetrahydro-1H-pyrrolo[3,4-d]pyrimidin-5-ylboronic acid Butyl lithium (1.26M, 28.4 mL, 35.8 mmol) was added dropwise to a solution of diisopropylamine (3.63 g, 35.8 mmol) in THF (20 mL) at −78° C., keeping the internal temperature below −40° C. Once the addition was complete, the contents of the flask were allowed to warm to −5° C., then were re-cooled to −78° C. The resulting mixture was cannulated over a period of about 30 minutes into a suspension of 1,3-dimethyl-6-((2-(trimethylsilyl)ethoxy)methyl)-1H-pyrrolo[3,4-d]pyrimidine-2,4(3H,6H)-dione (step 1) (6.93 g, 22.4 mmol) in THF (75 mL) at −78° C. The mixture was stirred at −78° C. for 30 minutes, then triisopropylborate (8.3 mL, 35.8 mmol) was added dropwise. The solution was stirred at −78° C. for 1.5 hours, then was quenched by carefully adding sat ammonium chloride (200 mL).

The mixture was allowed to reach room temperature and was extracted with ethyl acetate (3×100 mL). The combined organic extracts were dried with magnesium sulfate and the solvent was removed under vacuum. The crude material was triturated with ether/hexane and dried under vacuum at 50° C. The solid was recombined with the mother liquor which was reduced under vacuum. The resultant semi-solid material was triturated with iso-hexane and dried under vacuum at 50° C. to afford the title compound;

LC-MS: Rt 1.19 mins; MS m/z 354.4 [M+H]+; (Method 2minLowpHv01)

Step 3: 3-(1,3-Dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile A mixture of 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (step 2) (2.0 g, 5.7 mmol), 3-bromobenzonitrile (937 mg, 5.2 mmol), Pd-118 (168 mg, 0.26 mmol) and potassium carbonate (1.42 g, 10.3 mmol) in n-butyl acetate (40 mL) was heated to 80° C., then water (2.23 mL, 124.0 mmol) was added and the mixture was heated at 80° C. for 90 minutes. The reaction mixture was diluted with water (100 mL), the layers were separated as much as possible, and the aqueous phase (and residual organic portion) was extracted with DCM (1×100 mL, 2×50 mL). The combined organic extracts were washed with brine (1×100 mL), dried with magnesium sulfate and the solvent was removed under vacuum.

The resulting residue was re-crystallised from methanol and dried under vacuum at 50° C. to afford the title compound;

1H NMR (400 MHz, CDCl3) δ 7.87-7.82 (2H, mult), 7.74 (1H, d), 7.59 (1H, t), 6.59 (1H, s), 5.14 (2H, s), 3.50 (2H, t), 3.43 (3H, s), 3.56 (3H, s), 0.91 (2H, t), 0.00 (9H, s).

LC-MS: Rt 1.34 mins; MS m/z 411.4 [M+H]+; (Method 2minLowpHv01)

Step 4: 3-(1,3-Dimethyl-2,4-dioxo-2,3,4,6-tetrahydro-1H-pyrrolo[3,4-d]pyrimidin-5-yl)benzonitrile TBAF solution (20.3 mL, 20.3 mmol) was added to a suspension of 3-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile (step 3) (832 mg, 2.0 mmol) in THF (6 mL), giving a solution which was stirred at 60° C. for 1 hour. Most of the organic solvent was removed from the reaction mixture, water (100 mL) was added and the mixture was stirred for 5 minutes The aqueous suspension was extracted with choroform (4×100 mL). A large amount of the mixture remained as an emulsion. Sat brine (100 mL) was added to break up the emulsion, and the aqueous phase was extracted with more chloroform (4×100 mL). The combined organic extracts were dried with magnesium sulfate and the solvent was removed under vacuum to yield a red oil. The crude red oil was triturated with methanol to give a pink solid which was dried under vacuum at 50° C. The solid was triturated with methanol again and dried under vacuum at 50° C.

LC-MS: Rt 0.91 mins; MS m/z 281.4 [M+H]+; (Method 2minLowpHv01)

Step 5: Methyl 4-(5-(3-cyanophenyl)-1,3-dimethyl-2,4-dioxo-3,4-dihydro-1H-pyrrolo[3,4-d]pyrimidin-6(2H)-yl)butanoate A mixture of 3-(1,3-dimethyl-2,4-dioxo-2,3,4,6-tetrahydro-1H-pyrrolo[3,4-d]pyrimidin-5-yl)benzonitrile (step 4) (300 mg, 1.07 mmol), methyl 4-bromobutanoate (291 mg, 1.61 mmol) and cesium carbonate (697 mg, 2.14 mmol) in DMF (4 mL) was stirred at 80° C. for 2 hours. The reaction mixture was diluted with ethyl acetate (20 mL) and was washed with 1M HCl (3×10 mL). After the third wash, the mixture was concentrated in vacuo. The residue was triturated with diethyl ether and dried under vacuum at 50° C.

LC-MS: Rt 0.98 mins; MS m/z 381.5 [M+H]+; (Method 2minLowpHv01)

Step 6: 4-(5-(3-Cyanophenyl)-1,3-dimethyl-2,4-dioxo-3,4-dihydro-1H-pyrrolo[3,4-d]pyrimidin-6(2H)-yl)butanoic acid Lithium hydroxide (965 mg, 23.0 mmol) was added to a suspension of methyl 4-(5-(3-cyanophenyl)-1,3-dimethyl-2,4-dioxo-3,4-dihydro-1H-pyrrolo[3,4-d]pyrimidin-6(2H)-yl)butanoate (Step 5) (1.75 g, 4.6 mmol) in THF (9 mL)/water (9 mL). The mixture was stirred at room temperature for 4 hours. The organic solvent was largely removed under vacuum, the residue was acidified to pH 1, using 2M HCl. The resulting slurry was diluted with water (100 mL). The mixture was reduced under vacuum to give a white solid, which was further dried under vacuum at 50° C. overnight.

1H NMR (400 MHz, DMSO-d6) δ 12.14 (1H, v br), 7.95-7.89 (2H, mult), 7.78 (1H, d), 7.67 (1H, t), 7.05 (1H, s), 3.94 (2H, t), 3.16 (3H, s), 2.09 (2H, t), 1.82 (2H, t).

LC-MS: Rt 0.88 mins; MS m/z 367.2 [M+H]+; (Method 2minLowpHv02)

Step 7: 3-(1,3-Dimethyl-2,4,10-trioxo-1,2,3,4,7,8,9,10-octahydropyrimido[4,5-a]indolizin-5-yl)benzonitrile

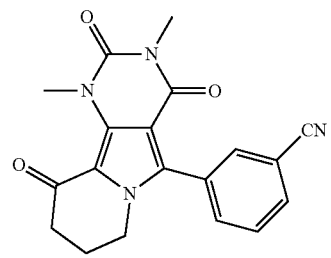 [SMILES: Cn1c(=O)c2c(-c3cccc(C#N)c3)n3c(c2n(C)c1=O)C(=O)CCC3]

T3P® solution (2.45 mL, 4.2 mmol) was added to a solution of 4-(5-(3-cyanophenyl)-1,3-dimethyl-2,4-dioxo-3,4-dihydro-1H-pyrrolo[3,4-d]pyrimidin-6(2H)-yl)butanoic acid (step 6) (1.54 g, assume 4.2 mmol) in DMF (9 mL) and the mixture was stirred at 100° C. for 5 hours.

A further 2.45 mL (4.2 mmol) of T3P® solution was added after 3 hours and a further portion (1.24 mL, 2.1 mmol) was added after 4 hours. The reaction mixture was diluted with ethyl acetate (100 mL) and washed with sat. sodium bicarbonate (2×50 mL) and brine (2×50 mL). The organic phase was dried with magnesium sulfate and the solvent was removed under vacuum.

1H NMR (400 MHz, CDCl3) δ 7.83 (1H, d), 7.78-7.72 (2H, mult), 7.67 (1H, t), 4.01 (2H, mult), 3.92 (3H, s), 3.36 (3H, s), 2.74 (2H, t), 2.26 (2H, mult).

LC-MS: Rt 0.94 mins; MS m/z 349.2 [M+H]+; (Method 2minLowpHv01)

Step 8: 5-(3-Cyanophenyl)-1,3-dimethyl-2,4-dioxo-1,2,3,4,7,8-hexahydropyrimido[4,5-a]indolizin-10-yl trifluoromethanesulfonate

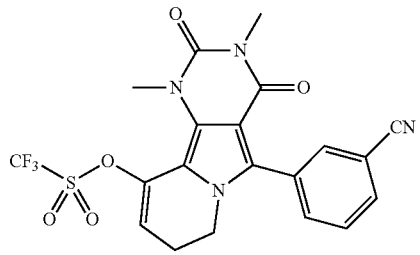 [SMILES: Cn1c(=O)c2c(-c3cccc(C#N)c3)n3c(c2n(C)c1=O)C(OS(=O)(=O)C(F)(F)F)=CCC3]

Trifluoromethanesulfonic anhydride (221 µL, 1.31 mmol) was added to an ice-cooled solution of 3-(1,3-dimethyl-2,4,10-trioxo-1,2,3,4,7,8,9,10-octahydropyrimido[4,5-a]indolizin-5-yl)benzonitrile (step 7) (350 mg, 1.01 mmol) and 2,6-lutidine (176 µL, 1.51 mmol) in DCM (5 mL). The solution was stirred at ice-bath temperature for 2 hours, further portions of 2,6-lutidine (88 µL, 0.78 mmol) and trifluoromethanesulfonic anhydride (85 µL, 0.50 mmol) were added. The reaction mixture was diluted with dichloromethane (40 mL) and was washed with water (2×20 mL) and sat. brine (1×20 mL). The organic phase was dried with magnesium sulfate and the solvent was removed under vacuum.

LC-MS: Rt 1.20 mins; MS m/z 481.5 [M+H]+; (Method 2minLowpHv01)

Step 9: 3-(1,3-Dimethyl-2,4-dioxo-10-(4,4,5,5-tetramethyl-1,3,2-dioxaborolan-2-yl)-1,2,3,4,7,8-hexahydropyrimido[4,5-a]indolizin-5-yl)benzonitrile

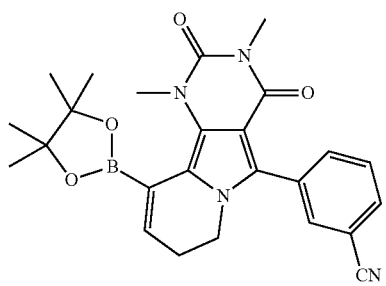 [SMILES: Cn1c(=O)c2c(-c3cccc(C#N)c3)n3c(c2n(C)c1=O)C(B1OC(C)(C)C(C)(C)O1)=CCC3]

A mixture of 5-(3-cyanophenyl)-1,3-dimethyl-2,4-dioxo-1,2,3,4,7,8-hexahydropyrimido[4,5-a]indolizin-10-yl trifluoromethanesulfonate (step 8) (480 mg, 1.0 mmol), bis(pinaolato)diboron (279 mg, 1.1 mmol), bis(triphenylphosphine)palladium(II) chloride (21 mg, 0.03 mmol), triphenylphosphine (16 mg, 0.06 mol) and potassium phenoxide (J. Am. Chem. Soc., 1959, Vol. 81, pp 2705-2715, 198 mg, 1.5 mmol) in toluene (10 mL) was stirred at 60° C., under nitrogen, for 3 hours. The reaction mixture was diluted with water (20 mL) and extracted with ethyl acetate (3×20 mL). The combined organic extracts were washed with water (2×20 mL), brine (1×20 mL), dried with magnesium sulfate and the solvent was removed under vacuum. Purified by chromatography on silica, eluting with 20-50% EtOAc/hexane. The combined fractions were concentrated in vacuo to yield title product.

1H NMR (400 MHz, CDCl3) δ 7.78 (1H, d), 7.75-7.71 (2H, mult), 7.60 (1H, t), 6.82 (1H, t), 3.81 (2H, t), 3.59 (3H, s), 3.37 (3H, s), 2.43 (2H, mult), 1.36 (12H, s).

LC-MS: Rt 1.25 mins; MS m/z 459.6 [M+H]+; (Method 2minLowpHv01)

Step 10: 3-(1,3-Dimethyl-10-(4-methylthiazol-2-yl)-2,4-dioxo-1,2,3,4,7,8-hexahydropyrimido[4,5-a]indolizin-5-yl)benzonitrile

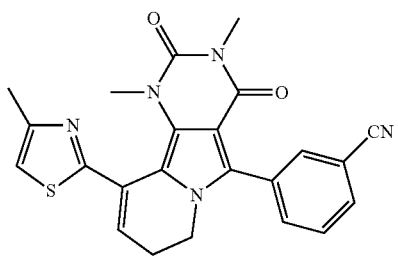 [SMILES: Cc1csc(C2=CCCn3c(-c4cccc(C#N)c4)c4c(=O)n(C)c(=O)n(C)c4c32)n1]

A mixture of 3-(1,3-dimethyl-2,4-dioxo-10-(4,4,5,5-tetramethyl-1,3,2-dioxaborolan-2-yl)-1,2,3,4,7,8-hexahydropyrimido[4,5-a]indolizin-5-yl)benzonitrile (step 9) (202 mg, 0.44 mmol), 2-iodo-4-methylthiazole (Intermediate O) (90 mg, 0.40 mmol), dichloro[1,1' bis(di-tert-butylphosphino)] ferrocene palladium (11) (13 mg, 0.02 mmol) and barium hydroxide (137 mg, 0.80 mmol) in acetonitrile/water (1:1, 2 mL) was stirred at room temperature for 45 minutes and at 80° C. for 1 hour. The reaction mixture was diluted with 1M HCl (10 mL) and was extracted with DCM (3×10 mL). The combined organic layers were filtered through a hydrophobic frit and the solvent removed under vacuum. Purified by chromatography on silica, eluting with 0.5% MeOH/DCM, 1% MeOH/DCM, 1.5-2.0% MeOH afforded the title product:

1H NMR (400 MHz, CDCl3) δ 7.82-7.74 (3H, mult), 7.62 (1H, t), 6.93 (1H, s), 6.52 (1H, t), 3.91 (2H, t), 3.34 (3H, s), 2.81 (3H, s), 2.60 (2H, mult), 2.50 (3H, s).

LC-MS: Rt 1.10 mins; MS m/z 430.1 [M+H]+; (Method 2minLowpHv01)

Step 11: 3-(1,3-Dimethyl-10-(4-methylthiazol-2-yl)-2,4-dioxo-1,2,3,4,7,8,9,10-octahydropyrimido[4,5-a]indolizin-5-yl)benzonitrile

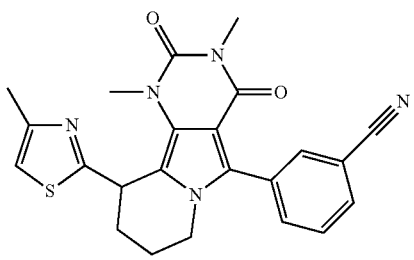 [SMILES: Cc1csc(C2CCCn3c(-c4cccc(C#N)c4)c4c(=O)n(C)c(=O)n(C)c4c32)n1]

A solution of 3-(1,3-dimethyl-10-(4-methylthiazol-2-yl)-2,4-dioxo-1,2,3,4,7,8-hexahydropyrimido[4,5-a]indolizin-5-yl)benzonitrile (step 10) (76 mg, 0.18 mmol) in ethanol/THF (1:1, 30 mL) was hydrogenated over 10% platinum on carbon, at room temperature and atmospheric pressure of hydrogen for 19 hours. A further portion of platinum on carbon catalyst was added (10 mg) and hydrogenation was continued as before for 24 hours. A further portion of platinum on carbon catalyst was added (60 mg) and hydrogenation was continued as before for a further 18 hours. The reaction mixture was filtered through GF/F paper to remove the catalyst, washing well with 20% MeOH/DCM. The filtrate was reduced under vacuum. The crude material was re-dissolved in EtOH/THF (1:1, 20 mL), the solution was de-gassed and 10% platinum on carbon (60 mg) was added. The mixture was hydrogenated at room temperature and atmospheric pressure of hydrogen for 20 hours. The reaction mixture was filtered through GF/F paper to remove the catalyst, washing well with 20% MeOH/DCM. The filtrate was reduced under vacuum. Purified by chromatography on silica, eluting with 0.5-1.5% MeOH/DCM afforded a yellow oily residue. Diethyl ether was added to the residue and removed under vacuum to give a white solid which was dried under vacuum at 50° C.

1H NMR (400 MHz, CDCl3) δ 7.81-7.70 (3H, mult), 7.62 (1H, mult), 6.81 (1H, s), 5.18 (1H, s), 4.06 (1H, d), 3.78 (1H, mult), 3.42 (3H, s), 3.36 (3H, s), 2.61 (1H, d), 2.49 (3H, s), 2.34 (1H, mult), 1.93 (2H, mult).

LC-MS: Rt 1.05 mins; MS m/z 432.1 [M+H]+; (Method 2minLowpHv02) 3-(1,3-Dimethyl-10-(4-methylthiazol-2-yl)-2,4-dioxo-1,2,3,4,7,8,9,10-octahydropyrimido[4,5-a]indolizin-5-yl)benzonitrile was purified by chiral separation under these conditions to afford the compound listed hereinafter:

Column: Chiralpak IB 250×10 mm, 5 um@35 degC
Mobile Phase: 35% MeOH/65% CO2
Flow: 10 ml/min
Detection: UV@220 um Example 9.1

Enantiomer 1 of 3-(1,3-dimethyl-10-(4-methylthiazol-2-yl)-2,4-dioxo-1,2,3,4,7,8,9,10-octahydropyrimido[4,5-a]indolizin-5-yl)benzonitrile
SFC Retention Time 4.09 mins
1H NMR (400 MHz, CDCl3) δ 7.82-7.73 (3H, m), 7.63 (1H, m), 6.79 (1H, s), 5.12 (1H, s), 4.05 (1H, m), 3.78 (1H, m), 3.42 (3H, s), 3.35 (3H, s), 2.59 (1H, m), 2.47 (3H, s), 2.32 (1H, m), 2.00-1.86 (2H, m).
LC-MS: Rt 1.08 mins; MS m/z 432.2 [M+H]+; (Method 2minLowpHv01)
100% ee Example 9.2

3-(1,3-Dimethyl-2,4-dioxo-5-phenyl-1,2,3,4,7,8,9,10-octahydropyrimido[4,5-a]indolizin-10-yl)benzonitrile

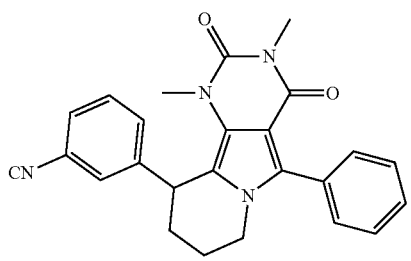

The title compound was prepared analogously to Example 9 by replacing 2-iodo-4-methylthiazole (step 10) with 3-bromobenzonitrile;

1H NMR (400 MHz, CDCl3) δ 7.58-7.44 (7H, mult), 7.32-7.24 (2H, mult), 4.91 (1H, mult), 4.10 (1H, mult), 3.80 (1H, mult), 3.35 (3H, s), 3.27 (3H, s), 2.37 (1H, mult), 2.10 (1H, mult), 1.85-1.70 (2H, mult).

LC-MS Rt 1.19 mins [M+H]+ 411.5 (Method 2minLowpHv01)

Example 10.0

1,3-Dimethyl-10-(4-methylthiazol-2-yl)-5-phenyl-7,8,9,10-tetrahydropyrimido[4',5':3,4]pyrrolo[1,2-b]pyridazine-2,4(1H,3H)-dione

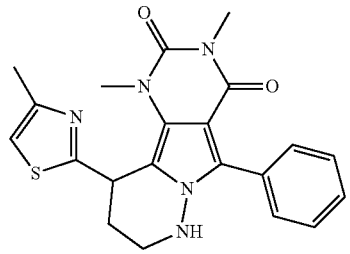 [SMILES: Cc1csc(C2CCNn3c(-c4ccccc4)c4c(=O)n(C)c(=O)n(C)c4c32)n1]

Step 1: (1,3-Dimethyl-2,4-dioxo-5-phenyl-1,2,3,4-tetrahydro-pyrrolo[3,4-d]pyrimidin-6-yl)-carbamic acid benzyl ester 5-Benzoyl-6-(bromomethyl)-1,3-dimethylpyrimidine-2,4(1H,3H)-dione (Intermediate C) (1.15 g, 3.41 mmol), benzyl carbazate (commercial) (2.83 g, 17.05 mmol) and triethylamine (1.426 ml, 10.23 mmol) were combined in EtOH (15 ml) and the mixture heated at reflux for 15 mins. The reaction mixture was cooled to RT and evaporated under reduced pressure. The residue was partitioned between water and DCM and the phases separated. The organic phase was passed through a hydrophobic frit and evaporated under reduced pressure. The residue was triturated with Et2O and cooled in ice until precipitation occurred. The precipitate was collected by filtration, affording the title compound as a white solid.

1H NMR (400 MHz, DMSO-d6) δ 11.16 (br s, 1H), 7.50-7.30 (m, 9H), 7.24 (br s, 1H), 7.09 (1H, br s), 5.11 (s, 2H), 3.19 (s, 3H), other 3H singlet obscured by water signal.

LC-MS Rt 1.00 mins; ES+ m/z 405 [M+H] (Method 2min-LowpH)

Step 2: (1,3-Dimethyl-2,4-dioxo-5-phenyl-1,2,3,4-tetrahydro-pyrrolo[3,4-d]pyrimidin-6-yl)-(3-hydroxy-propyl)-carbamic acid benzyl ester 3-Bromopropan-1-ol (0.645 ml, 7.14 mmol) was added to a suspension of (1,3-Dimethyl-2,4-dioxo-5-phenyl-1,2,3,4-tetrahydro-pyrrolo[3,4-d]pyrimidin-6-yl)-carbamic acid benzyl ester (step 1) (2.22 g, 5.49 mmol), K2CO3 (2.276 g, 16.47 mmol) and benzyltrimethylammonium chloride (0.102 g, 0.549 mmol) in acetonitrile (50 ml). The mixture was heated to 60° C. and stirred for 40 mins. The reaction mixture was cooled to RT and diluted with water. The mixture was extracted with EtOAc (2×) and the combined organic phases washed with brine, dried over sodium sulphate and evaporated under reduced pressure. Purification by chromatography on silica, eluting with EtOAc/hexane and then MeOH/EtOAc afforded the title compound as a white foam.

1H NMR (400 MHz, CDCl3) δ 7.34-7.18 (m, 10H), 6.32 (s, 1H), 5.24 (d, 1H), 5.14 (d, 1H), 3.61 (dt, 2H), 3.35 (m, 1H), 3.31 (s, 3H), 3.29 (m, 1H, partially obscured), 3.27 (s, 3H), 1.50 (m, 1H), 1.35 (m, 1H).

LC-MS Rt 0.98 mins; ES+ m/z 463.4 [M+H]+ (Method 2minLowpH).

Step 3: 3-[Benzyloxycarbonyl-(1,3-dimethyl-2,4-dioxo-5-phenyl-1,2,3,4-tetrahydro-pyrrolo[3,4-d]pyrimidin-6-yl)-amino]-propionic acid Tetrapropylammonium perruthenate (0.152 g, 0.432 mmol) was added to a solution of (1,3-Dimethyl-2,4-dioxo-5-phenyl-1,2,3,4-tetrahydro-pyrrolo[3,4-d]pyrimidin-6-yl)-(3-hydroxy-propyl)-carbamic acid benzyl ester (step 2) (2 g, 4.32 mmol) and N-methylmorpholine oxide monohydrate (commercial) (2.92 g, 21.62 mmol) in Acetonitrile (40 ml). The mixture was stirred at room temp. for 30 mins. The reaction mixture was quenched with isopropanol (50 mL) and stirred for 20 mins. The mixture was then evaporated under reduced pressure. Purification of the residue by chromatography on silica, eluting with EtOAc followed by 1% acetic acid/EtOAc afforded the title compound as a white solid.

1H NMR (400 MHz, CDCl3) δ 7.45-7.30 (m, 10H), 6.43 (s, 1H), 5.30 (m, 2H), 3.93 (m, 1H), 3.47 (m, 1H), 3.40 (s, 3H), 3.3 (s, 3H), 2.45 (m, 1H), 2.33 (m, 1H).

LC-MS Rt 0.98 mins; ES+ m/z 477.4 [M+H]+ (Method 2minLowpH)

Step 4: 1,3-Dimethyl-5-phenyl-8,9-dihydropyrimido[4',5':3,4]pyrrolo[1,2-b]pyridazine-2,4,10(1H,3H,7H)-trione 3-[Benzyloxycarbonyl-(1,3-dimethyl-2,4-dioxo-5-phenyl-1,2,3,4-tetrahydro-pyrrolo[3,4-d]pyrimidin-6-yl)-amino]-propionic acid (step 3) (1.09 g, 2.288 mmol) and Polyphosphoric acid (3 g, 2.288 mmol) were heated together at 100° C. (block temp) for 30 mins. The reaction mixture was cooled to RT and the residue dissolved in minimum volume of water. The mixture was basified by slow addition of 2M NaOH(aq), and extracted with chloroform (4x). The combined organic extracts were passed through a hydrophobic frit and evaporated under reduced pressure. Purification of the residue by chromatography on silica, eluting with MeOH/DCM afforded the title compound as a white solid.

1H NMR (400 MHz, CDCl3) δ 7.51-7.46 (m, 2H), 7.46-7.41 (m, 3H), 4.67 (t, 1H), 3.88 (s, 3H), 3.53 (dt, 2H), 3.29 (s, 3H), 2.68 (t, 2H).

LC-MS Rt 0.83 mins; ES+ m/z ion not evident [M+H]+ (Method 2minLowpH).

Step 5: Trifluoro-methanesulfonic acid 5,7-dimethyl-6,8-dioxo-9-phenyl-1,2,5,6,7,8-hexahydro-1,5,7,9a-tetraaza-fluoren-4-yl ester Trifluoromethanesulfonic anhydride (0.254 ml, 1.506 mmol) was added slowly to a solution of 1,3-dimethyl-5-phenyl-8,9-dihydropyrimido[4',5':3,4]pyrrolo[1,2-b]pyridazine-2,4,10(1H,3H,7H)-trione (step 4) (222 mg, 0.684 mmol) and 2,6-lutidine (commercial) (0.159 ml, 1.369 mmol) in DCM (10 ml) at 0° C. and the mixture stirred for 1.75 hours. The reaction mixture was quenched with sat. NaHCO3(aq) and extracted with DCM. The organic phase was passed through a hydrophobic frit and evaporated under reduced pressure. Purification of the residue by chromatography on silica, eluting with 20% EtOAc/hexane then 40% EtOAc/hexane afforded the title compound as a yellow solid.

1H NMR (400 MHz, CDCl3) δ 7.64-7.58 (m, 2H), 7.54-7.46 (m, 3H), 6.16 (m, 1H), 5.35 (m, 1H), 3.98 (m, 1H), 3.66 (s, 3H), 3.42 (s, 3H).

LC-MS Rt 1.07 mins; ES+ m/z 499.3 [M+H+MeCN]+ (Method 2minLowpH)

Step 6: 1,3-Dimethyl-10-(4-methylthiazol-2-yl)-5-phenyl-7,8-dihydropyrimido[4',5':3,4]pyrrolo[1,2-b]pyridazine-2,4(1H,3H)-dione Trifluoro-methanesulfonic acid 5,7-dimethyl-6,8-dioxo-9-phenyl-1,2,5,6,7,8-hexahydro-1,5,7,9a-tetraaza-fluoren-4-yl ester (step 5) (280 mg, 0.614 mmol), LiCl (2.60 mg, 0.061 mmol), copper iodide (11.68 mg, 0.061 mmol) and 4-methyl-2-tributylstannanyl-thiazole (Intermediate J) (4.45 g, 11.46 mmol) were combined in THF (15 ml) and PdCl2(dppf) (44.9 mg, 0.061 mmol) was added. The mixture was heated at reflux for 1 hour. The reaction mixture was cooled to RT and diluted with EtOAc. The mixture was washed with dil. NH4OH(aq), 1M KF(aq) and brine. The organic phase was dried over sodium sulphate and evaporated under reduced pressure. Purification of the residue by chromatography on silica, eluting with EtOAc/hexane, afforded the title compound as a crude pale brown solid.

LC-MS: Rt 0.97 mins; ES+ m/z 406.4 [M+H]+ (Method 2minLowpH).

Step 7: 1,3-Dimethyl-10-(4-methylthiazol-2-yl)-5-phenyl-7,8,9,10-tetrahydropyrimido[4',5':3,4]pyrrolo[1,2-b]pyridazine-2,4(1H,3H)-dione 1,3-Dimethyl-10-(4-methylthiazol-2-yl)-5-phenyl-7,8-dihydropyrimido[4',5':3,4]pyrrolo[1,2-b]pyridazine-2,4(1H,3H)-dione (step 6) (100 mg, 0.247 mmol), 10% wt. palladium on carbon (26.2 mg, 0.025 mmol) and ammonium formate (156 mg, 2.466 mmol) were combined in EtOH (10 ml) and the mixture heated at reflux for 24 hours. The reaction mixture was cooled to RT and filtered through a Celite® (filter material) cartridge (10 g), rinsing the residue with copious MeOH. The filtrates were evaporated under reduced pressure. The residue was triturated with EtOAc/hexane and the solid collected by filtration. Purification of the residue by chromatography on silica, eluting with EtOAc/hexane and MeOH/EtOAc yielded a crude material which was further purified by preparative HPLC using the following conditions:

Column: Waters Sunfire C18, 150 mm×30 mm, 5 μm

Mobile Phase: A=0.1% TFA in water; B=0.1% TFA in acetonitrile

Gradient: 0.0 min-0.5 min 30% B 30 mL/min, 0.5-1.0 min 30% B 30-50 mL/min, 1.0-7.25 min 30-70% B 50 mL/min, 7.25-7.3 70-98% B 50 mL/min, 7.3-8.3 min 98% B 50 mL/min, 8.3-8.5 min 98-30% B 50 mL/min Detection: UV@220 nm Flow rate: 10 mL/min Injection volume: 200 μl The title compound was obtained as an off-white solid 1H NMR (400 MHz, CDCl3) δ 8.26 (2H, br s), 7.62-7.57 (2H, mult), 7.52-7.43 (3H, mult), 6.96 (1H, d), 5.53 (1H, dd), 3.41 (3H, s), 3.37 (3H, s), 2.53 (3H, d), 2.50-2.42 (2H, mult).

LC-MS Rt 0.93 mins; ES+ m/z 408.3 [M+H] (Method 2minLowpH).

Chiral separation of the racemate by Supercritical Fluid Chromatography was carried out using the following conditions to afford the compound listed hereinafter:

Column: Chiralpak IB, 250×10 mm, 5 um;
Mobile Phase: 50% MeOH with 0.1% DEA/50% CO2
Flow Rate: 10 mL/min Example 10.1

Enantiomer 1 of 1,3-Dimethyl-10-(4-methylthiazol-2-yl)-5-phenyl-7,8,9,10-tetrahydropyrimido[4',5':3,4]pyrrolo[1,2-b]pyridazine-2,4(1H,3H)-dione SFC Retention time=2.76 mins
LC-MS: Rt 1.00 mins; MS 408.5 m/z [M+H] Method 2minLowpHv01
1H NMR (400 MHz, CDCl3) δ 7.62 (2H, d), 7.51-7.39 (3H, m), 6.79 (1H, d), 5.13 (1H, dd), 5.09 (1H, t), 3.49 (3H, s), 3.40 (1H, m), 3.36 (3H, s), 3.28 (1H, m), 2.54 (1H, m), 2.44 (3H, d), 2.36 (1H, m).

Example 10.2

5-(3-Chlorophenyl)-1,3-dimethyl-10-(4-methylthiazol-2-yl)-7,8,9,10-tetrahydropyrimido[4',5':3,4]pyrrolo[1,2-b]pyridazine-2,4(1H,3H)-dione

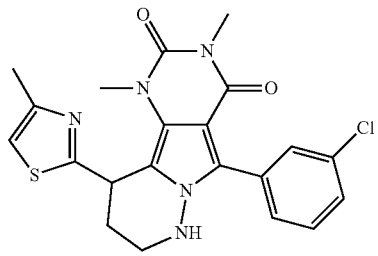 [SMILES: Cc1csc(C2CCNn3c(-c4cccc(Cl)c4)c4c(=O)n(C)c(=O)n(C)c4c32)n1]

The title compound was prepared analogously to Example 10 by replacing Intermediate C with the appropriate starting compound (prepared by a similar method to Intermediate C using the appropriate 3-chloro-benzoyl chloride in Step 2);
1H NMR (400 MHz, CDCl3) δ 7.61 (1H, m), 7.53 (1H, m), 7.40 (2H, m), 6.81 (1H, d), 5.17 (1H, dd), 3.48 (3H, s), 3.41 (1H, m), 3.37 (3H, s), 3.30 (1H, m), 2.56 (1H, m), 2.46 (3H, s), 2.38 (1H, m)
LC-MS Rt 1.16 mins; MS m/z 442.2 [M+H]+ (Method 2minLowpHv02)

Example 11.0

1,3-Dimethyl-9-(5-methylfuran-2-yl)-5-phenyl-8,9-dihydro-1H-pyrimido[4,5-a]pyrrolizine-2,4(3H,7H)-dione

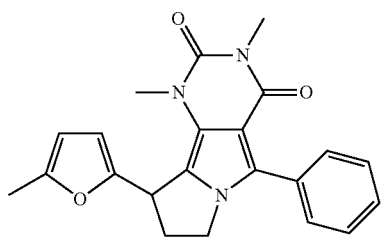 [SMILES: Cc1ccc(C2CCn3c(-c4ccccc4)c4c(=O)n(C)c(=O)n(C)c4c32)o1]

Step 1: Methyl 3-(1,3-dimethyl-2,4-dioxo-5-phenyl-3,4-dihydro-1H-pyrrolo[3,4-d]pyrimidin-6(2H)-yl)propanoate 5-Benzoyl-6-(bromomethyl)-1,3-dimethylpyrimidine-2,4(1H,3H)-dione (Intermediate C) (3 g, 8.90 mmol), beta alanine methyl ester hydrochloride (1.242 g, 8.90 mmol) and triethylamine (2.480 mL, 17.80 mmol) in EtOH (63.6 mL) was heated to 100° C. for 90 min using microwave radiation. The reaction mixture was diluted with of DCM (80 ml) and washed with water and 0.1M HCl. The organic portion was dried by passing through a phase separating cartridge and concentrated in vacuo to yield the title compound as a pale yellow oil.
LCMS: Rt 0.98 min; MS 342.6 [M+H]; (Method: 2min-lowpH)

Step 2: 3-(1,3-Dimethyl-2,4-dioxo-5-phenyl-3,4-dihydro-1H-pyrrolo[3,4-d]pyrimidin-6(2H)-yl)propanoic acid A mixture of methyl 3-(1,3-dimethyl-2,4-dioxo-5-phenyl-3,4-dihydro-1H-pyrrolo[3,4-d]pyrimidin-6(2H)-yl)propanoate (step 2) (3.24 g, 9.49 mmol) in THF (33.9 mL)/water (33.9 mL) and LiOH (2.273 g, 95 mmol) was heated to 50° C. for 1 hr. The reaction mixture was diluted with EtOAc (50 ml) and the layers separated. The organics were then washed with water (3×50 ml). The aqueous extracts were combined and the pH adjusted to approx. pH3 with 5M HCl. The resulting precipitate was isolated using suction filtration.
LC-MS: Rt 0.87 mins; MS 328.4 m/z [M+H]+ (Method 2minLowpHv01)
1H NMR: (400 MHz, CDCl3) δ 7.47 (5H, mult), 7.00 (1H, s), 4.09 (2H, t), 3.15 (3H, t), 2.70 (2H, t), 2.51 (3H, s).

Step 3: 1,3-Dimethyl-5-phenyl-7,8-dihydro-1H-pyrimido[4,5-a]pyrrolizine-2,4,9(3H)-trione 3-(1,3-Dimethyl-2,4-dioxo-5-phenyl-3,4-dihydro-1H-pyrrolo[3,4-d]pyrimidin-6(2H)-yl)propanoic acid (step 2) (2.11 g, 6.63 mmol) and propylphosphonic anhydride (4.34 g, 6.63 mmol) 50% in DMF was heated to 100° C. overnight. The reaction mixture was cooled to RT and the precipitate isolated using suction filtration. The isolated orange solid was washed with Et2O and dried in a vacuum oven at 50° C.
1H NMR: (400 MHz, CDCl3) δ 7.61 (2H, mult), 7.54 (3H, mult), 4.34 (2H, t), 3.94 (3H, s), 3.41 (3H, s), 3.17 (3H, t).
LC-MS: Rt 0.96 mins; MS 310.2 m/z [M+H]+ (Method 2minLowpHv01)

Step 4: 1,3-Dimethyl-2,4-dioxo-5-phenyl-2,3,4,7-tetrahydro-1H-pyrimido[4,5-a]pyrrolizin-9-yl trifluoromethanesulfonate 1,3-Dimethyl-5-phenyl-7,8-dihydro-1H-pyrimido[4,5-a]pyrrolizine-2,4,9(3H)-trione (step 3) (200 mg, 0.647 mmol) and 2,6-lutidine (0.113 ml, 0.970 mmol) in DCM (2 ml) were combined under nitrogen then cooled to 0° C. in a ice bath, and trifluoromethanesulfonic anhydride (219 mg, 0.776 mmol) was added dropwise over 5 mins. The reaction mixture and was allowed to stir at 0° C. for 35 mins then quenched with 10 ml of water. The aqueous was extracted with DCM (2×10 ml). The organics were combined and dried by passing through a phase separating cartridge. The crude product was concentrated under vacuum. The crude product was loaded onto a 40 g silica cartridge and the product eluted at 35% EtOAc/i-Hexane. The relevant fractions were combined and concentrated to yield a yellow gum. Diethyl ether was added to the gum and the mixture concentrated once more to yield the title compound as a yellow solid.

LC-MS: Rt 1.29 min; MS 443.2 m/z [M+H]+; (Method 2minLowpH)

1H NMR: av70431 (400 MHz, DMSO) δ 7.76 (2H, d), 7.49 (3H, mult), 6.36 (1H, s), 5.00 (2H, d), 3.48 (3H, s), 3.22 (3H, s).

19F NMR (400 MHz, DMSO) δ −66.3 (CF3).

Step 5: 1,3-Dimethyl-9-(5-methylfuran-2-yl)-5-phenyl-1H-pyrimido[4,5-a]pyrrolizine-2,4(3H,7H)-dione 1,3-Dimethyl-2,4-dioxo-5-phenyl-2,3,4,7-tetrahydro-1H-pyrimido[4,5-a]pyrrolizin-9-yl trifluoromethanesulfonate (step 4) (100 mg, 0.227 mmol), CuI (4.31 mg, 0.023 mmol), lithium bromide (39.4 mg, 0.453 mmol), tributyl(5-methylfuran-2-yl)stannane (168 mg, 0.453 mmol) in THF (2 ml) and Pd-118 (14.77 mg, 0.023 mmol) were heated to reflux for 10 mins. The reaction mixture was filtered through a glass filter paper and the filtrate concentrated in vacuo. The crude product was dissolved in the minimum amount DCM/EtOAc and loaded onto a 12 g silica cartridge and eluted with 0-80% EtOAc in iso-hexane. The desired product was eluted at 30% EtOAc. The relevant fractions were combined and concentrated to yield a yellow solid. The isolated solid was suspended in Et2O and the solid filtered to yield the title product.

LC-MS: Rt 1.30 mins; MS 374.3 m/z [M+H]+ (Method 2minLowpHv01)

1H NMR: (400 MHz, CDCl3) δ 7.68 (2H, d), 7.51 (2H, t), 7.43 (1H, t), 6.44 (1H, d), 6.16 (1H, t), 6.09 (1H, d), 4.71 (2H, d), 3.40 (3H, s), 3.19 (3H, s), 2.37 (3H, s).

Step 6: 1,3-Dimethyl-9-(5-methylfuran-2-yl)-5-phenyl-8,9-dihydro-1H-pyrimido[4,5-a]pyrrolizine-2,4(3H,7H)-dione To a mixture of ammonium formate (45.6 mg, 0.723 mmol), 1,3-dimethyl-9-(5-methylfuran-2-yl)-5-phenyl-1H-pyrimido[4,5-a]pyrrolizine-2,4(3H,7H)-dione (step 5) (27 mg, 0.072 mmol), and Pd/C (7.69 mg, 7.23 μmol) with a chip of dry ice was added ethanol (1446 μL). The reaction mixture was heated to 60° C. for 25 mins and allowed to stand at RT overnight. The reaction mixture was diluted with DCM and filtered through glass filter paper. The filtrate was washed with water and the organics collected and dried by passing through a phase separator cartridge. The organics were concentrated in vacuo. The crude product was loaded onto a 4 g silica cartridge and purified using an ISCO. The product was eluted with 0-80% EtOAc in iso-hexanes to afford the title compound;

LC-MS: Rt 1.22 mins; MS m/z 376.4 [M+H]+ (Method 2minLowpHv01)

1H NMR (400 MHz, CDCl3) δ 7.63 (2H, d), 7.47 (2H, t), 7.40 (1H, t), 5.89 (2H, mult), 4.66 (1H, mult), 4.19 (1H, mult), 4.06 (1H, mult), 3.43 (3H, s), 3.40 (3H, s), 2.89 (1H, mult), 2.69 (1H, mult), 2.30 (3H, s).

Chiral separation of the racemate by Supercritical Fluid Chromatography was carried out using the following conditions to afford the compound listed hereinafter:
Column: Chiralpak IB, 250×10 mm, 5 um
Mobile Phase: 25% MeOH with 0.1% DEA/75% CO2
Flow Rate: 10 mL/min Example 11.1

Enantiomer 1 of 1,3-dimethyl-9-(5-methylfuran-2-yl)-5-phenyl-8,9-dihydro-1H-pyrimido[4,5-a]pyrrolizine-2,4(3H,7H)-dione SFC Retention time=5.83 mins
LC-MS: Rt 1.23 mins; MS 376.9 m/z [M+H]+ (Method 2minLowpHv01)

1H NMR: (400 MHz, CDCl3) δ 7.63 (2H, d), 7.48 (2H, t), 7.40 (1H, t), 5.89 (2H, s), 4.66 (1H, d), 4.20 (1H, mult), 4.06 (1H, mult), 3.43 (3H, s), 3.40 (3H, s), 2.89 (1H, mult), 2.69 (1H, mult), 2.29 (3H, s).

Example 12.0

10-(5-Chlorofuran-2-yl)-8-(hydroxymethyl)-1,3-dimethyl-5-phenyl-7,8-dihydro-1H-pyrimido[4',5':3,4]pyrrolo[2,1-c][1,4]thiazine-2,4(3H,10H)-dione

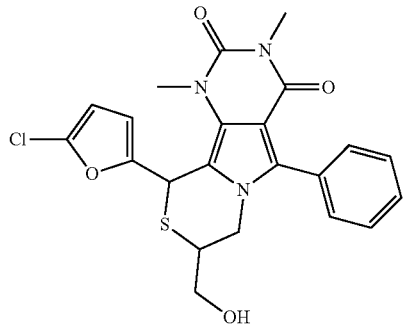 [SMILES: Cn1c(=O)c2c(-c3ccccc3)n3c(c2n(C)c1=O)C(c1ccc(Cl)o1)SC(CO)C3]

Step 1: 6-(2,3-Dihydroxypropyl)-1,3-dimethyl-5-phenyl-1H-pyrrolo[3,4-d]pyrimidine-2,4(3H,6H)-dione 5-Benzoyl-6-(bromomethyl)-1,3-dimethylpyrimidine-2,4(1H,3H)-dione (Intermediate C)(670 mg, 1.987 mmol), 3-aminopropane-1,2-diol (0.231 ml, 2.98 mmol) and TEA (0.554 ml, 3.97 mmol) were combined in EtOH (15 ml) and heated at reflux for 15 mins.

The reaction mixture was cooled to RT. and evaporated under vacuum. The residue was partitioned between DCM and diluted HCl(aq) and the phases separated. The organic phase was passed through a hydrophobic frit and evaporated under vacuum to afford the title compound;

LC-MS: MS Rt 0.76 mins [M+H]+ 330.3 Method 2minLowpHv01

Step 2: 6-(3-(tert-Butyldimethylsilyloxy)-2-hydroxypropyl)-1,3-dimethyl-5-phenyl-1H-pyrrolo[3,4-d]pyrimidine-2,4(3H,6H)-dione 6-(2,3-Dihydroxypropyl)-1,3-dimethyl-5-phenyl-1H-pyrrolo[3,4-d]pyrimidine-2,4(3H,6H)-dione (step 1)(1.66 g, 5.04 mmol), imidazole (0.686 g, 10.08 mmol) and DMAP (0.062 g, 0.504 mmol) were dissolved in DMF (25 ml) and TBS-Cl (0.836 g, 5.54 mmol) was added. The resulting mixture was stirred at RT overnight. Further TBS-Cl (0.836 g, 5.54 mmol) added and stirring continued for 2 hours. The reaction mixture was diluted with EtOAc and washed with sat. NaHCO3(aq) and brine (3×). The organic phase was dried over sodium sulphate and evaporated under vacuum. The residue was redissolved in DCM and evaporated onto silica. The silica was deposited onto a 25 g silica cartridge and the system eluted with 20% EtOAc/hexane, 40% EtOAc/hexane and 60% EtOAc/hexane. The product fractions were combined and evaporated to give tacky yellow solid. This solid was triturated with Et₂O/hexane to afford the title compound;
LC-MS: MS Rt 1.37 mins [M+H]+ 444.4 Method 2min-LowpHv01

Step 3: 1-((tert-Butyldimethylsilyl)oxy)-3-(1,3-dimethyl-2,4-dioxo-5-phenyl-3,4-dihydro-1H-pyrrolo[3,4-d]pyrimidin-6(2H)-yl)propan-2-yl methanesulfonate To a solution of 6-(3-(tert-butyldimethylsilyloxy)-2-hydroxypropyl)-1,3-dimethyl-5-phenyl-1H-pyrrolo[3,4-d]pyrimidine-2,4(3H,6H)-dione (step 2) (1 g, 2.25 mmol) in DCE (20 ml) was added triethylamine (1.57 ml, 11.27 mmol), DMAP (28 mg, 0.025 mmol) and methanesulfonyl chloride (0.89 ml, 11.3 mmol) at 0° C. and reaction stirred for 2 hours at RT. Solid K₂CO₃ was added to the reaction mixture and then it was diluted with water and extracted with DCM (3×20 ml). The organics were passed through a hydrophobic frit and concentrated in vacuo to yield the title compound as a brown oil which was used without further purification;
LC-MS: Rt 1.40 mins; MS m/z 522 [M+H]+; Method 2minLowpHv01

Step 4: S-(1-((tert-Butyldimethylsilyl)oxy)-3-(1,3-dimethyl-2,4-dioxo-5-phenyl-3,4-dihydro-1H-pyrrolo[3,4-d]pyrimidin-6(2H)-yl)propan-2-yl) ethanethioate 1-((tert-Butyldimethylsilyl)oxy)-3-(1,3-dimethyl-2,4-dioxo-5-phenyl-3,4-dihydro-1H-pyrrolo[3,4-d]pyrimidin-6 (2H)-yl)propan-2-yl methanesulfonate (step 3)(1.3 g, 2.63 mmol) in dry DMF (20 ml) was treated with potassium thioacetate (1.5 g, 13.1 mmol). The resulting solution stirred for 7 h at 70° C. and at RT for 3 days. The mixture was heated at 70° C. overnight and after cooling to RT, the mixture was partitioned between EtOAc (100 ml) and water (150 ml). The layers were separated and the aqueous was extracted with EtOAc (×3). The organics were combined, washed with water, brine (×3), passed through a hydrophobic frit and concentrated in vacuo to yield the title compound as a brown oil;
LCMS: Rt 1.52 mins; MS m/z 502 [M+H]+; Method 2min-LowpHv01;

Step 5: 6-(3-Hydroxy-2-mercaptopropyl)-1,3-dimethyl-5-phenyl-1H-pyrrolo[3,4-d]pyrimidine-2,4(3H,6H)-dione To a stirred solution of S-(1-((tert-butyldimethylsilyl) oxy)-3-(1,3-dimethyl-2,4-dioxo-5-phenyl-3,4-dihydro-1H-pyrrolo[3,4-d]pyrimidin-6(2H)-yl)propan-2-yl) ethanethioate (step 4) (1.62 g, 3.23 mmol) in EtOH (25 ml) was added sodium borohydride (0.61 g, 16.14 mmol) at 0° C. and the solution stirred overnight at RT. The reaction mixture was added slowly to TFA in water (20 ml, 50%). The resulting solid was removed by filtration and the filtrate was concentrated in vacuo to remove EtOH. The resulting mixture was diluted with water and extracted with DCM (×3). The combined organic extracts were passed through a hydrophobic frit and concentrated under reduced pressure to afford an oil. The oil was dissolved in a minimal volume of DCM and purified via ISCO column chromatography, 12 g, liquid load, 0-90% EtOAc in iso-hexane to afford the title compound;
LC-MS: Rt 0.90, 0.92 mins; MS m/z 346 [M+H]+; Method 2minLowpHv01;

Step 6: 10-(5-chlorofuran-2-yl)-8-(hydroxymethyl)-1,3-dimethyl-5-phenyl-7,8-dihydro-1H-pyrimido[4',5':3,4]pyrrolo[2,1-c][1,4]thiazine-2,4(3H,10H)-dione 6-(3-Hydroxy-2-mercaptopropyl)-1,3-dimethyl-5-phenyl-1H-pyrrolo[3,4-d]pyrimidine-2,4(3H,6H)-dione (step 5)(270 mg 0.78 mmol) was added to a microwave vial (2-5 mL) equipped with a stirrer bar. To the vial was added toluene (3 ml) followed by bismuth triflate (48.8 mg, 0.078 mmol) and 5-methylfuran-2-carbaldehyde (112 mg, 0.78 mmol). The vial was then sealed and heated to 100° C. in a microwave reactor for 30 min. The reaction mixture was reduced in vacuo and diluted with EtOAc. Water was added, the layers separated and the aqueous extracted with EtOAc. The organic extracts were combined, dried (MgSO₄), filtered and concentrated under reduced pressure to yield an oil. The oil was redissolved in a minimal volume of DCM and loaded onto silica. Purification by ISCO column chromatography, 24 g silica, eluting with 0-80% EtOAc in iso-hexane afford a diastereomeric mixture of the title compounds (Example 12.0);
LCMS: Rt 1.13 mins; MS m/z 458 [M+H]+; Method 2min-LowpHv01;

Chiral separation of the diastereomeric mixture (step 6) by Supercritical Fluid Chromatography was carried out using the following conditions to afford the compounds listed hereinafter:
Column: Chiralpak AD-H, 250×10 mm, 5 um@35 degC
Mobile phase: 30% Methanol/70% CO2
Flow: 10 ml/min
Detection: UV@220 nm
Instrument: Berger Minigram SFC1
Sample Concentration: 111 mg in 2 ml ethanol+1 ml THF (37 mg/ml)

Example 12a

Diastereoisomer 1 of 10-(5-chlorofuran-2-yl)-8-(hydroxymethyl)-1,3-dimethyl-5-phenyl-7,8-dihydro-1H-pyrimido [4',5':3,4]pyrrolo[2,1-c][1,4]thiazine-2,4(3H,10H)-dione
SFC Retention time=5.80 mins
LC-MS: Rt 1.12 mins; MS m/z 458 [M+H]+; Method 2minLowpHv01
1H NMR (400 MHz, CDCl3) δ 7.54-7.41 (5H, m); 6.15 (1H, d); 6.12 (1H, d); 5.78 (1H, s); 4.41 (1H, dd); 4.21 (1H, dd); 3.66 (3H, s); 3.47-3.36 (5H, m); 3.23-3.17 (1H, m).

Example 12b

Diastereoisomer 2 of 10-(5-chlorofuran-2-yl)-8-(hydroxymethyl)-1,3-dimethyl-5-phenyl-7,8-dihydro-1H-pyrimido [4',5':3,4]pyrrolo[2,1-c][1,4]thiazine-2,4(3H,10H)-dione
SFC Retention time=4.84 mins
LC-MS: Rt 1.11 mins; MS m/z 458 [M+H]+; Method 2minLowpHv01
1H NMR (400 MHz, CDCl3) δ 7.55-7.43 (5H, m); 6.14 (1H, d); 6.11 (1H, d); 5.79 (1H, s); 4.49 (1H, dd); 3.97 (1H, dd); 3.71 (2H, d); 3.67 (3H, s); 3.57-3.51 (1H, m); 3.37 (3H, s).
Also isolated were:
Diastereoisomer 3 of 10-(5-chlorofuran-2-yl)-8-(hydroxymethyl)-1,3-dimethyl-5-phenyl-7,8-dihydro-1H-pyrimido [4',5':3,4]pyrrolo[2,1-c][1,4]thiazine-2,4(3H,10H)-dione
SFC Retention time=3.98 mins
and Diastereoisomer 4 of 10-(5-chlorofuran-2-yl)-8-(hydroxymethyl)-1,3-dimethyl-5-phenyl-7,8-dihydro-1H-pyrimido[4,5':3,4]pyrrolo[2,1-c][1,4]thiazine-2,4(3H, 10H)-dione
SFC Retention time=5.80 mins

Example 12.1a, 12.1b, 12.1c and 12.1d (8R,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione, (8R,10S)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione, (8S,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione and (8S,10S)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione

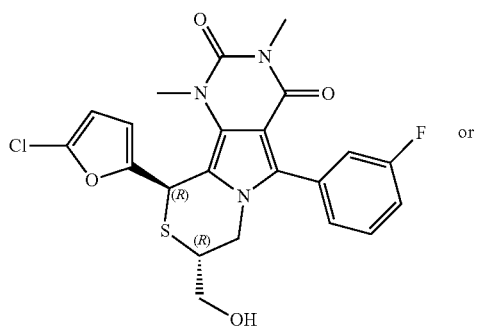

(8R,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione or

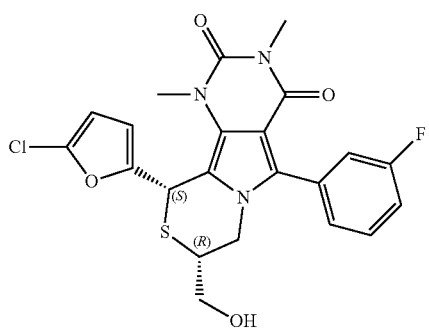

(8R,10S)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione -continued

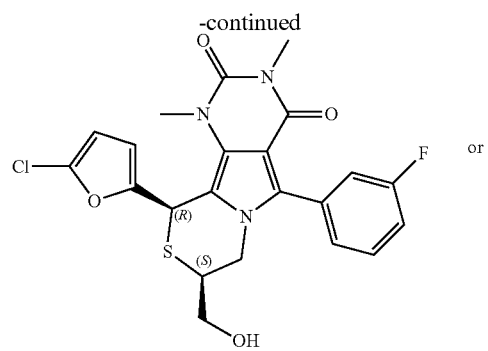

(8S,10R)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione or

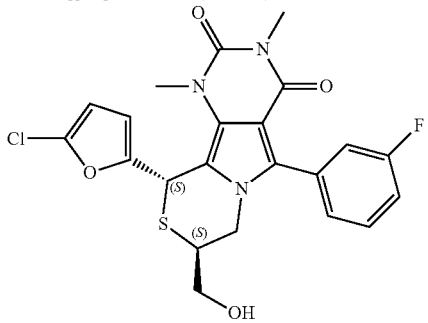

(8S,10S)-10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione

Step 1: (2,2-Dimethyl-1,3-dioxolan-4-yl)methyl trifluoromethanesulfonate

Trifluoromethylsulfonic anhydride (7.03 ml, 41.6 mmol) was added dropwise over 15 mins to a solution of solketal (4.70 ml, 37.8 mmol) and 2,6-lutidine (5.73 ml, 49.2 mmol) in DCM (126 mL) at 0° C. The mixture was stirred at 0° C. for 1 hour. The mixture was diluted with DCM (100 mL) and water (100 mL), the phases were separated and the aqueous phase extracted with DCM (3×50 mL). The combined organic extracts were dried over sodium sulfate and evaporated under vacuum to afford the title compound as a crude material which was used directly.

Step 2: 6-((2,2-Dimethyl-1,3-dioxolan-4-yl)methyl)-5-(3-fluorophenyl)-1,3-dimethyl-1H-pyrrolo[3,4-d]pyrimidine-2,4(3H,6H)-dione Sodium hydride (60% in mineral oil) (234 mg, 5.86 mmol) was added portionwise to a solution of 5-(3-fluorophenyl)-1,3-dimethyl-1H-pyrrolo[3,4-d]pyrimidine-2,4(3H,6H)-dione (Intermediate Nf) (1000 mg, 3.66 mmol) and dibenzo-18-crown-6 (132 mg, 0.366 mmol) in DMF (28.1 mL) at 0° C. The solution was warmed to room temperature and stirred for 20 minutes, then re-cooled to 0° C. (2,2-Dimethyl-1,3-dioxolan-4-yl)methyltrifluoromethane sulfonate (Intermediate Sb) (1547 mg, 5.86 mmol) was added dropwise over 5 minutes. The mixture was warmed to room temperature and stirred for 3 hours. The reaction was quenched with saturated NH$_4$Cl(aq) (10 mL) and extracted with DCM (3×30 mL). The combined organic extracts were dried over magnesium sulfate and evaporated under vacuum to afford the title compound as a red/brown amorphous solid.

LC-MS Rt 1.20 mins [M+H]+ 388.3 (Method 2minlowpHv03)

Step 3: 6-(2,3-Dihydroxypropyl)-5-(3-fluorophenyl)-1,3-dimethyl-1H-pyrrolo[3,4-d]pyrimidine-2,4(3H,6H)-dione HCl (2 M in diethyl ether) (92 ml, 185 mmol) was added dropwise to a solution of 6-((2,2-dimethyl-1,3-dioxolan-4-yl)methyl)-5-(3-fluorophenyl)-1,3-dimethyl-1H-pyrrolo[3,4-d]pyrimidine-2,4(3H,6H)-dione (7.15 g, 18.46 mmol) and water (6.65 g, 369 mmol) in acetonitrile (35.1 mL). The mixture was stirred at room temperature for 30 minutes. Evaporation of the reaction mixture under vacuum afforded the title compound.

LCMS Rt 0.85 mins [M+H]+ 348.3 (Method 2minlowpHV03)

Step 4: 6-(3-((tert-Butyldimethylsilyl)oxy)-2-hydroxypropyl)-5-(3-fluorophenyl)-1,3-dimethyl-1H-pyrrolo[3,4-d]pyrimidine-2,4(3H,6H)-dione Tert-butyldimethylsilyl chloride (0.695 g, 4.61 mmol) was added to a solution of 6-(2,3-dihydroxypropyl)-5-(3-fluorophenyl)-1,3-dimethyl-1H-pyrrolo[3,4-d]pyrimidine-2,4(3H,6H)-dione (1.82 g, 4.19 mmol), imidazole (0.571 g, 8.38 mmol) and DMAP (0.512 g, 4.19 mmol) in DMF (13.97 mL). The mixture was stirred at room temperature for 3 hours, then diluted with 10% aqueous citric acid solution (15 mL) and extracted with DCM (3×30 mL). The combined organic extracts were dried over magnesium sulfate and evaporated under vacuum. Purification by chromatography on silica, eluting with 0-50% EtOAc/hexane, afforded the title compound.

LC-MS Rt 1.52 mins [M+H]+ 462.4 (Method 2minlowpHv03)

Step 5: 1-((tert-Butyldimethylsilyl)oxy)-3-(5-(3-fluorophenyl)-1,3-dimethyl-2,4-dioxo-3,4-dihydro-1H-pyrrolo[3,4-d]pyrimidin-6(2H)-yl)propan-2-yl methanesulfonate Methanesulfonic anhydride (0.679 g, 3.90 mmol) in 1,2-dichloroethane (3.0 mL) was added dropwise to a solution of DMAP (0.016 g, 0.130 mmol), triethylamine (0.544 ml, 3.90 mmol) and 6-(3-((tert-butyldimethylsilyl)oxy)-2-hydroxypropyl)-5-(3-fluorophenyl)-1,3-dimethyl-1H-pyrrolo[3,4-d]pyrimidine-2,4(3H,6H)-dione (0.6 g, 1.300 mmol) in 1,2-dichloroethane (10 mL) at 0° C. The mixture was warmed to room temperature and stirred for 2 hours, then diluted with water (10 mL). The phases were separated and the aqueous phase was extracted with DCM (3×10 mL). The combined organic extracts were dried over magnesium sulfate and evaporated under vacuum to afford the title compound.

LC-MS Rt 1.52 mins [M+H]+ 540.6 (Method 2minlowpHv03)

Step 6: (1-((tert-Butyldimethylsilyl)oxy)-3-(5-(3-fluorophenyl)-1,3-dimethyl-2,4-dioxo-3,4-dihydro-1H-pyrrolo[3,4-d]pyrimidin-6(2H)-yl)propan-2-yl) ethanethioate A solution of 1-((tert-butyldimethylsilyl)oxy)-3-(5-(3-fluorophenyl)-1,3-dimethyl-2,4-dioxo-3,4-dihydro-1H-pyrrolo[3,4-d]pyrimidin-6(2H)-yl)propan-2-yl methanesulfonate (705 mg, 1.241 mmol) and potassium thioacetate (709 mg, 6.20 mmol) in DMF (4964 µL) was heated at 70° C. for 4 hours. Further portions of potassium thioacetate (709 mg, 6.20 mmol) were added as necessary to allow the reaction to run to completion. The reaction mixture was cooled to room temperature, diluted with water (15 mL) and extracted with DCM (3×20 mL). The combined organic extracts were dried over magnesium sulfate and evaporated under vacuum. Purification by chromatography on silica, eluting with 0-50% EtOAc/hexane, afforded the title compound.

LC-MS Rt 1.73 mins [M+H]+ 520.4 (2minlowpHv03)

Step 7: 6-(3-((tert-Butyldimethylsilyl)oxy)-2-mercaptopropyl)-5-(3-fluorophenyl)-1,3-dimethyl-1H-pyrrolo[3,4-d]pyrimidine-2,4(3H,6H)-dione Sodium borohydride (74.3 mg, 1.963 mmol) was added to a solution of (1-((tert-butyl dimethylsilyl)oxy)-3-(5-(3-fluorophenyl)-1,3-dimethyl-2,4-dioxo-3,4-dihydro-1H-pyrrolo[3,4-d]pyrimidin-6(2H)-yl)propan-2-yl) ethanethioate (340 mg, 0.654 mmol) in ethanol (6542 µL) at 0° C. The mixture was warmed to room temperature and stirred for 3 hours. The reaction was quenched at 0° C. with 1M HCl(aq), stirred for 10 mins, then extracted with DCM (3×10 mL). The combined organic extracts were dried over magnesium sulfate and evaporated under vacuum to afford the title compound.

LC-MS Rt 1.68 mins [M+H]+ 478.3 (Method 2minlowpHv03)

Step 8: 10-(5-Chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione Trifluoroacetic acid (161 µl, 2.094 mmol) was added to a solution of bismuth triflate (41.2 mg, 0.063 mmol), 5-chlorofuran-2-carbaldehyde (30.1 mg, 0.230 mmol) and 6-(3-((tert-butyldimethylsilyl)oxy)-2-mercaptopropyl)-5-(3-fluorophenyl)-1,3-dimethyl-1H-pyrrolo[3,4-d]pyrimidine-2,4(3H,6H)-dione (100 mg, 0.209 mmol) in toluene (2094 µL). The mixture was stirred at room temperature for 1 hour. The reaction mixture was diluted with DCM (10 mL) and 1M NaOH(aq) (10 mL). The phases were separated and the aqueous phase was extracted with DCM (3×10 mL). The combined organic extracts were dried over magnesium sulfate and evaporated under vacuum. Purification by chromatography on silica, eluting with 0-50% EtOAc/hexane, afforded the title compound as a mixture of diastereomers.

LC-MS Rt 1.26 mins [M+H]+ 476.1 (Method 2minlowpHv03)

The diastereomeric mixture was separated by SFC chromatographic resolution under the following conditions to afford the listed single diastereomer compounds.

Separation Conditions
Column: Chiralcel AD-H 250×10 mm, 5 um@35 degC
Mobile phase: 40% Methanol+0.1% v/v DEA/60% CO2
Flow: 10 ml/min
Detection: UV@220 nm

Example 12.1a

Diastereomer 1 of 10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H, 10H)-dione, Rt=4.41 mins 1H NMR (400 MHz, CD3OD): 7.55-7.46 (1H, m), 7.32-7.20 (3H, m), 6.25-6.21 (2H, m), 6.04 (1H, s), 4.40-4.32 (1H, m), 4.25-4.18 (1H, m), 3.62 (3H, s), 3.47-3.21 (6H, m), 3.20-3.10 (1H, m)

LC-MS Rt 1.26 mins [M+H]⁺ 476.1 (Method 2minlowpHv03)

Example 12.1b

Diastereomer 2 of 10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione, Rt=2.53 mins was further purified by SFC under the following conditions;

Column: 2 coupled Chiralpak IC 250×10 mm, 5 um

Mobile phase: 30% Methanol+0.1% v/v DEA/70% CO2

Flow: 10 ml/min

Detection: UV@220 nm

Rt=23.63 mins

1H NMR (400 MHz, CD3OD): δ 7.57-7.49 (1H, m), 7.30-7.22 (3H, m), 6.34 (1H, d), 6.25 (1H, d), 6.05 (1H, s), 4.58 (1H, dd), 3.89-3.80 (1H, m), 3.70-3.30 (10H, m).

LC-MS Rt 1.29 mins [M+H]⁺ 476.2 (2minlowpHV03)

Example 12.1c

Diastereomer 3 of 10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione, Rt=3.56 mins 1H NMR (400 MHz, CD3OD). 7.55-7.46 (1H, m), 7.32-7.20 (3H, m), 6.25-6.21 (2H, m), 6.04 (1H, s), 4.40-4.32 (1H, m), 4.25-4.18 (1H, m), 3.62 (3H, s), 3.47-3.21 (6H, m), 3.20-3.10 (1H, m)

LC-MS Rt 1.31 mins [M+H]⁺ 476.2 (2minlowpHv03)

Example 12.1 d

Diastereomer 4 of 10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione, Rt=4.43 mins 1H NMR (400 MHz, CD3OD): δ 7.57-7.49 (1H, m), 7.30-7.22 (3H, m), 6.34 (1H, d), 6.25 (1H, d), 6.05 (1H, s), 4.58 (1H, dd), 3.89-3.80 (1H, m), 3.70-3.30 (10H, m)

LC-MS Rt 1.29 mins [M+H]⁺ 476.2 (Method 2minlowpHv03)

The following listed examples were prepared in a similar manner to Example 12a-12d by replacing 5-(3-fluorophenyl)-1,3-dimethyl-1H-pyrrolo[3,4-d]pyrimidine-2,4(3H,6H)-dione (Intermediate Nf) in step 2 (except Example 12.4a-12.4c) with 3-(1,3-dimethyl-2,4-dioxo-2,3,4,6-tetrahydro-1H-pyrrolo[3,4-d]pyrimidin-5-yl)benzonitrile (Example 9 Step 4) and with the appropriate aldehyde (either commercially available or Intermediate described herein) in Step 8.

The diastereomeric mixtures were separated by SFC chromatographic resolution under the listed conditions to afford the title compounds.

Example 12.2a-12.2c 3-((8R,10R)-10-(5-Chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8S,10R)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8S,10S)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8R,10S)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile

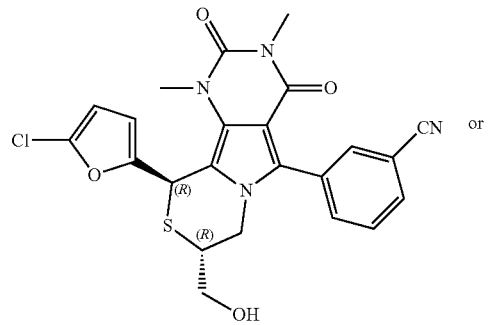

3-((8R,10R)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazine-5-yl)benzonitrile

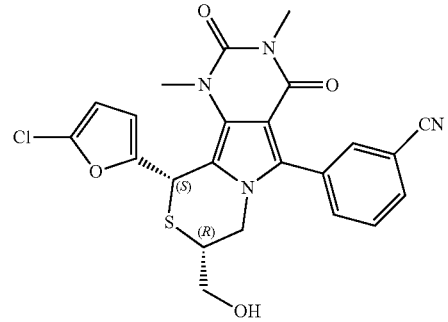

3-((8R,10S)-10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazine-5-yl)benzonitrile -continued

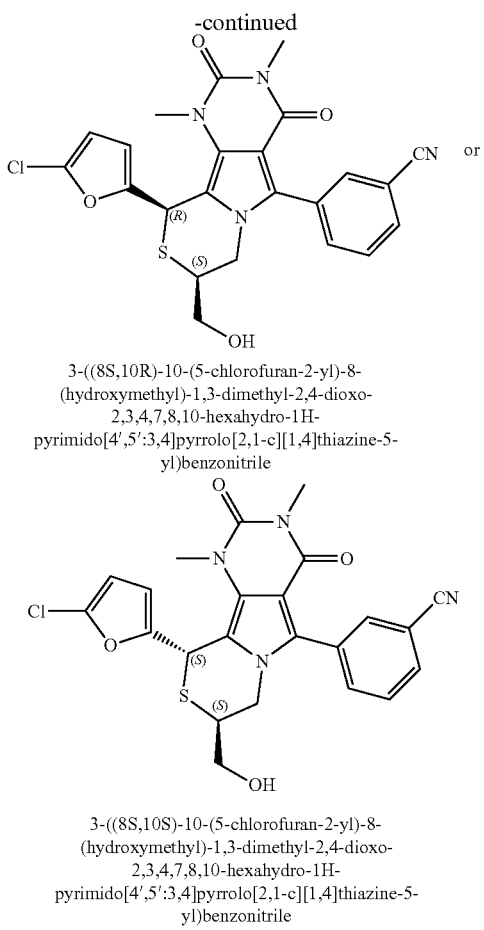

3-((8S,10R)-10-(5-chlorofuran-2-yl)-8-
(hydroxymethyl)-1,3-dimethyl-2,4-dioxo-
2,3,4,7,8,10-hexahydro-1H-
pyrimido[4',5':3,4]pyrrolo[2,1-c][1,4]thiazine-5-
yl)benzonitrile 3-((8S,10S)-10-(5-chlorofuran-2-yl)-8-
(hydroxymethyl)-1,3-dimethyl-2,4-dioxo-
2,3,4,7,8,10-hexahydro-1H-
pyrimido[4',5':3,4]pyrrolo[2,1-c][1,4]thiazine-5-
yl)benzonitrile Separation Conditions:
Column: Chiralpak AD-H, 250×10 mm, 5 um@35° C.
Mobile phase: 35% Methanol+0.1% v/v DEA/65% 002
Flow: 10 ml/min
Detection: UV@220 nm Example 12.2a Diastereomer 1 of 3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile was further purified under the following conditions:
Column: 2× Phenomenex LUX-C2 coupled, 250×10 mm, 5 um@35° C.
Mobile phase: 50% Methanol+0.1% v/v DEA/50% CO2
Flow: 10 ml/min
Detection: UV@220 nm
Rt=27.67 mins
1H NMR (400 MHz, CDCl3): δ 7.82-7.73 (3H, m), 7.65-7.60 (1H, m), 6.15 (2H, app. d), 5.79 (1H, s), 4.39 (1H, dd), 4.22-4.16 (1H, m), 3.97-3.90 (1H, m), 3.68 (3H, s), 3.55-3.45 (1H, m), 3.37 (3H, s), 3.22-3.13 (1H, m), 3.10-3.0 (1H, m)
LC-MS Rt 1.27 mins [M+H]⁺ 483.3 (Method 2minlowpHv03)

Example 12.2b

Diastereomer 2 of 3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile
Rt=3.04 mins
1H NMR (400 MHz, CDCl3): 7.65-7.60 (1H, m), 6.15 (2H, app. d), 5.79 (1H, s), 4.39 (1H, dd), 4.22-4.16 (1H, m), 3.97-3.90 (1H, m), 3.68 (3H, s), 3.55-3.45 (1H, m), 3.37 (3H, s), 3.22-3.13 (1H, m), 3.10-3.0 (1H, m).
LC-MS Rt 1.25 mins [M+H]⁺ 483.3 (Method 2minlowpHv03)

Example 12.2c

Diastereomer 3 of 3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile, Rt=6.47 mins
1H NMR (400 MHz, CDCl3): δ 7.80-7.70 (3H, m), 7.65-7.60 (1H, m), 6.17-6.14 (2H, m), 5.79 (1H, s), 4.41-4.36 (1H, m), 4.05-3.97 (1H, m), 3.78-3.70 (2H, m), 3.67 (3H, s), 3.57-3.47 (1H, m), 3.41-3.31 (4H, m).
LC-MS Rt 1.27 mins [M+H]⁺ 483.2 (2minlowpHv03)

Example 12.3a-12.3d 3-((8R,10R)-10-(4-Chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8R,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8S,10R)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile or 3-((8S,10S)-10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile

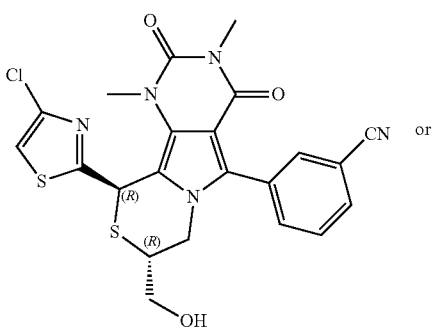

3-((8R,10R)-10-(5-chlorothiazol-2-yl)-8-
(hydroxymethyl)-1,3-dimethyl-2,4-dioxo-
2,3,4,7,8,10-hexahydro-1H-
pyrimido[4',5':3,4]pyrrolo[2,1-c][1,4]thiazine-5-
yl)benzonitrile

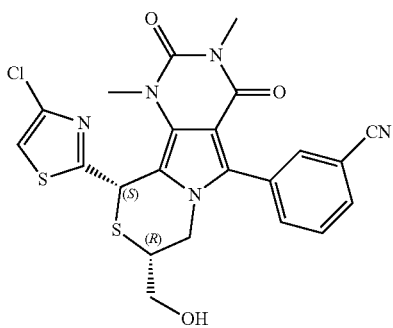

3-((8R,10S)-10-(5-chlorothiaziol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazine-5-yl)benzonitrile

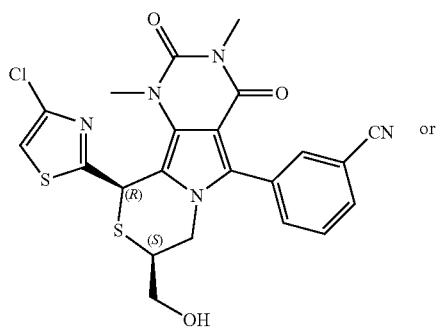

3-((8S,10R)-10-(5-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazine-5-yl)benzonitrile

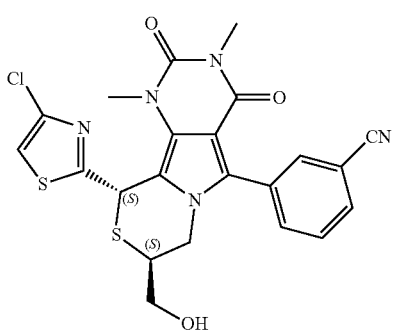

3-((8S,10S)-10-(5-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazine-5-yl)benzonitrile Separation Conditions:
Column: Chiralpak AD-H, 250×10 mm, 5 um@34.6° C.
Mobile phase: 22% Methanol+0.1% v/v DEA/78% 002
Flow: 10 ml/min
Detection: UV@220 nm

Example 12.3a

Diastereomer 1 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile, Rt=16.37 mins 1H NMR (400 MHz, DMSO-d6): δ7.99 (1H, s), 7.94-7.90 (1H, m), 7.82-7.77 (2H, m), 7.68-7.63 (1H, m), 6.47 (1H, s), 5.02 (1H, dd), 4.27 (1H, dd), 3.98-3.90 (1H, m), 3.59 (3H, s), 3.50-3.43 (1H, m), 3.18 (3H, s), 3.0-2.90 (1H, m)

LC-MS Rt 1.17 mins [M+H]$^+$ 500.2 (Method 2minlowpHv03)

Example 12.3b

Diastereomer 2 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile, Rt=11.37 mins 1H NMR (400 MHz, DMSO-d6): δ 8.0-7.96 (1H, m), 7.94-7.90 (1H, m), 7.83-7.76 (2H, m), 7.71-7.65 (1H, m), 6.47 (1H, s), 5.23-5.17 (1H, m), 4.43-4.36 (1H, m), 3.64 (3H, s), 3.63-3.53 (3H, m), 3.19 (3H, s)

LC-MS Rt 1.14 mins [M+H]$^+$ 500.5 (Method 2minlowpHv03)

Example 12.3c

Diastereomer 3 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile, Rt=14.48 mins 1H NMR (400 MHz, DMSO-d6): δ 8.0-7.96 (1H, m), 7.94-7.90 (1H, m), 7.83-7.76 (2H, m), 7.71-7.65 (1H, m), 6.47 (1H, s), 5.23-5.17 (1H, m), 4.43-4.36 (1H, m), 3.64 (3H, s), 3.63-3.53 (3H, m), 3.19 (3H, s)

LC-MS Rt 1.16 mins [M+H]$^+$ 500.2 (2minlowpHv03)

Example 12.3d

Diastereomer 4 of 3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile, Rt=14.48 mins LC-MS Rt 1.17 mins [M+H]$^+$ 500.2 (Method 2minlowpHv03)

1H NMR (400 MHz, DMSO-d6): δ 7.99 (1H, s), 7.94-7.90 (1H, m), 7.82-7.77 (2H, m), 7.68-7.63 (1H, m), 6.47 (1H, s), 5.02 (1H, dd), 4.27 (1H, dd), 3.98-3.90 (1H, m), 3.59 (3H, s), 3.50-3.43 (1H, m), 3.18 (3H, s), 3.0-2.90 (1H, m)

Example 12.4a-12.4c (8R,10R)-10-(4-Chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione or (8R,10S)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione or (8S,10R)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione or (8S,10S)-10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione

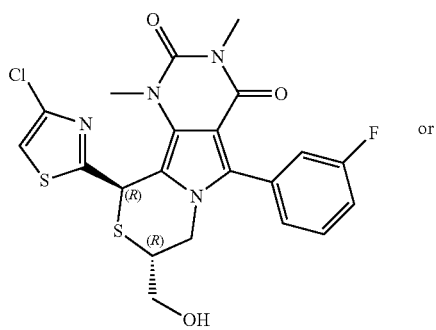

(8R,10R)-10-(5-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,3(3H,10H)-dione

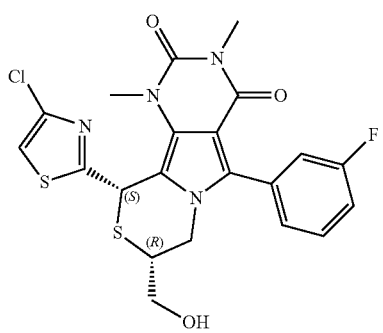

(8R,10S)-10-(5-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,3(3H,10H)-dione

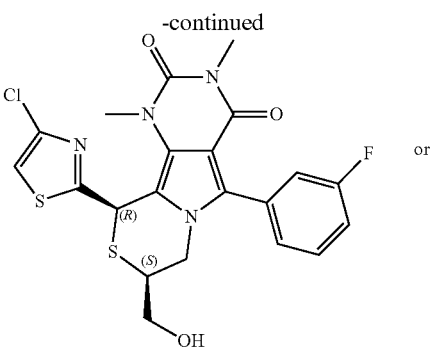

(8S,10R)-10-(5-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,3(3H,10H)-dione

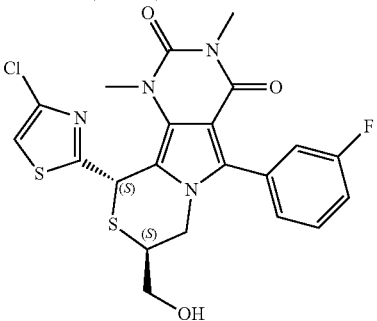

(8S,10S)-10-(5-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,3(3H,10H)-dione Separation Conditions:
Column: Chiralpak IC 250×10 mm, 5 um
Mobile phase: 45% Isopropanol+0.1% v/v DEA/55% CO2
Flow: 10 ml/min
Detection: UV@220 nm Example 12.4a Diastereomer 1 of 10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione Rt=6.99 mins was further purified under the following conditions:
Column: Chiralpak AD-H 250×10 mm, 5 um
Mobile phase: 30% Methanol+0.1% v/v DEA/70% C02
Flow: 10 ml/min
Detection: UV@220 nm
Rt=12.88 mins
1H NMR (400 MHz, DMSO-d6): δ 7.78 (1H, s), 7.52-7.44 (1H, m), 7.37-7.26 (3H, m), 6.47 (1H, s), 5.05-4.99 (1H, m), 4.32-4.25 (1H, m), 3.96-3.91 (1H, m), 3.58 (3H, s), 3.50-3.43 (1H, m), 3.17 (3H, s), 3.04-2.95 (1H, m)
LC-MS Rt 1.19 mins [M+H]+ 493.2 (Method 2minlowpHv03)

Example 12.4b

Diastereomer 2 of 10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione Rt=13.85 mins
LC-MS Rt 1.20 mins [M+H]+ 493.1 (2minlowpHv03)
1H NMR (400 MHz, DMSO-d6): δ 7.78 (1H, s), 7.56-7.47 (1H, m), 7.38-7.26 (3H, m), 6.46 (1H, s), 5.23-5.17 (1H, m), 4.49-4.42 (1H, m), 3.63 (3H, s), 3.61-3.48 (3H, m), 3.18 (3H, m)

Example 12.4c

Diastereomer 3 of 10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione
Rt=8.69 mins
1H NMR (400 MHz, DMSO-d6): δ 7.78 (1H, s), 7.52-7.44 (1H, m), 7.37-7.26 (3H, m), 6.47 (1H, s), 5.05-4.99 (1H, m), 4.32-4.25 (1H, m), 3.96-3.91 (1H, m), 3.58 (3H, s), 3.50-3.43 (1H, m), 3.17 (3H, s), 3.04-2.95 (1H, m)
LC-MS Rt 1.20 mins [M+H]+ 493.1 (Method 2minlowpHv03)

Example 13

3-(10-(4-Chlorothiazol-2-yl)-1,3-dimethyl-2,4-dioxo-1,2,3,4,7,8,9,10-octahydropyrimido[4,5-a]indolizin-5-yl)benzonitrile

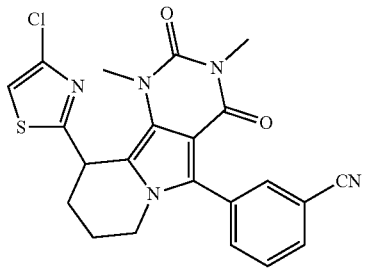 [SMILES: Cn1c(=O)c2c(-c3cccc(C#N)c3)n3c(c2n(C)c1=O)C(c1nc(Cl)cs1)CCC3]

Step 1: Lithium 4-(5-(3-cyanophenyl)-1,3-dimethyl-2,4-dioxo-3,4-dihydro-1H-pyrrolo[3,4-d]pyrimidin-6(2H)-yl)butanoate Lithium hydroxide monohydrate (1.158 g, 27.6 mmol) was added to a suspension of methyl 4-(5-(3-cyanophenyl)-1,3-dimethyl-2,4-dioxo-3,4-dihydro-1H-pyrrolo[3,4-d]pyrimidin-6(2H)-yl)butanoate (Example 9 Step 5) (10 g, 26.3 mmol) in THF (99 ml) and water (32.9 ml). The mixture was stirred for 2 hours and evaporated under vacuum to afford the title compound.
LC-MS Rt 0.94 mins; [M-Li+H]+ 367.4; (Method 2minlowpHv03)

Step 2: 4-(5-(3-Cyanophenyl)-1,3-dimethyl-2,4-dioxo-3,4-dihydro-1H-pyrrolo[3,4-d]pyrimidin-6(2H)-yl)-N-methoxy-N-methylbutanamide T3P® (31.3 ml, 52.6 mmol) was added dropwise to a solution of N,O-dimethyllhydroxylamine hydrochloride (2.70 g, 27.6 mmol), DIPEA (18.39 ml, 105 mmol) and lithium 4-(5-(3-cyanophenyl)-1,3-dimethyl-2,4-dioxo-3,4-dihydro-1H-pyrrolo[3,4-d]pyrimidin-6(2H)-yl)butanoate (9.8 g, 26.3 mmol) in DMF (263 mL). The mixture was stirred at room temperature for 40 minutes and quenched with water (250 mL). The resultant precipitate was collected by filtration under reduced pressure to afford the title compound.
LC-MS Rt 1.03 mins [M+H]+ 410.5 (2minlowpHv03)

Step 3: 3-(6-(4-(4-Chlorothiazol-2-yl)-4-oxobutyl)-1,3-dimethyl-2,4-dioxo-2,3,4,6-tetrahydro-1H-pyrrolo[3,4-d]pyrimidin-5-yl)benzonitrile Isopropylmagnesium chloride lithium chloride complex solution (1.3 M in THF, 2.067 ml, 2.69 mmol) was added dropwise to a solution of 4-(5-(3-cyanophenyl)-1,3-dimethyl-2,4-dioxo-3,4-dihydro-1H-pyrrolo[3,4-d]pyrimidin-6(2H)-yl)-N-methoxy-N-methylbutanamide (1 g, 2.442 mmol) and 2-bromo-4-chlorothiazole (Intermediate Q, step 2) (0.533 g, 2.69 mmol) in THF (24.42 mL) at 0° C. The mixture was stirred at 0° C. for 30 minutes. A further portion of isopropylmagnesium chloride lithium chloride complex solution (1.3 M in THF, 2.067 ml, 2.69 mmol) was added at 0° C. and the mixture was stirred for a further 30 minutes at 0° C. The reaction was quenched with saturated NH4Cl(aq) (20 mL) and extracted with DCM (3×20 mL). The combined organic extracts were washed with saturated NaHCO3(aq) (10 mL), dried over magnesium sulfate and evaporated under reduced pressure. Trituration with methanol afforded the title compound.
LC-MS Rt 1.26 mins [M+H]+ 468.4 2minlowpHv03.

Step 4: 3-(6-(4-(4-Chlorothiazol-2-yl)-4-hydroxybutyl)-1,3-dimethyl-2,4-dioxo-2,3,4,6-tetrahydro-1H-pyrrolo[3,4-d]pyrimidin-5-yl)benzonitrile Sodium borohydride (0.606 g, 16.03 mmol) was added portionwise to a suspension of 3-(6-(4-(4-chlorothiazol-2-yl)-4-oxobutyl)-1,3-dimethyl-2,4-dioxo-2,3,4,6-tetrahydro-1H-pyrrolo[3,4-d]pyrimidin-5-yl)benzonitrile (2.5 g, 5.34 mmol) in ethanol (53.4 mL) at 0° C. The reaction mixture was stirred for 15 minutes at 0° C., the quenched with water (25 mL) and extracted with DCM (3×50 mL). The combined organic fractions were dried over magnesium sulfate and evaporated under reduced pressure to afford the title compound.
LC-MS Rt 1.15 mins [M+H]+ 470.4 (2minlowpHv03).

Step 5: 3-(10-(4-Chlorothiazol-2-yl)-1,3-dimethyl-2,4-dioxo-1,2,3,4,7,8,9,10-octahydropyrimido[4,5-a]indolizin-5-yl)benzonitrile Trifluoromethanesulfonic anhydride (3.95 ml, 23.41 mmol) was added dropwise to a solution of 3-(6-(4-(4-chlorothiazol-2-yl)-4-hydroxybutyl)-1,3-dimethyl-2,4-dioxo-2,3,4,6-tetrahydro-1H-pyrrolo[3,4-d]pyrimidin-5-yl)benzonitrile (5 g, 10.64 mmol) and triethylamine (3.56 ml, 25.5 mmol) in DCM (213 mL) at −78° C. The mixture was stirred for 1 min at −78° C. The reaction was quenched with saturated aqueous NaHCO3(aq) (100 mL) and extracted with DCM (3×100 mL). The combined organic extracts were dried over magnesium sulfate and evaporated under reduced pressure to afford crude racemic 3-(10-(4-chlorothiazol-2-yl)-1,3-dimethyl-2,4-dioxo-1,2,3,4,7,8,9,10-octahydropyrimido[4,5-a]indolizin-5-yl)benzonitrile.
1H NMR (400 MHz, CDCl3) δ 7.80-7.72 (3H, mult), 7.63 (1H, t), 7.05 (1H, s), 5.17 (1H, mult), 4.05 (1H, mult), 3.79 (1H, mult), 3.44 (6H, br s), 2.63 (1H, mult), 2.34 (1H, mult), 1.98-1.84 (2H, mult).
LC-MS Rt 1.15 mins [M+H]+ 452.4 (Cl isotopes)(Method 2minLowHv01)

Example 13a (R)-3-(10-(4-chlorothiazol-2-yl)-1,3-dimethyl-2,4-dioxo-1,2,3,4,7,8,9,10-octahydropyrimido[4,5-a]indolizin-5-yl)benzonitrile

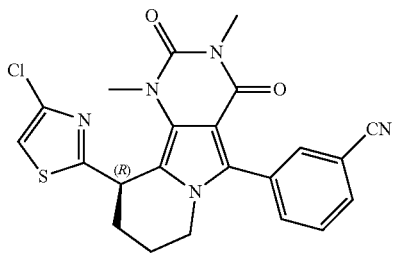

Column: Chiralcel OJ-H 250×10 mm, 5 um@35 C
Mobile phase: 40% Methanol/60% CO2
Flow: 10 ml/min
Detection: UV@220 nm
Enantiomer (R)-3-(10-(4-chlorothiazol-2-yl)-1,3-dimethyl-2,4-dioxo-1,2,3,4,7,8,9,10-octahydropyrimido[4,5-a]indolizin-5-yl)benzonitrile Rt=5.48 mins
NMR (400 MHz, DMSO-d6) δ 8.00 (1H, s), 7.93 (1H, d), 7.84 (1H, d), 7.68 (1H, t), 7.65 (1H, s), 5.31 (1H, mult), 3.98 (1H, mult), 3.90 (1H, mult), 3.31 (3H, s), 3.16 (3H, s), 2.36 (1H, mult), 2.26 (1H, mult), 1.84 (1H, mult), 1.68 (1H, mult).
LC-MS Rt 1.28 mins [M+H]+ 452.5 (Method 2minLowpHv03) The other enantiomer (S) was isolated at Rt=4.54 mins The compounds of the following examples were prepared by a similar method to that of Example 13 and 13a from the appropriate starting material (prepared by an analogous method to methyl 4-(5-(3-cyanophenyl)-1,3-dimethyl-2,4-dioxo-3,4-dihydro-1H-pyrrolo[3,4-d]pyrimidin-6(2H)-yl) butanoate (Example 9 Step 5) using the appropriate halo compound in Step 3) and using the appropriate halo compound in step 3). The racemate were resolved by SFC chromatographic according the conditions described.

Example 13.1

10-(4-Chlorothiazol-2-yl)-5-(4-(hydroxymethyl) thiazol-2-yl)-1,3-dimethyl-7,8,9,10-tetrahydropyrimido[4,5-a]indolizine-2,4(1H,3H)-dione

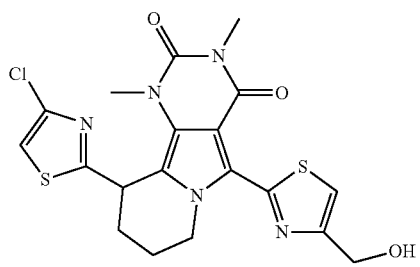 [SMILES: Cn1c(=O)c2c(-c3nc(CO)cs3)n3c(c2n(C)c1=O)C(c1nc(Cl)cs1)CCC3]

1H NMR (400 MHz, DMSO-d6) δ 7.72 (1H, s), 7.71 (1H, s), 5.50-5.38 (2H, m), 4.71 (2H, s), 4.64 (1H, d), 4.05 (1H, td), 3.38 (3H, s), 3.27 (3H, s), 2.44-2.27 (2H, m), 1.95 (1H, d), 1.76 (1H, m).
LC-MS Rt 1.02 mins [M+H]+ 464.4/466.4 (Method 2min-LowpHv03).

Example 13.1a (R)-10-(4-chlorothiazol-2-yl)-5-(4-(hydroxymethyl) thiazol-2-yl)-1,3-dimethyl-7,8,9,10-tetrahydropyrimido[4,5-a]indolizine-2,4(1H,3H)-dione or (S)-10-(4-chlorothiazol-2-yl)-5-(4-(hydroxymethyl) thiazol-2-yl)-1,3-dimethyl-7,8,9,10-tetrahydropyrimido[4,5-a]indolizine-2,4(1H,3H)-dione

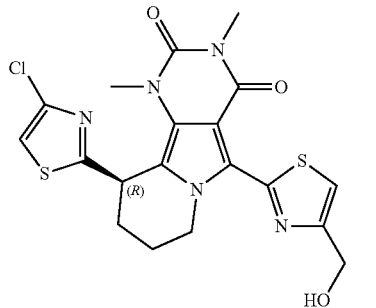 or (R)-10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione

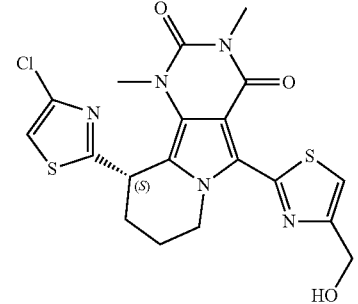

(S)-10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione Column: Phenomenex LUX-C4, 250×10 mm, 5 um@35 degC
Mobile phase: 50% Methanol/50% CO2
Flow: 10 ml/min
Detection: UV@220 nm

Example 13.1a

Enantiomer 1 of 10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione: Rt=3.25 mins
1H NMR (400 MHz, DMSO-d6) δ 7.66 (1H, s), 7.65 (1H, s), 5.39 (1H, t), 5.36 (1H, m), 4.65 (2H, d), 4.58 (1H, m), 3.99 (1H, td), 3.32 (3H, s), 3.21 (3H, s), 2.38-2.21 (2H, m), 1.89 (1H, s), 1.69 (1H, obs q).
LC-MS Rt 1.06 mins [M+H]+ 464.3/466.3 (Method 2min-LowpHv03
The second enantiomer was isolated at Rt=4.20 mins

Example 13.2

1,3-Dimethyl-5,10-bis(4-methylthiazol-2-yl)-7,8,9,10-tetrahydropyrimido[4,5-a]indolizine-2,4(1H,3H)-dione

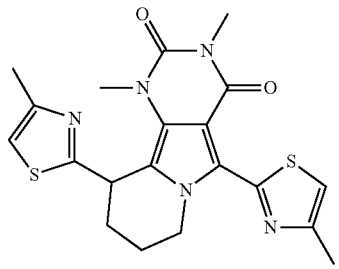 [SMILES: Cc1csc(-c2c3c(=O)n(C)c(=O)n(C)c3c3n2CCCC3c2nc(C)cs2)n1]

1H NMR (400 MHz, CDCl3) δ 7.02 (1H, s), 6.69 (1H, s), 5.04 (1H, mult), 4.60 (1H, mult), 4.01 (1H, mult), 3.32 (6H, s), 2.45 (3H, s), 2.37 (3H, s), 2.32 (1H, mult), 2.21 (1H, mult), 1.86 (2H, mult).

LC-MS Rt 1.23 mins [M+H]$^+$ 428.3 (Method 2minLowpHv03)

Example 13.3

10-(4-Chlorothiazol-2-yl)-1,3-dimethyl-5-(4-methylthiazol-2-yl)-7,8,9,10-tetrahydropyrimido[4,5-a]indolizine-2,4(1H,3H)-dione

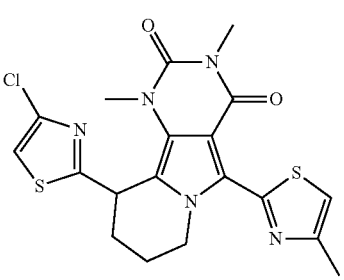 [SMILES: Cc1csc(-c2c3c(=O)n(C)c(=O)n(C)c3c3n2CCCC3c2nc(Cl)cs2)n1]

1H NMR (400 MHz, CDCl3) δ 7.31-7.26 (5H, mult), 7.20 (1H, s), 7.04 (1H, s), 5.15 (1H, mult), 4.67 (1H, mult), 4.24 (1H, mult), 3.43 (3H, s), 3.42 (3H, s), 2.60 (3H, s), 2.59 (1H, mult), 2.34 (1H, mult), 2.04-1.89 (2H, mult).

LC-MS Rt 1.30 mins; [M+H]$^+$ 433.1 (Method 2minLowpHv03).

Example 13.3a (R)-10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione or (S)-10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione

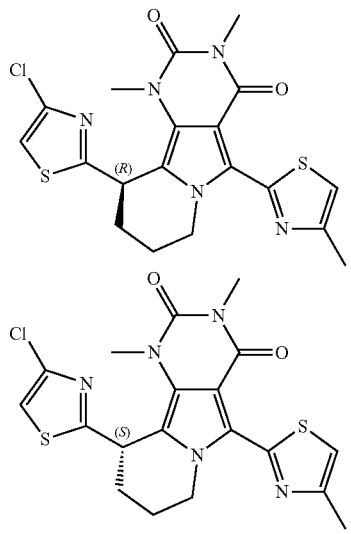

Column: Chiralpak AD-H 250×10 mm, 5 um@35 degC
Mobile phase: 45% Methanol+0.1% v/v DEA/55% CO2
Flow: 10 ml/min
Detection: 220 nm

Example 13.3a

Enantiomer 1 of 10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione Rt=4.34 mins 1H NMR (400 MHz, CDCl3) δ 7.12 (1H, s), 7.03 (1H, s), 5.13 (1H, dd), 4.71 (1H, mult), 4.08 (1H, mult), 3.42 (3H, s), 3.41 (3H, s), 2.61 (1H, mult), 2.54 (3H, s), 2.31 (1H, mult), 2.02-1.82 (2H, mult)

LC-MS Rt 1.27 mins [M+H]$^+$ 448.1 (Method 2minLowpHv03).

The second enantiomer was isolated at Rt=6.38 mins

Example 13.4

10-(4-Chlorothiazol-2-yl)-1,3-dimethyl-5-(2-methylthiazol-4-yl)-7,8,9,10-tetrahydropyrimido[4,5-a]indolizine-2,4(1H,3H)-dione

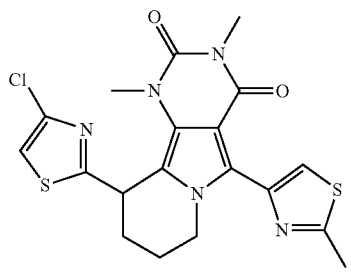 [SMILES: Cc1nc(-c2c3c(=O)n(C)c(=O)n(C)c3c3n2CCCC3c2nc(Cl)cs2)cs1]

1H NMR (400 MHz, DMSO-d6) δ 7.90 (1H, s), 7.63 (1H, s), 5.30 (1H, m), 4.04 (1H, d), 3.87 (1H, td), 3.31 (3H, s), 3.19 (3H, s), 2.73 (3H, s), 2.36 (1H, d), 2.25 (1H, t), 1.87 (1H, d), 1.68 (1H, q).

LCMS Rt 1.24 min [M+H]+ 448.4 (Method 2minLow-pHv03)

Example 13.4a (R)-10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione or (S)-10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione

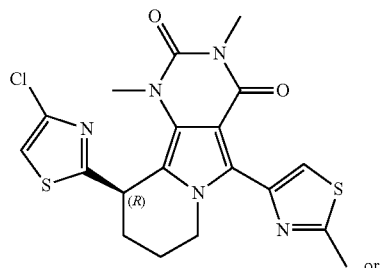

(R)-10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione or

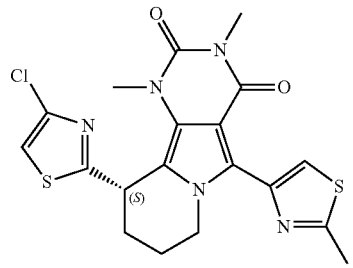

(S)-10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione Column: Chiralcel AD-H 250×10 mm×5 um@35° C.
Mobile phase: 50% Methanol/50% CO2
Flow: 10 ml/min
Detection: UV@220 nm

Example 13.4a

Enantiomer 1 of 10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione: Rt=3.82 mins 1H NMR (400 MHz, DMSO-d6) δ 7.90 (s, 1H), 7.63 (s, 1H), 5.30 (t, 1H), 4.40 (d, 1H), 3.87 (td, 1H), 3.31 (s, 3H), 3.20 (s, 3H), 2.73 (s, 3H), 2.36 (d, 1H), 2.26 (s, 1H), 1.86 (s, 1H), 1.69 (s, 1H).

LC-MS Rt 1.18 min [M+H]+ 448.3 (Method 2minLow-pHv04) The second enantiomer was isolated at Rt=4.91 mins.

Example 14

(8S,10R)-10-(5-Chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione or (8R,10R)-10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione or (8R,10S)-10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione or (8S,10S)-10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione

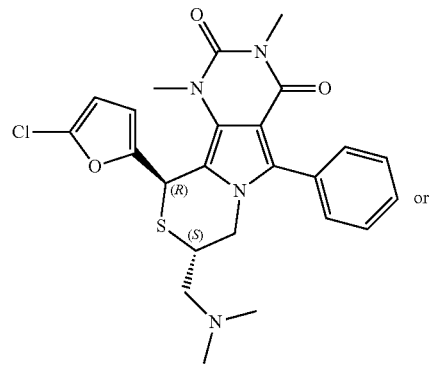

(8S,10R)-10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione or

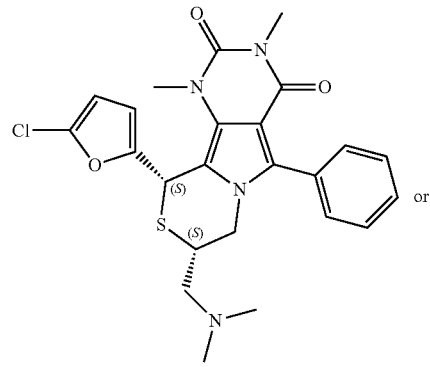

(8S,10S)-10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione

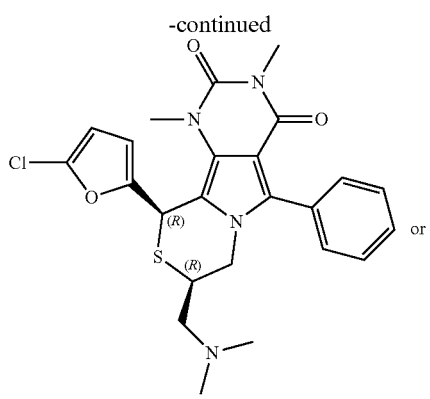

(8R,10R)-10-(5-chlorofuran-2-yl)-8-
((dimethylamino)methyl)-1,3-dimethyl-5-
phenyl-7,8-dihydro-1H-
pyrimido[4',5':3,4]pyrrolo[2,1-
c][1,4]thiazine-2,4(3H,10H)-dione

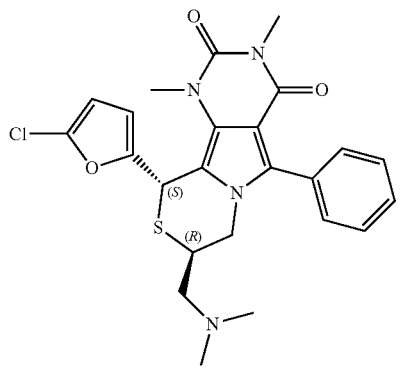

(8R,10S)-10-(5-chlorofuran-2-yl)-8-
((dimethylamino)methyl)-1,3-dimethyl-5-
phenyl-7,8-dihydro-1H-
pyrimido[4',5':3,4]pyrrolo[2,1-
c][1,4]thiazine-2,4(3H,10H)-dione Methanesulfonic anhydride (60.9 mg, 0.35 mmol) was added to a solution of 10-(5-chlorofuran-2-yl)-8-(hydroxymethyl)-1,3-dimethyl-5-phenyl-7,8-dihydro-1H-pyrimido[4',5':3,4]pyrrolo[2,1-c][1,4]thiazine-2,4(3H,10H)-dione (Example 12.0) (160 mg, 0.35 mmol) and 2,6-lutidine (0.041 ml, 0.35 mmol) in DCM (16 ml) at 0°. The mixture was stirred at room temperature for 2 hours. The mixture was evaporated under vacuum and the residue redissolved in THF (6 ml). Dimethylamine solution (2M in THF, 6 ml, 12.0 mmol) was added and mixture stirred at room temperature for 1 h, at 35° C. for 16 hours, at 55° C. for 6 hours, again at room temperature for 3 days, then at 55° C. for 4 hours, and finally heated under microwave irradiation at 80° C. for 20 mins. The mixture was evaporated under vacuum. The residue was redissolved in DCM and methanol and loaded onto an Isolute™SCX-2 cartridge. The column was first rinsed with methanol/DCM (1:1, 50 ml) then eluted with 3.5 M NH$_3$/methanol (50 ml). The basic eluent was evaporated under vacuum to afford the title compounds as a mixture of diastereomers LC-MS: Rt 0.75 and 0.78 mins [M+H]$^+$ 485 (Method 2minLowpHv01)

The diastereomers were separated by SFC chromatographic resolution under the following conditions to afford the title compounds.

Column: Chiralcel AD 250×10 mm 5 u@35 degC
Mobile phase: 20% Methanol+0.1% DEA/80% CO2
Flow: 10 ml/min
Detection: UV@220 nm

Example 14a

Diastereoisomer 1 of 10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione Rt=4.85 mins 1H NMR (400 MHz, DMSO) δ 7.50-7.44 (5H, m); 6.43 (1H, d); 6.26 (1H, d); 6.14 (1H, s); 4.16-4.06 (2H, m); 3.52-3.47 (4H, s); 3.15 (3H, s); 2.02 (2H, dd); 1.94 (6H, s).

LC-MS Rt 0.84 mins [M+H]$^+$ 485 (Method 2minLowpHv03)

Example 14b

Diastereoisomer 2 of 10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione Rt=6.88 mins 1H NMR (400 MHz, DMSO) δ 7.50-7.43 (5H, m); 6.42 (1H, d); 6.32 (1H, d); 6.15 (1H, s); 4.35 (1H, dd); 3.70 (1H, dd); 3.64-3.55 (1H, m); 3.53 (3H, s); 3.15 (3H, s); 2.38 (2H, dd); 2.06 (6H, s)

LC-MS Rt 0.81 mins [M+H]$^+$ 485 (Method 2minLowpHv03)

Example 15

(R)-10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione or (S)-10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione

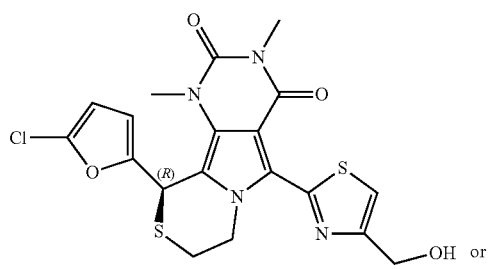

(R)-10-(5-chlorofuran-2-yl)-5-(4-
hydroxymethyl)thiazol-2-yl)-1,3-dimethyl-7,8-
dihydro-1H-pyrimido[4',5':3,4]pyrrolo[2,1-
c][1,4]thiazine-2,4(3H,10H)-dione

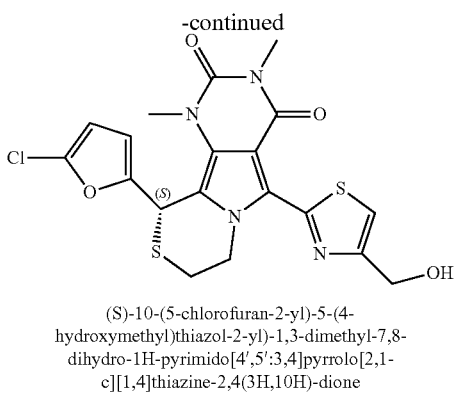

(S)-10-(5-chlorofuran-2-yl)-5-(4-hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Step 1: Ethyl 2-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylate TFA (0.858 ml, 11.14 mmol) was added to a mixture of ethyl 2-(1,3-dimethyl-2,4-dioxo-6-(2-(tritylthio)ethyl)-2,3,4,6-tetrahydro-1H-pyrrolo[3,4-d]pyrimidin-5-yl)thiazole-4-carboxylate (Intermediate GB) (473 mg, 0.743 mmol), triethylsilane (0.119 ml, 0.743 mmol) and bismuth triflate (244 mg, 0.371 mmol) in toluene (5.4 ml). The mixture was stirred at room temperature for 48 hours. The mixture was diluted with saturated NaHCO$_3$(aq) (30 ml) and extracted with EtOAc (3×20 ml). The combined organic extracts were washed with water (20 ml) and brine (20 ml), dried over sodium sulfate and evaporated under vacuum. Purification by chromatography on silica, eluting with 30-50% EtOAc/hexane afforded the title compound.

1H NMR (400 MHz, DMSO-d6) δ 8.73 (1H, s), 6.42 (1H, d), 6.22 (1H, s), 6.21 (1H, d), 4.58 (1H, dt), 4.42 (1H, m), 4.38 (2H, q), 3.45 (3H, s), 3.21 (3H, s), 2.98 (1H, m), 1.33 (3H, t).

LC-MS Rt 1.41 mins [M+H]$^+$ 507.3/509.3 (Method 2min-LowpHv03)

Step 2: rac-10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Sodium borohydride (45.1 mg, 1.191 mmol) was added to a solution of ethyl 2-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylate (302 mg, 0.596 mmol) and lithium chloride (50.5 mg, 1.191 mmol) in ethanol (7.50 ml) and THF (15 ml) at 0° C. The mixture was warmed to room temperature and stirred for 7 hours. Further portions of lithium chloride (50.5 mg, 1.191 mmol) and sodium borohydride (45.1 mg, 1.191 mmol) were added to allow the reaction to run to completion. The reaction was quenched with saturated NaHCO$_3$(aq) solution (50 ml), diluted with water (20 ml) and extracted with DCM (3×75 ml). The combined organic extracts were washed with water (20 ml), passed though a hydrophobic frit and evaporated under vacuum to afford the title compound.

1H NMR (400 MHz, DMSO-d6) δ 7.68 (1H, s), 6.42 (1H, d), 6.20 (1H, s), 6.17 (1H, d), 5.40 (1H, t), 4.65 (2 h, d), 4.54 (1H, dt), 4.38 (1H, m), 3.45 (3H, s), 3.20 (3H, s), 3.03-2.96 (2H, m)

LC-MS Rt 1.22 mins [M+H]$^+$ 465.3/467.3 (Method 2min-LowpHv03)

Step 3: (R)-10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Separation of racemic 10-(5-chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione was carried out under the following conditions to afford the title compound.

Column: Chiralcel OD-H 250×10 mm, 5 um@35 degC

Mobile phase: 50% Methanol/50% CO2

Flow: 10 ml/min

Detection: UV@220 nm

Enantiomer 1 of 10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione or (S)-10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Rt=6.73 mins 1H NMR (400 MHz, DMSO-d6) δ 7.68 (1H, s), 6.41 (1H, d), 6.19 (1H, s), 6.16 (1H, dd), 5.39 (1H, t), 4.65 (2H, d), 4.53 (1H, dt), 4.38 (1H, m), 3.45 (3H, s), 3.20 (3H, s), 3.04-2.96 (2H, m).

LC-MS Rt 1.17 mins [M+H]$^+$ 465.2 (Method 2minLowpHv03)

Chiral purity>99% e.e.

The other enantiomer was isolated at Rt=5.07 mins

The compounds of the following examples were prepared analogously to Example 15 (steps 1 and 2) by replacing Intermediate GB (step 1) with the appropriate starting compound (prepared by a similar method to Intermediate GB from Intermediate F and the appropriate halo compound in and the commercially available aldehyde.

Example 15.1

10-(4-Chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione

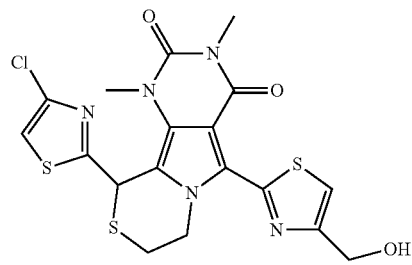 [SMILES: Cn1c(=O)c2c(-c3nc(CO)cs3)n3c(c2n(C)c1=O)C(c1nc(Cl)cs1)SCC3]

1H NMR (400 MHz, DMSO-d6) δ 7.379 (1H, s), 7.69 (1H, s), 6.51 (1H, s), 5.39 (1H, t), 4.72-4.60 (3H, m), 4.30 (1H, m), 3.53 (3H, s), 3.22 (3H, s), 3.19-3.02 (2H, m)

LC-MS Rt 1.07 mins [M+H]$^+$ 482.0 (Method 2minLowpHv03)

Example 15.2

10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione

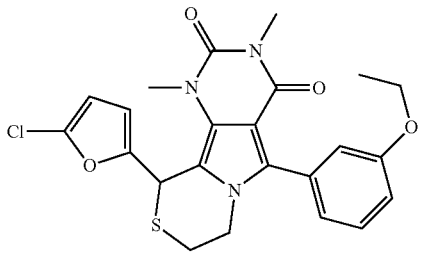 [SMILES: CCOc1cccc(-c2c3c(=O)n(C)c(=O)n(C)c3c3n2CCSC3c2ccc(Cl)o2)c1]

LC-MS Rt 1.32 mins [M+H]+ 472.5 (Method 2minLow-pHv01)
1H NMR (400 MHz, CDCl3) δ 7.40 (1H, t), 6.99 (2H, t), 6.94 (1H, d), 6.11 (1H, d), 5.93 (1H, d), 5.72 (1H, s), 4.21 (1H, mult), 4.10 (3H, mult), 3.59 (3H, s), 3.36 (3H, s), 3.08 (1H, mult), 2.83 (1H, mult), 1.45 (3H, t)

Example 15.3

5-(3-Methoxyphenyl)-1,3-dimethyl-10-(4-methylthiazol-2-yl)-7,8-dihydro-1H-pyrimido[4',5':3,4]pyrrolo[2,1-c][1,4]thiazine-2,4(3H,10H)-dione

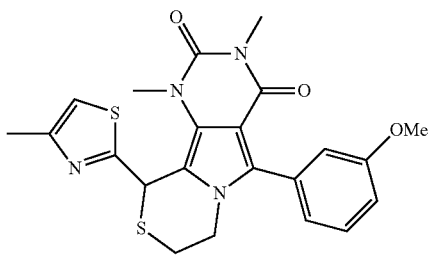 [SMILES: COc1cccc(-c2c3c(=O)n(C)c(=O)n(C)c3c3n2CCSC3c2nc(C)cs2)c1]

1H NMR (400 MHz, DMSO-d6) δ 7.39 (1H, t), 7.24 (1H, s), 7.04 (1H, dd), 7.01-6.96 (2H, m), 6.37 (1H, s), 4.12 (1H, m), 4.03 (1H, m), 3.79 (3H, s), 3.52 (3H, s), 3.15 (3H, s), 3.11 (1H, m), 3.01 (1H, m)
LC-MS Rt 1.12 mins [M+H]+ 455.3 (Method 2minLow-pHv01)

Example 15.4

10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione

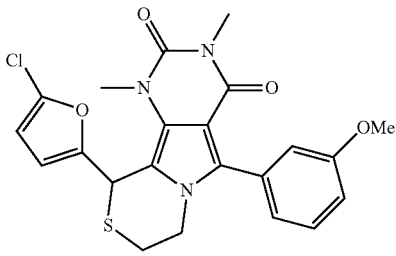 [SMILES: COc1cccc(-c2c3c(=O)n(C)c(=O)n(C)c3c3n2CCSC3c2ccc(Cl)o2)c1]

1H NMR (400 MHz, DMSO-d6) δ 7.38 (1H, t), 7.02 (3H, obs t), 6.41 (1H, d), 6.15-6.11 (2H, m), 4.12 (1H, dt), 3.97 (1H, m), 3.79 (3H, s), 3.44 (3H, s), 3.13 (3H, s), 2.98-2.92 (2H, m)
LC-MS Rt 1.26 mins [M+H]+ 458.2 (Method 2minLow-pHv01)

Example 15.5

10-(2-Chlorothiazol-4-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione

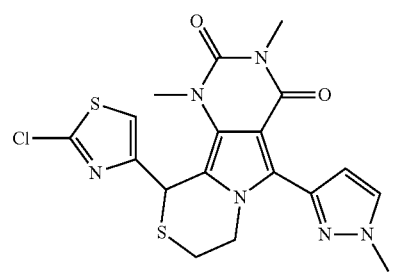 [SMILES: Cn1ccc(-c2c3c(=O)n(C)c(=O)n(C)c3c3n2CCSC3c2csc(Cl)n2)n1]

1H NMR (400 MHz, DMSO) δ 7.80 (1H, s), 7.23 (1H, s), 6.69 (1H, s), 6.15 (1H, s), 4.48 (1H, mult), 4.37 (1H, mult), 3.94 (3H, s), 3.45 (3H, s), 3.18 (3H, s), 2.99 (2H, mult)
LC-MS Rt 1.13 mins [M+H]+ 449.5 (Method 2minLow-pHv03)

Example 15.6

10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione

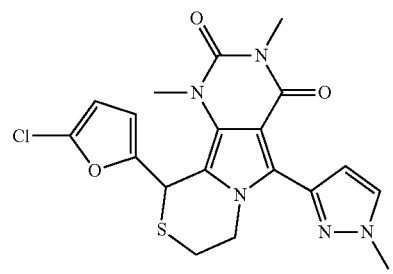 [SMILES: Cn1ccc(-c2c3c(=O)n(C)c(=O)n(C)c3c3n2CCSC3c2ccc(Cl)o2)n1]

1H NMR (400 MHz, CDCl3) δ 7.49 (1H, d), 6.81 (1H, d), 6.09 (1H, d), 5.96 (1H, d), 5.71 (1H, s), 4.61 (1H, mult), 4.46 (1H, mult), 3.99 (3H, s), 3.58 (3H, s), 3.39 (3H, s), 3.12 (1H, mult), 2.89 (1H, mult)
LC-MS Rt 1.11 mins [M+H]+ 432.6 (Method 2minLow-pHv01)

Example 15.7

10-(5-Chlorofuran-2-yl)-1,3-dimethyl-5-(1-methyl-1H-imidazol-4-yl)-7,8-dihydro-1H-pyrimido[4',5':3,4]pyrrolo[2,1-c][1,4]thiazine-2,4(3H,10H)-dione

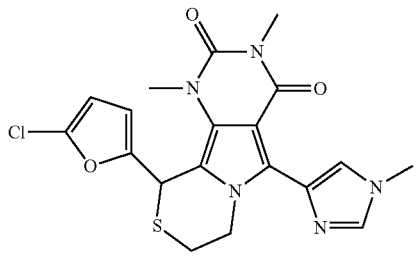 [SMILES: Cn1cnc(-c2c3c(=O)n(C)c(=O)n(C)c3c3n2CCSC3c2ccc(Cl)o2)c1]

1H NMR (400 MHz, CDCl3) δ 8.53 (1H, s), 7.94 (1H, s), 6.11 (1H, mult), 6.00 (1H, mult), 5.72 (1H, s), 4.66 (1H, mult), 4.25 (1H, mult), 4.05 (3H, s), 3.59 (3H, s), 3.44 (3H, s), 3.19 (1H, mult), 3.02 (1H, mult)
LC-MS Rt 0.76 mins [M+H]+ 432.6 (Method 2minLow-pHv01)

Example 15.8

10-(5-Chlorofuran-2-yl)-1,3-dimethyl-5-(1-methyl-1H-pyrazol-4-yl)-7,8-dihydro-1H-pyrimido[4',5':3,4]pyrrolo[2,1-c][1,4]thiazine-2,4(3H,10H)-dione

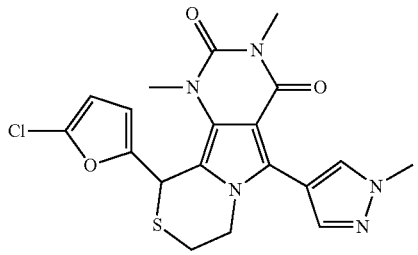 [SMILES: Cn1cc(-c2c3c(=O)n(C)c(=O)n(C)c3c3n2CCSC3c2ccc(Cl)o2)cn1]

1H NMR (400 MHz, CDCl3) δ 7.88 (1H, s), 7.64 (1H, s), 6.08 (1H, d), 5.92 (1H, d), 5.71 (1H, s), 4.38 (1H, m), 4.26 (1H, m) 4.01 (3H, s), 3.56 (3H, s), 3.37 (3H, s), 3.08 (1H, ddd), 2.89 (1H, dt).
LC-MS Rt 0.80 mins [M+H]+ 430.2 (Method 2minLow-pHv02)

Example 15.9

10-(5-Chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione

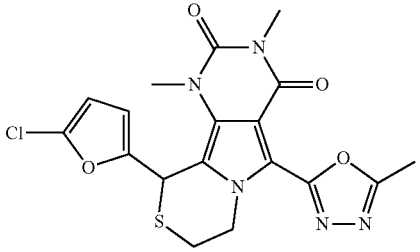 [SMILES: Cc1nnc(-c2c3c(=O)n(C)c(=O)n(C)c3c3n2CCSC3c2ccc(Cl)o2)o1]

1H NMR (400 MHz, CDCl3) δ 6.12 (1H, d), 5.97 (1H, mult), 5.72 (1H, s), 4.78 (1H, mult), 4.60 (1H, mult), 3.60 (3H, s), 3.43 (3H, s), 3.19 (1H, mult), 2.97 (1H, mult), 2.71 (3H, s)
LC-MS Rt 0.98 mins [M+H]+ 465.3 (Method 2minLow-pHv01)

Example 15.10

10-(5-Chlorofuran-2-yl)-1,3-dimethyl-5-(4-methyloxazol-2-yl)-7,8-dihydro-1H-pyrimido[4',5':3,4]pyrrolo[2,1-c][1,4]thiazine-2,4(3H,10H)-dione

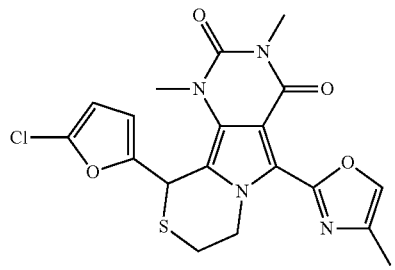 [SMILES: Cc1coc(-c2c3c(=O)n(C)c(=O)n(C)c3c3n2CCSC3c2ccc(Cl)o2)n1]

1H NMR (400 MHz, CD3OD+5 drops DMSO-d6) δ 7.68 (1H, s), 6.25 (1H, d), 6.09 (1H, d), 6.04 (1H, s), 4.85 (1H, dt), 4.35 (1H, m), 3.55 (3H, s), 3.33 (3H, s), 3.15 (1H, m), 3.00 (1H, dt), 2.29 (3H, s)
LC-MS Rt 1.27 mins [M+H]+ 433.1 (Method 2minLow-pHv03) The compounds of the following examples were prepared analogously to Example 15a and 15b by replacing Intermediate GB (step 1) with the appropriate starting compound (prepared by a similar method to Intermediate GB starting from Intermediate F and the appropriate halo compound) and the commercially available aldehyde. The resulting racemates were separated by SFC chromatographic resolution to yield single enantiomers.

Example 15.11

(R)-10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione
or
(S)-10-(5-chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione

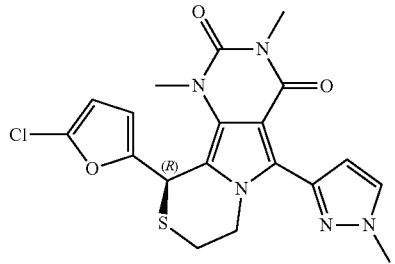

(R)-10-(5-chlorofuran-2-yl)-1,3-dimethyl-5-(1-methyl-1H-pyrazol-3-yl)-7,8-dihydro-1H-pyrimido(4',5':3,4)pyrrolo[2,1-c][1,4]thiazine-2,4(3H,10H)-dione          or

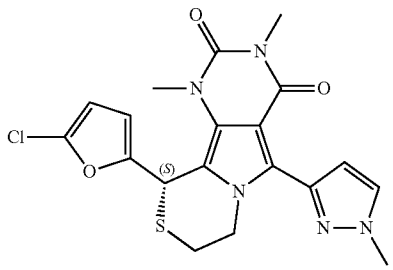

(S)-10-(5-chlorofuran-2-yl)-1,3-dimethyl-
5-(1-methyl-1H-pyrazol-3-yl)-7,8-dihydro-
1H-pyrimido(4',5':3,4]pyrrolo[2,1-
c][1,4]thiazine-2,4(3H,10H)-dione Column: Chiralcel OD 250×10 mm 5 μm@35.1° C.
Eluent: 50% MeOH/50% scCO2
Flow: 10 ml/min
Detection: UV@220 nm
Enantiomer 1 of 10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione Rt=7.67 mins
LC-MS Rt 1.12 mins [M+H]$^+$ 432.1 (Method 2minLowpHv01)
1H NMR (400 MHz, DMSO-d6) δ 7.79 (1H, d), 6.67 (1H, d), 6.39 (1H, d), 6.13 (1H, s), 6.07 (1H, dd), 4.44 (1H, dt), 4.29 (1H, m), 3.91 (3H, s), 3.43 (3H, s), 3.16 (3H, s), 3.00-2.94 (2H, m)

Example 15.12

(S)-10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione or (R)-10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione

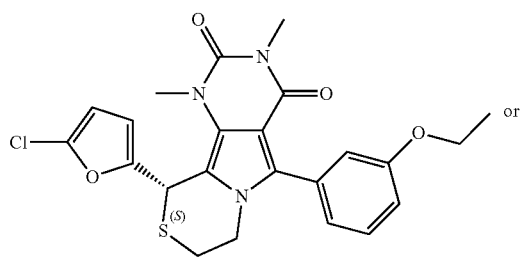

(S)-10-(5-chlorofuran-2-yl)-5-(3-ethyoxyphenyl)-
1,3-dimethyl-7,8-dihydro-1H-
pyrimido[4',5':3,4]pyrrolo[2,1-c][1,4]thiazine-
2,4(3H,10H)-dione

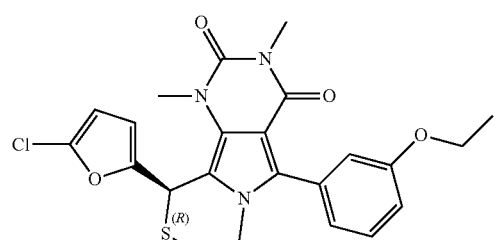

(R)-10-(5-chlorofuran-2-yl)-5-(3-ethyoxyphenyl)-
1,3-dimethyl-7,8-dihydro-1H-
pyrimido[4',5':3,4]pyrrolo[2,1-c][1,4]thiazine-
2,4(3H,10H)-dione Separation Conditions:
Column: Chiralcel OD-3, 150×2.1 mm 3 um@40 C,
Eluent: 40% MeOH/60% CO2
Flow: 0.4 ml/min
Detection: UV@220 nm and 254 nm
Enantiomer 1 of 10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione Rt=6.85 mins
1H NMR (400 MHz, CDCl3) δ 7.41 (1H, t), 6.98 (3H, mult), 6.10 (1H, d), 5.93 (1H, mult), 5.72 (1H, s), 4.32 (4H, mult), 3.59 (3H, s), 3.35 (3H, s), 3.08 (1H, mult), 2.83 (1H, mult), 1.45 (3H, t)

Example 15.13

(S)-10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione or (R)-10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione

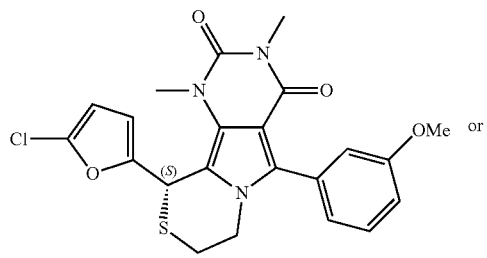

(S)-10-(5-chlorofuran-2-yl)-5-(3-methoxyphenyl)-
1,3-dimethyl-7,8-dihydro-1H-
pyrimido[4',5':3,4]pyrrolo[2,1-c][1,4]thiazine-
2,4(3H,10H)-dione -continued

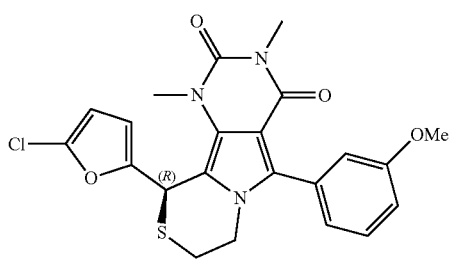

(R)-10-(5-chlorofuran-2-yl)-5-(3-methoxyphenyl)-
1,3-dimethyl-7,8-dihydro-1H-
pyrimido[4',5':3,4]pyrrolo[2,1-c][1,4]thiazine-
2,4(3H,10H)-dione Separation Conditions:
Column: Chiralcel OD 250×10 mm 5 um@34.8° C.
Mobile phase: 35% Methanol/65% CO2
Flow: 10 ml/min
Detection: UV@220-260 nm
Enantiomer 1 of 10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione Rt=5.40 mins 1H NMR (400 MHz, DMSO-d6) δ 7.38 (1H, td), 7.07-6.98 (3H, m), 6.41 (1H, d), 6.16-6.10 (2H, m), 4.12 (1H, dt), 3.98 (1H, m), 3.79 (3H, s), 3.44 (3H, s), 3.14 (3H, s), 2.98—2.92 (2H, m)

LC-MS Rt 1.26 mins [M+H]+ 458.3 (Method 2minLow-pHv01)

Example 15.14

(S)-10-(5-Chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione or (R)-10-(5-chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione

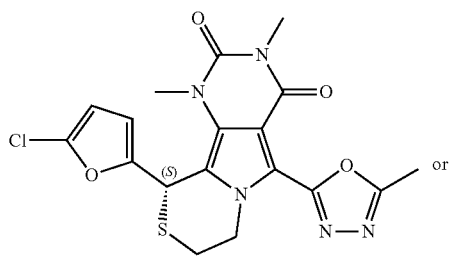

(S)-10-(5-chlorofuran-2-yl)-1,3-dimethyl-
5-(5-methyl-1,3,4-oxadiazol-2-yl)-7,8-
dihydro-1H-pyrimido(4',5':3,4]pyrrolo[2,1-
c][1,4]thiazine-2,4(3H,10H)-dione -continued

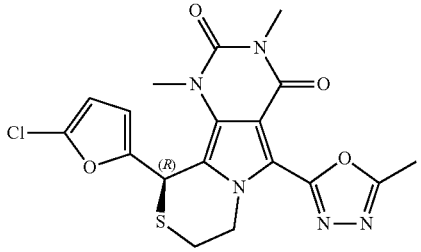

(R)-10-(5-chlorofuran-2-yl)-1,3-dimethyl-
5-(5-methyl-1,3,4-oxadiazol-2-yl)-7,8-
dihydro-1H-pyrimido(4',5':3,4]pyrrolo[2,1-
c][1,4]thiazine-2,4(3H,10H)-dione Separation Conditions:
Column: Chiralpak ID, 250×10 mm, 5 um@35 degC
Mobile phase: 50% Methanol/50% CO2
Flow: 10 ml/min
Detection: UV@220 nm
Enantiomer 1 of 10-(5-Chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione Rt=6.64 mins 1H NMR (400 MHz, DMSO-d6) δ 6.42 (1H, d), 6.23 (1H, s), 6.15 (1H, dd), 4.55 (1H, dt), 4.27 (1H, m), 3.43 (3H, s), 3.20 (3H, s), 3.07 (1H, dt), 2.98 (1H, m), 2.61 (3H, s)

LC-MS Rt 1.15 mins [M+H]+ 434.3 (Method 2minLow-pHv01)

Example 15:15

(R)-10-(5-Chlorofuran-2-yl)-5-(4-((S)-1-hydroxyethyl)thiazol-2-yl)-1,3-dimethyl-7,8-dihydro-1H-pyrimido[4',5':3,4]pyrrolo[2,1-c][1,4]thiazine-2,4 (3H,10H)-dione or (R)-10-(5-chlorofuran-2-yl)-5-(4-((R)-1-hydroxyethyl)thiazol-2-yl)-1,3-dimethyl-7,8-dihydro-1H-pyrimido[4',5':3,4]pyrrolo[2,1-c][1,4]thiazine-2,4 (3H,10H)-dione or (S)-10-(5-chlorofuran-2-yl)-5-(4-((S)-1-hydroxyethyl)thiazol-2-yl)-1,3-dimethyl-7,8-dihydro-1H-pyrimido[4',5':3,4]pyrrolo[2,1-c][1,4]thiazine-2,4 (3H,10H)-dione or (S)-10-(5-chlorofuran-2-yl)-5-(4-((R)-1-hydroxyethyl)thiazol-2-yl)-1,3-dimethyl-7,8-dihydro-1H-pyrimido[4',5':3,4]pyrrolo[2,1-c][1,4]thiazine-2,4 (3H,10H)-dione

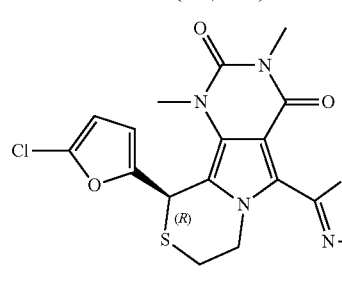

(R)-10-(5-chlorofuran-2-yl)-5-(4-((S)-1-
hydroxyethyl)thiazol-2-yl)-1,3-dimethyl-7,8-
dihydro-1H-pyrimido[4',5':3,4]pyrrolo[2,1-
c][1,4]thiazine-2,4(3H,10H)-dione -continued

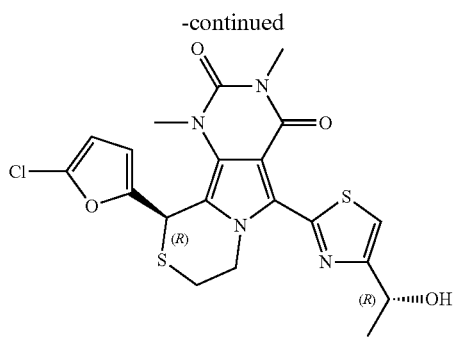

(R)-10-(5-chlorofuran-2-yl)-5-(4-((R)-1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione

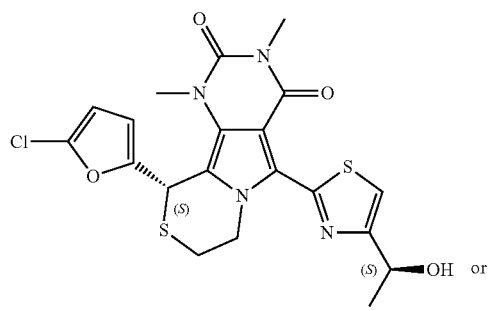

(S)-10-(5-chlorofuran-2-yl)-5-(4-((S)-1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione or

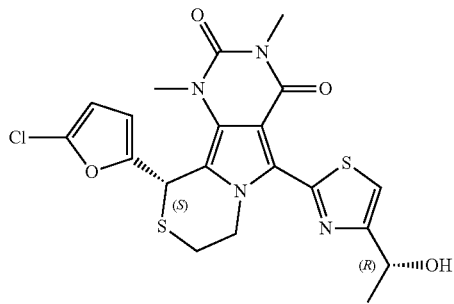

(S)-10-(5-chlorofuran-2-yl)-5-(4-((R)-1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione Separation Conditions:
Column: Chiralcel OJ-H 250×10 mm, 5 um@35 degC
Mobile phase: 30% Methanol+0.1% v/v DEA/70% CO2
Flow: 10 ml/min
Detection: UV@220 nm
Diastereoisomer 1 of 10-(5-Chlorofuran-2-yl)-5-(4-((S)-1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione Rt=5.72 mins 1H NMR (400 MHz, DMSO-d6) δ 7.64 (1H, s), 6.42 (1H, d), 6.20 (1H, s), 6.18 (1H, d), 5.39 (1H, br s), 4.89 (1H, m), 4.53 (1H, dt), 4.41 (1H, m), 3.45 (3H, s), 3.20 (3H, s), 3.05-2.95 (2H, m), 1.45 (3H, d)

LC-MS Rt 1.25 mins [M+H]+ 495.2 (Method 2minLow-pHv03)

Example 15.16

(R)-10-(4-Chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione or (S)-10-(4-chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione

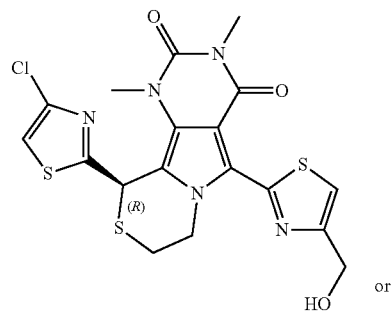

(R)-10-(4-chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione or

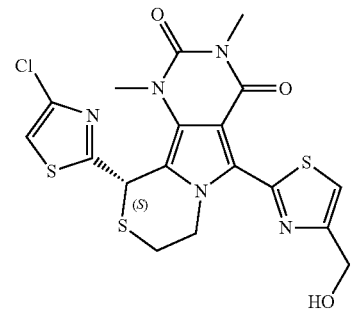

(S)-10-(4-chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Separation Conditions:
Column: Chiralpak IF 250×10 mm, 5 um@35.1° C.
Mobile Phase: 50% MeOH/50% CO2
Flow: 15 ml/min
Detection: UV@220 nm
Enantiomer 1 of 10-(4-Chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione Rt=4.40 mins 1H NMR (400 MHz, DMSO-d6) δ 7.78 (1H, s), 7.68 (1H, s), 6.50 (1H, s), 5.38 (1H, t), 4.67 (1H, m), 4.63 (2H, d), 4.30 (1H, m), 3.52 (3H, s), 3.31 (3H, s), 3.14 (1H, m), 3.06 (1H, m).

LC-MS Rt 1.08 mins [M+H]+ 482.3 (Method 2minLow-pHv03).

Example 16

9-(4-Chlorothiazol-2-yl)-1,3-dimethyl-5-phenyl-8,9-dihydro-1H-pyrimido[4,5-a]pyrrolizine-2,4(3H,7H)-dione

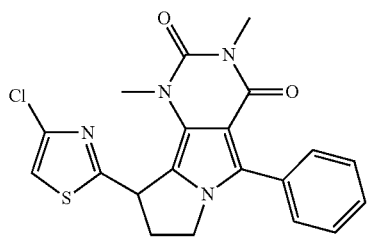 [SMILES: Cn1c(=O)c2c(-c3ccccc3)n3c(c2n(C)c1=O)C(c1nc(Cl)cs1)CC3]

Step 1: 3-(1,3-Dimethyl-2,4-dioxo-5-phenyl-3,4-dihydro-1H-pyrrolo[3,4-d]pyrimidin-6(2H)-yl)-N-methoxy-N-methylpropanamide Isopropylmagnesium bromide solution (2.9M, 3.03 mL, 8.79 mmol) was added slowly to a suspension of methyl 3-(1,3-dimethyl-2,4-dioxo-5-phenyl-3,4-dihydro-1H-pyrrolo[3,4-d]pyrimidin-6(2H)-yl)propanoate (Example 11.0 step 1) (1.5 g, 4.39 mmol) and commercially available N,O-dimethylhydroxylamine hydrochloride (0.514 g, 5.27 mmol) in THF (50 mL) at 0° C. The mixture was warmed to room temperature and stirred for 30 mins. A further portion of isopropylmagnesium bromide solution (2.9M, 3.03 mL, 8.79 mmol) was added slowly and the mixture stirred for a further 60 mins. The reaction was quenched with saturated NH₄Cl (aq) and extracted with EtOAc (2×). The combined organic extracts were washed with brine, dried over sodium sulfate and evaporated under vacuum. Purification by chromatography on silica, eluting with 50-100% EtOAc/hexane, then 1-8% MeOH/EtOAc afforded the title compound.

LC-MS Rt 0.99 mins [M+H]⁺ 371.2 (Method 2minLow-pHv03)

1H NMR (400 MHz, CDCl3) δ 7.47-7.29 (5H, mult), 6.42 (1H, br s), 4.19 (2H, t), 3.45 (3H, s), 3.26 (3H, s), 3.07 (3H, s), 2.64 (2H, t).

Step 2: 6-(3-(4-Chlorothiazol-2-yl)-3-oxopropyl)-1,3-dimethyl-5-phenyl-1H-pyrrolo[3,4-d]pyrimidine-2,4(3H,6H)-dione Isopropylmagnesium chloride lithium chloride complex solution (1.3M, 2.93 mL, 3.81 mmol) was added dropwise to a solution of 3-(1,3-dimethyl-2,4-dioxo-5-phenyl-3,4-dihydro-1H-pyrrolo[3,4-d]pyrimidin-6(2H)-yl)-N-methoxy-N-methylpropanamide (470 mg, 1.269 mmol) and 2-bromo-4-chlorothiazole (Intermediate Q) (252 mg, 1.269 mmol) in THF (20 mL). The mixture was stirred at room temperature for 45 mins. The reaction was quenched with saturated NH₄Cl(aq) and extracted with EtOAc (2×). The combined organic extracts were washed with brine, dried over sodium sulfate and evaporated under vacuum. Purification by chromatography on silica, eluting with 20-70% EtOAc/hexane afforded the title compound.

LC-MS Rt 1.29 mins; [M+H]⁺ 429.2 (Method 2minLow-pHv03)

Step 3: 6-(3-(4-Chlorothiazol-2-yl)-3-hydroxypropyl)-1,3-dimethyl-5-phenyl-1H-pyrrolo[3,4-d]pyrimidine-2,4(3H,6H)-dione Sodium borohydride (415 mg, 10.96 mmol) was added to a suspension of 6-(3-(4-chlorothiazol-2-yl)-3-oxopropyl)-1,3-dimethyl-5-phenyl-1H-pyrrolo[3,4-d]pyrimidine-2,4(3H,6H)-dione (470 mg, 1.096 mmol) in methanol (20 mL). The mixture was stirred at room temperature for 15 mins. The reaction was quenched with saturated NH₄Cl(aq) and extracted with chloroform (3×). The combined organic extracts were passed through a hydrophobic frit and evaporated under vacuum to afford the title compound.

1H NMR (400 MHz, CDCl3) δ 7.56-7.43 (5H, mult), 7.06 (1H, s), (1H, br s), 4.81 (1H, mult), 4.24 (1H, mult), 4.14 (1H, mult), 3.44 (3H, s), 3.36 (3H, s), 2.35 (1H, mult), 2.14 (1H, mult).

LC-MS Rt 1.14 mins [M+H]⁺ 431.1 (Method 2minLow-pHv03)

Step 4: 9-(4-Chlorothiazol-2-yl)-1,3-dimethyl-5-phenyl-8,9-dihydro-1H-pyrimido[4,5-a]pyrrolizine-2,4(3H,7H)-dione Trifluromethanesulfonic anhydride (0.576 mL, 3.41 mmol) in DCM (3 mL) was added slowly to a solution of 6-(3-(4-chlorothiazol-2-yl)-3-hydroxypropyl)-1,3-dimethyl-5-phenyl-1H-pyrrolo[3,4-d]pyrimidine-2,4(3H,6H)-dione (490 mg, 1.137 mmol) and triethylamine (0.792 mL, 5.69 mmol) in DCM (40 mL) at 0° C. Further portions of triethylamine (0.792 mL, 5.69 mmol) and trifluoromethanesulfonic anhydride (0.576 mL, 3.41 mmol) were added to allow the reaction to run to completion. The reaction was quenched with saturated NaHCO₃(aq) and extracted with DCM. The organic phase was passed through a hydrophobic frit and evaporated under vacuum. Purification by mass-directed HPLC under the following conditions afforded the title compound.

Column: XSelect CSH Prep C18 column, 30×100 mm, 5 um.

Mobile phase: A=0.1% DEA in water, B=0.1% DEA in MeCN

Gradient:

0.0-0.5 min: 30% B 30 mL/min 0.5-1.0 min: 30% B 30-50 mL/min 1.0-7.2 min: 30-70% B, 7.2-7.3 min: 70-98% B, 7.3-9.4 min: 98% B 9.4-9.5 min: 30% B 50 mL/min 1H NMR (400 MHz, CDCl3) δ 7.62 (2H, d), 7.49 (2H, t), 7.42 (1H, t), 7.06 (1H, s), 5.02 (1H, dd), 4.21 (1H, ddd), 4.11 (1H, ddd), 3.40 (6H, apparent s), 3.12 (1H, mult), 2.82 (1H, dddd).

LC-MS Rt 1.27 mins; [M+H]⁺ 413.2 (Method 2minLow-pHv03)

Example 16a (R)-9-(4-Chlorothiazol-2-yl)-1,3-dimethyl-5-phenyl-8,9-dihydro-1H-pyrimido[4,5-a]pyrrolizine-2,4(3H,7H)-dione or (S)-9-(4-chlorothiazol-2-yl)-1,3-dimethyl-5-phenyl-8,9-dihydro-1H-pyrimido[4,5-a]pyrrolizine-2,4(3H,7H)-dione

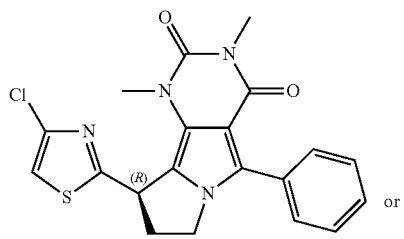

(R)-9-(4-chlorothiazol-2-yl)-1,3-dimethyl-5-phenyl-8,9-dihydro-1H-pyrimido[4,5-a]pyrrolizine-2,4(3H,7H)-dione or

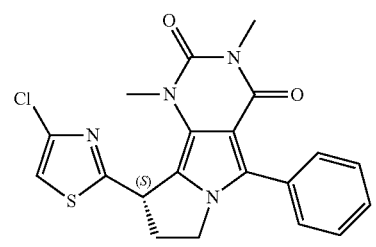

(S)-9-(4-chlorothiazol-2-yl)-1,3-dimethyl-5-phenyl-8,9-dihydro-1H-pyrimido[4,5-a]pyrrolizine-2,4(3H,7H)-dione Chiral separation of racemic 9-(4-chlorothiazol-2-yl)-1,3-dimethyl-5-phenyl-8,9-dihydro-1H-pyrimido[4,5-a]pyrrolizine-2,4(3H,7H)-dione (Example 16) by Supercritical Fluid Chromatography under the following conditions afforded the title compound;

Column: Chiralpak AD-H, 250×10 mm, 5 um@35 degC
Mobile phase: 50% Methanol+0.1% v/v DEA/50% CO2
Flow: 10 ml/min
Detection: UV@220 nm

Example 16a

Enantiomer 1 of 9-(4-chlorothiazol-2-yl)-1,3-dimethyl-5-phenyl-8,9-dihydro-1 H-pyrimido[4,5-a]pyrrolizine-2,4(3H,7H)-dione Rt=3.68 mins 1H NMR (400 MHz, CDCl3) δ 7.62 (2H, d), 7.48 (2H, t), 7.42 (1H, t), 7.06 (1H, s), 5.02 (1H, d), 4.21 (1H, mult), 4.11 (1H, mult), 3.40 (6H, apparent s), 3.12 (1H, mult), 2.881 (1H, dd)

LC-MS Rt 1.30 mins [M+H]$^+$ 413.2 (Method 2minLow-pHv03)

The second enantiomer was isolated at Rt=5.70 mins

The following examples were prepared analogously to Example 16 and 16a by replacing 2-bromo-4-chlorothiazole (Intermediate Q) in step 2 with 2-iodo-4-methylthiazole (Intermediate O).

Example 16.1

1,3-Dimethyl-9-(4-methylthiazol-2-yl)-5-phenyl-8,9-dihydro-1H-pyrimido[4,5-a]pyrrolizine-2,4(3H,7H)-dione

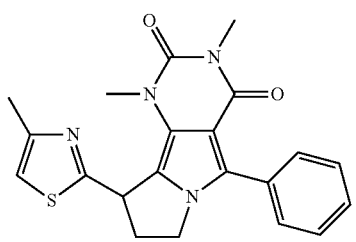 [SMILES: Cc1csc(C2CCn3c(-c4ccccc4)c4c(=O)n(C)c(=O)n(C)c4c32)n1]

LC-MS Rt 1.19 mins [M+H] 393.2 (Method 2minLow-pHv03)

1H NMR (400 MHz, CDCl3) δ 7.62 (2H, d), 7.56-7.41 (3H, mult), 7.03 (1H, s), 5.45 (1H, mult), 4.17 (2H, mult), 3.40 (3H, s), 3.37 (3H, s), 3.31 (1H, mult), 2.94 (1H, mult), 2.65 (3H, s)

Example 16.1a (R)-1,3-Dimethyl-9-(4-methylthiazol-2-yl)-5-phenyl-8,9-dihydro-1H-pyrimido[4,5-a]pyrrolizine-2,4(3H,7H)-dione or (S)-1,3-dimethyl-9-(4-methylthiazol-2-yl)-5-phenyl-8,9-dihydro-1H-pyrimido[4,5-a]pyrrolizine-2,4(3H,7H)-dione

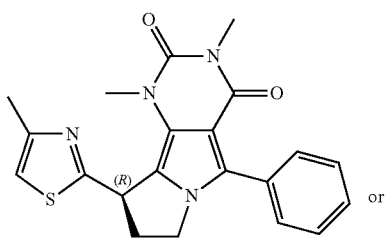

(R)-1,3-dimethyl-9-(4-methylthiazol-2-yl)-5-phenyl-8,9-dihydro-1H-pyrimido[4,5-a]pyrrolizine-2,4(3H,7H)-dione or

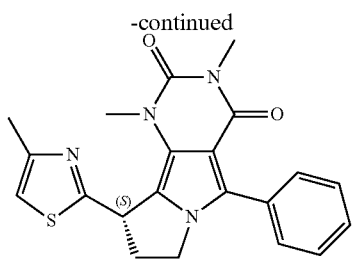

(S)-1,3-dimethyl-9-(4-methylthiazol-2-yl)-5-phenyl-8,9-dihydro-1H-pyrimido[4,5-a]pyrrolizine-2,4(3H,7H)-dione Column: Chiralpak AD 250 mm×10 mm×5 μm@35 degC
Mobile phase: 40% MeOH (containing 0.1% DEA)/60 CO2
Flow: 10 ml/min
Detection: UV@220 nm Example 16.1a Enantiomer of 1,3-dimethyl-9-(4-methylthiazol-2-yl)-5-phenyl-8,9-dihydro-1H-pyrimido[4,5-a]pyrrolizine-2,4(3H,7H)-dione Rt=4.01 mins
1H NMR (400 MHz, CDCl3) δ 7.64 (2H, d), 7.49 (2H, t), 7.43 (1H, t), 6.89 (1H, s), 5.16 (1H, d), 4.23 (1H, mult), 4.12 (1H, mult), 3.40 (3H, s), 3.38 (3H, s), 3.16 (1H, mult), 2.83 (1H, mult), 2.53 (3H, s)
LC-MS Rt 1.20 mins [M+H]+ 393.3 m/z (Method 2min-LowpHv03) The second enantiomer was isolated at Rt=5.52 mins Example 17

(8R,10R)-10-(5-Chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8R,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione

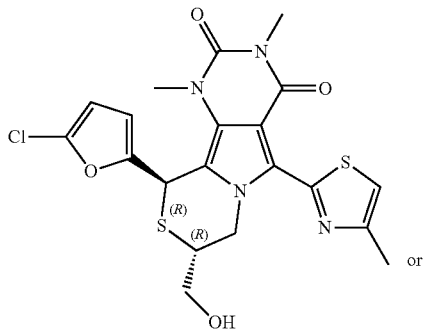

(8R,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione

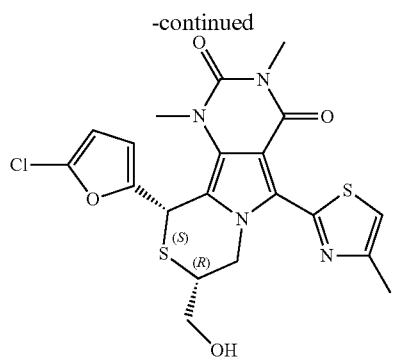

(8R,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione

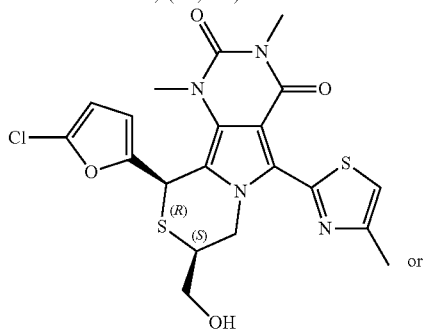

(8S,10R)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione

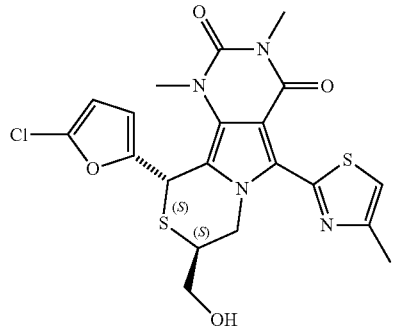

(8S,10S)-10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione Step 1: 2-(((4-Methoxybenzyl)oxy)methyl)oxirane p-Methoxybenzyl chloride (2.326 g, 14.85 mmol) was added slowly to a suspension of sodium hydride (60% dispersion in mineral oil, 0.594 g, 14.85 mmol) in DMF (25 mL) at 0° C. and the mixture stirred for 25 mins. Glycidol (1 g, 13.50 mmol) was then added dropwise over 25 mins, the mixture was allowed to warm to room temperature and stirred for 3 days. The mixture was diluted with EtOAc (50 ml) and washed with saturated NH4Cl (aq) (30 ml), saturated NaHCO3 (aq) (50 ml) and brine (100 ml). The organic phase was dried over magnesium sulfate and evaporated under vacuum. Purification by chromatography on silica, eluting with 0-10% EtOAc/hexane, afforded the title compound.

LC-MS Rt 1.05 min [M+H]+ 195.8 (Method 2minLow-pHv03)

Step 2: 2-(((4-Methoxybenzyl)oxy)methyl)thiirane

Thiourea (0.935 g, 12.28 mmol) was added to a solution of 2-(((4-methoxybenzyl)oxy)methyl) oxirane (1.084 g, 5.58 mmol) in methanol (30 mL) and the mixture stirred at room temperature for 16 hours, then evaporated under vacuum. Purification by chromatography on silica, eluting with 0-10% EtOAc/hexane, afforded the title compound.

LC-MS Rt 1.29 min [M−H]⁻ 209.0 (Method 2minLow-pHv03)

Step 3: (1-Chloro-3-((4-methoxybenzyl)oxy) propan-2-yl) (trityl)sulfane 2-(((4-Methoxybenzyl)oxy)methyl)thiirane (496 mg, 2.359 mmol) was added to a solution of trityl chloride (598 mg, 2.144 mmol) in dichloromethane (10 mL). The mixture was stirred at room temperature for 16 hours, then evaporated under vacuum. Purification by chromatography on silica, eluting with 0-5% EtOAc/hexane, gave a crude material which was triturated with methanol to afford the title compound.

Step 4: 6-(3-((4-Methoxybenzyl)oxy)-2-(tritylthio) propyl)-1,3-dimethyl-5-(4-methylthiazol-2-yl)-1H-pyrrolo[3,4-d]pyrimidine-2,4(3H,6H)-dione Potassium iodide (9.80 mg, 0.059 mmol) was added to a mixture of 1,3-dimethyl-5-(4-methylthiazol-2-yl)-1H-pyrrolo[3,4-d]pyrimidine-2,4(3H,6H)-dione (Intermediate Nd) (81 mg, 0.294 mmol), (1-chloro-3-((4-methoxybenzyl)oxy) propan-2-yl)(trityl)sulfane (158 mg, 0.323 mmol) and cesium carbonate (191 mg, 0.587 mmol) in dimethylacetamide (2 ml). The mixture was stirred at 50° C. for 3 days. The reaction mixture was partitioned between water (20 ml) and ethyl acetate (20 ml), the phases were separated and the aqueous phase extracted with ethyl acetate (10 ml). The combined organic extracts were washed with brine (20 ml), dried over magnesium sulfate and evaporated under vacuum. Purification by chromatography on silica, eluting with 0-50% EtOAc/hexane, afforded the title compound.

LC-MS Rt 1.82 min [M+H]⁺ 729.3 (Method 2minLow-pHv03)

Step 5: 10-(5-Chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4 (3H,10H)-dione Trifluoroacetic acid (0.155 ml, 2.017 mmol) was added to a suspension of 6-(3-((4-methoxybenzyl)oxy)-2-(tritylthio) propyl)-1,3-dimethyl-5-(4-methylthiazol-2-yl)-1H-pyrrolo [3,4-d]pyrimidine-2,4(3H,6H)-dione (98 mg, 0.134 mmol), 5-chlorofuran-2-carbaldehyde (19.30 mg, 0.148 mmol) and bismuth triflate (44.1 mg, 0.067 mmol) in toluene (2 ml) The resulting mixture was stirred at room temperature for 30 mins. A further portion of 5-chlorofuran-2-carbaldehyde (26 mg) was added and the mixture stirred for a further 16 hours. The mixture was diluted with 1M NaOH(aq) (10 ml) and DCM (20 ml). The organic phase was separated and washed with saturated NH₄Cl(aq) (20 ml), passed through a hydrophobic frit and evaporated under vacuum. Purification by chromatography on silica, eluting with 0-90% EtOAc/hexane, afforded the title racemic compound.

LC-MS Rt 1.26 min [M+H]⁺ 479.4 (Method 2minLow-pHv03)

The racemate was separated by SFC chromatographic resolution under the following conditions to afford the title compound as a single enantiomer.

Column: Chiralcel OJ-H 250×10 mm, 5 um@35 degC
Mobile phase: 45% Methanol/55% CO2
Flow: 10 ml/min
Detection: UV@220 nm Diastereomer 1 of 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4 (3H,10H)-dione SFC Rt=4.68 mins 1H NMR1 (400 MHz, CDCl3) δ 7.20 (s, 1H), 6.26 (dd, 1H), 6.14 (d, 1H), 5.75 (s, 1H), 5.42 (dd, 1H), 4.04 (dd, 1H), 3.74 (m, 1H), 3.70 (s, 3H), 3.49 (dd, 1H), 3.44 (s, 3H), 3.21 (t, 1H), 2.53 (s, 3H).

LC-MS Rt 1.29 min [M+H]⁺ 479.1 (Method 2minLow-pHv03)

The following listed examples were prepared in a similar manner to Example 17, by replacing 1,3-dimethyl-5-(4-methylthiazol-2-yl)-1H-pyrrolo[3,4-d]pyrimidine-2,4(3H,6H)-dione (step 4) (Intermediate Nd) with the appropriate starting material (prepared in a similar manner to intermediate Nd using the appropriate halo compound). The diastereomers were separated by SFC chromatographic resolution to afford the title compounds.

Example 17.1

(8R,10R)-10-(5-Chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione or (8R,10S)-10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione or (8S,10R)-10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione or (8S,10S)-10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione

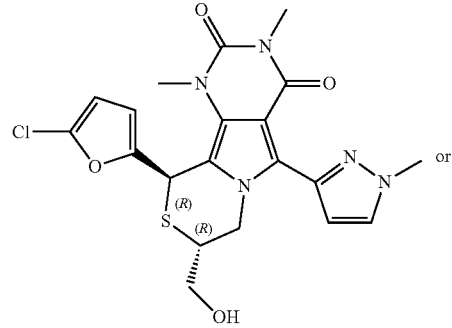

(8R,10R)-10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione -continued

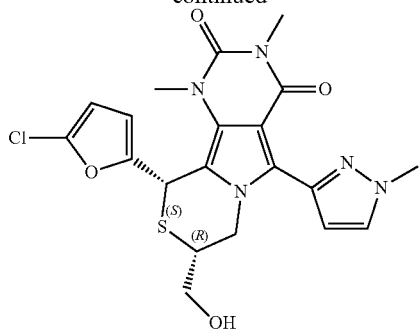

(8R,10S)-10-(5-chlorofuran-2-yl)-8-
(hydroxymethyl)-1,3-dimethyl-5-(1-methyl-
1H-pyrazol-3-yl)-7,8-dihydro-1H-
pyrimido[4',5':3,4]pyrrolo[2,1-
c][1,4]thiazine-2,4(3H,10H)-dione

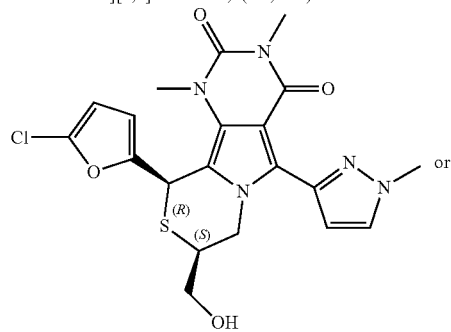

(8S,10R)-10-(5-chlorofuran-2-yl)-8-
(hydroxymethyl)-1,3-dimethyl-5-(1-methyl-
1H-pyrazol-3-yl)-7,8-dihydro-1H-
pyrimido[4',5':3,4]pyrrolo[2,1-
c][1,4]thiazine-2,4(3H,10H)-dione

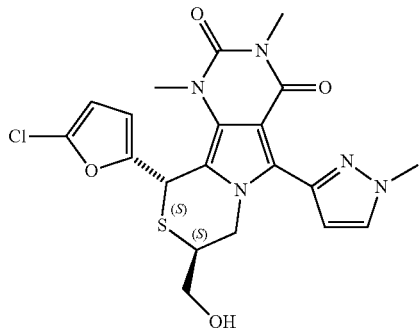

(8S,10S)-10-(5-chlorofuran-2-yl)-8-
(hydroxymethyl)-1,3-dimethyl-5-(1-methyl-
1H-pyrazol-3-yl)-7,8-dihydro-1H-
pyrimido[4',5':3,4]pyrrolo[2,1-
c][1,4]thiazine-2,4(3H,10H)-dione Separation Conditions:
Column: Chiralcel OJ-H 250×10 mm, 5 um@35 degC
Mobile phase: 40% Methanol+0.1% v/v DEA/60% 002
Flow: 10 ml/min
Detection: UV@220 nm
Diastereoisomer 1 of 10-(5-Chlorofuran-2-yl)-8-(hydroxymethyl)-1,3-dimethyl-5-(1-methyl-1H-pyrazol-3-yl)-7,8-dihydro-1H-pyrimido[4,5':3,4]pyrrolo[2,1-c][1,4]thiazine-2,4(3H,10H)-dione
Rt=4.28 mins.
1H NMR (400 MHz, DMSO-d6) δ 7.82 (1H, d), 6.70 (1H, d), 6.42 (1H, d), 6.20 (1H, d), 6.15 (1H, s), 5.21 (1H, br s), 4.63 (1H, dd), 4.22 (1H, dd), 3.92 (3H, s), 3.48 (3H, s), 3.46-3.40 (2H, m), 3.22-3.16 (4H, m).
LC-MS Rt 1.17 mins [M+H]$^+$ 462.1 (Method 2minLow-pHv03)

Example 17.2

(8R,10R)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione or (8R,10S)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione or (8S,10R)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione or (8S,10S)-10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione

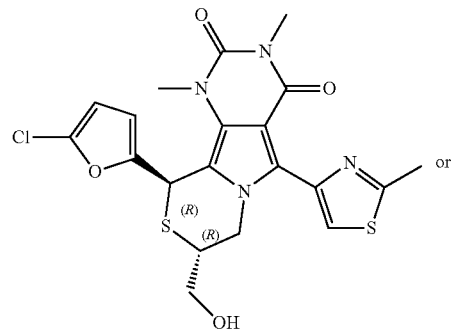

(8R,10R)-10-(5-chlorofuran-2-yl)-8-
(hydroxymethyl)-1,3-dimethyl-5-(2-methylthiazol-
4-yl)-7,8-dihydro-1H-
pyrimido[4',5':3,4]pyrrolo[2,1-c][1,4]thiazine-
2,4(3H,10H)-dione

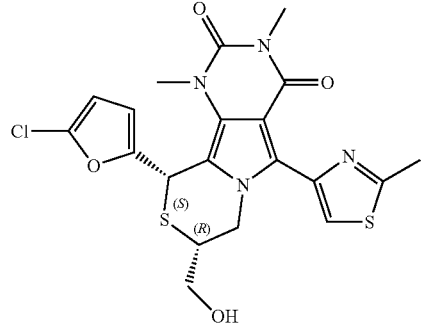

(8R,10S)-10-(5-chlorofuran-2-yl)-8-
(hydroxymethyl)-1,3-dimethyl-5-(2-methylthiazol-
4-yl)-7,8-dihydro-1H-
pyrimido[4',5':3,4]pyrrolo[2,1-c][1,4]thiazine-
2,4(3H,10H)-dione -continued

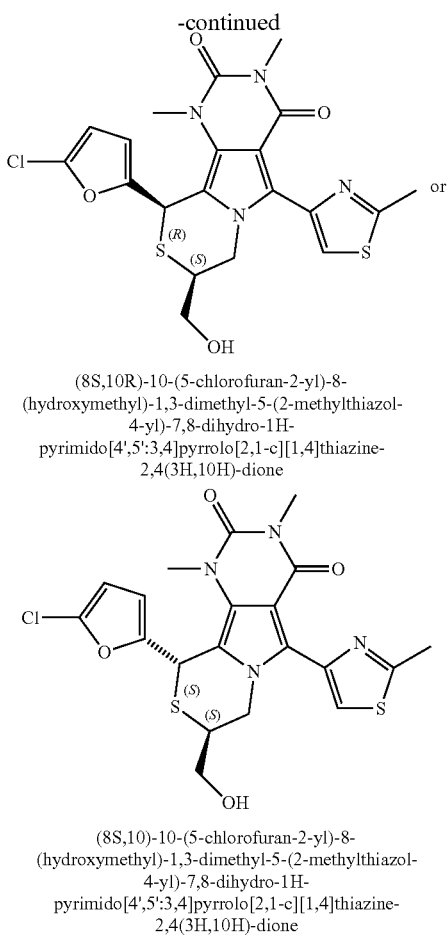

(8S,10R)-10-(5-chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione (8S,10)-10-(5-chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione Separation Conditions:
Column: Chiralpak AD-H 250×10 mm, 5 um@35 degC
Mobile phase: 40% Isopropanol+0.1% v/v DEA/60% CO2
Flow: 10 ml/min
Detection: UV@220 nm
Diastereoisomer 1 of 10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione
Rt=4.69 mins
1H NMR (400 MHz, CDCl3) δ 7.96 (s, 1H), 6.21 (dd, 1H), 6.11 (d, 1H), 5.72 (s, 1H), 5.17 (dd, 1H), 4.08 (dd, 1H), 3.68 (s, 3H), 3.64 (dd, 1H), 3.46 (dd, 1H), 3.40 (s, 3H), 3.22 (t, 1H), 2.78 (s, 3H).
LC-MS Rt 1.25 min [M+H]$^+$ 479.0 (Method 2minLowpHv03)

Example 18

9,9-Difluoro-5-(3-fluorophenyl)-1,3-dimethyl-10-(5-methylfuran-2-yl)-7,8,9,10-tetrahydropyrimido[4,5-a]indolizine-2,4(1H,3H)-dione

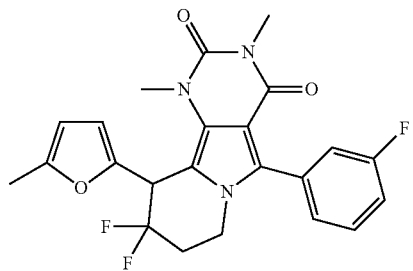 [SMILES: Cc1ccc(C2c3c4c(c(-c5cccc(F)c5)n3CCC2(F)F)c(=O)n(C)c(=O)n4C)o1]

Step 1: 9,9-Difluoro-5-(3-fluorophenyl)-1,3-dimethyl-8,9-dihydropyrimido[4,5-a]indolizine-2,4,10(1H,3H,7H)-trione A solution of commercially available N-fluorobenzenesulfonimide (2.77 g, 8.8 mmol) in THF (7 mL) was added to a suspension of manganese(II) bromide (1.89 g, 8.8 mmol) in THF (5 mL) and cooled to −78° C. A suspension of 5-(3-fluorophenyl)-1,3-dimethyl-8,9-dihydropyrimido[4,5-a]indolizine-2,4,10(1H,3H,7H)-trione (Intermediate L, step 1) (750 mg, 2.2 mmol) in THF (10 mL) was added dropwise, followed by potassium hexamethyldisilazide solution (1M, 11 mL, 11 mmol). The mixture was stirred at −60° C. for 2 hours and at room temperature for 1 hour. The reaction was quenched with saturated NaHCO3(aq) (150 mL) and extracted with DCM (3×50 mL). The combined organic extracts were dried over magnesium sulfate and evaporated under vacuum. Purification by mass-directed HPLC using the following conditions afforded the title compound.

Column: XSelect CSH Prep C18 column, 30×100 mm, 5 um.

Mobile phase: A=0.1% formic acid in water, B=0.1% formic acid in MeCN

Elution Gradient:

0.0-0.5 min: 30% B 30 mL/min 0.5-1.0 min: 30% B 30-50 mL/min 1.0-7.2 min: 30-70% B, 7.2-7.3 min: 70-98% B, 7.3-9.4 min: 98% B 9.4-9.5 30% B 50 mL/min 1H NMR (400 MHz, CDCl3) δ 7.55 (1H, mult), 7.31-7.16 (3H, mult), 4.21 (2H, t), 3.95 (3H, s), 3.37 (3H, s), 2.67 (2H, mult).

19F NMR (376 MHz, CDCl3) δ −108.7, −110.9.

LC-MS Rt 1.19 mins [M+H]$^+$ 378.1 (Method 2minLowpHv03)

Step 2: 9,9-Difluoro-5-(3-fluorophenyl)-10-hydroxy-1,3-dimethyl-7,8,9,10-tetrahydropyrimido[4,5-a]indolizine-2,4(1H,3H)-dione Sodium borohydride (7.2 mg, 0.19 mmol) was added to solution of 9,9-difluoro-5-(3-fluorophenyl)-1,3-dimethyl-8,9-dihydropyrimido[4,5-a]indolizine-2,4,10(1H,3H,7H)-trione (55 mg, 0.15 mmol) in methanol (1 mL) and tetrahydrofuran (1 mL) at 0° C. The mixture was stirred at room temperature for 30 mins. The reaction was quenched with water (10 mL) and extracted with DCM (6×5 mL). The combined organic extracts were passed through a hydrophobic frit and evaporated under vacuum to afford the title compound.

1H NMR (400 MHz, CDCl3) δ 7.47 (1H, mult), 7.24-7.12 (3H, mult), 5.29 (1H, t), 4.20-4.13 (1H, mult), 3.97 (1H, mult), 3.77 (3H, s), 3.36 (3H, s), 2.90-2.69 (2H, mult), 2.34 (1H, mult).

LC-MS Rt 1.10 mins [M+H]$^+$ 380.1 (Method 2minLowpHv03)

Step 3: 9,9-Difluoro-5-(3-fluorophenyl)-1,3-dimethyl-10-(5-methylfuran-2-yl)-7,8,9,10-tetrahydropyrimido[4,5-a]indolizine-2,4(1H,3H)-dione Gold (III) chloride (4 mg, 0.012 mmol) was added to a suspension of 9,9-difluoro-5-(3-fluorophenyl)-10-hydroxy-1,3-dimethyl-7,8,9,10-tetrahydropyrimido[4,5-a]indolizine-2,4(1H,3H)-dione (47 mg, 0.12 mmol) and 2-methylfuran (15 µL, 0.16 mmol) in acetonitrile (1 mL). The mixture was stirred at room temperature for 1 hour. The mixture was evaporated under vacuum, the residue was dissolved in DCM (5 mL) and washed with water (5 mL). The organic phase was passed through a hydrophobic frit evaporated under vacuum. Purification by mass directed HPLC using the following conditions afforded the title compound.

Column: XSelect CSH Prep C18 column, 30×100 mm, 5 um.

Mobile phase: A=0.1% formic acid in water, B=0.1% formic acid in MeCN

Elution Gradient:

0.0-0.5 min: 40% B 30 mL/min 0.5-1.0 min: 40% B 30-50 mL/min 1.0-7.2 min: 40-80% B, 7.2-7.3 min: 80-98% B, 7.3-9.4 min: 98% B 9.4-9.5 40% B 50 mL/min 1H NMR (400 MHz, CDCl3) δ 7.48 (1H, mult), 7.26 (1H, d), 7.22-7.16 (2H, mult), 5.94 (1H, d), 5.90 (1H, d), 5.04 (1H, t), 4.23 (1H, mult), 3.99 (1H, mult), 3.42 (3H, s), 3.34 (3H, s), 2.60 (1H, mult), 2.33-2.23 (4H, mult).

19F NMR (376 MHz, CDCl3) δ −99.9, −112.3.

LC-MS Rt 1.39 mins [M+H]+ 444.2 (Method 2minLowpHv03)

Example 19

(8R,10R)-8-(Aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8R,10S)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10R)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10S)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (8S,10R)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (8S,10S)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (8R,10R)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (8R,10S)-8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione Step 1: 2-(Thiiran-2-ylmethyl)isoindoline-1,3-dione Thiourea (1.873 g, 24.61 mmol) was added to a solution of N-(2,3-epoxypropyl)phthalimide (2 g, 9.84 mmol) in methanol (25 mL). The mixture was stirred at room temperature for 16 hours, then concentrated under vacuum. The residue was diluted with water (50 ml) and extracted with ethyl acetate (50 ml). The organic extract was washed with brine (50 ml) passed through a hydrophobic frit and evaporated under vacuum. Purification by chromatography on silica, eluting with 0-50% EtOAc/hexane, afforded the title compound.

LC-MS Rt 1.13 min [M+H]⁺ 220.4 (Method 2minLow-pHv03)

Step 2: 2-(3-Bromo-2-(tritylthio)propyl)isoindoline-1,3-dione

Trityl bromide (1147 mg, 3.55 mmol) was added portionwise over 5 mins to a solution of 2-(thiiran-2-ylmethyl)isoindoline-1,3-dione (778 mg, 3.55 mmol) in DCM (15 mL). The mixture was stirred for at room temperature for 16 hours, diluted with DCM (30 ml) and washed with brine (50 ml). The organic layer was separated, passed through a hydrophobic frit and evaporated under vacuum to afford the title compound.

Step 3: 6-(3-(1,3-Dioxoisoindolin-2-yl)-2-(tritylthio) propyl)-1,3-dimethyl-5-(4-methylthiazol-2-yl)-1H-pyrrolo[3,4-d]pyrimidine-2,4(3H,6H)-dione Cesium carbonate (1.537 g, 4.72 mmol) was added to a solution of 1,3-dimethyl-5-(4-methylthiazol-2-yl)-1H-pyrrolo[3,4-d]pyrimidine-2,4(3H,6H)-dione (Intermediate Nd) (0.652 g, 2.359 mmol) and 2-(3-bromo-2-(tritylthio)propyl)isoindoline-1,3-dione (2.011 g, 2.59 mmol) in dimethylacetamide (10 ml) and the mixture was stirred at 55° C. for 16 hours. The mixture was cooled to room temperature, partitioned between water (150 ml) and ethyl acetate (150 ml). The organic layer was separated, washed with brine (150 ml), dried over magnesium sulfate and evaporated under vacuum. Purification by chromatography on silica, eluting with 0-75% EtOAc/hexane afforded the title compound.

LC-MS Rt 1.71 min [M+H]⁺ 738.2 (Method 2minLow-pHv03)

Step 4: 10-(5-Chlorofuran-2-yl)-8-((1,3-dioxoisoindolin-2-yl)methyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione Trifluoroacetic acid (0.399 ml, 5.18 mmol) was added to a solution of 6-(3-(1,3-dioxoisoindolin-2-yl)-2-(tritylthio)propyl)-1,3-dimethyl-5-(4-methylthiazol-2-yl)-1H-pyrrolo[3,4-d]pyrimidine-2,4(3H,6H)-dione (764 mg, 1.035 mmol) in toluene (15 ml) and the mixture was stirred at room temperature for 30 minutes. Bismuth triflate (340 mg, 0.518 mmol) and 5-chlorofuran-2-carbaldehyde (203 mg, 1.553 mmol) were then added and the mixture was stirred at room temperature for 16 hours. The mixture was then diluted with ethyl acetate (150 ml) and washed with water (150 ml), saturated NaHCO₃(aq) (150 ml) and brine (150 ml). The organic layer was dried over magnesium sulfate and evaporated under vacuum. Purification by chromatography on silica, eluting with 0-100% EtOAc/hexane, afforded the title compound as a mixture of diastereomers.

LC-MS Rt 1.48 min [M+H]⁺ 608.6 (Method 2minLow-pHv03)

Step 5: 8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione as a mixture of stereoisomers Ethanolamine (0.320 mL, 5.30 mmol) was added to a solution of 10-(5-chlorofuran-2-yl)-8-((1,3-dioxoisoindolin-2-yl)methyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (537 mg, 0.883 mmol) in toluene (10 mL). The mixture was stirred at 70° C. for 3 hours and then cooled to room temperature for 16, then heated at 70° C. for a further 2.5 hours and again cooled to room temperature. The mixture was diluted with water (100 ml) and ethyl acetate (100 ml). The organic phase was separated, washed with 1M NaOH(aq) (50 ml) passed through a hydrophobic frit and evaporated under vacuum to afford the title compound as a mixture of diastereomers.

LC-MS Rt 0.82 min [M+H]+ 478.3 and Rt 0.89 min [M+H]+ 478.2 (Method 2minLowpHv03) The mixture was separated by SFC chromatographic resolution under the following conditions to afford the title compound as a single enantiomer Separation Conditions:
Column: Chiralcel OJ-H 250×10 mm, 5 um@35 degC
Mobile phase: 40% Methanol+0.1% v/v DEA/60% CO2
Flow: 10 ml/min
Detection: UV@220 nm Diastereoisomer 1 8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4 (3H,10H)-dione Rt=3.23 mins LC-MS Rt 0.81 min [M+H]⁺ 478.1 (Method 2minLow-pHv03)

1H NMR (400 MHz, CDCl3) δ 7.15 (s, 1H), 6.34 (dd, 1H), 6.17 (t, 2H), 4.63 (dd, 1H), 3.79 (dd, 1H), 3.69 (s, 3H), 3.61 (m, 1H), 3.41 (s, 3H), 2.69 (d, 2H), 2.53 (s, 3H)

Example 20

3-(9-(4-Chlorothiazol-2-yl)-1,3-dimethyl-2,4-dioxo-2,3,4,7,8,9-hexahydro-1H-pyrimido[4,5-a]pyrrolizin-5-yl)benzonitrile

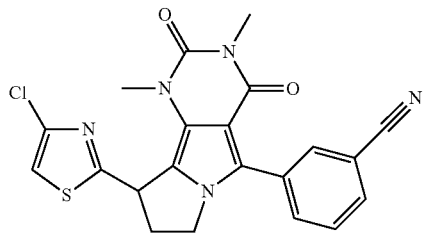 [SMILES: Cn1c(=O)c2c(-c3cccc(C#N)c3)n3c(c2n(C)c1=O)C(c1nc(Cl)cs1)CC3]

Step 1: Methyl 3-(5-(3-cyanophenyl)-1,3-dimethyl-2,4-dioxo-3,4-dihydro-1H-pyrrolo[3,4-d]pyrimidin-6 (2H)-yl)propanoate DBU (0.656 mL, 4.35 mmol) was added to a solution of 3-(1,3-dimethyl-2,4-dioxo-2,3,4,6-tetrahydro-1H-pyrrolo[3,4-d]pyrimidin-5-yl)benzonitrile (Example 9 Step 4) (1.22 g, 4.35 mmol) and methyl acrylate (0.392 mL, 4.35 mmol) in acetonitrile (15 mL). The mixture was stirred at room temperature for 4 days. Further portions of methyl acrylate (0.392 mL, 4.35 mmol) and DBU (0.656 mL, 4.35 mmol) were added as required to allow the reaction to run to completion. The reaction was quenched with saturated NH₄Cl(aq) and extracted with DCM (2×). The combined organic extracts were passed through a hydrophobic frit and evaporated under vacuum. Purification by chromatography on silica, eluting with 20-100% EtOAc/hexane afforded a crude material which was triturated with DCM/diethyl ether/hexane to afford the title compound.

LC-MS Rt 1.03 mins [M+H]+ 367.1 (Method 2minLow-pHv03)

1H NMR (400 MHz, CDCl3) δ 7.80-7.71 (3H, mult), 7.64 (1H, t), 6.51 (1H, s), 4.24 (2H t), 3.70 (3H, s), 3.43 (3H, s), 3.36 (3H, s), 2.69 (2H, t)

Step 2: 3-(5-(3-Cyanophenyl)-1,3-dimethyl-2,4-dioxo-3,4-dihydro-1H-pyrrolo[3,4-d]pyrimidin-6(2H)-yl)-N-methoxy-N-methylpropanamide Isopropylmagnesium bromide (2.82 mL, 8.19 mmol) was added slowly to a suspension of methyl 3-(5-(3-fluorophenyl)-1,3-dimethyl-2,4-dioxo-3,4-dihydro-1H-pyrrolo[3,4-d]pyrimidin-6(2H)-yl)propanoate (1 g, 2.73 mmol) and N,O-dimethylhydroxylamine hydrochloride (0.319 g, 3.28 mmol) in THF (30 mL) and the mixture was stirred at room temperature for 30 mins. The reaction was quenched with saturated NH4Cl(aq) and extracted with DCM (2×). The combined organic extracts were passed through a hydrophobic frit and evaporated under vacuum. Trituration with DCM/hexane afforded the title compound.

1H NMR (400 MHz, CDCl3) δ 7.76 (3H, mult), 7.64 (1H, t), 6.57 (1H, s), 4.27 (2H, t), 3.62 (3H, s), 3.44 (3H, s), 3.36 (3H, s), 3.18 (3H, s), 2.78 (2H, t).

LC-MS Rt 0.97 mins [M+H]+ 396.5 (Method 2minLow-pHv03)

Step 3: 3-(6-(3-(4-Chlorothiazol-2-yl)-3-oxopropyl)-1,3-dimethyl-2,4-dioxo-2,3,4,6-tetrahydro-1H-pyrrolo[3,4-d]pyrimidin-5-yl)benzonitrile Isopropylmagnesium chloride lithium chloride complex solution (4.58 mL, 5.95 mmol) was added slowly to a suspension of 3-(5-(3-cyanophenyl)-1,3-dimethyl-2,4-dioxo-3,4-dihydro-1H-pyrrolo[3,4-d]pyrimidin-6(2H)-yl)-N-methoxy-N-methylpropanamide (784 mg, 1.983 mmol) and 2-bromo-4-chlorothiazole (Intermediate Q, step 2) (394 mg, 1.983 mmol) in THF (30 mL). The mixture was stirred at room temperature for 40 mins. The reaction mixture was quenched with saturated NH4Cl(aq) and extracted with EtOAc (2×). The combined organic extracts were washed with brine, dried over sodium sulphate and evaporated under vacuum. Purification by chromatography on silica, eluting with 10-60% EtOAc/hexane afforded the title compound.

1H NMR (400 MHz, CDCl3) δ 7.79-7.59 (4H, mult), 7.51 (1H, s), 6.51 (1H, s), 4.41 (2H, t), 3.50 (2H, t), 3.41 (3H, s), 3.35 (3H, s)

LC-MS Rt 1.20 mins [M+H]+ 454.0 (Method 2minLow-pHv03)

Step 4: 3-(6-(3-(4-Chlorothiazol-2-yl)-3-hydroxypropyl)-1,3-dimethyl-2,4-dioxo-2,3,4,6-tetrahydro-1H-pyrrolo[3,4-d]pyrimidin-5-yl)benzonitrile Sodium borohydride (408 mg, 10.80 mmol) was added to a solution of 3-(6-(3-(4-chlorothiazol-2-yl)-3-oxopropyl)-1,3-dimethyl-2,4-dioxo-2,3,4,6-tetrahydro-1H-pyrrolo[3,4-d]pyrimidin-5-yl)benzonitrile (490 mg, 1.080 mmol) in methanol (20 mL). The mixture was stirred at room temp. for 25 mins, then quenched with saturated NaHCO3(aq) and extracted with chloroform (3×). The combined organic extracts were passed through a hydrophobic frit and evaporated under vacuum to afford the title compound.

1H NMR (400 MHz, CDCl3) δ 7.80-7.59 (4H, mult), 7.09 (1H, s), 6.51 (1H, s), 4.91 (1H, mult), 4.16 (2H, mult), 3.43 (3H, s), 3.37 (3H, s), 2.33 (1H, mult), 2.24 (1H, mult).

LC-MS Rt 1.11 mins [M+H]+ 456.1 (Method 2minLow-pHv03)

Step 5: 3-(9-(4-Chlorothiazol-2-yl)-1,3-dimethyl-2,4-dioxo-2,3,4,7,8,9-hexahydro-1H-pyrimido[4,5-a]pyrrolizin-5-yl)benzonitrile Trifluoromethanesulfonic anhydride (0.445 mL, 2.63 mmol) was added to a solution of 3-(6-(3-(4-chlorothiazol-2-yl)-3-hydroxypropyl)-1,3-dimethyl-2,4-dioxo-2,3,4,6-tetrahydro-1H-pyrrolo[3,4-d]pyrimidin-5-yl)benzonitrile (600 mg, 1.316 mmol) and triethylamine (0.550 mL, 3.95 mmol) in DCM (20 mL). The mixture was stirred at room temperature for 90 mins. Further portions of triethylamine (0.550 mL, 3.95 mmol) and trifluoromethanesulfonic anhydride (0.445 mL, 2.63 mmol) were added to allow the reaction to run to completion. The reaction mixture was quenched with saturated NaHCO3(aq) and extracted with DCM (3×). The combined organic extracts were passed through a hydrophobic frit and evaporated under vacuum. Purification by chromatography on silica, eluting with 20-80% EtOAc/hexane gave a crude material which was triturated with DCM/diethyl ether/hexane to afford the title compound.

1H NMR (400 MHz, CDCl3) δ 7.92 (1H, mult), 7.88 (1H, mult), 7.71 (1H, mult), 7.61 (1H, mult), 7.08 (1H, s), 5.04 (1H, dd), 4.26 (1H, mult), 4.11 (1H, mult), 3.41 (3H, s), 3.40 (3H, s), 3.15 (1H, mult), 2.86 (1H, mult).

LC-MS Rt 1.23 mins [M+H]+ 438.1 (Method 2minLow-pHv03)

Example 20a (R)-3-(9-(4-Chlorothiazol-2-yl)-1,3-dimethyl-2,4-dioxo-2,3,4,7,8,9-hexahydro-1H-pyrimido[4,5-a]pyrrolizin-5-yl)benzonitrile or (S)-3-(9-(4-chlorothiazol-2-yl)-1,3-dimethyl-2,4-dioxo-2,3,4,7,8,9-hexahydro-1H-pyrimido[4,5-a]pyrrolizin-5-yl)benzonitrile

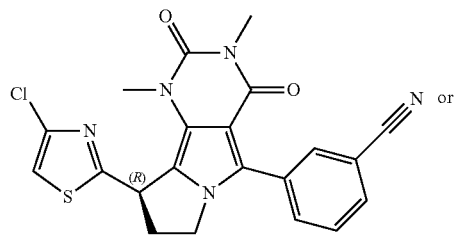

(R)-3-(9-(4-chlorothiazol-2-yl)-1,3-dimethyl-2,4-dioxo-2,3,4,7,8,9-hexahydro-1H-pyrimido[4,5-a]pyrrolizin-5-yl)benzonitrile

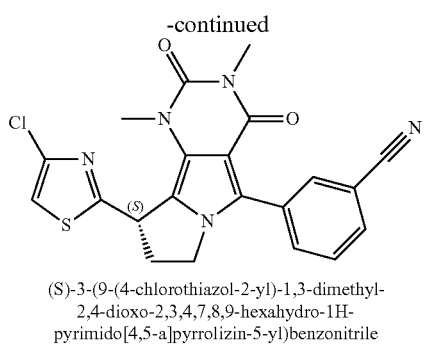

(S)-3-(9-(4-chlorothiazol-2-yl)-1,3-dimethyl-
2,4-dioxo-2,3,4,7,8,9-hexahydro-1H-
pyrimido[4,5-a]pyrrolizin-5-yl)benzonitrile Chiral separation of the racemic Example 20 by Supercritical Fluid Chromatography using the following conditions afforded the title compound:
Column: Chiralpak IA, 250×10 mm, 5 um@35° C.,
Mobile phase: 50% Methanol/50% CO2
Flow: 10 ml/min
Detection: UV@220 nm

Example 20a

Enantiomer 1 of 3-(9-(4-chlorothiazol-2-yl)-1,3-dimethyl-2,4-dioxo-2,3,4,7,8,9-hexahydro-1H-pyrimido[4,5-a]pyrrolizin-5-yl)benzonitrile SFC Rt=4.77 mins,
1H NMR (400 MHz, CDCl3) δ 7.93 (1H, mult), 7.88 (1H, s), 7.71 (1H, mult), 7.61 (1H, t), 7.08 (1H, s), 5.04 (1H, d), 4.26 (1H, mult), 4.11 (1H, mult), 3.41 (3H, s), 3.41 (3H, s, distinct peak), 3.16 (1H, mult), 2.86 (1H, mult)
LC-MS Rt 1.24 mins [M+H]+ 438.0 m/z (Method 2minLowpHv03)
The other enantiomer was isolated at Rt=6.97 mins
The following compounds were prepared analogously to Examples 20 by replacing 3-(1,3-dimethyl-2,4-dioxo-2,3,4,6-tetrahydro-1H-pyrrolo[3,4-d]pyrimidin-5-yl)benzonitrile with the appropriate starting compound (described hereinafter). Example 20.2 was separated by SFC chromatography to afford Example 20.2a

Example 20.1

9-(4-Chlorothiazol-2-yl)-1,3-dimethyl-5-(4-methylthiazol-2-yl)-8,9-dihydro-1H-pyrimido[4,5-a]pyrrolizine-2,4(3H,7H)-dione

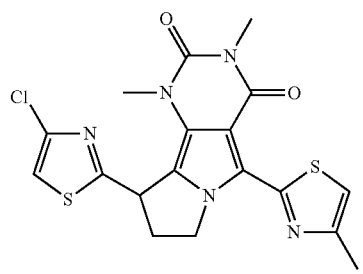 [SMILES: Cc1csc(-c2c3c(=O)n(C)c(=O)n(C)c3c3n2CCC3c2nc(Cl)cs2)n1]

1H NMR (400 MHz, CDCl3) δ 7.04 (1H, s), 7.02 (1H, s), 5.04 (1H, mult), 4.97 (1H, mult), 4.52 (1H, mult), 3.47 (3H, s), 3.40 (3H, s), 3.18 (1H, mult), 2.83 (1H, mult), 2.51 (3H, s)

LC-MS Rt 1.39 mins [M+H]+ 434.4 (Method 2minLowpHv03)

Example 20.2

9-(4-Chlorothiazol-2-yl)-5-(3-fluorophenyl)-1,3-dimethyl-8,9-dihydro-1H-pyrimido[4,5-a]pyrrolizine-2,4(3H,7H)-dione

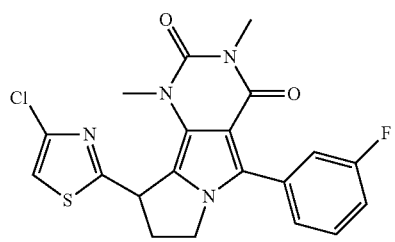 [SMILES: Cn1c(=O)c2c(-c3cccc(F)c3)n3c(c2n(C)c1=O)C(c1nc(Cl)cs1)CC3]

LC-MS Rt 1.30 mins [M+H]+ MS 431.5 (Method 2minLowpHv03)
1H NMR (400 MHz, CDCl3) δ 7.49-7.39 (2H, mult), 7.34 (1H, mult), 7.12 (1H, mult), 7.06 (1H, s), 5.02 (1H, dd), 4.21 (1H, mult), 4.11 (1H, mult), 3.40 (6H, apparent s), 3.12 (1H, mult), 2.83 (1H, mult).

Example 20.2a (R)-9-(4-Chlorothiazol-2-yl)-5-(3-fluorophenyl)-1,3-dimethyl-8,9-dihydro-1H-pyrimido[4,5-a]pyrrolizine-2,4(3H,7H)-dione or (S)-9-(4-Chlorothiazol-2-yl)-5-(3-fluorophenyl)-1,3-dimethyl-8,9-dihydro-1H-pyrimido[4,5-a]pyrrolizine-2,4(3H,7H)-dione

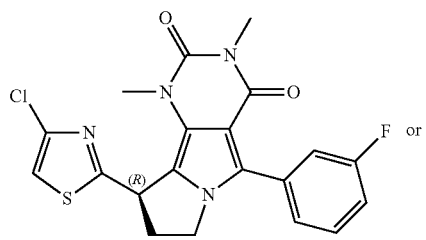

(R)-9-(4-chlorothiazol-2-yl)-5-(3-fluorophenyl)-1,3-dimethyl-8,9-dihydro-1H-pyrimido[4,5-a]pyrrolizine-2,4(3H,7H)-dione

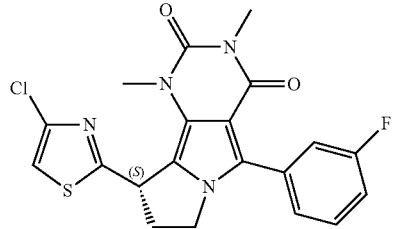

(S)-9-(4-chlorothiazol-2-yl)-5-(3-fluorophenyl)-1,3-dimethyl-8,9-dihydro-1H-pyrimido[4,5-a]pyrrolizine-2,4(3H,7H)-dione Separation Conditions:
Column: Chiralpak AD-H, 250×10 mm, 5 um@35 degC
Mobile phase: 50% Methanol/50% CO2
Flow: 10 ml/min
Detection: UV@220 nm Example 20.2a Enantiomer 1 of 9-(4-Chlorothiazol-2-yl)-5-(3-fluorophenyl)-1,3-dimethyl-8,9-dihydro-1H-pyrimido[4,5-a]pyrrolizine-2,4(3H,7H)-dione
Rt=3.24 mins
1H NMR (400 MHz, CDCl3) δ 7.49-7.37 (2H, mult), 7.34 (1H, d), 7.11 (1H, t), 5.02 (1H, d), 4.22 (1H, mult), 4.11 (1H, t), 3.39 (3H, s), 3.39 (3H, s, distinct peak), 3.12 (1H, mult), 2.82 (1H, dd)
LC-MS Rt 1.30 mins [M+H]$^+$ 431.1 (Method 2minLowpHv03)

Example 21

9-(4-Chlorothiazol-2-yl)-1,3,8,8-tetramethyl-5-phenyl-8,9-dihydro-1H-pyrimido[4,5-a]pyrrolizine-2,4(3H,7H)-dione

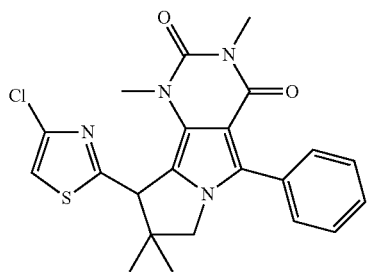 [SMILES: Cn1c(=O)c2c(-c3ccccc3)n3c(c2n(C)c1=O)C(c1nc(Cl)cs1)C(C)(C)C3]

Step 1: 7-((4-Chlorothiazol-2-yl)(hydroxy)methyl)-1,3-dimethyl-5-phenyl-1H-pyrrolo[3,4-d]pyrimidine-2,4(3H,6H)-dione Isopropylmagnesium chloride lithium chloride complex solution (1.3M, 2.82 mL, 3.67 mmol) was added slowly to 2-bromo-4-chlorothiazole (Intermediate Q, step 2) (729 mg, 3.67 mmol) in THF (2 mL) at 0° C. The mixture was stirred at 0° C. for 5 mins, then added dropwise to 1,3-dimethyl-2,4-dioxo-5-phenyl-2,3,4,6-tetrahydro-1H-pyrrolo[3,4-d]pyrimidine-7-carbaldehyde (Intermediate Na) (416 mg, 1.469 mmol) in THF (8 mL) at 0° C. and the resultant mixture stirred for 15 mins. The reaction mixture was quenched with saturated NH$_4$Cl(aq) and extracted with DCM (3×). The combined organic extracts were evaporated under vacuum. Purification by chromatography on silica, eluting with 40-100% EtOAc/hexane then 5-10% MeOH/EtOAc afforded a crude material which was triturated with DCM/EtOAc/diethyl ether/hexane to afford the title compound.
LC-MS Rt 1.11 mins; [M+H]$^+$ 403.1 (Method 2minLowpHv03)
1H NMR (400 MHz, DMSO-d6) δ 12.04 (1H, s), 7.79-7.73 (3H, mult), 7.48-7.38 (3H, mult), 7.25 (1H, d), 6.39 (1H, d), 3.47 (3H, s), 3.22 (3H, s).

Step 2: Methyl 3-(4-chlorothiazol-2-yl)-3-(1,3-dimethyl-2,4-dioxo-5-phenyl-2,3,4,6-tetrahydro-1H-pyrrolo[3,4-d]pyrimidin-7-yl)-2,2-dimethylpropanoate Boron trifluoride THF complex (0.028 mL, 0.255 mmol) was added to a solution of 7-((4-chlorothiazol-2-yl)(hydroxy)methyl)-1,3-dimethyl-5-phenyl-1H-pyrrolo[3,4-d]pyrimidine-2,4(3H,6H)-dione (114 mg, 0.283 mmol) and commercially available ((1-methoxy-2-methylprop-1-en-1-yl)oxy)trimethylsilane (0.143 mL, 0.707 mmol) in THF (5 mL). The mixture was stirred at room temperature for 5 minutes. The reaction was quenched with saturated NaHCO$_3$(aq) and extracted with DCM (2×). The combined organic extracts were passed through a hydrophobic frit and evaporated under vacuum. Purification by chromatography on silica, eluting with 20-80% EtOAc/hexane afforded the title compound.
1H NMR (400 MHz, DMSO-d6) δ 10.83 (1H, s), 7.92 (2H, d), 7.51 (2H, t), 7.43 (1H, t), 7.04 (1H, s), 5.11 (1H, s), 3.75 (3H, s), 3.73 (3H, s), 3.44 (3H, s), 1.53 (3H, s), 1.33 (3H, s).
LC-MS Rt 1.49 mins [M+H]$^+$ 487.5 (Method 2minLowpHv03)

Step 3: 7-(1-(4-Chlorothiazol-2-yl)-3-hydroxy-2,2-dimethylpropyl)-1,3-dimethyl-5-phenyl-1H-pyrrolo[3,4-d]pyrimidine-2,4(3H,6H)-dione Sodium borohydride (46.6 mg, 1.232 mmol) was added to a mixture of methyl 3-(4-chloro thiazol-2-yl)-3-(1,3-dimethyl-2,4-dioxo-5-phenyl-2,3,4,6-tetrahydro-1H-pyrrolo[3,4-d]pyrimidin-7-yl)-2,2-dimethylpropanoate (120 mg, 0.246 mmol) and lithium chloride (52.2 mg, 1.232 mmol) in methanol (10 mL). The mixture was stirred at room temp. for 30 mins. The reaction was quenched with saturated NaHCO$_3$ (aq) and extracted with DCM (3×). The combined organic extracts were passed through a hydrophobic frit and evaporated under vacuum to afford the title compound.
1H NMR (400 MHz, CDCl3) δ 10.71 (1H, s), 7.89 (2H, d), 7.50 (2H, t), 7.41 (1H, t), 7.04 (1H, s), 5.05 (1H, s), 3.73 (3H, s), 3.50 (1H, d), 3.43 (3H, s), 3.38 (1H, d), 1.19 (3H, s), 1.10 (3H, s).
LC-MS Rt 1.37 mins [M+H]$^+$ 459.1 (Method 2minLowpHv03)

Step 4: 3-(4-Chlorothiazol-2-yl)-3-(1,3-dimethyl-2,4-dioxo-5-phenyl-2,3,4,6-tetrahydro-1H-pyrrolo[3,4-d]pyrimidin-7-yl)-2,2-dimethylpropyl methanesulfonate Methanesulfonyl chloride (0.034 mL, 0.436 mmol) was added to a solution of 7-(1-(4-chlorothiazol-2-yl)-3-hydroxy-2,2-dimethylpropyl)-1,3-dimethyl-5-phenyl-1H-pyrrolo[3,4-d]pyrimidine-2,4(3H,6H)-dione (100 mg, 0.218 mmol) and triethylamine (0.076 mL, 0.545 mmol) in DCM (6 mL). The mixture was stirred at room temperature for 5 mins.
The reaction was quenched with saturated NaHCO$_3$(aq) and extracted with DCM. The organic phase was passed through a hydrophobic frit and evaporated under vacuum to afford the title compound as a crude material which was used without further purification;
LC-MS Rt 1.40 mins [M+H]$^+$ 537.5 (Method 2minLowpHv03)

Step 5: 9-(4-Chlorothiazol-2-yl)-1,3,8,8-tetramethyl-5-phenyl-8,9-dihydro-1H-pyrimido[4,5-a]pyrrolizine-2,4(3H,7H)-dione Sodium hydride (60% wt., 38.0 mg, 0.950 mmol) was added to a solution of 3-(4-chlorothiazol-2-yl)-3-(1,3-dimethyl-2,4-dioxo-5-phenyl-2,3,4,6-tetrahydro-1H-pyrrolo[3,4-d]pyrimidin-7-yl)-2,2-dimethylpropyl methanesulfonate (170 mg, 0.317 mmol) in THF (10 mL). The mixture was stirred at room temperature for 5 mins. The reaction was quenched with water and extracted with DCM (2×). The combined organic extracts were passed through a hydrophobic frit and evaporated under vacuum. Purification by chromatography on silica, eluting with 20-100% EtOAc/hexane afforded the title compound.

1H NMR (400 MHz, CDCl3) δ 7.66 (2H, d), 7.50 (2H, t), 7.44 (1H, t), 7.09 (1H, s), 4.55 (1H, s), 4.10 (1H, d), 3.78 (1H, d), 3.40 (3H, s), 3.33 (3H, s), 1.37 (3H, s), 1.06 (3H, s)

LC-MS Rt 1.40 mins [M+H]+ 441.1 (Method 2minLowpHv03)

Example 21a (S)-9-(4-Chlorothiazol-2-yl)-1,3,8,8-tetramethyl-5-phenyl-8,9-dihydro-1H-pyrimido[4,5-a]pyrrolizine-2,4(3H,7H)-dione or (R)-9-(4-chlorothiazol-2-yl)-1,3,8,8-tetramethyl-5-phenyl-8,9-dihydro-1H-pyrimido[4,5-a]pyrrolizine-2,4(3H,7H)-dione

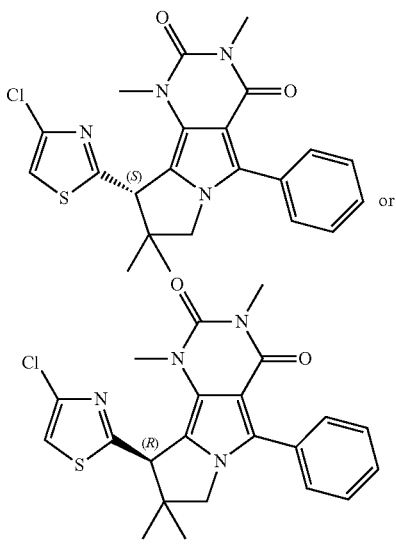

Chiral separation of the racemic Example 21 by Supercritical Fluid Chromatography was carried out using the following conditions to afford the title compound:
Column: Chiralcel OJ-H 250×10 mm, 5 um@35 degC
Mobile phase: 30% Methanol/70% CO2
Flow: 10 ml/min
Detection: UV@220 nm Example 21a Enantiomer 1 of 9-(4-chlorothiazol-2-yl)-1,3,8,8-tetramethyl-5-phenyl-8,9-dihydro-1H-pyrimido[4,5-a]pyrrolizine-2,4(3H,7H)-dione
Rt=5.48 mins
1H NMR (400 MHz, CDCl3) δ 7.55 (2H, d), 7.40 (2H, t), 7.33 (1H, t), 7.00 (1H, s), 4.45 (1H, s), 4.00 (1H, d), 3.68 (1H, d), 3.30 (3H, s), 3.23 (3H, s), 1.27 (3H, s), 0.96 (3H, s)

LC-MS Rt 1.39 mins [M+H]+ 441.1 (Method 2minLowpHv03)

The other enantiomer was isolated at Rt=4.27 mins

The following listed compounds were prepared in a similar manner to Example 21, using the appropriate starting material (the preparations of which are described hereinafter):

Example 21.1

9-(4-Chlorothiazol-2-yl)-5-(3-fluorophenyl)-1,3,8,8-tetramethyl-8,9-dihydro-1H-pyrimido[4,5-a]pyrrolizine-2,4(3H,7H)-dione

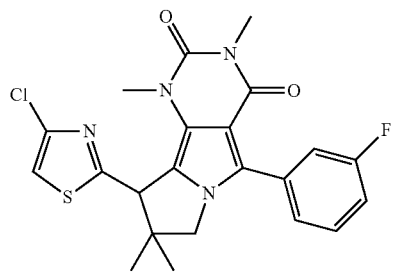 [SMILES: Cn1c(=O)c2c(-c3cccc(F)c3)n3c(c2n(C)c1=O)C(c1nc(Cl)cs1)C(C)(C)C3]

1H NMR (400 MHz, CDCl3) δ 7.50-7.43 (2H, mult), 7.38 (1H, mult), 7.15 (1H, mult), 7.10 (1H, s), 4.55 (1H, s), 4.11 (1H, d), 3.77 (1H, d), 3.40 (3H, s), 3.33 (3H, s), 1.37 (3H, s), 1.07 (3H, s).

LC-MS Rt 1.42 mins [M+H]+ 459.4 (Method 2minLowpHv03)

Example 21.2

9-(4-Chlorothiazol-2-yl)-1,3,8,8-tetramethyl-5-phenyl-8,9-dihydro-1H-pyrimido[4,5-a]pyrrolizine-2,4(3H,7H)-dione

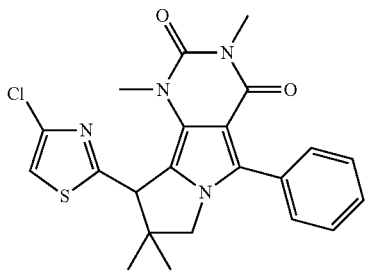 [SMILES: Cn1c(=O)c2c(-c3ccccc3)n3c(c2n(C)c1=O)C(c1nc(Cl)cs1)C(C)(C)C3]

1H NMR (400 MHz, CDCl3) δ 7.66 (2H, d), 7.50 (2H, t), 7.44 (1H, t), 7.09 (1H, s), 4.55 (1H, s), 4.10 (1H, d), 3.78 (1H, d), 3.40 (3H, s), 3.33 (3H, s), 1.37 (3H, s), 1.06 (3H, s)

LC-MS Rt 1.40 mins [M+H]+ 441.1 (Method 2minLowpHv03)

Example 21.3

3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile

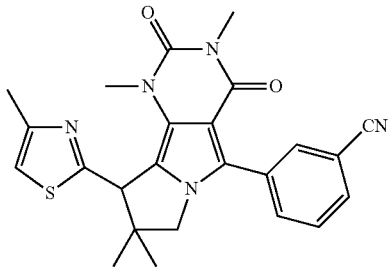 [SMILES: Cc1csc(C2c3c4c(c(-c5cccc(C#N)c5)n3CC2(C)C)c(=O)n(C)c(=O)n4C)n1]

1H NMR (400 MHz, CDCl3) δ 7.99 (1H, d), 7.88 (1H, s), 7.71 (1H, d), 7.62 (1H, t), 6.99 (1H, s), 4.88 (1H, s), 4.16 (1H, d), 3.76 (1H, d), 3.40 (3H, s), 3.33 (3H, s), 2.59 (3H, s), 1.43 (3H, s), 1.11 (3H, s)

LC-MS Rt 1.30 mins; [M+H]+ 446.4 (Method 2minLow-pHv03)

Example 21.4

5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione

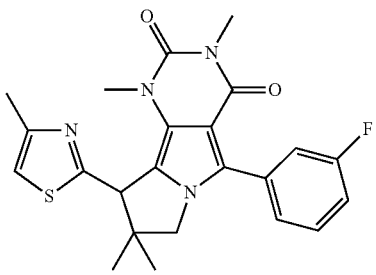 [SMILES: Cc1csc(C2c3c4c(c(-c5cccc(F)c5)n3CC2(C)C)c(=O)n(C)c(=O)n4C)n1]

1H NMR (400 MHz, CDCl3) δ 7.50-7.43 (2H, mult), 7.37 (1H, d), 7.14 (1H, mult), 7.00 (1H, s), 4.95 (1H, s), 4.10 (1H, d), 3.79 (1H, d), 3.40 (3H, s), 3.32 (3H, s), 2.61 (3H, s), 1.44 (3H, s), 1.12 (3H, s).

LC-MS Rt 1.35 mins [M+H]+ 439.3 (Method 2minLow-pHv03)

Example 21.5

1,3,8,8-Tetramethyl-9-(4-methylthiazol-2-yl)-5-phenyl-8,9-dihydro-1H-pyrimido[4,5-a]pyrrolizine-2,4(3H,7H)-dione

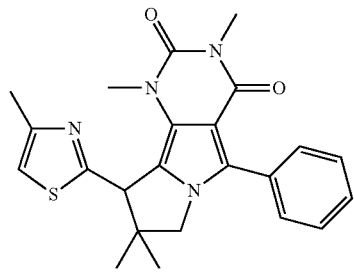 [SMILES: Cc1csc(C2c3c4c(c(-c5ccccc5)n3CC2(C)C)c(=O)n(C)c(=O)n4C)n1]

1H NMR (400 MHz, CDCl3) δ 7.65 (2H, d), 7.51 (2H, t), 7.45 (1H, t), 7.03 (1H, s), 5.03 (1H, s), 4.08 (1H, d), 3.81 (1H, d), 3.40 (3H, s), 3.32 (3H, s), 2.64 (3H, s), 1.45 (3H, s), 1.13 (3H, s)

LC-MS Rt 1.34 mins [M+H]+ 421.5 (Method 2minLow-pHv03)

The compounds of the following listed Examples were prepared by SFC chromatographic resolution of the appropriate racemate.

Example 21.6

(R)-9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione or (S)-9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione

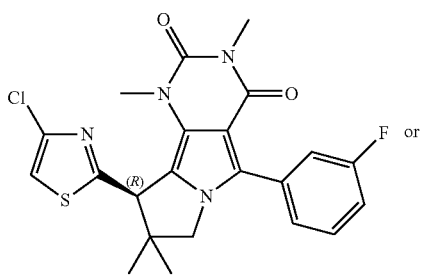

(R)-9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione

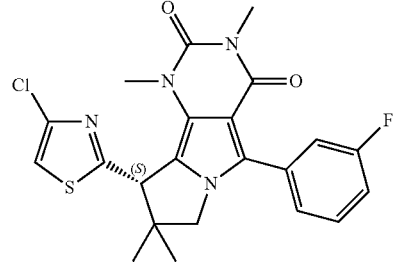

(S)-9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione Separation Conditions:

Column: Chiralpak AD-H 250×10 mm, 5 um@35 degC

Mobile phase: 50% Methanol/50% CO2

Flow: 10 ml/min

Detection: UV@220 nm

Enantiomer 1 of 9-(4-chlorothiazol-2-yl)-5-(3-fluorophenyl)-1,3,8,8-tetramethyl-8,9-dihydro-1H-pyrimido[4,5-a]pyrrolizine-2,4(3H,7H)-dione Rt=1.99 mins 1H NMR (400 MHz, CDCl3) δ 7.50-7.42 (2H, mult), 7.37 (1H, mult), 7.13 (1H, mult), 7.09 (1H, s), 4.54 (1H, s), 4.11 (1H, d), 3.77 (1H, d), 3.39 (3H, s), 3.32 (3H, s), 1.36 (3H, s), 1.06 (3H, s)

LC-MS Rt 1.45 mins [M+H]+ 459.3 (Method 2minLow-pHv03)

Example 21.7

(R)-5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione or (S)-5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione

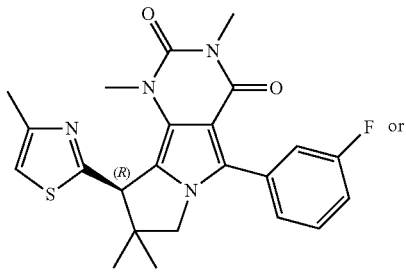

(R)-5-(3-fluorophenyl)-1,3,8,8-tetramethyl-9-(4-methylthiazol-2-yl)-8,9-dihydro-1H-pyrimidio[4,5-a]pyrrolizine-2,4(3H,7H)-dione

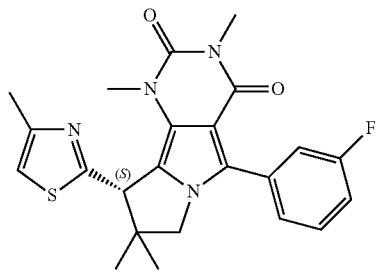

(S)-5-(3-fluorophenyl)-1,3,8,8-tetramethyl-9-(4-methylthiazol-2-yl)-8,9-dihydro-1H-pyrimidio[4,5-a]pyrrolizine-2,4(3H,7H)-dione Separation Conditions:

Column: Chiralpak AD-H 250×10 mm, 5 um@35 degC

Mobile phase: 20% methanol/80% CO2

Flow: 10 ml/min

Detection: UV@220 nm

Enantiomer 1 of 5-(3-fluorophenyl)-1,3,8,8-tetramethyl-9-(4-methylthiazol-2-yl)-8,9-dihydro-1H-pyrimido[4,5-a]pyrrolizine-2,4(3H,7H)-dione Rt=3.13 mins 1H NMR (400 MHz, CDCl3) δ 7.45 (2H, mult), 7.38 (1H, mult), 7.12 (1H, mult), 6.85 (1H, s), 4.54 (1H, s), 4.14 (1H, d), 3.75 (1H, d), 3.39 (3H, s), 3.31 (3H, s), 2.48 (3H, s), 1.35 (3H, s), 1.02 (3H, s)

LC-MS Rt 1.39 mins [M+H]+ 439.3 (Method 2minLow-pHv03)

Example 21.8

(R)-3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile or (S)-3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile

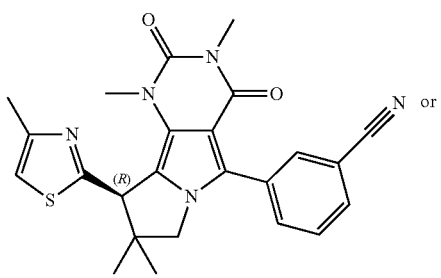

(R)-3-(1,3,8,8-tetramethyl-9-(4-methylthiazol-2-yl)-2,4-dioxo-2,3,4,7,8,9-hexahydro-1H-pyrimidio[4,5-a]pyrrolizin-5-yl)benzonitrile

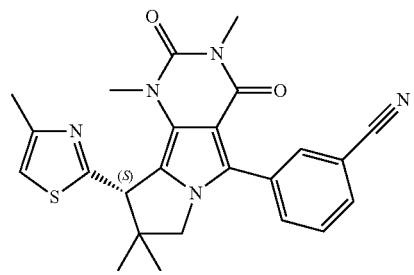

(S)-3-(1,3,8,8-tetramethyl-9-(4-methylthiazol-2-yl)-2,4-dioxo-2,3,4,7,8,9-hexahydro-1H-pyrimidio[4,5-a]pyrrolizin-5-yl)benzonitrile Separation Conditions:

Column: Chiralpak AD-H, 250×10 mm, 5 um@35 degC

Mobile phase: 20% Methanol/80% CO2

Flow: 10 ml/min

Detection: UV@220 nm

Enantiomer 1 of 3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile Rt=3.80 mins 1H NMR (400 MHz, CDCl3) δ 7.99 (1H, d), 7.88 (1H, s), 7.72 (1H, d), 7.63 (1H, t), 7.02 (1H, s), 4.97 (1H, s), 4.15 (1H, d), 3.76 (1H, d), 3.40 (3H, s), 3.33 (3H, s), 2.62 (3H, s), 1.45 (3H, s), 1.13 (3H, s).

LC-MS Rt 1.30 mins; [M+H]+ 446.4 (Method 2minLow-pHv03)

Example 21.9

(R)-1,3,8,8-Tetramethyl-9-(4-methylthiazol-2-yl)-5-phenyl-8,9-dihydro-1H-pyrimido[4,5-a]pyrrolizine-2,4(3H,7H)-dione or (S)-1,3,8,8-Tetramethyl-9-(4-methylthiazol-2-yl)-5-phenyl-8,9-dihydro-1H-pyrimido[4,5-a]pyrrolizine-2,4(3H,7H)-dione

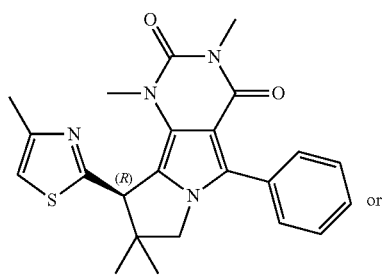

(R)-1,3,8,8-tetramethyl-9-(4-methylthiazol-2-yl)-5-phenyl-8,9-dihydro-1H-pyrimido[4,5-a]pyrrolizine-2,4(3H,7H)-dione

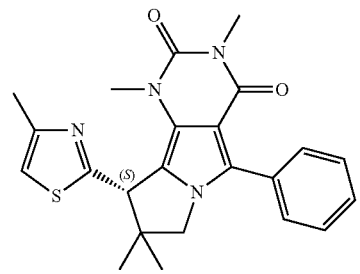

(S)-1,3,8,8-tetramethyl-9-(4-methylthiazol-2-yl)-5-phenyl-8,9-dihydro-1H-pyrimido[4,5-a]pyrrolizine-2,4(3H,7H)-dione Separation Conditions:

Column: Chiralpak AD-H 250×10 mm, 5 um@35 degC

Mobile phase: 25% Methanol/75% CO2

Flow: 10 ml/min

Detection: UV@220 nm

Enantiomer 1 of 1,3,8,8-Tetramethyl-9-(4-methylthiazol-2-yl)-5-phenyl-8,9-dihydro-1H-pyrimido[4,5-a]pyrrolizine-2,4(3H,7H)-dione Rt=2.89 mins 1H NMR (400 MHz, CDCl3) δ 7.65 (2H, d), 7.48 (2H, t), 7.41 (1H, t), 6.83 (1H, s), 4.54 (1H, s), 4.13 (1H, d), 3.74 (1H, d), 3.38 (3H, s), 3.31 (3H, s), 2.48 (3H, s), 1.35 (3H, s), 1.00 (3H, s)

LC-MS Rt 1.33 mins; [M+H]+ 421.3 (Method 2minLow-pHv03)

Example 22

10-(4-Chlorothiazol-2-yl)-1,3-dimethyl-5-(1-methyl-1H-pyrazol-3-yl)-7,8,9,10-tetrahydropyrimido[4,5-a]indolizine-2,4(1H,3H)-dione

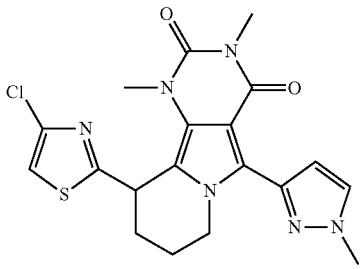 [SMILES: Cn1ccc(-c2c3c(=O)n(C)c(=O)n(C)c3c3n2CCCC3c2nc(Cl)cs2)n1]

Step 1: 1,3-Dimethyl-5-(1-methyl-1H-pyrazol-3-yl)-1H-pyrrolo[3,4-d]pyrimidine-2,4(3H,6H)-dione The title compound was prepared by a similar method to 3-(1,3-Dimethyl-2,4-dioxo-2,3,4,6-tetrahydro-1H-pyrrolo[3,4-d]pyrimidin-5-yl)benzonitrile (Example 9.0 Step 4), replacing 3-bromobenzonitrile with 3-iodo-1-methyl-1H-pyrazole in Step 3.

1H NMR (400 MHz, DMSO-d6) δ 12.07 (1H, s), 7.74 (1H, d), 7.36 (1H, d), 6.67 (1H, s), 3.91 (3H, s), 3.30 (3H, s), 3.24 (3H, s).

LC-MS Rt 1.85 mins [M+H]+ 259.0 (Method 5minLow-pHv01)

Step 2: 4-(1,3-Dimethyl-5-(1-methyl-1H-pyrazol-3-yl)-2,4-dioxo-3,4-dihydro-1H-pyrrolo[3,4-d]pyrimidin-6(2H)-yl)-N-methoxy-N-methylbutanamide 1,3-Dimethyl-5-(1-methyl-1H-pyrazol-3-yl)-1H-pyrrolo[3,4-d]pyrimidine-2,4(3H,6H)-dione (800 mg, 3.09 mmol), 4-bromo-N-methoxy-N-methylbutanamide (Intermediate P) (843 mg, 4.01 mmol) and cesium carbonate (2011 mg, 6.17 mmol) were suspended in DMF (11.100 ml) and the mixture was stirred at room temperature for 22 hours. The mixture was poured into water (50 ml) and extracted with DCM (3×100 ml). The combined organic extracts were washed with water (2×50 ml) and brine (50 ml), dried over sodium sulfate and evaporated under vacuum. Purification by mass-directed HPLC under the following conditions afforded the title compound.

Column: XSelect CSH Prep C18 column, 30×100 mm, 5 um.

Mobile phase: A=0.1% DEA in water, B=0.1% DEA in MeCN

Gradient:

0.0-0.5 min: 10% B 30 mL/min 0.5-1.0 min: 10% B 30-50 mL/min 1.0-7.2 min: 10-35% B, 7.2-7.3 min: 35-98% B, 7.3-9.4 min: 98% B 9.4-9.5 10% B 50 mL/min 1H NMR (400 MHz, DMSO-d6) δ 7.76 (1H, d), 6.91 (1H, s), 6.84 (1H, d), 4.27 (2H, t), 3.91 (3H, s), 3.59 (3H, s), 3.30 (3H, s), 3.19 (3H, s), 3.05 (3H, s), 2.32 (2H, t), 1.92 (2H, quint).

LC-MS Rt 0.87 mins [M+H]+ 389.6 (Method 2minLow-pHv03)

Step 3: 6-(4-(4-Chlorothiazol-2-yl)-4-oxobutyl)-1,3-dimethyl-5-(1-methyl-1H-pyrazol-3-yl)-1H-pyrrolo[3,4-d]pyrimidine-2,4(3H,6H)-dione Isopropylmagnesium chloride lithium chloride complex (3M solution in THF, 1.188 ml, 1.545 mmol) was added slowly to a solution of 4-(1,3-dimethyl-5-(1-methyl-1H-pyrazol-3-yl)-2,4-dioxo-3,4-dihydro-1H-pyrrolo[3,4-d]pyrimidin-6(2H)-yl)-N-methoxy-N-methylbutanamide (200 mg, 0.515 mmol) and 2-bromo-4-chlorothiazole (Intermediate Q, step 2) (112 mg, 0.566 mmol) in THF (3.280 ml) at 0° C. The mixture was then stirred at room temperature for 2 hours. A further portion of isopropylmagnesium chloride lithium chloride complex (3M solution in THF, 300 µl) was added and the mixture stirred for a further 15 mins. The reaction was quenched with saturated NH$_4$Cl(aq) (6 ml), diluted with water (20 ml) and extracted with EtOAc (3×30 ml). The combined organic extracts were washed with brine (10 ml), dried over sodium sulfate and evaporated under vacuum. Purification by chromatography on silica, eluting with 50-70% EtOAc/hexane, afforded the title compound.

1H NMR (400 MHz, DMSO-d6) δ 8.22 (1H, s), 7.70 (1H. d), 6.93 91H, s), 6.82 (1H, d), 4.35 (2H, t), 3.86 (3H, s), 3.26 (3H, s), 3.19 (3H, s), 306 (2H, t), 2.09 (2H, t)

LC-MS Rt 1.15 mins [M+H]+ 447.2 (Method 2minLow-pHv03)

Step 4: 10-(4-Chlorothiazol-2-yl)-1,3-dimethyl-5-(1-methyl-1H-pyrazol-3-yl)-7,8-dihydropyrimido[4,5-a]indolizine-2,4(1H,3H)-dione Pyridine hydrochloride (6.02 g, 52.1 mmol) was added to a suspension of 6-(4-(4-chlorothiazol-2-yl)-4-oxobutyl)-1,3-dimethyl-5-(1-methyl-1H-pyrazol-3-yl)-1H-pyrrolo[3,4-d]pyrimidine-2,4(3H,6H)-dione (2.33 g, 5.21 mmol) in methanol (82 ml) and water (8.17 ml) and the mixture stirred at room temperature for 3 days. The mixture was then diluted with chloroform (300 ml), washed with 1M HCl(aq) (3×100 ml) and saturated NaHCO$_3$(aq) (100 ml). The organic phase was passed through a hydrophobic frit and evaporated under vacuum. Purification by chromatography on silica, eluting with 50-80% EtOAc/hexane afforded a crude material which was triturated with methanol to afford the title compound.

1H NMR (400 MHz, DMSO-d6) δ 7.83 (1H, d), 7.80 (1H, s), 6.94 (1H, d), 6.66 (1H, t), 4.15 (2H, t), 3.96 (3H, s), 3.19 (3H, s), 2.68 (3H, s), 2.57 (2H, q).

LC-MS Rt 1.16 mins [M+H]+ 429.3 (Method 2minLow-pHv03)

Step 5: 10-(4-Chlorothiazol-2-yl)-1,3-dimethyl-5-(1-methyl-1H-pyrazol-3-yl)-7,8,9,10-tetrahydropyrimido[4,5-a]indolizine-2,4(1H,3H)-dione A suspension of 10-(4-chlorothiazol-2-yl)-1,3-dimethyl-5-(1-methyl-1H-pyrazol-3-yl)-7,8-dihydropyrimido[4,5-a]indolizine-2,4(1H,3H)-dione (25 mg, 0.058 mmol) and 10% platinum on carbon (12 mg, 6.15 µmol) in ethanol (2.2 ml) and THF (6.6 ml) was stirred under an atmosphere of hydrogen for 7 days. The mixture was filtered and the residue rinsed thoroughly with ethanol and the combined filtrates evaporated under vacuum. Purification by chromatography on silica, eluting with 80% EtOAc/hexane afforded a crude material which was triturated with diethyl ether to afford the title compound.

1H NMR (400 MHz, DMSO-d6) δ 7.79 (1H, d), 7.61 (1H, s), 6.72 (1H, d), 5.28 (1H, m), 4.46 (1H, obs d), 3.39 (3H, s), 3.88 (1H, m), 3.30 (3H, s), 3.19 (3H, s), 2.39-2.31 (2H, m), 2.25 (1H, t), 1.87 (1H, d), 1.64 (1H, q)

LC-MS Rt 1.14 mins [M+H]+ 431.4 (Method 2minLow-pHv03)

Example 23a, 23b and 23c (8R,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8R,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8S,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8S,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione

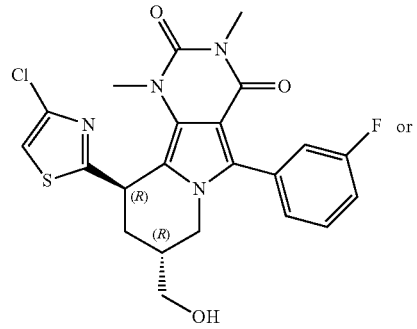

(8R,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4-(1H,3H)-dione

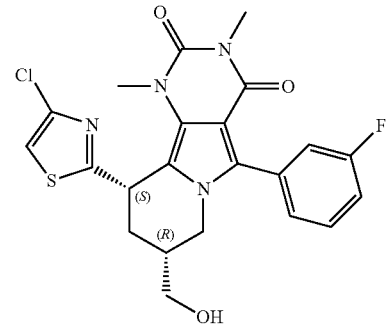

(8R,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4-(1H,3H)-dione -continued

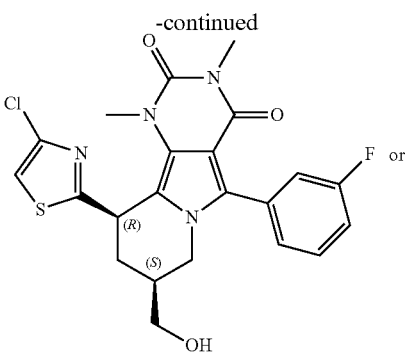

(8S,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4-(1H,3H)-dione

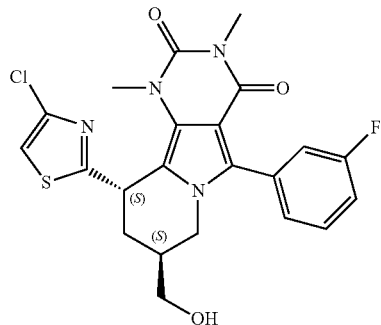

(8S,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4-(1H,3H)-dione Step 1: 4-(Hydroxymethyl)furan-2(5H)-one (Carbethoxymethylene)triphenylphosphorane (63.8 g, 183 mmol) was added in four portions to a suspension of 1,3-dihydroxyacetone (15.0 g, 167 mmol) in DCM (165 mL). The mixture was stirred at room temperature for 18 hours. The reaction mixture was extracted with water (4×150 mL). The combined aqueous phases were treated with 3 g of decolourising charcoal and filtered, washing the residue with a little water. The filtrates were evaporated under vacuum, then evaporated again from toluene to afford the title compound.

1H NMR (400 MHz, CDCl3) δ 6.05 (1H, s), 4.88 (2H, s), 4.61 (2H, s), 2.46 (1H, br).

Step 2: 4-(Hydroxymethyl)dihydrofuran-2(3H)-one

A mixture of 4-(hydroxymethyl)furan-2(5H)-one (1.0 g, 8.8 mmol) and 10% palladium on carbon (100 mg) in 2-methyltetrahydrofuran (9 mL) was stirred under an atmosphere of hydrogen for 23 hours. The reaction mixture was filtered and the residue rinsed with ethyl acetate. The filtrates were evaporated under vacuum to afford the title compound.

1H NMR (400 MHz, CDCl3) δ 4.14 (1H, dd), 4.24 (1H, dd), 3.74-3.66 (2H, mult), 2.78 (1H, mult), 2.63 (1H, dd), 2.41 (1H, dd), 2.26 (1H, br).

Step 3: (5-Oxotetrahydrofuran-3-yl)methyl trifluoromethanesulfonate

A solution of trifluoromethanesulfonic anhydride (15.0 g, 53.2 mmol) in DCM (25 mL) was added dropwise to a solution of 4-(hydroxymethyl)dihydrofuran-2(3H)-one (4.75 g, 41.0 mmol) and 2,6-lutidine (7.15 mL, 61.4 mmol) in DCM (111 mL) at 0° C. The mixture was stirred at 0° C. for 20 minutes. The product mixture was diluted with DCM (100 mL) and was washed with water (3×100 mL). The organic phase was dried over magnesium sulfate and evaporated under vacuum.

Purification by chromatography on silica, eluting with 30-50% EtOAc/hexane, afforded the title compound.

1H NMR (400 MHz, CDCl3) δ 4.60-4.49 (3H, mult), 4.22 (1H, dd), 3.13 (1H, mult), 2.79 (1H, dd), 2.43 (1H, dd).
19F NMR (376 MHz, CDCl3) δ −74.2.

Step 4: 5-(3-fluorophenyl)-1,3-dimethyl-6-((5-oxotetrahydrofuran-3-yl)methyl)-1H-pyrrolo[3,4-d]pyrimidine-2,4(3H,6H)-dione 5-(3-Fluorophenyl)-1,3-dimethyl-1H-pyrrolo[3,4-d]pyrimidine-2,4(3H,6H)-dione (2.50 g, 9.2 mmol) was added portionwise to a mixture of potassium tert-butoxide (1.18 g, 10.5 mmol) and 18-crown-6 (242 mg, 0.92 mmol) in THF (15 mL), and stirred at room temperature for 15 minutes. A solution of (5-oxotetrahydrofuran-3-yl)methyl trifluoromethanesulfonate (2.61 g, 10.5 mmol) in THF (7.5 mL) was then added, maintaining the temperature at ~20° C. using a water bath. The solution was stirred at room temperature for 1 hour. The reaction was quenched with saturated NH4Cl(aq) (10 mL), diluted with dichloromethane (100 mL) and washed with saturated NH4Cl(aq) (2×50 mL). The organic phase was dried over magnesium sulfate and the solvent evaporated under vacuum. Purification by chromatography on silica, eluting with 40-100% EtOAc/hexane, afforded the title compound.

LC-MS Rt 1.01 mins [M+H]+ 372.3 (Method 2minLowpHv03)

Step 5: Sodium 4-(5-(3-fluorophenyl)-1,3-dimethyl-2,4-dioxo-3,4-dihydro-1H-pyrrolo[3,4-d]pyrimidin-6(2H)-yl)-3-(hydroxymethyl)butanoate Sodium hydroxide (2M, 2.00 mL, 4.0 mmol) was added to a suspension of 5-(3-fluorophenyl)-1,3-dimethyl-6-((5-oxotetrahydrofuran-3-yl)methyl)-1H-pyrrolo[3,4-d]pyrimidine-2,4(3H,6H)-dione (1.35 g, 3.6 mmol) in ethanol (27 mL). The mixture was stirred at room temperature for 2 hours. The solvents were evaporated under vacuum to afford the title compound.

LC-MS Rt 0.93 mins [M-Na+H]+ 390.4 (Method 2minLowpHv03)

Step 6: 4-((tert-Butyldimethylsilyl)oxy)-3-((5-(3-fluorophenyl)-1,3-dimethyl-2,4-dioxo-3,4-dihydro-1H-pyrrolo[3,4-d]pyrimidin-6(2H)-yl)methyl)butanoic acid A solution of tert-butyldimethylsilyl trifluoromethanesulfonate (3.37 mL, 14.7 mmol) in DCM (5 mL) was added dropwise to a suspension of sodium 4-(5-(3-fluorophenyl)-1,3-dimethyl-2,4-dioxo-3,4-dihydro-1H-pyrrolo[3,4-d]pyrimidin-6(2H)-yl)-3-(hydroxymethyl)butanoate (1.51 g, 3.7 mmol) and 2,6-lutidine (2.57 mL, 22.0 mmol) in DCM (20 mL) at 0° C. The mixture was stirred at room temperature for 3 hours. Further portions of 2,6-lutidine (641 μL, 5.5 mmol) and tert-butyldimethylsilyl trifluoromethanesulfonate (843 μL, 3.7 mmol) were added and the mixture stirred for a further 2 hours. The reaction was diluted with DCM (50 mL), washed with water (2×25 mL) and 1M HCl(aq) (1×25 mL), the organic phase was dried over magnesium sulfate and evaporated under vacuum. The residue was suspended in methanol (25 mL) and pyridine hydrochloride (424 mg, 3.7 mmol) and water (2.5 mL) were added. The mixture was stirred at room temperature for 2 hours then concentrated under vacuum. The residue was dissolved in DCM (50 mL) and washed with 1M HCl (aq) (2×25 mL) and brine (1×25 mL). The organic phase was dried over magnesium sulfate and evaporated under vacuum. Trituration with diethyl ether afforded the title compound.

LC-MS Rt 1.51 mins [M+H]$^+$ 504.5 (Method 2minLowpHv03)

Step 7: 4-((tert-Butyldimethylsilyl)oxy)-3-((5-(3-fluorophenyl)-1,3-dimethyl-2,4-dioxo-3,4-dihydro-1H-pyrrolo[3,4-d]pyrimidin-6(2H)-yl)methyl)-N-methoxy-N-methylbutanamide T3P® (2.62 mL, 4.5 mmol) was added to a suspension of 4-((tert-butyldimethylsilyl)oxy)-3-((5-(3-fluorophenyl)-1,3-dimethyl-2,4-dioxo-3,4-dihydro-1H-pyrrolo[3,4-d]pyrimidin-6(2H)-yl)methyl)butanoic acid (1.13 g, 2.2 mmol), DIPEA (2.16 mL, 12.3 mmol) and N,O-dimethylhydroxylamine hydrochloride (263 mg, 2.7 mmol) in DMF (8 mL) at 0° C. The mixture was stirred at room temperature for 30 minutes. The reaction was diluted with ethyl acetate (40 mL) and was washed with water (1×20 mL), 1M HCl(aq) (1×20 mL) and saturated NaHCO$_3$(aq) (1×20 mL). The organic phase was dried over magnesium sulfate and the solvent was removed under vacuum. Purification by chromatography on silica, eluting with 0-3% MeOH/DCM, afforded the title compound.

LC-MS Rt 1.62 mins [M+H]$^+$ 547.4 (Method 2minLowpHv03)

Step 8: 6-(2-(((tert-Butyldimethylsilyl)oxy)methyl)-4-(4-chlorothiazol-2-yl)-4-oxobutyl)-5-(3-fluorophenyl)-1,3-dimethyl-1H-pyrrolo[3,4-d]pyrimidine-2,4(3H,6H)-dione Isopropylmagnesium chloride lithium chloride complex solution (1.3M, 1.6 mL, 2.1 mmol) was added to a solution of 4-((tert-butyldimethylsilyl)oxy)-3-((5-(3-fluorophenyl)-1,3-dimethyl-2,4-dioxo-3,4-dihydro-1H-pyrrolo[3,4-d]pyrimidin-6(2H)-yl)methyl)-N-methoxy-N-methylbutanamide (823 mg, 1.5 mmol) and 2-bromo-4-chlorothiazole (Intermediate Q, step 2) (418 mg, 2.1 mmol) in THF (8 mL) at 0° C. The mixture was stirred at room temperature for 1 hour. A further portion of isopropylmagnesium chloride lithium chloride complex solution (1.3M, 116 µL, 0.15 mmol) was added the mixture stirred for a further 1 hour. The reaction was quenched with saturated NH$_4$Cl(aq) (5 mL), diluted with ethyl acetate (40 mL) and washed with saturated NH$_4$Cl(aq) (3×20 mL). The organic phase was dried over magnesium sulfate and evaporated under vacuum. Purification by chromatography on silica, eluting with 20-40% EtOAc/hexane, afforded the title compound.

LC-MS Rt 1.80 mins [M+H]$^+$ 605.4 (Method 2minLowpHv03)

Step 9: 10-(4-Chlorothiazol-2-yl)-5-(3-fluorophenyl)-8-(hydroxymethyl)-1,3-dimethyl-7,8-dihydropyrimido[4,5-a]indolizine-2,4(1H,3H)-dione Pyridine hydrochloride (516 mg, 4.5 mmol) was added to a solution of 6-(2-(((tert-butyldimethylsilyl)oxy)methyl)-4-(4-chlorothiazol-2-yl)-4-oxobutyl)-5-(3-fluorophenyl)-1,3-dimethyl-1H-pyrrolo[3,4-d]pyrimidine-2,4(3H,6H)-dione (540 mg, 0.89 mmol) in methanol (14 mL) and water (1.4 mL). The mixture was stirred at room temperature for 18 hours. The reaction was concentrated under vacuum. The residue was diluted with ethyl acetate (30 mL) and washed with 1M HCl (3×15 mL). The organic phase was dried over magnesium sulfate, warmed at 35° C. for 15 minutes, then evaporated under vacuum.

Trituration with diethyl ether afforded the title compound.

LC-MS Rt 1.17 mins [M+H]$^+$ 473.4 (Method 2minLowpHv03)

Step 10: 10-(4-Chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione A mixture of 10-(4-Chlorothiazol-2-yl)-5-(3-fluorophenyl)-8-(hydroxymethyl)-1,3-dimethyl-7,8-dihydropyrimido[4,5-a]indolizine-2,4(1H,3H)-dione (310 mg, 0.66 mmol) and 10% platinum on carbon (310 mg) in ethanol (22 mL) and tetrahydrofuran (22 mL) was stirred under an atmosphere of hydrogen for 3 days. The reaction mixture was filtered and the filtrates concentrated under vacuum. The residue was dissolved in ethanol (22 mL) and tetrahydrofuran (22 mL), fresh 10% platinum on carbon (310 mg) was added and the mixture further stirred under an atmosphere of hydrogen for 5 days. The reaction mixture was filtered and the filtrates evaporated under vacuum. The residue was dissolved in 10 mL of 5% MeOH/DCM and the solution was treated with silica-TMT (trimercaptotriazine functionalized silica, ~1 g) for 5 minutes, then filtered. The residue was washed with 5% MeOH/DCM and the filtrates evaporated under vacuum.

Purification by chromatography on silica, eluting with 50-100% EtOAc/hexane afforded the title compound as a mixture of diastereomers.

LC-MS Rt 1.15 mins [M+H]$^+$ 475.3 (Method 2minLowpHv03)

Step 10: (8R,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8R,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8S,10R)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione or (8S,10S)-10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione The mixture of diastereomers was separated by SFC chromatographic resolution using the following combination of two SFC conditions in series to afford the title compounds as single diastereomers.

The first separation resolves Diastereoisomer 2 and another diastereoisomer.

The second separation resolves Diastereoisomer 1 and Diastereoisomer 3

Separation condition 1:
Column: Chiralpak OJ-H 250×10 mm, 5 μm
Mobile Phase: 40% MeOH/60% CO2
Flow: 10 mL/min
Detection: UV@220 nm Example 23b Diastereomer 2 of 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione, Rt=5.70 mins (First separation)

1H NMR (400 MHz, DMSO-d6) b 7.65 (1H, s), 7.53 (1H, mult), 7.41-7.28 (3H, mult), 5.29 (1H, t), 4.75 (1H, t), 3.89 (1H, mult), 3.74 (1H, t), 3.42 (1H, mult), 3.18-3.14 (6H, mult), 2.03 (1H, mult), 1.72 (1H, mult).

LC-MS Rt 1.15 mins [M+H]+ 475.4 (Method 2minLowpHv03)

Another Diastereomer of 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione, Rt=2.42 mins was isolated (First separation)

Second Separation Resolves Diastereomer 1 and Diastereomer 3

Column: Chiralcel OD-H 250×10 mm, 5 μm
Mobile Phase: 30% MeOH/70% CO2
Flow: 10 mL/min
Detection: UV@220 nm Example 23a Diastereomer 1 of 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione, Rt=6.02 mins (Second separation)

1H NMR (400 MHz, DMSO-d6) δ 7.63 (1H, s), 7.53 (1H, mult), 7.36-7.29 (3H, mult), 5.36 (1H, mult), 4.69 (1H, br t), 3.98 (1H, dd), 3.62 (1H, t), 3.29 (3H, s), 3.16 (3H, s), 2.35 (1H, d), 2.02 (1H, mult), 1.91 (1H, mult).

LC-MS Rt 1.15 mins [M+H]+ 475.3 (Method 2minLowpHv03)

Example 23c

Diastereomer 3 of 10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione, Rt=7.03 mins (Second separation)

1H NMR (400 MHz, DMSO-d6) δ 7.63 (1H, s), 7.53 (1H, mult), 7.36-7.28 (3H, mult), 5.36 (1H, mult), 4.69 (1H, br t), 3.98 (1H, dd), 3.62 (1H, t), 3.30 (3H, s), 3.16 (3H, s), 2.35 (1H, d), 2.02 (1H, mult), 1.91 (1H, mult).

LC-MS Rt 1.15 mins [M+H]+ 475.5 (Method 2minLowpHv03) The following listed examples were prepared in a similar manner to Example 23a, 23b and 23c replacing 5-(3-fluorophenyl)-1,3-dimethyl-1H-pyrrolo[3,4-d]pyrimidine-2,4(3H,6H)-dione in step 4 with the appropriate material (preparation described hereinafter). The mixtures of diastereomers were separated by SFC chromatographic resolution under the listed conditions to afford the title compounds as single diastereomers.

Example 23.1a, 23b and 23c 3-((8R,10R)-10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile or 3-((8S,10R)-10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile or 3-((8R,10S)-10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile or 3-((8S,10S)-10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile

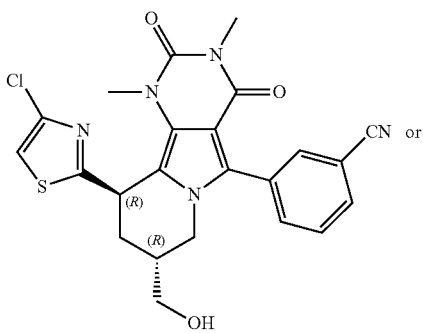

3-((8R,10R)-10-(4-chlorothiazol-2-yl)-8-(hydroxymethyl)-1,3-dimethyl-2,4-dioxo-1,2,3,4,7,8,9,10-octahydropyrimido[4,5-a]indolizine-5-yl)benzonitrile

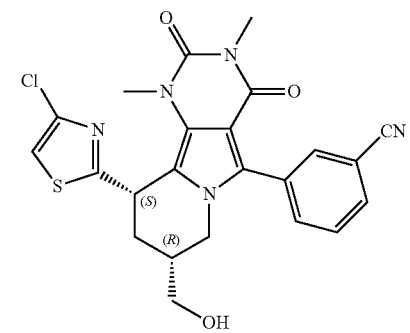

3-((8R,10S)-10-(4-chlorothiazol-2-yl)-8-(hydroxymethyl)-1,3-dimethyl-2,4-dioxo-1,2,3,4,7,8,9,10-octahydropyrimido[4,5-a]indolizine-5-yl)benzonitrile -continued

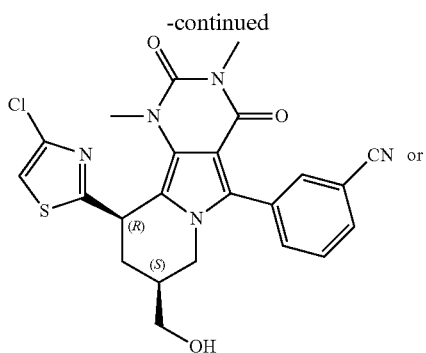

3-((8S,10R)-10-(4-chlorothiazol-2-yl)-8-
(hydroxymethyl)-1,3-dimethyl-2,4-dioxo-
1,2,3,4,7,8,9,10-octahydropyrimido[4,5-
a]indolizine-5-yl)benzonitrile

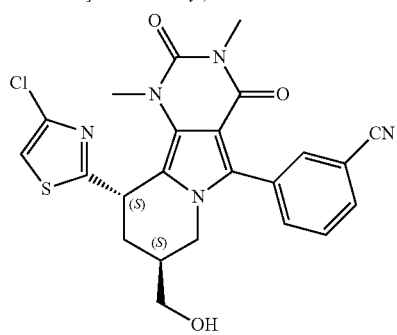

3-((8S,10S)-10-(4-chlorothiazol-2-yl)-8-
(hydroxymethyl)-1,3-dimethyl-2,4-dioxo-
1,2,3,4,7,8,9,10-octahydropyrimido[4,5-
a]indolizine-5-yl)benzonitrile Separation Conditions:

Column: LUX 250×10 mm, 5 μm

Mobile Phase: 50% MeOH/50% 002

Flow: 10 mL/min

Detection: UV@220 nm

Example 23.1a

Diastereomer 1 of 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile, Rt=17.26 mins 1H NMR (400 MHz, CDCl3) δ 7.79-7.72 (3H, mult), 7.63 (1H, t), 7.04 (1H, s), 5.18 (1H, mult), 4.14 (1H, dd), 3.73 (1H, dd), 3.65-3.55 (2H, mult), 3.45 (3H, s), 3.36 (3H, s), 2.63 (1H, d), 2.21-2.10 (2H, mult).

LC-MS Rt 1.11 mins [M+H]+ 482.5 (Method 2minLow-pHv03)

Example 23.1b

Diastereomer 2 of 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile, Rt=9.43 mins 1H NMR (400 MHz, CDCl3) δ 7.80-7.74 (3H, mult), 7.62 (1H, t), 7.07 (1H, s), 5.10 (1H, t), 4.02 (1H, dd), 3.75-3.66 (2H, mult), 3.61 (1H, dd), 3.37-3.35 (6H, mult), 2.66 (1H, mult), 2.26 (1H, mult), 2.17-2.08 (1H, mult).

LC-MS Rt 1.10 mins [M+H]+ 482.4 (Method 2minLow-pHv03)

Example 23.1c

Diastereomer 3 of 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile, Rt=14.67 mins 1H NMR (400 MHz, CDCl3) δ 7.80-7.74 (3H, mult), 7.62 (1H, t), 7.07 (1H, s), 5.10 (1H, t), 4.02 (1H, dd), 3.75-3.67 (2H, mult), 3.61 (1H, dd), 3.37-3.34 (6H, mult), 2.66 (1H, mult), 2.26 (1H, mult), 2.16-2.08 (1H, mult).

LC-MS Rt 1.10 mins [M+H]+ 482.4 (Method 2minLow-pHv03)

Diastereomer 4 was isolated at Rt=27.87 mins

Example 24

(7S)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione or (7R)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione

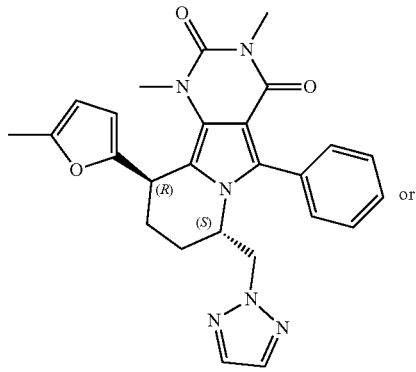

(7S,10R)-7-((2H-1,2,3-triazol-2-
yl)methyl)-1,3-dimethyl-10-(5-
methylfuran-2-yl)-5-phenyl-7,8,9,10-
tetrahydropyrimido[4,5-a]indolizine-
2,4(1H,3H)-dione

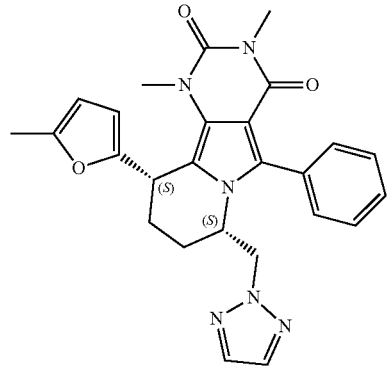

(7S,10S)-7-((2H-1,2,3-triazol-2-
yl)methyl)-1,3-dimethyl-10-(5-
methylfuran-2-yl)-5-phenyl-7,8,9,10-
tetrahydropyrimido[4,5-a]indolizine-
2,4(1H,3H)-dione

Step 1: (S)-Dibenzyl 2-(1,3-dimethyl-2,4-dioxo-5-phenyl-3,4-dihydro-1H-pyrrolo[3,4-d]pyrimidin-6(2H)-yl)pentanedioate 5-benzoyl-6-(bromomethyl)-1,3-dimethylpyrimidine-2,4 (1H,3H)-dione (Intermediate C) (2.04 g, 6.05 mmol), (S)-dibenzyl 2-aminopentanedioate (commercially available) (4.53 g, 9.08 mmol) and triethylamine (3.37 mL, 24.20 mmol) were suspended in dioxane (30 mL) and the mixture was heated at reflux for 2 hours. The mixture was cooled to room temperature and evaporated under vacuum. The residue was partitioned between DCM and 0.1M HCl(aq) and the phases separated. The organic phase was passed through a hydrophobic frit. Purification by chromatography on silica, eluting with 20-60% EtOAc/hexane, afforded the title compound.

1H NMR (400 MHz, CDCl3) δ 7.50-7.25 (15H, mult), 6.44 (1H, s), 5.24 (1H, d), 5.20 (1H, d), 4.99 (1H, d), 4.95 (1H, mult), 4.92 (1H, mult), 3.39 (3H, s), 3.35 (3H, s), 2.48 (1H, mult), 2.31 (1H, mult), 2.20 (1H, mult), 2.09 (1H, mult).

LC-MS Rt 1.33 mins [M+H]$^+$ 566.4 (Method 2minLowpHv01)

Step 2: (S)-2-(1,3-Dimethyl-2,4-dioxo-5-phenyl-3,4-dihydro-1H-pyrrolo[3,4-d]pyrimidin-6(2H)-yl)pentanedioic acid A suspension of (S)-dibenzyl 2-(1,3-dimethyl-2,4-dioxo-5-phenyl-3,4-dihydro-1H-pyrrolo[3,4-d]pyrimidin-6(2H)-yl)pentanedioate (3 g, 5.30 mmol) and 10% palladium on carbon (0.564 g, 0.530 mmol) in ethanol (100 mL) was stirred under a hydrogen atmosphere for 140 mins. The mixture was filtered through a Celite® cartridge (10 g, filter material) and the residue rinsed well with methanol and 7N NH$_3$/methanol. The combined filtrates were evaporated under vacuum to afford the title compound.

1H NMR (MHz, DMSO-d6) δ 7.45-7.38 (5H, mult), 6.90 (1H, s), 4.33 (1H, t), 3.33 (3H, s), 3.15 (3H, s), 2.31 (1H, mult), 2.11-1.87 (3H, mult).

LC-MS Rt 0.78 mins [M+H]$^+$ 386.3 (Method 2minLowpHv01)

Step 3: (S)-1,3-Dimethyl-2,4,10-trioxo-5-phenyl-1,2,3,4,7,8,9,10-octahydropyrimido[4,5-a]indolizine-7-carboxylic acid (S)-2-(1,3-Dimethyl-2,4-dioxo-5-phenyl-3,4-dihydro-1H-pyrrolo[3,4-d]pyrimidin-6(2H)-yl)pentanedioic acid (2.44 g, 6.33 mmol) and polyphosphoric acid (4.85 ml, 6.33 mmol) were combined and heated at 110° C. for 85 mins. The reaction mixture was cooled to ~50° C. and diluted with water to give a fluid mixture. The mixture was then cooled to room temperature, further diluted with water and extracted with chloroform (5×). The combined organic extracts were passed through a hydrophobic frit and evaporated under vacuum to afford the title compound.

LC-MS Rt 0.88 mins [M−H]$^−$ 366.2 (Method 2minLowpHv01)

Step 4: (S)-Methyl 1,3-dimethyl-2,4,10-trioxo-5-phenyl-1,2,3,4,7,8,9,10-octahydropyrimido[4,5-a]indolizine-7-carboxylate (S)-1,3-Dimethyl-2,4,10-trioxo-5-phenyl-1,2,3,4,7,8,9,10-octahydropyrimido[4,5-a]indolizine-7-carboxylic acid (1.85 g, 5.04 mmol), potassium carbonate (2.088 g, 15.11 mmol) and dimethyl sulfate (1.444 mL, 15.11 mmol) were combined in acetone (50 mL) and water (5 mL). The mixture was heated at reflux for 1.5 hours, then cooled to room temperature and evaporated under vacuum. The residue was partitioned between DCM and water and the phases separated. The organic phase was passed through a hydrophobic frit and evaporated under vacuum. Purification by chromatography on silica, eluting with 40-80% EtOAc/hexane, afforded the title compound.

LC-MS Rt 1.01 mins [M+H]$^+$ 382.3 (Method 2minLowpHv01)

Step 5: (7S)-Methyl 10-hydroxy-1,3-dimethyl-2,4-dioxo-5-phenyl-1,2,3,4,7,8,9,10-octahydropyrimido[4,5-a]indolizine-7-carboxylate Sodium borohydride (0.179 g, 4.72 mmol) was added slowly to a suspension of (S)-1,3-dimethyl-2,4,10-trioxo-5-phenyl-1,2,3,4,7,8,9,10-octahydropyrimido[4,5-a]indolizine-7-carboxylic acid (1.8 g, 4.72 mmol) in methanol (40 mL). The mixture was stirred at room temperature for 30 mins. The reaction was quenched with saturated NaHCO$_3$ (aq) and extracted with DCM. The organic phase was passed through a hydrophobic frit and evaporated under vacuum to afford the title compound.

LC-MS Rt 0.94 mins [M+H]$^+$ 384.3 (Method 2minLowpHv01)

Step 6: (7S)-Methyl 1,3-dimethyl-10-(5-methylfuran-2-yl)-2,4-dioxo-5-phenyl-1,2,3,4,7,8,9,10-octahydropyrimido[4,5-a]indolizine-7-carboxylate Gold (III) chloride (0.142 g, 0.469 mmol) was added to a solution of (7S)-methyl 10-hydroxy-1,3-dimethyl-2,4-dioxo-5-phenyl-1,2,3,4,7,8,9,10-octahydropyrimido[4,5-a]indolizine-7-carboxylate (1.8 g, 4.69 mmol) and 2-methylfuran (0.466 mL, 5.16 mmol) in acetonitrile (30 mL). The mixture was stirred at room temperature for 25 mins, then quenched with saturated NaHCO$_3$(aq). The mixture was extracted with DCM, the organic phase passed through a hydrophobic frit and evaporated under vacuum.

Purification by chromatography on silica, eluting with 20-40% EtOAc/hexane, afforded the title compound.

LC-MS Rt 1.22 mins [M+H]$^+$ 448.5 (Method 2minLowpHv01)

Step 7: (7S)-7-(Hydroxymethyl)-1,3-dimethyl-10-(5-methylfuran-2-yl)-5-phenyl-7,8,9,10-tetrahydropyrimido[4,5-a]indolizine-2,4(1H,3H)-dione Lithium aluminium hydride (1M in THF, 3.44 mL, 3.44 mmol) was added to a solution of (7S)-methyl 1,3-dimethyl-10-(5-methylfuran-2-yl)-2,4-dioxo-5-phenyl-1,2,3,4,7,8,9,10-octahydro pyrimido[4,5-a]indolizine-7-carboxylate (1.4 g, 3.13 mmol) in THF (30 mL) at 0° C. The mixture was stirred at room temp. for 1 hour. The reaction mixture was quenched at 0° C. by the slow dropwise addition of water (1 mL), stirred vigourously at 0° C. for 5 mins, then diluted with EtOAc and further stirred vigourously for 20 mins. The mixture was filtered, rinsing the residue with EtOAc. The filtrates were passed through a hydrophobic frit and evaporated under vacuum to afford the title compound.

LC-MS Rt 1.10 mins [M+H]+ 420.3 (Method 2minLow-pHv01)

Step 8: ((7S)-1,3-Dimethyl-10-(5-methylfuran-2-yl)-2,4-dioxo-5-phenyl-1,2,3,4,7,8,9,10-octahydropyrimido[4,5-a]indolizin-7-yl)methyl methanesulfonate Methanesulfonyl chloride (0.483 mL, 6.20 mmol) was added to a solution of (7S)-7-(hydroxyl methyl)-1,3-dimethyl-10-(5-methylfuran-2-yl)-5-phenyl-7,8,9,10-tetrahydropyrimido[4,5-a]indolizine-2,4(1H,3H)-dione (1.3 g, 3.10 mmol) and triethylamine (1.296 mL, 9.30 mmol) in DCM (30 mL). The mixture was stirred at room temp. for 105 mins. The reaction was quenched with saturated NaHCO$_3$(aq) and extracted with DCM. The organic extract was passed through a hydrophobic frit and evaporated under vacuum. Purification by chromatography on silica, eluting with 40-75% EtOAc/hexane, afforded the title compound.

LC-MS Rt 1.20 mins [M+H]+ 498.3 (Method 2minLow-pHv01)

Step 9: (7S)-7-((2H-1,2,3-tTriazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione ((7S)-1,3-Dimethyl-10-(5-methylfuran-2-yl)-2,4-dioxo-5-phenyl-1,2,3,4,7,8,9,10-octahydro pyrimido[4,5-a]indolizin-7-yl)methyl methanesulfonate (200 mg, 0.402 mmol), potassium carbonate (167 mg, 1.206 mmol) and 1,2,3-triazole (0.070 mL, 1.206 mmol) were combined in DMF (3 mL) and the mixture heated at 120° C. under microwave irradiation for 1 hour. The mixture was partitoned between EtOAc and water, and extracted with EtOAc (2×). The organic phase was washed with brine (4×), dried over sodium sulfate and evaporated under vacuum. Purification by chromatography on silica, eluting with 20-100% EtOAc/hexane, afforded the title compound as a mixture of diastereomers LC-MS Rt 1.34 mins [M+H]+ 471.3 (Method 2minLow-pHv04)

Step 10: (7S)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione or (7R)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione The diastereomeric mixture of (7S)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione was separated by SFC under the following conditions to afford the title compound as a single diastereomers.

Separation Conditions:
Column: Chiralcel OD-H 250×10 mm×5 um@34.5° C., UV@220 nm
Eluent: 25% MeOH/75% CO2
Flow: 10 mL/min
Detection: UV@220 nm Example 24

Enantiomer 1 of (7S)-7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione Rt=12.29 mins LC-MS Rt 1.37 mins [M+H]+ 471.6 (Method 2minLow-pHv03)

1H NMR (400 MHz, CDCl3) δ 7.52-7.39 (5H, mult), 7.20 (2H, s), 5.78 (1H, mult), 5.62 (1H, mult), 4.99 (1H, mult), 4.68 (1H, mult), 4.24 (1H, mult), 4.22 (1H, mult), 3.40 (3H, s), 3.27 (3H, s), 2.25 (1H, mult), 2.21 (3H, s), 2.07 (1H, mult), 1.81-1.62 (2H, mult).

The second diastereomer was isolated at Rt=5.93 mins.

Example 25

2-(10-(5-Chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylic acid

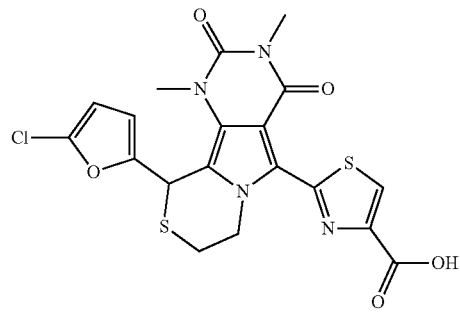 [SMILES: Cn1c(=O)c2c(-c3nc(C(=O)O)cs3)n3c(c2n(C)c1=O)C(c1ccc(Cl)o1)SCC3]

Ethyl 2-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylate (Example 15 Step 1)(72 mg, 0.142 mmol) and lithium hydroxide monohydrate (5.96 mg, 0.142 mmol) were suspended in THF (5 mL) and the mixture stirred at room temperature for 24 hours. Two portions of lithium hydroxide monohydrate (5.96 mg, 0.142 mmol) were added during this period. Water (2 mL) was then added and the mixture stirred for a further 30 mins. The resulting mixture was evaporated under vacuum. The residue was partitioned between water (20 ml) and DCM (20 mL) and brought to pH 1 with HCl(aq). The phases were separated and the aqueous phase was extracted with DCM (2×20 ml). The combined organic extracts were passed through a hydrophobic frit and evaporated under vacuum. The residue was re-suspended in DCM (5 ml) and loaded to a Isolute PE-AX ion exchange cartridge (1 g). The cartridge was eluted with DCM (50 ml), 1:1 MeOH:DCM (20 ml) and 4 M HCl/dioxane. The acidic eluent was evaporated under vacuum and the residue triturated with TBME:iso-hexane to afford the title compound.

1H NMR (400 MHz, DMSO-d6) δ 13.15 (1H, br s), 8.66 (1H, s), 6.42 (1H, d), 6.22 (1H, s), 6.20 (1H, dd), 4.61 (1H, dt), 4.45 (1H, m), 3.45 (3H, s), 3.21 (3H, s), 3.10-2.94 (2H, m)

LC-MS Rt 1.25 mins [M+H]+ 479.2 (Method 2minLow-pHv03)

Example 26a, 26b and 26c

N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide or N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide or N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide or N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8)methyl)methanesulfonamide

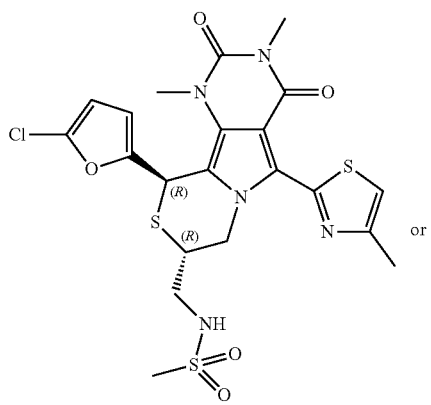

N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide

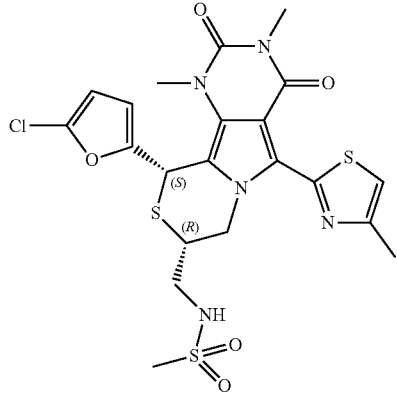

N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide

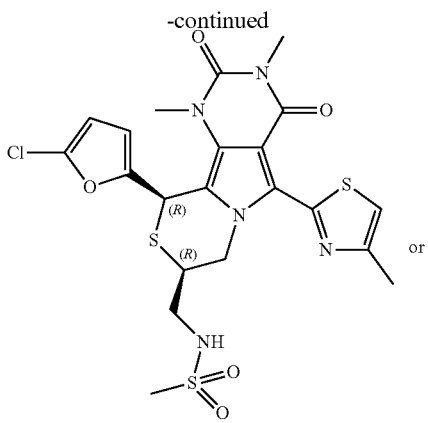

N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide

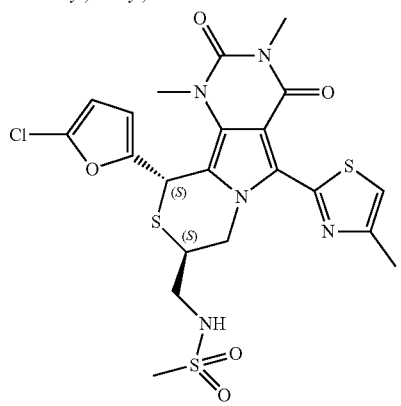

N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)methanesulfonamide Methanesulfonyl chloride (0.112 mL, 1.444 mmol) was added to a solution of 8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (Example 19) (69 mg, 0.144 mmol) and DIPEA (0.504 mL, 2.89 mmol) in DCM (2 mL). The mixture was stirred at room temperature for 16 hours, then diluted with ethyl acetate (20 ml) and washed with water (20 ml), 10% w/w citric acid (aq) (20 ml) and brine (20 ml). The organic layer was passed through a hydrophobic frit and evaporated under vacuum. Purification by mass-directed HPLC under the following conditions afforded two racemic diastereomers.

Column: XSelect CSH Prep C18 column, 30×100 mm, 5 um.

Mobile phase: A=0.1% DEA in water, B=0.1% DEA in MeCN

Gradient:
0.0-0.5 min: 30% B 30 mL/min
0.5-1.0 min: 30% B 30-50 mL/min
1.0-7.2 min: 30-70% B, 7.2-7.3 min: 70-98% B, 7.3-9.4 min: 98% B
9.4-9.5 30% B 50 mL/min Diastereomer pair 1 of N-((10-(5-chlorofuran-2-yl)-1,3-dimethyl-5-(4-methylthiazol-2-yl)-2,4-dioxo-2,3,4,7,8,10- hexahydro-1H-pyrimido[4',5':3,4]pyrrolo[2,1-c][1,4]thi-azin-8-yl)methyl)methanesulfonamide LC-MS Rt 1.21 min [M+H]+ 556.5 (Method 2minLow-pHv03)

Diastereomer pair 2 of N-((10-(5-chlorofuran-2-yl)-1,3-dim-ethyl-5-(4-methylthiazol-2-yl)-2,4-dioxo-2,3,4,7,8,10-hexahydro-1H-pyrimido[4',5':3,4]pyrrolo[2,1-c][1,4]thi-azin-8-yl)methyl)methanesulfonamide LCMS Rt 1.31 min [M+H]+ 556.5 (Method 2minLow-pHv03)

Diastereomer pair 1 was resolved into enantiomers by SFC chromatographic resolution under the following conditions to afford the listed compound.
  Column: OJ CHIRALCEL, 250×10 mm, 5 um@35° C.
  Mobile phase: 50% Methanol/50% CO2
  Flow: 10 ml/min
  Detection: UV@220 nm

Example 26b

Diastereomer 2 of N-((10-(5-chlorofuran-2-yl)-1,3-dim-ethyl-5-(4-methylthiazol-2-yl)-2,4-dioxo-2,3,4,7,8,10-hexahydro-1H-pyrimido[4',5':3,4]pyrrolo[2,1-c][1,4]thi-azin-8-yl)methyl)methanesulfonamide Rt=3.32 mins LC-MS Rt 1.23 min [M+H]+ 556.3 (Method 2minLow-pHv03)

1H NMR (400 MHz, CDCl3) δ 7.16 (s, 1H), 6.14 (d, 1H), 6.08 (d, 1H), 5.75 (s, 1H), 5.49 (dd, 1H), 5.26 (s, 1H), 4.21 (dd, 1H), 3.73 (m, 1H), 3.59 (s, 3H), 3.43 (s, 5H), 3.00 (s, 3H), 2.57 (s, 3H).

Diastereomer pair 2 was resolved into enantiomers by SFC chromatographic resolution under the following conditions to afford the listed compounds;
  Column: Chiralpak AD-H 250×10 mm, 5 um@35 degC
  Mobile phase: 50% Methanol/50% CO2
  Flow: 10 ml/min
  Detection: UV@220 nm

Example 26a

Diastereomer 1 of N-((10-(5-chlorofuran-2-yl)-1,3-dim-ethyl-5-(4-methylthiazol-2-yl)-2,4-dioxo-2,3,4,7,8,10-hexahydro-1H-pyrimido[4',5':3,4]pyrrolo[2,1-c][1,4]thi-azin-8-yl)methyl)methanesulfonamide, Rt=5.69 mins 1H NMR (400 MHz, CDCl3) δ 8.23 (s, 1H), 7.22 (s, 1H), 6.26 (dd, 1H), 6.13 (d, 1H), 5.79 (s, 1H), 5.41 (dd, 1H), 4.06 (dd, 1H), 3.85 (dd, 1H), 3.72 (s, 3H), 3.43 (s, 3H), 3.29 (m, 1H), 2.92 (s, 3H), 2.62 (s, 4H), 2.59 (m, 1H).

LC-MS Rt 1.32 min [M+H]+ 556.3 (Method 2minLow-pHv03)

Example 26c

Diastereomer 3 of N-((10-(5-chlorofuran-2-yl)-1,3-dim-ethyl-5-(4-methylthiazol-2-yl)-2,4-dioxo-2,3,4,7,8,10-hexahydro-1H-pyrimido[4',5':3,4]pyrrolo[2,1-c][1,4]thi-azin-8-yl)methyl)methanesulfonamide Rt=4.45 mins 1H NMR (400 MHz, CDCl3) δ 8.22 (s, 1H), 7.22 (s, 1H), 6.26 (dd, 1H), 6.13 (d, 1H), 5.79 (s, 1H), 5.41 (dd, 1H), 4.06 (d, 1H), 3.85 (dd, 1H), 3.72 (s, 3H), 3.43 (s, 3H), 3.29 (d, 1H), 2.92 (s, 3H), 2.62 (s, 3H), 2.59 (m, 1H).

LC-MS Rt 1.30 min [M+H]+ 556.3 (Method 2minLow-pHv03)

The following listed examples were prepared in a similar manner to Example 26a, b and c by replacing methanesulfonyl chloride with the appropriate acyl chloride. Purification and chromatographic conditions as described.

Example 26.1a, 26.1b and 26.1c

N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide or N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide or N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide or N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide

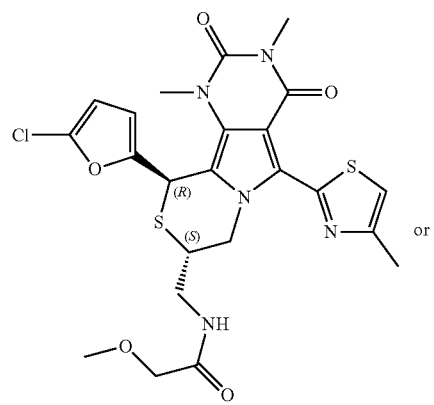

N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide

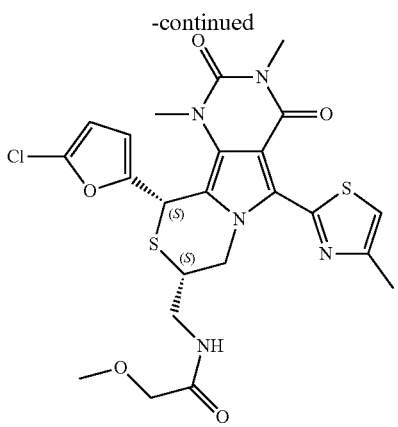

N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide

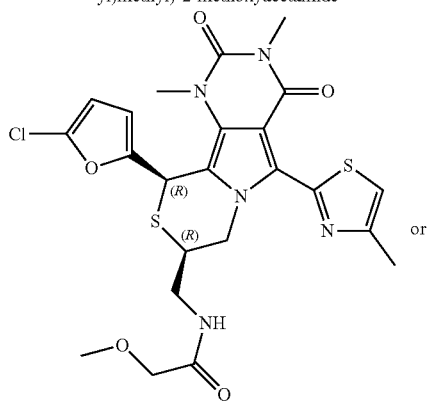

N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide or

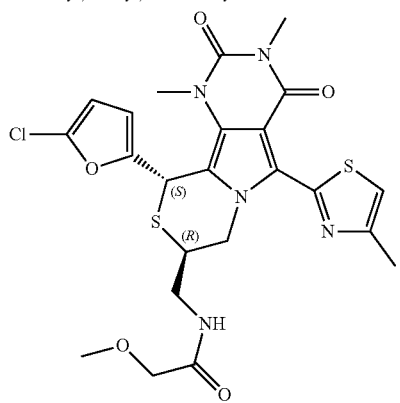

N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide Separation of the racemic diastereomers by achiral SFC:
Column: Princeton DEAP 21.2×150 mm, 5 um
Mobile Phase: A=Methanol, B=002
Flow: 100 mL/min Gradient:
0-0.5 min: 1% A
0.5-8.0 min: 1-10% A
8.0-8.1 min: 10-40% A
8.1-8.6 min: 40% A
8.6-8.7 min: 40-1% A Diastereomer pair 1 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide LC-MS Rt=1.21 mins [M+H]$^+$ 550.5 (Method 2minLow-pHv03)

Diastereomer pair 2 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide LC-MS Rt=1.21 mins [M+H]$^+$ 550.5 (Method 2minLow-pHv03)

Diastereomer pair 1 was separated by SFC chromatographic resolution under the following conditions to afford the listed compound;
Column: Chiralcel OJ-H 250×10 mm, 5 um@35 degC
Mobile phase: 45% Methanol/55% CO2
Flow: 10 ml/min
Detection: UV@220 nm Example 26.1b Diastereomer 2 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide, Rt=2.88 mins 1H NMR (400 MHz, Chloroform-d) δ 7.12 (s, 1H), 6.92 (t, 1H), 6.22 (dd, 1H), 6.13 (d, 1H), 5.77 (d, 1H), 5.70 (dd, 1H), 3.89 (s, 2H), 3.87-3.82 (m, 1H), 3.72 (m, 1H), 3.66 (s, 3H), 3.66 (m, 1H), 3.55 (m, 1H), 3.43 (s, 3H), 3.43 (s, 3H), 2.52 (s, 3H)

LC-MS Rt 1.31 min [M+H]$^+$ 550.4 (Method 2minLow-pHv03)

Diastereomer pair 2 was separated by SFC chromatographic resolution under the following conditions to afford the listed compounds;
Column: Chiralpak AD-H 250×10 mm, 5 um@35 degC
Mobile phase: 40% Isopropanol/60% CO2
Flow: 10 ml/min
Detection: UV@220 nm Example 26.1a Diastereomer 1 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide, Rt=5.21 mins 1H NMR (400 MHz, CDCl3) δ 7.18 (m, 1H), 7.16 (s, 1H), 6.24 (dd, 1H), 6.12 (d, 1H), 5.77 (d, 1H), 5.49 (dd, 1H), 4.19 (dd, 1H), 3.93 (d, 1H), 3.84 (d, 1H), 3.76 (m, 1H), 3.70 (s, 3H), 3.44 (s, 3H), 3.39 (m, 1H), 3.36 (s, 3H), 3.03 (m, 1H), 2.57 (s, 3H)

LC-MS Rt 1.23 min [M+H]+ 550.2 (Method 2minLow-pHv03)

Example 26.1c

Diastereomer 3 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide, Rt=3.55 mins 1H NMR (400 MHz, CDCl3) δ 7.18 (m, 1H), 7.16 (s, 1H), 6.24 (dd, 1H), 6.12 (d, 1H), 5.77 (d, 1H), 5.49 (dd, 1H), 4.19 (dd, 1H), 3.93 (d, 1H), 3.84 (d, 1H), 3.76 (m, 1H), 3.70 (s, 3H), 3.44 (s, 3H), 3.39 (m, 1H), 3.36 (s, 3H), 3.03 (m, 1H), 2.57 (s, 3H)

LC-MS Rt 1.23 min [M+H]+ 550.2 (Method 2minLow-pHv03)

Example 26.2a and 26.2b

Methyl (((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate or Methyl (((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate or Methyl (((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate or Methyl (((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate

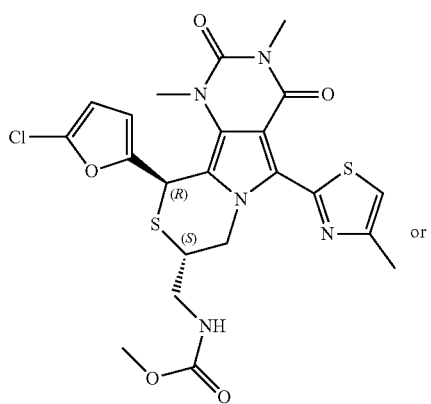

methyl (((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate or

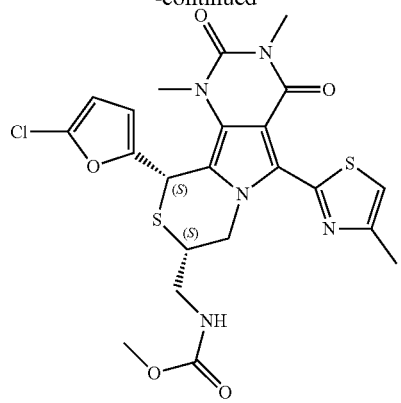

methyl (((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate

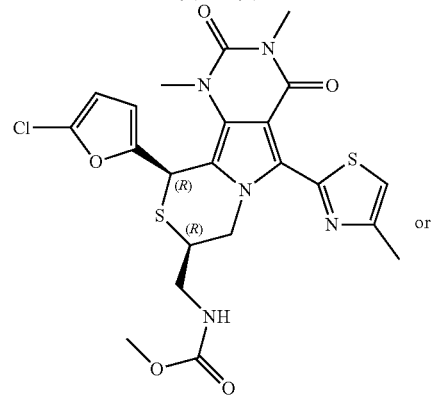

methyl (((8R,10R)-10-(5-chlorofuran-2-yl)-1,3-dimethyl-5-(4-methylthiazol-2-yl)-1,4-dioxo-2,3,4,7,8,10-hexahydro-1H-pyrimido[4',5':3,4]pyrrolo[2,1-c][1,4]thiazin-8-yl)methyl)carbamate or

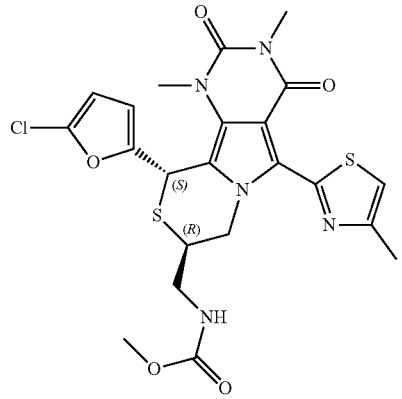

methyl (((8R,10S)-10-(5-chlorofuran-2-yl)-1,3-dimethyl-5-(4-methylthiazol-2-yl)-1,4-dioxo-2,3,4,7,8,10-hexahydro-1H-pyrimido[4',5':3,4]pyrrolo[2,1-c][1,4]thiazin-8-yl)methyl)carbamate The mixture of diastereomers was separated into two racemic diastereomers by mass-directed HPLC under the following conditions;
Column: XSelect CSH Prep C18 column, 30×100 mm, 5 um.
Mobile phase: A=0.1% DEA in water, B=0.1% DEA in MeCN
Gradient:
0.0-0.5 min: 40% B 30 mL/min
0.5-1.0 min: 40% B 30-50 mL/min
1.0-7.2 min: 40-80% B, 7.2-7.3 min: 80-98% B, 7.3-9.4 min: 98% B
9.4-9.5 40% B 50 mL/min
Diastereomer pair 1 of methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate
LC-MS Rt 1.28 mins [M+H]+ 536.2 (Method 2minLow-pHv03)
Diastereomer pair 2 of methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate
LC-MS Rt 1.36 mins [M+H]+ 536.2 (Method 2minLow-pHv03)
Diastereomer pair 1 was resolved into single diastereomers by SFC chromatographic resolution under the following conditions to give the listed compound;
Column: OJ CHIRALCEL, 250×10 mm, 5 um@35° C.
Mobile phase: 50% Methanol/50% CO2
Flow: 10 ml/min
Detection: UV@220 nm Example 26.2a Diastereomer 1 of methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate, Rt=3.46 mins
1H NMR (400 MHz, CDCl3) δ 7.12 (d, 1H), 6.13 (d, 2H), 5.74 (s, 1H), 5.66 (dd, 1H), 5.22 (s, 1H), 3.90 (dd, 1H), 3.70 (s, 1H), 3.68 (s, 3H), 3.64 (s, 3H), 3.54 (m, 1H), 3.44 (m, 1H), 3.43 (s, 3H), 2.53 (s, 3H)
LC-MS Rt 1.29 min [M+H]+ 536.3 (Method 2minLow-pHv03)
Diastereomer pair 2 was resolved into single diastereomers by SFC chromatographic resolution under the following conditions to give the listed compound;
Column: Chiralpak AD-H, 250×10 mm, 5 um@35 degC
Mobile phase: 40% Methanol/60% CO2
Flow: 10 ml/min
Detection: UV@220 nm Example 26.2b Diastereomer 2 of methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate, Rt=6.10 mins
1H NMR (400 MHz, CDCl3) δ 7.65 (s, 1H), 7.20 (s, 1H), 6.25 (d, 1H), 6.12 (d, 1H), 5.77 (s, 1H), 5.41 (d, 1H), 3.99 (d, 1H), 3.71 (s, 6H), 3.69 (m, 1H), 3.59 (d, 1H), 3.43 (s, 3H), 2.60 (s, 3H), 2.55 (dd, 1H)
LC-MS Rt 1.36 min [M+H]+ 536.2 (Method 2minLow-pHv03)

Example 26.3a, 26.3b, 26.3c and 26d

N-(((8S,10R)-10-(5-Chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl) acetamide or N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl) acetamide or N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl) acetamide or N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl) acetamide

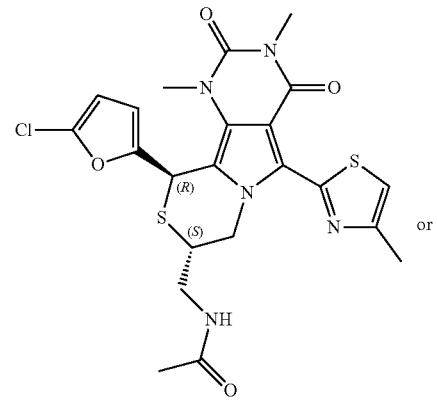

N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide

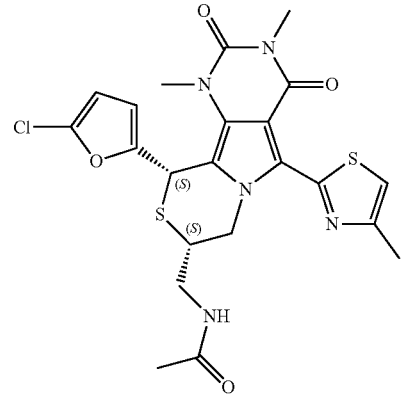

N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide

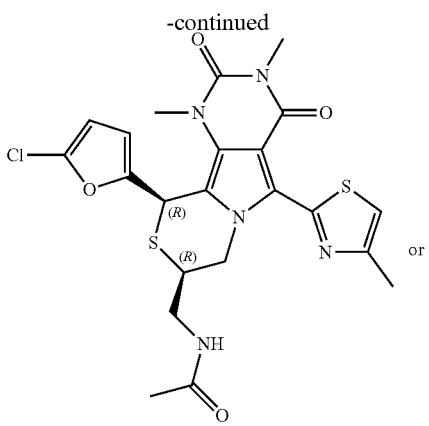

N-(((8R,10R)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)acetamide

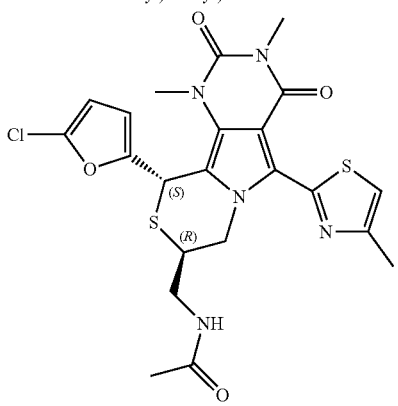

N-(((8R,10S)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)acetamide The mixture of diastereomers was separated by single-step SFC chromatographic resolution under the listed conditions to give the title compounds.
Column: Chiralpak AD-H 250×10 mm, 5 um@35 degC
Mobile phase: 30% Isopropanol/70% CO2
Flow: 10 ml/min
Detection: UV@220 nm Example 26.3a Diastereomer 1 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide, Rt=9.38 mins
1H NMR (400 MHz, CDCl3) δ 7.14 (s, 1H), 6.14 (d, 1H), 6.12 (dd, 1H), 5.99 (t, 1H), 5.75 (d, 1H), 5.57 (dd, 1H), 3.85 (dd, 1H), 3.74 (m, 1H), 3.64 (m, 1H), 3.63 (s, 3H), 3.45 (dd, 1H), 3.42 (s, 3H), 2.53 (s, 3H), 1.97 (s, 3H)
LC-MS Rt 1.23 min [M+H]+ 520.4 (Method 2minLow-pHv03)

Example 26.3b

Diastereomer 2 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide, Rt=12.03 mins
1H NMR (400 MHz, CDCl3) δ 7.59 (dd, 1H), 7.23 (s, 1H), 6.25 (dd, 1H), 6.11 (d, 1H), 5.78 (s, 1H), 5.37 (dd, 1H), 4.05 (m, 1H), 3.72 (m, 2H), 3.71 (s, 3H), 3.42 (s, 3H), 2.59 (s, 3H), 2.45 (m, 1H), 2.06 (s, 3H)
LC-MS Rt 1.19 min [M+H]+ 520.3 (Method 2minLow-pHv03)

Example 26.3c

Diastereomer 3 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide, Rt=4.82 mins
1H NMR (400 MHz, CDCl3) δ 7.14 (s, 1H), 6.14 (d, 1H), 6.12 (dd, 1H), 6.01 (t, 1H), 5.75 (d, 1H), 5.57 (dd, 1H), 3.85 (dd, 1H), 3.74 (m, 1H), 3.64 (m, 1H), 3.63 (s, 3H), 3.45 (dd, 1H), 3.42 (s, 3H), 2.53 (s, 3H), 1.97 (s, 3H)
LC-MS Rt 1.15 min [M+H]+ 520.3 (Method 2minLow-pHv03)

Example 26.3d

Diastereomer 4 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide, Rt=5.82 mins
1H NMR (400 MHz, CDCl3) δ 7.59 (dd, 1H), 7.23 (s, 1H), 6.25 (dd, 1H), 6.11 (d, 1H), 5.78 (s, 1H), 5.37 (dd, 1H), 4.05 (m, 1H), 3.72 (m, 2H), 3.71 (s, 3H), 3.42 (s, 3H), 2.59 (s, 3H), 2.45 (m, 1H), 2.06 (s, 3H)
LC-MS Rt 1.20 min [M+H]+ 520.5 (Method 2minLow-pHv03)

Example 26.4a and 26.4b

N-(((8S,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide or N-(((8S,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide or N-(((8R,10R)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide or N-(((8R,10S)-10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide

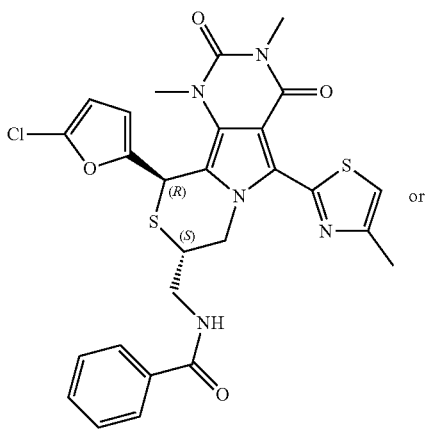

N-(((8S,10R)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)benzamide

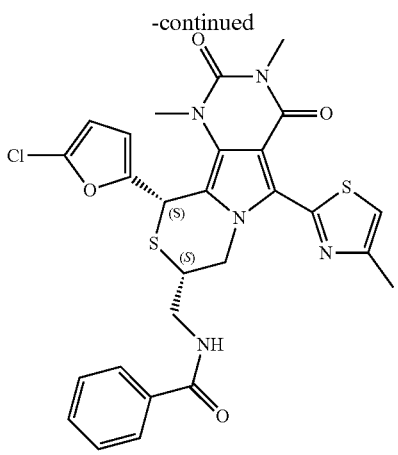

N-(((8S,10S)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)benzamide

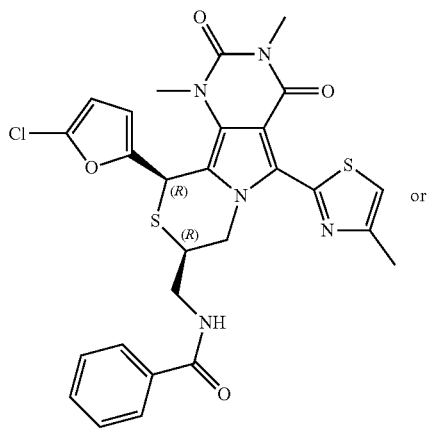

or

N-(((8R,10R)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)benzamide

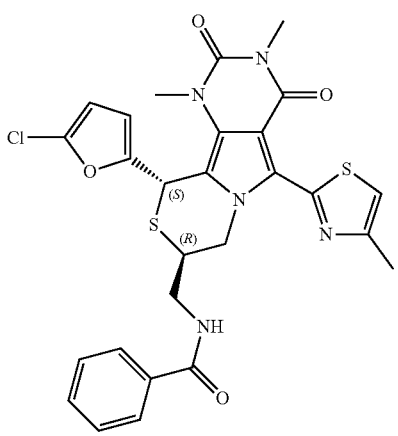

N-(((8R,10S)-10-(5-chlorofuran-2-yl)-
1,3-dimethyl-5-(4-methylthiazol-2-yl)-
2,4-dioxo-2,3,4,7,8,10-hexahydro-1H-
pyrimido[4',5':3,4]pyrrolo[2,1-c][1,4]
thiazin-8-yl)methyl)benzamide The mixture of diastereomers was separated by single-step SFC chromatographic resolution under the listed conditions to give the title compounds.

Column: Phenomenex LUX-A2 250×10 mm, 5 um@35 degC
Mobile phase: 50% Isopropanol/50% CO2
Flow: 10 ml/min
Detection: UV@220 nm Example 26.4a Diastereomer 1 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide, Rt=6.94 mins
LC-MS Rt 1.38 min [M+H]+ 582.4 (Method 2minLow-pHv03)
1H NMR (400 MHz, CDCl3) δ 7.57 (d, 2H), 7.47 (t, 1H), 7.41 (d, 1H), 7.33 (t, 2H), 7.02 (s, 1H), 6.18 (dd, 1H), 6.03 (d, 1H), 5.73 (s, 1H), 5.48 (dd, 1H), 4.03 (dd, 1H), 3.83 (m, 1H), 3.70 (m, 1H), 3.64 (s, 3H), 3.35 (s, 3H), 2.70 (ddd, 1H), 1.99 (d, 3H)

Example 26.4b

Diastereomer 2 of N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide, Rt=6.94 mins
LC-MS Rt 1.36 min [M+H]+ 582.4 (Method 2minLow-pHv03)
1H NMR (400 MHz, CDCl3) δ 7.71 (d, 2H), 7.55 (t, 1H), 7.47 (dd, 2H), 7.10 (s, 1H), 6.63 (t, 1H), 6.11 (dd, 1H), 6.02 (d, 1H), 5.79 (d, 1H), 5.66 (d, 1H), 3.99 (dd, 1H), 3.86 (m, 1H), 3.74 (m, 2H), 3.63 (s, 3H), 3.42 (s, 3H), 2.29 (s, 3H)

Example 27a and 27b (7R,9R)-9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione and (7S,9R)-9-(4-Chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione

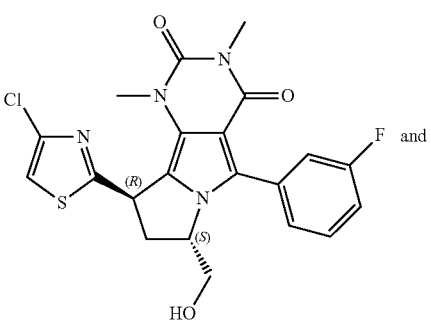

and (7S,9R)-9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4-(3H,7H)-dione

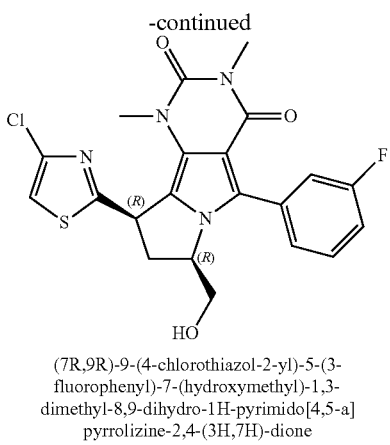

(7R,9R)-9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4-(3H,7H)-dione Step 1: 7-((4-Chlorothiazol-2-yl)(hydroxy)methyl)-5-(3-fluorophenyl)-1,3-dimethyl-1H-pyrrolo[3,4-d]pyrimidine-2,4(3H,6H)-dione The title compound was prepared by an analogous method to 7-((4-chlorothiazol-2-yl)(hydroxy)methyl)-1,3-dimethyl-5-phenyl-1H-pyrrolo[3,4-d]pyrimidine-2,4(3H,6H)-dione (Example 21 Step 1) from 5-(3-fluorophenyl)-1,3-dimethyl-2,4-dioxo-2,3,4,6-tetrahydro-1H-pyrrolo[3,4-d]pyrimidine-7-carbaldehyde (Intermediate Nc) and 2-bromo-4-chlorothiazole (Intermediate Q, step 2);
1H NMR (400 MHz, CDCl3) δ 12.16 (1H, s), 7.75 (1H, s), 7.69 (2H, d), 7.64 (2H, d), 7.48 (1H, mult), 7.29 (1H, d), 7.22 (1H, mult), 6.40 (1H, d), 3.48 (3H, s), 3.23 (3H, s)
LC-MS Rt 1.18 mins [M+H]+ 421.2 m/z (Method 2min-LowpHv03)

Step 2: 7-(1-(4-Chlorothiazol-2-yl)but-3-en-1-yl)-5-(3-fluorophenyl)-1,3-dimethyl-1H-pyrrolo[3,4-d]pyrimidine-2,4(3H,6H)-dione Boron trifluoride THF complex (0.205 mL, 1.861 mmol) was added to a solution of 7-((4-chlorothiazol-2-yl)(hydroxy)methyl)-5-(3-fluorophenyl)-1,3-dimethyl-1H-pyrrolo[3,4-d]pyrimidine-2,4(3H,6H)-dione (870 mg, 2.067 mmol) and allyltri-n-butyltin (0.641 mL, 2.067 mmol) were dissolved in THF (15 mL). The mixture was stirred at room temp. for 20 mins. The reaction mixture was quenched with saturated NaHCO3(aq) and extracted with EtOAc. The organic extracts were washed with 1M KF(aq) (1×), brine (1×), dried over sodium sulfate and evaporated under vacuum. Purification by chromatography on silica, eluting with 10-60% EtOAc/hexane, afforded the title compound.
LC-MS Rt 1.42 mins [M+H]+ 445.3 (Method 2minLowpHv03)
1H NMR (400 MHz, CDCl3) δ 9.92 (1H, s), 7.66 (1H, dt), 7.60 (1H, d), 7.44 (1H, mult), 7.10 (1H, td), 7.05 (1H, s), 5.72 (1H, mult), 5.17-5.09 (2H, mult), 4.85 (1H, t), 3.68 (3H, s), 3.42 (3H, s), 2.92 (2H, mult).

Step 3: 7-(1-(4-Chlorothiazol-2-yl)-3,4-dihydroxybutyl)-5-(3-fluorophenyl)-1,3-dimethyl-1H-pyrrolo[3,4-d]pyrimidine-2,4(3H,6H)-dione Osmium tetroxide (2.5% w.t., 2.032 mL, 0.162 mmol) was added to a solution of 7-(1-(4-chlorothiazol-2-yl)but-3-en-1-yl)-5-(3-fluorophenyl)-1,3-dimethyl-1H-pyrrolo[3,4-d]pyrimidine-2,4(3H,6H)-dione (720 mg, 1.618 mmol) and N-methyl morpholine oxide (284 mg, 2.427 mmol) in acetonitrile (20 mL,) and water (2 mL). The mixture was stirred at room temperature for 105 mins. The reaction was quenched with saturated aqueous sodium metabisulfite solution and extracted with chloroform (3×). The combined organic extracts were passed through a hydrophobic frit and evaporated under vacuum to afford the title compound as a mixture of diastereomers.
LC-MS Rt 1.12 mins [M+H]+ 479.3 (Method 2minLowpHv03)

Step 4: 7-(4-((tert-Butyldimethylsilyl)oxy)-1-(4-chlorothiazol-2-yl)-3-hydroxybutyl)-5-(3-fluorophenyl)-1,3-dimethyl-1H-pyrrolo[3,4-d]pyrimidine-2,4(3H,6H)-dione tert-Butyldimethylsilyl chloride (309 mg, 2.047 mmol) was added to a solution of 7-(1-(4-chlorothiazol-2-yl)-3,4-dihydroxybutyl)-5-(3-fluorophenyl)-1,3-dimethyl-1H-pyrrolo[3,4-d]pyrimidine-2,4(3H,6H)-dione (817 mg, 1.706 mmol), imidazole (232 mg, 3.41 mmol) and DMAP (20.84 mg, 0.171 mmol) in DMF (15 mL). The mixture was stirred at room temperature for 50 mins. A further portion of tert-butyldimethylsilyl chloride (100 mg, 0.662 mmol) was added and the mixture stirred for a further 1 hour. The reaction mixture was diluted with EtOAc and washed with 0.1M HCl (aq) (1×) and brine (3×). The organic phase was dried over sodium sulfate and evaporated under vacuum. Purification by chromatography on silica, eluting with 0-60% EtOAc/hexane, afforded the title compound as a mixture of diastereomers.
LC-MS Rt 1.68 mins [M+H]+ 593.5 (Method 2minLowpHv03)

Step 5: 1-((tert-Butyldimethylsilyl)oxy)-4-(4-chlorothiazol-2-yl)-4-(5-(3-fluorophenyl)-1,3-dimethyl-2,4-dioxo-2,3,4,6-tetrahydro-1H-pyrrolo[3,4-d]pyrimidin-7-yl)butan-2-yl methanesulfonate Methanesulfonic anhydride (347 mg, 1.989 mmol) was added to a solution of 7-(4-(((tert-butyldimethylsilyl)oxy)-1-(4-chlorothiazol-2-yl)-3-hydroxybutyl)-5-(3-fluorophenyl)-1,3-dimethyl-1H-pyrrolo[3,4-d]pyrimidine-2,4(3H,6H)-dione (590 mg, 0.995 mmol) and triethylamine (0.416 mL, 2.98 mmol) in DCM (30 mL). The mixture was stirred at room temperature 20 mins. The reaction was quenched with saturated NaHCO3(aq) and extracted with DCM (3×). The combined organic extracts were passed through a hydrophobic frit and evaporated under vacuum to afford the title compound as a crude material which was used directly.

Step 6: 7-(((tert-Butyldimethylsilyl)oxy)methyl)-9-(4-chlorothiazol-2-yl)-5-(3-fluorophenyl)-1,3-dimethyl-8,9-dihydro-1H-pyrimido[4,5-a]pyrrolizine-2,4(3H,7H)-dione Sodium hydride (127 mg, 3.18 mmol) was added to a solution of 1-((tert-butyldimethylsilyl)oxy)-4-(4-chlorothiazol-2-yl)-4-(5-(3-fluorophenyl)-1,3-dimethyl-2,4-dioxo-2,3,4,6-tetrahydro-1H-pyrrolo[3,4-d]pyrimidin-7-yl)butan-2-yl methanesulfonate (712 mg, 1.061 mmol) in THF (30 mL). The mixture was stirred at room temperature for 35 mins. The reaction was quenched with water and extracted with DCM (3×). The combined organic extracts were passed through a hydrophobic frit and evaporated under vacuum. Purification by chromatography on silica, eluting with 0-100% EtOAc/hexane afforded the title compound as a mixture of diastereomers.

LC-MS Rt 1.77 mins [M+H]+ 575.4 (Method 2minLowpHv03)

Step 7: Diastereoisomeric mixture of 9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione Trifluoroacetic acid (2 mL, 26.0 mmol) was added to a solution of 7-(((tert-butyldimethylsilyl)oxy)methyl)-9-(4-chlorothiazol-2-yl)-5-(3-fluorophenyl)-1,3-dimethyl-8,9-dihydro-1H-pyrimido[4,5-a]pyrrolizine-2,4(3H,7H)-dione (570 mg, 0.991 mmol) in methanol (20 mL) and water (3 mL). The mixture stirred at room temperature 20 mins. Further portions of water (1 mL) and trifluoroacetic acid (1 mL) were added and the mixture stirred for a further 3 hours. The reaction was quenched with saturated NaHCO$_3$(aq) and extracted with chloroform (3×). The combined organic extracts were passed through a hydrophobic frit and evaporated under vacuum. Purification by chromatography on silica, eluting with 0-100% EtOAc/hexane afforded the title compounds as a mixture of diastereomers.

Resolution of the diastereomers was carried out by serial SFC chromatographic resolution under the following conditions;
Column: Chiralpak AD-H 250×10 mm 5 um
Eluent: 30% MeOH/60% CO2
Flow: 10 mL/min
Detection: UV@225 nm
followed by the following conditions;
Column: Chiralcel OJ-H 250×10 mm 5 um
Eluent: 30% MeOH/60% CO2
Flow: 10 mL/min
Detection: UV@225 nm Example 27a Diastereomer (7R,9R)-9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione, Rt=5.24 min LC-MS Rt 1.12 mins [M+H]+ 461.4 (Method 2minLowpHv03)

1H NMR (400 MHz, CDCl3) δ 7.46 (1H, mult), 7.37 (1H, mult), 7.30 (1H, mult), 7.15 (1H, dt), 7.06 (1H, s), 5.07 (1H, dd), 4.82 (1H, mult), 3.52-3.44 (2H, mult), 3.38 (1H, mult), 3.38 (3H, s), 3.34 (3H, s), 2.83 (1H, dt)

Example 27b

Diastereomer (7S,9R)-9-(4-chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione, Rt=4.30 min 1H NMR (400 MHz, CDCl3) δ 7.46 (1H, mult), 7.39 (1H, mult), 7.31 (1H, mult), 7.16 (1H, td), 7.09 (1H, s), 5.11 (1H, dd), 4.86 (1H, mult), 3.52 (1H, dd), 3.47 (1H, dd), 3.37 (3H, s), 3.27 (3H, s), 3.22 (1H, mult), 2.88 (1H, mult)

LC-MS Rt 1.15 mins [M+H]+ 461.4 (Method 2minLowpHv03)

The compounds of the following listed examples were prepared by a similar method to that of Example 27a and 27b from the appropriate starting material in step 1 (described hereinafter) and appropriate halo compound. The resulting diastereomeric mixtures were separated by SFC chromatographic under the listed conditions.

Example 27.1a and 27.1b (7R,9R)-9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione or (7S,9R)-9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione or (7R,9S)-9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione or (7S,9S)-9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione

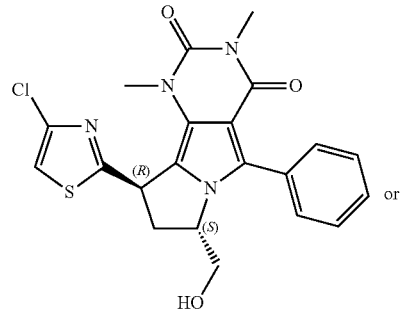

(7S,9R)-9-(4-chlorothiazol-2-yl)-7-(hydroxymethyl)-1,3-dimethyl-5-phenyl-8,9-dihydro-1H-pyrimido[4,5-a]pyrrolizine-2,4-(3H,7H)-dione

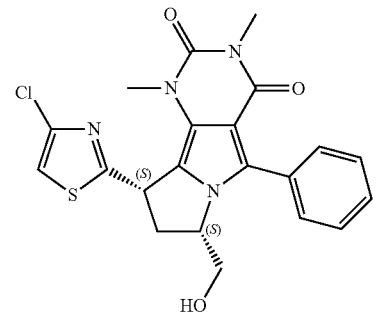

(7S,9S)-9-(4-chlorothiazol-2-yl)-7-(hydroxymethyl)-1,3-dimethyl-5-phenyl-8,9-dihydro-1H-pyrimido[4,5-a]pyrrolizine-2,4-(3H,7H)-dione

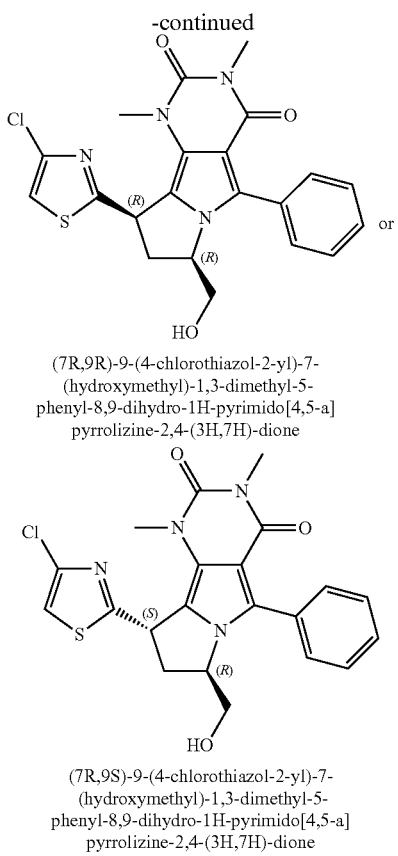

(7R,9R)-9-(4-chlorothiazol-2-yl)-7-
(hydroxymethyl)-1,3-dimethyl-5-
phenyl-8,9-dihydro-1H-pyrimido[4,5-a]
pyrrolizine-2,4-(3H,7H)-dione (7R,9S)-9-(4-chlorothiazol-2-yl)-7-
(hydroxymethyl)-1,3-dimethyl-5-
phenyl-8,9-dihydro-1H-pyrimido[4,5-a]
pyrrolizine-2,4-(3H,7H)-dione Separation Conditions: Serial Separation
First Separation:
Column: Chiralcel OJ-H 250×10 mm, 5 um@35 C
Eluent: 40% Methanol/60% CO2
Flow: 10 ml/min
Detection: UV@220 nm
Second Separation:
Column: Chiralcel OD-H 500×10 mm, 5 um@35 C
Eluent: 30% Methanol/60% CO2
Flow: 10 ml/min
Detection: UV@220 nm Example 27.1a Diastereomer 1 of 9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione
Rt=13.03 mins
1H NMR (400 MHz, CDCl3) δ 7.58-7.52 (2H, mult), 7.50-7.39 (3H, mult), 7.04 (1H, s), 5.05 (1H, mult), 4.79 (1H, mult), 3.49-3.36 (2H, mult), 3.33 (3H, s), 3.30 (3H, s), 2.81 (1H, mult), 2.36 (1H, mult)
LC-MS Rt 1.09 mins [M+H]+ 443.4 (Method 2minLow-pHv03)

Example 27.1b

Diastereomer 2 of 9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione
Rt=14.56 mins
LC-MS Rt 1.12 mins [M+H]+ 443.3 (Method 2minLow-pHv03)

1H NMR (400 MHz, CDCl3) δ 7.61-7.55 (2H, mult), 7.51-7.41 (3H, mult), 7.09 (1H, s), 5.09 (1H, dd), 4.84 (1H, mult), 3.50-3.38 (2H, mult), 3.34 (3H, s), 3.26 (3H, s), 3.21 (1H, mult), 2.84 (1H, mult)

Example 27.2a and 27.2b (7S,9R)-7-(hydroxymethyl)-1,3-dimethyl-9-(4-methylthiazol-2-yl)-5-phenyl-8,9-ddihydro-1H-pyrimido[4,5-a]pyrrolizine-2,4(3H,7H)-dione or (7R,9R)-7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione or (7S,9S)-7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione or (7R,9S)-7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione

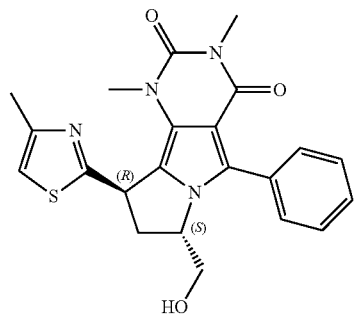

(7S,9R)-7-(hydroxymethyl)-1,3-dimethyl-
9-(4-methylthiazol-2-yl)-5-phenyl-8,9-dihydro-
1H-pyrimido[4,5-a]pyrrolizine-2,4(3H,7H)-dione or

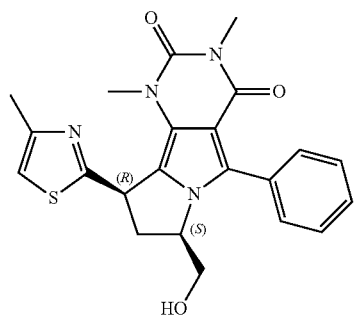

(7R,9R)-7-(hydroxymethyl)-1,3-dimethyl-
9-(4-methylthiazol-2-yl)-5-phenyl-8,9-dihydro-
1H-pyrimido[4,5-a]pyrrolizine-2,4(3H,7H)-dione

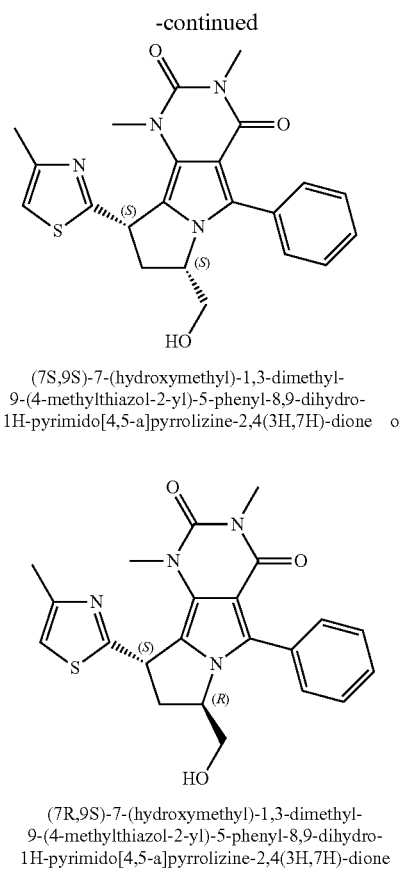

(7S,9S)-7-(hydroxymethyl)-1,3-dimethyl-
9-(4-methylthiazol-2-yl)-5-phenyl-8,9-dihydro-
1H-pyrimido[4,5-a]pyrrolizine-2,4(3H,7H)-dione  or (7R,9S)-7-(hydroxymethyl)-1,3-dimethyl-
9-(4-methylthiazol-2-yl)-5-phenyl-8,9-dihydro-
1H-pyrimido[4,5-a]pyrrolizine-2,4(3H,7H)-dione Separation Conditions:

Column: Chiralcel OJ-H 250×10 mm, 5 um@35 degC

Mobile phase: 35% Methanol/65% CO2

Flow: 10 ml/min

Detection: UV@220 nm

Example 27.2a

Diastereomer 1 of 7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione Rt=4.78 mins LC-MS Rt 1.04 mins [M+H]$^+$ 423.4 (Method 2minLow-pHv03)

1H NMR (400 MHz, CDCl3) δ 7.58 (2H, d), 7.50-7.38 (3H, mult), 6.81 (1H, s), 5.01 (1H, d), 4.80 (1H, mult), 4.27 (1H, mult), 3.55-3.34 (3H, mult), 3.32 (3H, s), 3.31 (3H, s), 2.69 (1H, mult), 2.39 (3H, s).

Example 27.2b

Diastereomer 2 of 7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione Rt=4.49 mins 1H NMR (400 MHz, CDCl3) δ 7.59 (2H, d), 7.51-7.41 (3H, mult), 6.85 (1H, s), 5.10 (1H, dd), 4.86 (1H, mult), 3.76 (1H, mult), 3.51, 3.37 (2H, mult), 3.34 (3H, s), 3.22 (3H, s), 3.18 (1H, mult), 2.84 (1H, mult), 2.47 (3H, s).

LC-MS Rt 1.06 mins [M+H]$^+$423.5 (Method 2minLow-pHv03)

Example 27.3a and 27.3b 3-((7S,9R)-9-(4-Chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile
or 3-((7S,9S)-9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile
or 3-((7R,9R)-9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile
or 3-((7R,9S)-9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile

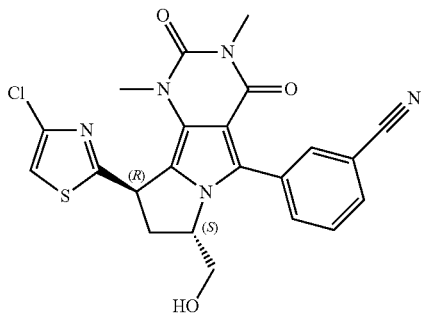

3-((7S,9R)-9-(4-chlorothiazol-2-yl)-7-
(hydroxymethyl)-1,3-dimethyl-2,4-dioxo-
2,3,4,7,8,9-hexahydro-1H-pyrimido[4,5-a]
pyrrolizin-5-yl)benzonitrile      or

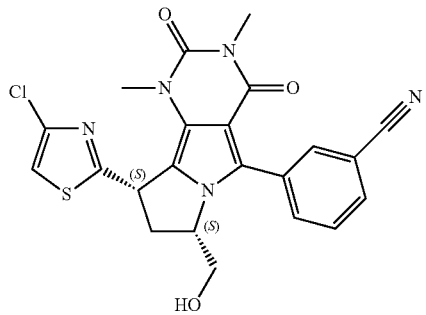

3-((7S,9S)-9-(4-chlorothiazol-2-yl)-7-
(hydroxymethyl)-1,3-dimethyl-2,4-dioxo-
2,3,4,7,8,9-hexahydro-1H-pyrimido[4,5-a]
pyrrolizin-5-yl)benzonitrile -continued

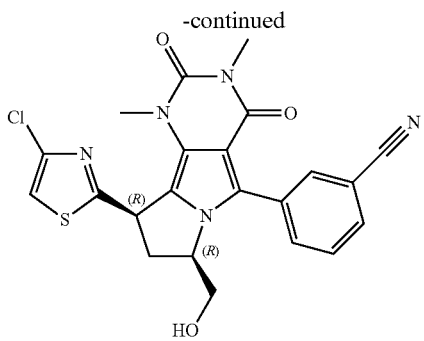

3-((7R,9R)-9-(4-chlorothiazol-2-yl)-7-
(hydroxymethyl)-1,3-dimethyl-2,4-dioxo-
2,3,4,7,8,9-hexahydro-1H-pyrimido[4,5-a]
pyrrolizin-5-yl)benzonitrile or

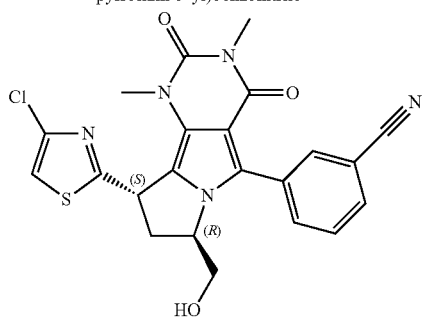

3-((7R,9S)-9-(4-chlorothiazol-2-yl)-7-
(hydroxymethyl)-1,3-dimethyl-2,4-dioxo-
2,3,4,7,8,9-hexahydro-1H-pyrimido[4,5-a]
pyrrolizin-5-yl)benzonitrile Separation Conditions:
Column: Chiralcel OJ-H 250×10 mm, 5 um@35 degC
Mobile phase: 35% Methanol/65% CO2
Flow: 10 ml/min
Detection: UV@220 nm Example 27.3a Diastereomer 1 of 3-(9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile
Rt=4.81 mins
1H NMR (400 MHz, CDCl3) δ 7.82-7.74 (2H, mult), 7.62 (1H, d), 7.51 (1H, t), 6.99 (1H, s), 4.98 (1H, d), 4.72 (1H, mult), 3.46-3.33 (2H, mult), 3.27 (1H, mult, obscured), 3.25 (3H, s, distinct), 3.25 (3H, s, distinct) 2.73 (1H, d), 2.46 (1H, br s)
LC-MS Rt 1.07 mins [M+H]+ 468.3 (Method 2minLowpHv03)

Example 27.3b

Diastereomer 2 of 3-(9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile
Rt=5.03 mins
1H NMR (400 MHz, CDCl3) δ 7.89-7.83 (2H, mult), 7.70 (1H, d), 7.59 (1H, t), 7.11 (1H, s), 5.13 (1H, dd), 4.87 (1H, mult), 3.50 (1H, dd), 3.40 (1H, dd), 3.31 (3H, s), 3.22 (1H, mult, obscured) 3.22 (3H, s), 2.87 (1H, mult), 2.16 (1H, br s).
LC-MS Rt 1.10 mins [M+H]+ 468.4 (Method 2minLowpHv03)

Example 28a and 28b (8R,10R)-8-((1H-Imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8R,10S)-8-((1H-imidazol-1-yl)methyl)-1-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10R)-8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione or (8S,10S)-8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione

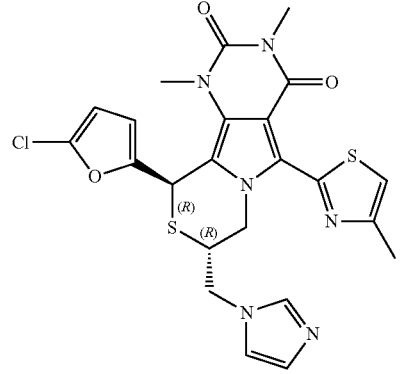

(8R,10R)-8-((1H-imidazol-1-yl)metyl)-10-
(5-chlorofuran-2-yl)-1,3-dimethyl-5-(4-
methylthiazol-2-yl)-7,8-dihyro-1H-pyrimido
[4',5':3,4]pyrrolo[2,1-c][1,4]thiazine-2,4
(3H,10H)-dione or

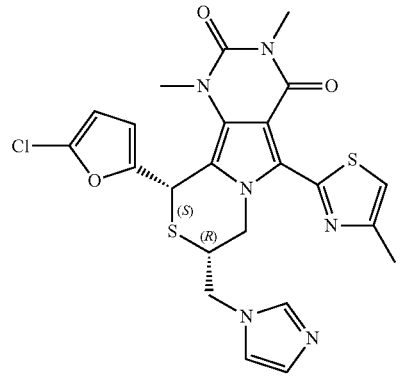

(8R,10S)-8-((1H-imidazol-1-yl)metyl)-10-
(5-chlorofuran-2-yl)-1,3-dimethyl-5-(4-
methylthiazol-2-yl)-7,8-dihyro-1H-pyrimido
[4',5':3,4]pyrrolo[2,1-c][1,4]thiazine-2,4
(3H,10H)-dione

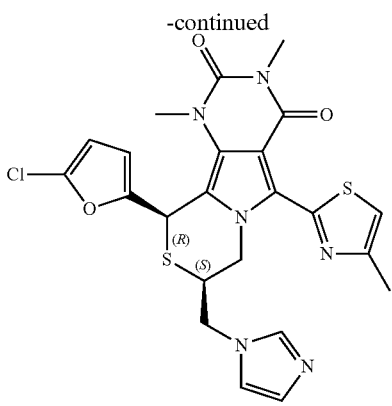

(8S,10R)-8-((1H-imidazol-1-yl)metyl)-10-
(5-chlorofuran-2-yl)-1,3-dimethyl-5-(4-
methylthiazol-2-yl)-7,8-dihyro-1H-pyrimido
[4',5':3,4]pyrrolo[2,1-c][1,4]thiazine-2,4
(3H,10H)-dione   or

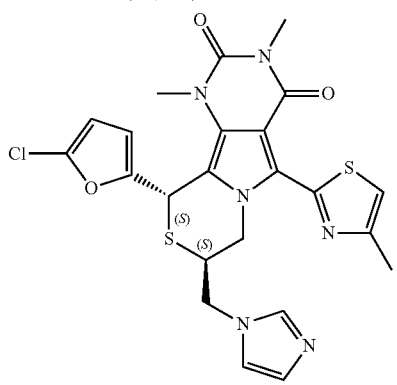

(8S,10S)-8-((1H-imidazol-1-yl)metyl)-10-
(5-chlorofuran-2-yl)-1,3-dimethyl-5-(4-
methylthiazol-2-yl)-7,8-dihyro-1H-pyrimido
[4',5':3,4]pyrrolo[2,1-c][1,4]thiazine-2,4
(3H,10H)-dione Sodium imidazolide (86 mg, 0.960 mmol) was added to a solution of racemic 10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione (115 mg, 0.240 mmol) (Example 17) in DCM (24 ml) at 0° C. The mixture was stirred for 30 minutes, then trifluoromethanesulfonic anhydride (0.049 ml, 0.288 mmol) was added dropwise. The mixture was warmed to room temperature and stirred for 3 hours. The mixture was diluted with DCM (10 ml) washed with water (30 ml) and brine (30 ml). The organic layer was passed through a hydrophobic frit and evaporated under vacuum. Purification by chromatography on silica, eluting with 0-20% methanol/DCM, afford the title compound as a mixture of diastereomers.

LC-MS Rt 0.90 min [M+H]$^+$ 529.3 (Method 2minLow-pHv03)

The mixture of diastereomers was separated by SFC chromatographic resolution under this following conditions to afford the title compounds.
Column: Chiralpak IF 250×10 mm, 5 um@35 deg C
Mobile phase: 50% methanol+0.1% DEA/50% CO2
Flow: 10 ml/min
Detection: UV@220 nm Example 28a Diastereomer 1 of 8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione, Rt=12.05 mins 1H NMR (400 MHz, CDCl3) δ 7.32 (d, 1H), 7.26 (s, 1H), 7.00 (s, 1H), 6.73 (s, 1H), 6.19 (dd, 1H), 6.13 (d, 1H), 5.82 (s, 1H), 5.59 (dd, 1H), 4.37 (dd, 1H), 3.96 (dt, 1H), 3.85 (m, 2H), 3.69 (s, 3H), 3.46 (s, 3H), 2.47 (s, 3H)

LC-MS Rt 0.93 min [M+H]+ 529.5 (Method 2minLow-pHv03)

Example 28b

Diastereomer 2 of 8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione Rt=7.40 mins LC-MS Rt 0.90 min [M+H]+ 529.4 (Method 2minLow-pHv03)

1H NMR (400 MHz, CDCl3) δ 7.33 (dd, 2H), 7.15 (d, 1H), 7.00 (s, 1H), 6.72 (s, 1H), 6.19 (dt, 1H), 6.13 (d, 1H), 5.81 (d, 1H), 5.59 (dd, 1H), 4.36 (dd, 1H), 3.98 (m, 1H), 3.85 (m, 2H), 3.69 (s, 3H), 3.46 (s, 3H), 2.47 (d, 3H)

Example 29

9-(4-Chlorothiazol-2-yl)-5-(3-fluorophenyl)-1,3-dimethyl-8-methylene-8,9-dihydro-1H-pyrimido[4,5-a]pyrrolizine-2,4(3H,7H)-dione

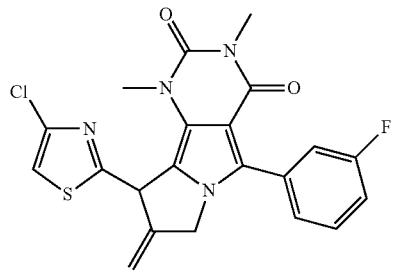 [SMILES: C=C1Cn2c(-c3cccc(F)c3)c3c(=O)n(C)c(=O)n(C)c3c2C1c1nc(Cl)cs1]

Step 1: Dimethyl 2-((4-chlorothiazol-2-yl)(5-(3-fluorophenyl)-1,3-dimethyl-2,4-dioxo-2,3,4,6-tetrahydro-1H-pyrrolo[3,4-d]pyrimidin-7-yl)methyl)malonate NaHMDS solution (1M in THF, 7.13 mL, 7.13 mmol) was added slowly to a mixture of 7-((4-chlorothiazol-2-yl) (hydroxy)methyl)-5-(3-fluorophenyl)-1,3-dimethyl-1H-pyrrolo[3,4-d]pyrimidine-2,4(3H,6H)-dione (Example 27, step 1) (1 g, 2.376 mmol), dimethyl malonate (0.819 mL, 7.13 mmol) and boron trifluoride THF complex (0.236 mL, 2.139 mmol) in THF (30 mL).

The mixture was stirred at room temperature for 15 mins. The reaction was quenched with saturated NaHCO$_3$(aq) and extracted with DCM (3×). The combined organic extracts were passed through a hydrophobic frit and evaporated under vacuum. Purification by chromatography on silica, eluting with 20-40% EtOAc/hexane, afforded the title compound.

LC-MS Rt 1.37 mins [M+H]$^+$ 535.4 (Method 2minLow-pHv03)

Step 2: 7-(1-(4-Chlorothiazol-2-yl)-3-hydroxy-2-(hydroxymethyl)propyl)-5-(3-fluorophenyl)-1,3-dimethyl-1H-pyrrolo[3,4-d]pyrimidine-2,4(3H,6H)-dione Sodium borohydride (190 mg, 5.02 mmol) was added to a suspension of dimethyl 2-((4-chlorothiazol-2-yl) (5-(3-fluorophenyl)-1,3-dimethyl-2,4-dioxo-2,3,4,6-tetrahydro-1H-pyrrolo[3,4-d]pyrimidin-7-yl)methyl)malonate (895 mg, 1.673 mmol) and lithium chloride (213 mg, 5.02 mmol) in methanol (20 mL). The mixture was stirred at room temperature for 30 mins. Further portions of lithium chloride (213 mg, 5.02 mmol) and sodium borohydride (190 mg, 5.02 mmol) were added to allow the reaction to run to completion. The reaction was quenched with saturated NaHCO$_3$(aq) and extracted with chloroform (3×). The combined organic extracts were passed through a hydrophobic frit and evaporated under vacuum to afford the title compound.

LC-MS Rt 1.18 mins [M+H]$^+$ 479.5 (Method 2minLowpHv03)

Step 3: 2-((4-Chlorothiazol-2-yl)(5-(3-fluorophenyl)-1,3-dimethyl-2,4-dioxo-2,3,4,6-tetrahydro-1H-pyrrolo[3,4-d]pyrimidin-7-yl)methyl)allyl methanesulfonate Methanesulfonic anhydride (1699 mg, 9.75 mmol) was added to a solution of 7-(1-(4-chlorothiazol-2-yl)-3-hydroxy-2-(hydroxymethyl)propyl)-5-(3-fluorophenyl)-1,3-dimethyl-1H-pyrrolo[3,4-d]pyrimidine-2,4(3H,6H)-dione (934 mg, 1.950 mmol) and triethylamine (1.631 mL, 11.70 mmol) in DCM (20 mL). The mixture was stirred at room temperature for 16 hours. Further portions of triethylamine (1.631 mL, 11.70 mmol) and methanesulfonic anhydride (1699 mg, 9.75 mmol) were added as necessary to allow the reaction to run to completion. The reaction was quenched with saturated NaHCO$_3$(aq) and extracted with DCM (3×). The combined organic extracts were passed through a hydrophobic frit and evaporated under vacuum. Purification by chromatography on silica, eluting with 20-100% EtOAc/hexane, afforded the title compound.

LC-MS Rt 1.27 mins [M+H]$^+$ 539.5 (Method 2minLowpHv03)

Step 4: 9-(4-Chlorothiazol-2-yl)-5-(3-fluorophenyl)-1,3-dimethyl-8-methylene-8,9-dihydro-1H-pyrimido[4,5-a]pyrrolizine-2,4(3H,7H)-dione Sodium hydride (60% wt. in mineral oil, 31.2 mg, 0.779 mmol) was added to a solution of 2-((4-chlorothiazol-2-yl)(5-(3-fluorophenyl)-1,3-dimethyl-2,4-dioxo-2,3,4,6-tetrahydro-1H-pyrrolo[3,4-d]pyrimidin-7-yl)methyl)allyl methanesulfonate (140 mg, 0.260 mmol) in THF (8 mL). The mixture was stirred at room temperature for 2 hours. A further portion of sodium hydride (31.2 mg, 0.779 mmol) was added to allow the reaction to run to completion. The reaction was quenched with water and extracted with DCM (3×). The combined organic extracts were passed through a hydrophobic frit and evaporated under vacuum. Purification by chromatography on silica, eluting with 20-100% EtOAc/hexane, afforded the title compound.

1H NMR (400 MHz, CDCl3) δ 7.45 (1H, mult), 7.39 (1H, mult), 7.34-7.25 (2H, mult), 7.13 (1H, mult), 7.10 (1H, s), 4.65 (1H, dd), 3.97 (1H, d), 3.39 (3H, s), 3.23 (3H, s), 2.64 (1H, mult), 2.61 (1H, mult)

LC-MS Rt 1.35 mins [M+H]$^+$ 443.4 (Method 2minLowpHv03)

Example 30a, 30b, 30c and 30d (8R,10R)-10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione or (8S,10R)-10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione or (8S,10S)-10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione or (8R,10S)-10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione

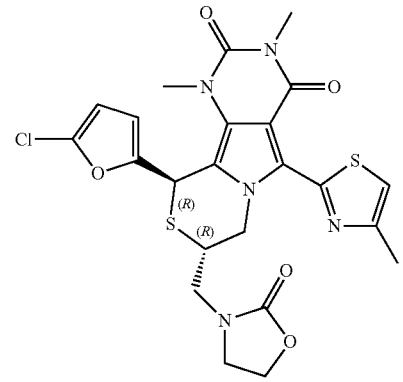

(8R,10R)-10-(5-chlorofuran-2-yl(-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione or

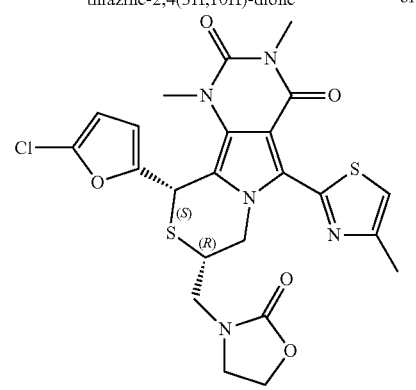

(8R,10S)-10-(5-chlorofuran-2-yl(-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione

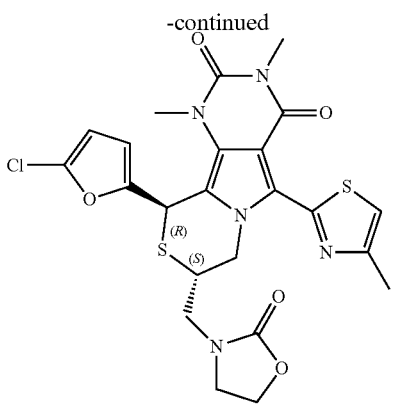

(8S,10R)-10-(5-chlorofuran-2-yl(-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione    or

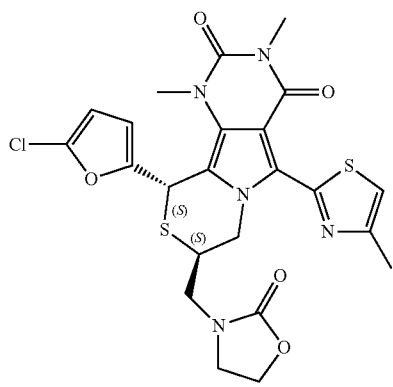

(8S,10S)-10-(5-chlorofuran-2-yl(-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione Step 1: 2-Chloroethyl((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate The title compound was prepared in a similar manner to Example 26 step 1, replacing methanesulfonyl chloride with 2-chloroethyl chloroformate.

LC-MS Rt 1.36 min [M+H]+ 584.3 (Method 2minLow-pHv03)

Step 2: 10-(5-Chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione Sodium hydride (60% wt in mineral oil, 6.69 mg, 0.167 mmol) was added to a solution of 2-chloroethyl((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate (48.9 mg, 0.084 mmol) in THF (4 mL). The mixture was heated at reflux for 18 hours. A further portion of sodium hydride (60% wt in mineral oil, 33.4 mg, 0.836 mmol) was added and the mixture heated at reflux for a further 2 days. The mixture was cooled to room temperature, quenched with water (20 ml) and extracted with ethyl acetate (2×30 ml). The combined organic extracts were washed with brine, passed through a hydrophobic frit and evaporated under vacuum. Purification by mass-directed HPLC under the following conditions afforded the title compound as a mixture of diastereomers.

Column: XSelect CSH Prep C18 column, 30×100 mm, 5 um.
Mobile phase: A=0.1% FA in water, B=0.1% FA in MeCN
Gradient:
0.0-0.5 min: 30% B 30 mL/min
0.5-1.0 min: 30% B 30-50 mL/min
1.0-7.2 min: 30-70% B, 7.2-7.3 min: 70-98% B, 7.3-9.4 min: 98% B
9.4-9.5 30% B 50 mL/min The mixture of diastereomers was separated by SFC chromatographic resolution under the listed conditions to afford the title compounds as single diastereomers.
Column: Chiralpak IA, 250×10 mm, 5 um@35° C.
Mobile phase: 40% Methanol/60% CO2
Flow: 10 ml/min
Detection: UV@220 nm Example 30a Diastereomer 1 of 10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione, Rt=7.02 mins
1H NMR (400 MHz, CDCl3) δ 7.13 (s, 1H), 6.16 (d, 1H), 6.13 (d, 1H), 5.79 (s, 1H), 5.34 (dd, 1H), 4.47 (dd, 1H), 4.26 (m, 2H), 3.92 (q, 1H), 3.66 (s, 3H), 3.61 (m, 1H), 3.44 (s, 3H), 3.37 (m, 2H), 3.10 (dd, 1H), 2.53 (s, 3H)
LC-MS Rt 1.24 min [M+H]+ 548.3 (Method 2minLow-pHv03)

Example 30b

Diastereomer 2 of 10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione, Rt=9.45 mins
1H NMR (400 MHz, CDCl3) δ 7.13 (s, 1H), 6.22 (t, 1H), 6.15 (d, 1H), 5.90 (dd, 1H), 5.80 (s, 1H), 4.39 (td, 2H), 3.77 (m, 4H), 3.67 (s, 3H), 3.63 (m, 1H), 3.48 (dd, 1H), 3.44 (s, 3H), 2.52 (s, 3H)
LC-MS Rt 1.24 min [M+H]+ 548.4 (Method 2minLow-pHv03)

Example 30c

Diastereomer 3 of 10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione, Rt=7.91 mins
1H NMR (400 MHz, CDCl3) δ 7.13 (s, 1H), 6.22 (t, 1H), 6.15 (d, 1H), 5.90 (dd, 1H), 5.80 (s, 1H), 4.39 (td, 2H), 3.77 (m, 4H), 3.67 (s, 3H), 3.63 (m, 1H), 3.48 (dd, 1H), 3.44 (s, 3H), 2.52 (s, 3H)
LC-MS Rt 1.24 min [M+H]+ 548.4 (Method 2minLow-pHv03)

Example 30d

Diastereomer 4 of 10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione, Rt=6.25 mins 1H NMR (400 MHz, CDCl3) δ 7.13 (s, 1H), 6.16 (d, 1H), 6.13 (d, 1H), 5.79 (s, 1H), 5.34 (dd, 1H), 4.47 (dd, 1H), 4.26 (m, 2H), 3.92 (q, 1H), 3.66 (s, 3H), 3.61 (m, 1H), 3.44 (s, 3H), 3.37 (m, 2H), 3.10 (dd, 1H), 2.53 (s, 3H)

LC-MS Rt 1.24 min [M+H]$^+$ 520.3 (Method 2minLow-pHv03) The following examples were prepared in a similar manner to Example 30 a-d, replacing 2-chloroethyl chloroformate in step 1 with 4-bromobutyryl chloride. The mixture of diastereomers was separated by SFC chromatographic resolution under the listed conditions to afford the title compounds as single diastereomers.

Example 30.1a, 30.1b, 30.1c and 30.1d (8R,10R)-10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,1H)-dione or (8S,10R)-10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione or (8R,10S)-10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione or (8S,10S)-10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione

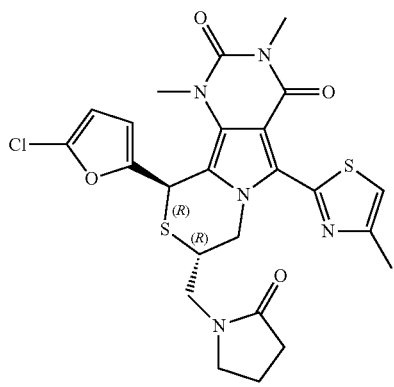

(8R,10R)-10-(5-chlorofuran-2-yl)-1,3-dimethyl-5-(4-methylthiazol-2-yl)-8-((2-oxooxazolidin-1-yl)methyl)-7,8-dihydro-1H-pyrimido[4',5':3,4]pyrrolo[2,1-c][1,4]thiazine-2,4(3H,10H)-dione or

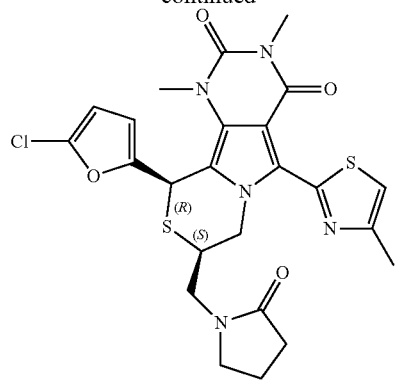

(8S,10R)-10-(5-chlorofuran-2-yl)-1,3-dimethyl-5-(4-methylthiazol-2-yl)-8-((2-oxooxazolidin-1-yl)methyl)-7,8-dihydro-1H-pyrimido[4',5':3,4]pyrrolo[2,1-c][1,4]thiazine-2,4(3H,10H)-dione

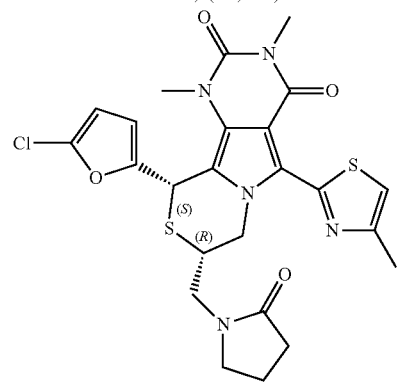

(8R,10S)-10-(5-chlorofuran-2-yl)-1,3-dimethyl-5-(4-methylthiazol-2-yl)-8-((2-oxooxazolidin-1-yl)methyl)-7,8-dihydro-1H-pyrimido[4',5':3,4]pyrrolo[2,1-c][1,4]thiazine-2,4(3H,10H)-dione or

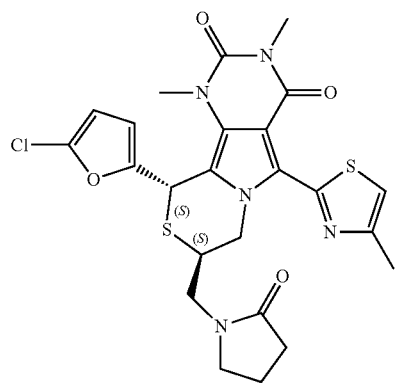

(8S,10S)-10-(5-chlorofuran-2-yl)-1,3-dimethyl-5-(4-methylthiazol-2-yl)-8-((2-oxooxazolidin-1-yl)methyl)-7,8-dihydro-1H-pyrimido[4',5':3,4]pyrrolo[2,1-c][1,4]thiazine-2,4(3H,10H)-dione Separation Conditions:
Column: Chiralcel OD-H 250×10 mm, 5 um@35° C.
Mobile phase: 40% Methanol/60% CO2
Flow: 10 ml/min
Detection: UV@220 nm

Example 30.1a

Diastereomer 1 of 10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione, Rt=5.25 mins 1H NMR (400 MHz, CDCl3) δ 7.13 (s, 1H), 6.12 (s, 2H), 5.76 (s, 1H), 5.08 (dd, 1H), 4.51 (dd, 1H), 3.87 (m, 1H), 3.65 (s, 3H), 3.43 (s, 3H), 3.39 (m, 2H), 3.22 (dd, 1H), 3.12 (dd, 1H), 2.53 (s, 3H), 2.33 (t, 2H), 1.97 (m, 2H)

LC-MS Rt 1.25 min [M+H]+ 546.4 (Method 2minLowpHv03)

Example 30.1 d

Diastereomer 4 of 10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione, Rt=7.69 mins LC-MS Rt 1.25 min [M+H]+ 546.4 (Method 2minLowpHv03)

1H NMR (400 MHz, CDCl3) δ 7.16 (s, 1H), 6.29 (d, 1H), 6.15 (d, 1H), 5.78 (s, 1H), 5.60 (d, 1H), 3.85 (d, 2H), 3.68 (s, 3H), 3.68 (m, 1H), 3.60 (dd, 1H), 3.51 (dd, 1H), 3.44 (m, 1H), 3.43 (s, 3H), 2.55 (s, 3H), 2.39 (t, 2H), 2.09 (q, 2H)

Diastereomers 2 and 3 were further separated under the following conditions to afford single diasteromers
Column: LUX A2, 250×10 mm, 5 um@35° C.
Mobile phase: 50% Methanol/50% CO2
Flow: 10 ml/min
Detection: UV@220 nm

Example 30.1b

Diastereomer 2 of 10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione, Rt=14.80 mins 1H NMR (400 MHz, CDCl3) δ 7.16 (s, 1H), 6.29 (d, 1H), 6.15 (d, 1H), 5.78 (s, 1H), 5.60 (d, 1H), 3.85 (d, 2H), 3.68 (s, 3H), 3.68 (m, 1H), 3.60 (dd, 1H), 3.51 (dd, 1H), 3.44 (m, 1H), 3.43 (s, 3H), 2.55 (s, 3H), 2.39 (t, 2H), 2.09 (q, 2H)

LC-MS Rt 1.25 min [M+H]+ 546.4 (Method 2minLowpHv03)

Example 30.1c

Diastereomer 3 of 10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione, Rt=10.38 mins 1H NMR (400 MHz, CDCl3) δ 7.13 (s, 1H), 6.12 (s, 2H), 5.76 (s, 1H), 5.08 (dd, 1H), 4.51 (dd, 1H), 3.87 (m, 1H), 3.65 (s, 3H), 3.43 (s, 3H), 3.39 (m, 2H), 3.22 (dd, 1H), 3.12 (dd, 1H), 2.53 (s, 3H), 2.33 (t, 2H), 1.97 (m, 2H)

LC-MS Rt 1.25 min [M+H]+ 546.4 (Method 2minLowpHv03)

Example 31

(R)-3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile or (S)-3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile

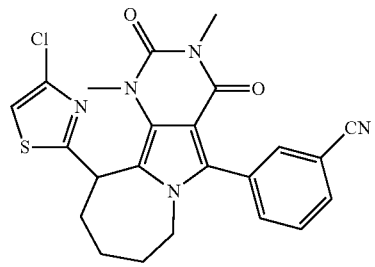 [SMILES: Cn1c(=O)c2c(-c3cccc(C#N)c3)n3c(c2n(C)c1=O)C(c1nc(Cl)cs1)CCCC3]

Step 1: Ethyl 5-(5-(3-cyanophenyl)-1,3-dimethyl-2,4-dioxo-3,4-dihydro-1H-pyrrolo[3,4-d]pyrimidin-6(2H)-yl)pentanoate The title compound was prepared from 3-(1,3-dimethyl-2,4-dioxo-2,3,4,6-tetrahydro-1H-pyrrolo[3,4-d]pyrimidin-5-yl)benzonitrile (Example 9, step 4) and ethyl 5-bromopentanoate (0.712 mL, 4.50 mmol) by an analogous method to Example 9 step 5;

LC-MS: Rt 1.18 mins; MS 409.6 m/z [M+H] Method 2minLowpHv03

1H NMR (400 MHz, CDCl3) δ 7.79-7.69 (3H, mult), 7.62 (1H, t), 6.47 (1H, s), 4.14 (2H, q), 3.93 (2H, t), 3.45 (3H, s), 3.36 (3H, s), 2.25 (2H, t), 1.74 (2H, mult), 1.52 (2H, mult), 1.26 (3H, t).

Step 2: 5-(5-(3-Cyanophenyl)-1,3-dimethyl-2,4-dioxo-3,4-dihydro-1H-pyrrolo[3,4-d]pyrimidin-6(2H)-yl)-N-methoxy-N-methylpentanamide The title compound was prepared from ethyl 5-(5-(3-cyanophenyl)-1,3-dimethyl-2,4-dioxo-3,4-dihydro-1H-pyrrolo[3,4-d]pyrimidin-6(2H)-yl)pentanoate by a method similar to Example 13, step 2;

LC-MS: Rt 1.06 mins; MS 424.3 m/z [M+H] Method 2minLowpHv03

1H NMR (400 MHz, CDCl3) δ 7.77-7.70 (3H, mult), 7.61 (1H, mult), 6.49 (1H, s), 3.92 (2H, t), 3.66 (3H, s), 3.43 (3H, s), 3.36 (3H, s), 3.17 (3H, s), 2.38 (2H, t), 1.75 (2H, mult), 1.54 (2H, mult).

Step 3: 3-(6-(5-(4-Chlorothiazol-2-yl)-5-oxopentyl)-1,3-dimethyl-2,4-dioxo-2,3,4,6-tetrahydro-1H-pyrrolo[3,4-d]pyrimidin-5-yl)benzonitrile The title compound was prepared from 5-(5-(3-cyanophenyl)-1,3-dimethyl-2,4-dioxo-3,4-dihydro-1H-pyrrolo[3,4-d]pyrimidin-6(2H)-yl)-N-methoxy-N-methylpentanamide and 2-bromo-4-chlorothiazole by a method similar to Example 13, step 3;

LC-MS: Rt 1.30 mins; MS 482.2 m/z [M+H] Method 2minLowpHv03
1H NMR (400 MHz, CDCl3) δ 7.78-7.70 (3H, mult), 7.62 (1H, t), 7.49 (1H, s), 6.49 (1H, s), 3.97 (2H, t), 3.44 (3H, s), 3.36 (3H, s), 3.06 (2H, t), 1.79 (2H, mult), 1.64 (2H, mult).

Step 4: 3-(6-(5-(4-Chlorothiazol-2-yl)-5-hydroxypentyl)-1,3-dimethyl-2,4-dioxo-2,3,4,6-tetrahydro-1H-pyrrolo[3,4-d]pyrimidin-5-yl)benzonitrile The title compound was prepared from 3-(6-(5-(4-Chlorothiazol-2-yl)-5-oxopentyl)-1,3-dimethyl-2,4-dioxo-2,3,4,6-tetrahydro-1H-pyrrolo[3,4-d]pyrimidin-5-yl)benzonitrile by a method similar to Example 13, step 4;

Step 5: 3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile The title compound was prepared from 3-(6-(5-(4-chlorothiazol-2-yl)-5-hydroxypentyl)-1,3-dimethyl-2,4-dioxo-2,3,4,6-tetrahydro-1H-pyrrolo[3,4-d]pyrimidin-5-yl)benzonitrile by a method similar to Example 13, step 5;
LC-MS: Rt 1.34 mins; MS 466.4 m/z [M+H] Method 2minLowpHv04.

Step 6: (R) or (S)-3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile Chiral separation of racemic 3-(11-(4-chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile by Supercritical Fluid Chromatography was carried out using the following conditions to afford the title compound;
Column: Chiralcel AD-H 250×10 mm, 5 um@35 C
Mobile phase: 15% Methanol/85% CO2
Flow: 10 ml/min
Detection: UV@220 nm
Enantiomer 1 of 3-(11-(4-chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile SFC Retention time=26.26 mins
LC-MS: Rt 1.36 mins; MS 466.5 m/z [M+H] Method 2minLowpHv03
1H NMR (400 MHz, CDCl3) δ 7.70-7.49 (4H, mult), 7.01 (1H, s), 5.23 (1H, dd), 3.93 (1H, dd), 3.54 (3H, s), 3.39 (1H, dd), 3.26 (3H, s), 2.90 (1H, mult), 2.02-1.89 (5H, mult) The second enantiomer was isolated at SFC Rt=32.07 min Example 32

(R)-11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione or (S)-11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione

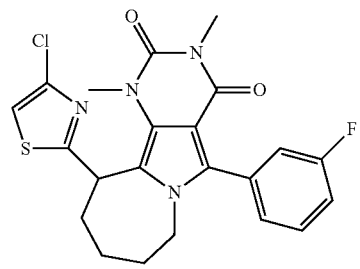 [SMILES: Cn1c(=O)c2c(-c3cccc(F)c3)n3c(c2n(C)c1=O)C(c1nc(Cl)cs1)CCCC3]

Step 1: 5-(3-Fluorophenyl)-1,3-dimethyl-6-((2-(trimethylsilyl)ethoxy)methyl)-1H-pyrrolo[3,4-d]pyrimidine-2,4(3H,6H)-dione The title compound was prepared from 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (Example 9, step 2) and 1-bromo-3-fluorobenzene by a similar method to Example 9 step 3;
LCMS; Rt 1.54 mins; MS m/z 404.4 [M+H]+; 2minlowpHV03.

Step 2: 5-(3-Fluorophenyl)-1,3-dimethyl-1H-pyrrolo[3,4-d]pyrimidine-2,4(3H,6H)-dione The title compound was prepared from 5-(3-Fluorophenyl)-1,3-dimethyl-6-((2-(trimethylsilyl)ethoxy)methyl)-1H-pyrrolo[3,4-d]pyrimidine-2,4(3H,6H)-dione by a similar method to Example 9, step 4;
LC-MS: Rt 1.05 mins; MS m/z 274.3 [M+H]+; Method 2minLowpHv03

Step 3-9: (R)- or (S)-11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione The title compound was prepared by a similar method to Example 31 steps 1-6;
Enantiomer 1 of 11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione
SFC Rt=4.38 mins SFC Chiralcel OJ-H 250×10 mm, 5 um@35 degC, 35% Methanol/65% CO2, 10 ml/min, Detection: UV@220 nm, >99% e.e.
LC-MS Rt 1.45 mins; MS 459.4 m/z [M+H] Method 2min-LowpHv03
1H NMR (400 MHz, CDCl3) δ 7.46 (1H, mult), 7.23-7.10 (3H, mult), 7.09 (1H, s), 5.30 (1H, mult), 4.11 (1H, mult), 3.64 (3H, s), 3.43 (1H, mult), 3.37 (3H, s), 3.01 (1H, mult), 2.11-1.88 (5H, mult)

Example 33

1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione

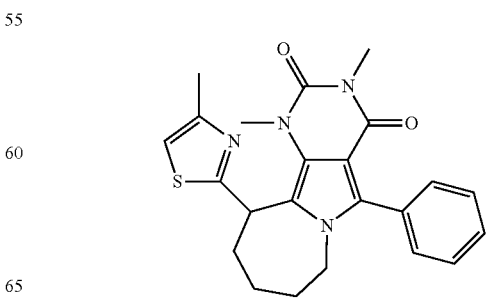

Step 1: Ethyl 5-(1,3-dimethyl-2,4-dioxo-5-phenyl-3,4-dihydro-1H-pyrrolo[3,4-d]pyrimidin-6(2H)-yl)pentanoate 5-Benzoyl-6-(bromomethyl)-1,3-dimethylpyrimidine-2,4(1H,3H)-dione (Intermediate C) (1.38 g, 4.09 mmol), ethyl 5-aminovalerate hydrochloride (1.109 g, 6.14 mmol) and triethylamine (1.711 mL, 12.28 mmol) were combined in ethanol (20 mL) and the mixture heated at reflux for 40 mins. The reaction mixture was cooled to room temperature and evaporated under vacuum. The residue was partitioned between water and DCM and the phases separated. The organic phase was passed through a hydrophobic frit and evaporated onto silica. The silica was deposited onto a 25 g silica cartridge and the system eluted with 20% EtOAc/hexane, 40% EtOAc/hexane, 60% EtOAc/hexane and 80% EtOAc/hexane. The product fractions were combined and concentrated under reduced pressure to afford the title compound;

LC-MS: Rt 1.29 mins; MS 384.3 m/z [M+H] Method 2minLowpHv03

1H NMR (400 MHz, CDCl3) δ 7.54-7.37 (5H, mult), 6.41 (1H, br s), 4.12 (2H, q), 3.93 (2H, t), 3.44 (3H, s), 3.36 (3H, s), 2.22 (2H, t), 1.74 (2H, mult), 1.53 (2H, mult), 1.26 (3H, t).

Step 2-5: 1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione The title compound was prepared from ethyl 5-(1,3-dimethyl-2,4-dioxo-5-phenyl-3,4-dihydro-1H-pyrrolo[3,4-d]pyrimidin-6(2H)-yl)pentanoate by a similar method to Example 31 steps 2-5;

LC-MS: Rt 1.34 mins; MS 421.2 m/z [M+H] Method 2minLowpHv03

1H NMR (400 MHz, CDCl3) δ 7.55-7.34 (5H, mult), 6.95 (1H, s), 5.45 (1H, mult), 4.18 (1H, mult), 3.63 (3H, s), 3.36 (3H, s), 3.25 (1H, mult), 2.61 (3H, s), 2.19-1.79 (5H, mult).

Example 33a (R)-1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione or (S)-1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione

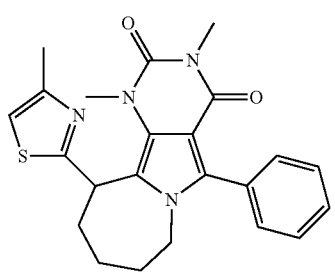 [SMILES: Cc1csc(C2CCCCn3c(-c4ccccc4)c4c(=O)n(C)c(=O)n(C)c4c32)n1]

Chiral separation of racemic 1,3-dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione (Example 33) by Supercritical Fluid Chromatography was carried out using the following conditions to afford the title compound;

SFC Chiralcel OJ-H 250 mm×10 mm×5 µm, Eluent 35% IPA (containing 0.1% DEA)/65% CO2, 10 ml/min@35° C., detection@220 nm, Enantiomer 1 of 1,3-Dimethyl-1-(4-methylthiazol-2-yl)-5-phenyl-8,9,10,11-tetrahydro-1H-pyrimido[4',5':3,4]pyrrolo[1,2-a]azepine-2,4(3H,7H)-dione SFC Retention time=3.96 min, >99% ee LC-MS: Rt 1.39 mins; MS 421.3 m/z [M+H] Method 2minLowpHv03

1H NMR (av81851, 400 MHz, CDCl3) δ 7.52-7.37 (5H, mult), 6.88 (1H, s), 5.37 (1H, dd), 4.14 (1H, dd), 3.63 (3H, s), 3.45 (1H, dd), 3.36 (3H, s), 3.10 (1H, mult), 2.54 (3H, s), 2.08 (1H, mult), 1.91 (2H, mult), 1.57 (2H, mult).

The second entantiomer was isolated at SFR Rt=6.31 mins

Example 34

(R)-11-(4-Chlorothiazol-2-yl)-1,3-dimethyl-5-phenyl-8,9,10,11-tetrahydro-1H-pyrimido[4',5':3,4]pyrrolo[1,2-a]azepine-2,4(3H,7H)-dione or (S)-11-(4-Chlorothiazol-2-yl)-1,3-dimethyl-5-phenyl-8,9,10,11-tetrahydro-1H-pyrimido[4',5':3,4]pyrrolo[1,2-a]azepine-2,4(3H,7H)-dione

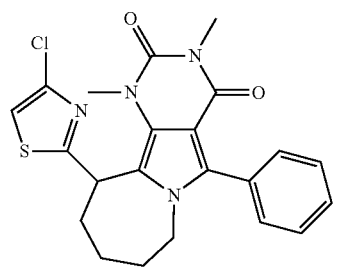 [SMILES: Cc1csc(C2CCCCn3c(-c4ccccc4)c4c(=O)n(C)c(=O)n(C)c4c32)n1]

The title compound was prepared by a similar method to Example 33a by replacing 2-iodo-4-methylthiazole (Example 33, step 3) with 2-bromo-4-chlorothiazole (Intermediate Q, step 2);

Enantiomer 1 of 11-(4-chlorothiazol-2-yl)-1,3-dimethyl-5-phenyl-8,9,10,11-tetrahydro-1H-pyrimido[4',5':3,4]pyrrolo[1,2-a]azepine-2,4(3H,7H)-dione LC-MS: Rt 1.45 mins; MS 441.3 m/z [M+H] Method 2minLowpHv03

1H NMR (400 MHz, CDCl3) δ 7.54-7.34 (5H, mult), 7.08 (1H, s), 5.03 (1H, mult), 4.14 (1H, mult), 3.63 (3H, s), 3.37 (1H, mult), 3.36 (3H, s), 3.00 (1H, mult), 2.12-1.85 (5H, mult).

SFC Chiralcel OJ-H 250×10 mm, 5 um@35 degC, 45% Methanol+0.1% v/v DEA/55% CO2, 10 ml/min, Detection: UV@220 nm, Rt 4.79 min, >99% e.e.

PREPARATION OF INTERMEDIATES

Intermediate A 6-(2-Mercapto-ethyl)-1,3-dimethyl-5-phenyl-1,6-dihydro-pyrrolo[3,4-d]pyrimidine-2,4-dione

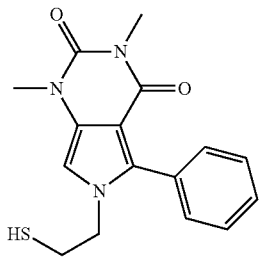 [SMILES: Cn1c(=O)c2c(-c3ccccc3)n(CCS)cc2n(C)c1=O]

Step 1: 1,3-Dimethyl-5-phenyl-6-(2-tritylsulfanyl-ethyl)-1,6-dihydro-pyrrolo[3,4-d]pyrimidine-2,4-dione Triethylamine (0.211 ml, 1.513 mmol) was added to a solution of 5-Benzoyl-6-(bromomethyl)-1,3-dimethylpyrimidine-2,4(1H,3H)-dione (Intermediate C) (510 mg, 1.513 mmol) and 2-tritylsulfanyl-ethylamine (Intermediate D) (483 mg, 1.513 mmol) in EtOH (5 ml) and the mixture heated at 100° C. under microwave irradiation for 2 hours. The reaction mixture was diluted with DCM (10 mL) and was washed with water (3×10 mL). The organic phase was passed through a hydrophobic frit and the solvent was evaporated under reduced pressure. The title product was obtained as a pale yellow solid and used without further purification.

LC-MS Rt 1.37 mins [M+H]⁺ 558.3 (Method 2min-LowpH)

Step 2: 6-(2-Mercapto-ethyl)-1,3-dimethyl-5-phenyl-1,6-dihydro-pyrrolo[3,4-d]pyrimidine-2,4-dione TFA (5.975 ml, 78 mmol) was added to a solution of 1,3-dimethyl-5-phenyl-6-(2-tritylsulfanyl-ethyl)-1,6-dihydro-pyrrolo[3,4-d]pyrimidine-2,4-dione (step 1) (865 mg, 1.551 mmol) and triethylsilane (2.477 ml, 15.51 mmol) in DCM (20 ml) and the mixture stirred at RT for 3 hours. The solvent was evaporated under reduced pressure. The residue was partitioned between DCM (10 mL) and sat. NaHCO₃ (10 mL) and the phases separated. The organic phase was dried over magnesium sulfate and the solvent evaporated under reduced pressure. The residue was triturated with diethyl ether and the solid collected by filtration. The title compound was obtained as a white solid.

¹H NMR (400 MHz, DMSO-d6) δ 7.45 (5H, s), 7.01 (1H, s), 4.02 (2H, t), 3.31 (3H, s), 3.15 (3H, s), 2.80 (2H, q), 2.33 (SH, t).

LC-MS Rt 0.95 mins; [M+H]⁺ 316.5 (Method 2min-LowpH)

Intermediate B (S)-6-(1-(Dimethylamino)-3-mercaptopropan-2-yl)-1,3-dimethyl-5-phenyl-1H-pyrrolo[3,4-d]pyrimidine-2,4(3H,6H)-dione

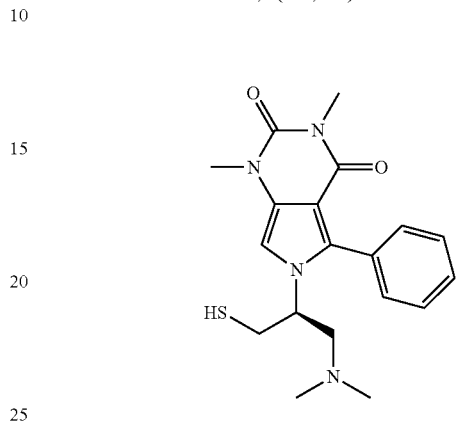

Step 1: (S)-2-Amino-3-(tritylthio)propan-1-ol

D-Cysteine (2.36 g, 19.48 mmol) was suspended in THF (40 mL) and cooled to 0° C. Borane-tetrahydrofuran complex (1 M in THF, 78 mL, 78 mmol) was added over 20 mins and the mixture was stirred at RT for 6 hours. The reaction was quenched with DMF (7 mL) and stirred for 25 mins. Trityl chloride (5.97 g, 21.43 mmol) was added and the mixture stirred for a further 16 hours. The reaction mixture was evaporated under vacuum. The residue was partitioned between DCM and water and the phases separated. The organic phase was passed through a hydrophobic frit and evaporated under vacuum. Purification by chromatography on silica, eluting with 50% EtOAc/hexane, EtOAc, 10% MeOH/EtOAc and 20% MeOH/EtOAc gave the title compound.

1H NMR (400 MHz, CDCl3) δ 7.49-7.17 (1%, mult), 3.55 (1H, mult), 3.40 (1H, mult), 2.74 (1H, mult), 2.49 (2H, mult).

Step 2: (S)-6-(1-Hydroxy-3-(tritylthio)propan-2-yl)-1,3-dimethyl-5-phenyl-1H-pyrrolo[3,4-d]pyrimidine-2,4(3H,6H)-dione (S)-2-Amino-3-(tritylthio)propan-1-ol (step 1) (1.58 g, 4.52 mmol), triethylamine (1.454 mL, 10.43 mmol) and 5-benzoyl-6-(bromomethyl)-1,3-dimethylpyrimidine-2,4 (1H,3H)-dione (Intermediate C) (1.173 g, 3.48 mmol) were combined in EtOH (60 mL) and the mixture heated at reflux for 1 hour. The reaction mixture was cooled to RT and evaporated under vacuum. The residue was partitioned between DCM and water and the phases separated. The organic phase was passed through a hydrophobic frit and evaporated under vacuum to give the title compound which was used without further purification.

¹H NMR (400 MHz, CDCl3) δ 7.56-7.17 (20H, mult), 6.37 (1H, s), 4.17 (1H, mult), 3.67 (2H, mult), 3.43 (3H, s), 3.35 (3H, s), 2.70 (1H, mult), 2.51 (1H, mult).

LC-MS Rt=1.40 min [M+H]+ 588.6 (Method 2minLowpHv01).

Step 3: (S)-2-(1,3-Dimethyl-2,4-dioxo-5-phenyl-3,4-dihydro-1H-pyrrolo[3,4-d]pyrimidin-6(2H)-yl)-3-(tritylthio)propyl methanesulfonate (S)-6-(1-Hydroxy-3-(tritylthio)propan-2-yl)-1,3-dimethyl-5-phenyl-1H-pyrrolo[3,4-d]pyrimidine-2,4(3H,6H)-dione (step 2) (2.5 g, 4.25 mmol) was dissolved in DCM (80 mL) and triethylamine (1.186 mL, 8.51 mmol) was added followed by methanesulfonyl chloride (0.398 mL, 5.10 mmol). The mixture was stirred at room temperature for 2 hours, further methanesulfonyl chloride was added and the mixture stirred for 50 mins. The reaction mixture was quenched with sat. NaHCO$_3$(aq) and extracted with DCM. The organic phase was passed through a hydrophobic frit and evaporated under vacuum. Purification by chromatography on silica, eluting with 20-100% EtOAc in iso-hexane gave the title compound.

$^1$H NMR (400 MHz, CDCl3) δ 7.50 (4H, mult), 7.39 (2H, mult), 7.35-7.22 (9H, mult), 6.30 (1H, s), 4.33 (1H, mult), 4.17 (1H, mult), 4.09 (1H, mult), 3.43 (3H, s), 3.34 (3H, s), 2.82 (3H, s), 2.73 (1H, mult), 2.49 (1H, mult).

LC-MS Rt=1.45 min [M+H]+ 666.3 (Method 2minLowpHv01).

Step 4: 6-((S)-1-Dimethylaminomethyl-2-tritylsulfanyl-ethyl)-1,3-dimethyl-5-phenyl-1,6-dihydro-pyrrolo[3,4-d]pyrimidine-2,4-dione (S)-2-(1,3-Dimethyl-2,4-dioxo-5-phenyl-3,4-dihydro-1H-pyrrolo[3,4-d]pyrimidin-6(2H)-yl)-3-(tritylthio)propyl methanesulfonate (step 3)(1.7 g, 2.55 mmol) was dissolved in DMF (12 mL) and dimethylamine (40% wt. aqueous solution) (1.455 mL, 11.49 mmol) was added. The mixture was heated under microwave irradiation at 120° C. for 15 h. The reaction mixture was diluted with EtOAc and washed with brine (4×). The organic phase was dried over sodium sulphate and evaporated under vacuum. The residue was redissolved in DCM and evaporated onto silica. Purification by chromatography on silica, eluting with 20-100% EtOAc in iso-hexane gave the title compound.

$^1$H NMR (400 MHz, CDCl3) δ 7.51 (5H, mult), 6.42 (1H, s), 4.35 (1H, mult), 3.45 (3H, s), 3.36 (3H, s), 2.95 (2H, mult), 2.64 (2H, mult), 1.57 (6H, mult).

LC-MS: Rt 1.07 mins; MS 615.7 m/z [M+H] Method 2minLowpHv01

Step 5: (S)-6-(1-(Dimethylamino)-3-mercaptopropan-2-yl)-1,3-dimethyl-5-phenyl-1H-pyrrolo[3,4-d]pyrimidine-2,4(3H,6H)-dione

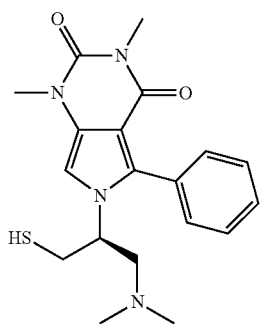 [SMILES: CN(C)C[C@@H](CS)n1cc2c(c1-c1ccccc1)c(=O)n(C)c(=O)n2C]

6-((S)-1-Dimethylaminomethyl-2-tritylsulfanyl-ethyl)-1,3-dimethyl-5-phenyl-1,6-dihydro-pyrrolo[3,4-d]pyrimidine-2,4-dione (step 4) (1.3 g, 2.115 mmol) was dissolved in DCM (50 mL) and TFA (5 mL, 64.9 mmol) and triethylsilane (0.675 mL, 4.23 mmol) were added. The mixture was stirred at RT for 1 hour 20 mins. The reaction mixture was rigorously evaporated under vacuum. Purification by chromatography on silica, eluting with 20-100% EtOAc/hexane, 10% MeOH/EtOAc and 10% (7N NH3 in MeOH)/EtOAc gave the title compound.

$^1$H NMR (400 MHz, CDCl3) δ 7.51 (5H, mult), 6.42 (1H, s), 4.35 (1H, mult), 3.45 (3H, s), 3.36 (3H, s), 2.95 (2H, mult), 2.64 (2H, mult), 1.57 (6H, mult)

LC-MS: Rt 0.64 mins; MS 373.5 m/z [M+H] Method 2minLowpHv01

Intermediate C

5-Benzoyl-6-(bromomethyl)-1,3-dimethylpyrimidine-2,4(1H,3H)-dione

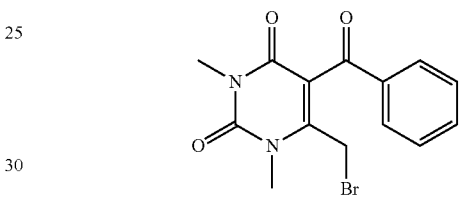

Step 1: 1,3,6-Trimethylpyrimidine-2,4(1H,3H)-dione

To a stirred suspension of N,N'-dimethylurea (commercial) (72.1 g, 819 mmol) and DMAP (100 g, 819 mmol) in pyridine (300 mL) under N$_2$ was added dropwise with stirring acetic anhydride (255 mL, 2701 mmol). On complete addition the reaction mixture was allowed to stir at RT for 3 hours. After this time, the volatiles were removed under reduced pressure to afford a viscous orange pyridine solution, which was seeded with product. The mixture was stored at 0-4° C. for 7 days. The resulting crystalline solid was then filtered under reduced pressure, washed with diethyl ether and dried to afford the title compound as colourless crystals. The mother liquors were further purified by chromatography on silica eluting with 30-50% EtOAc in iso-hexane. The resulting solid was diluted with diethyl ether (500 mL) and was stored at 0-4° C. overnight. The resulting crystals were filtered off and washed with iso-hexane, then dried to afford the title compound as colourless crystals and combined. The title product was obtained as white crystals.

$^1$H NMR (400 MHz, CDCl$_3$) δ 5.58 (1H, s), 3.38 (3H, s), 3.30 (3H, s), 2.22 (3H, s);

LC-MS Rt=0.55 min [M+H]+ 155.4 (Method: 2min-LC_v003).

Step 2: 5-Benzoyl-1,3,6-trimethylpyrimidine-2,4(1H,3H)-dione 1,3,6-Trimethylpyrimidine-2,4(1H,3H)-dione (step 1) (5 g, 32.4 mmol) and chlorobenzene (50 mL) were charged to a 3 necked flask, and the vessel evacuated with nitrogen. Benzoyl chloride (commercial) (11.2 mL, 97 mmol) was added followed by zinc (11) chloride (5 g, 36.7 mmol) in one portion and the reaction was then heated to 110° C. for 16 h.

The reaction was cooled to RT then poured into water (100 mL) and EtOAc (100 mL). The layers were separated and the aqueous extracted with EtOAc (2×150 mL). The combined organics were washed with water (100 mL) and dried (Na$_2$SO$_4$), filtered under reduced pressure and evaporated to leave an orange solid. The solid was washed with hexane followed by hot diethyl ether, affording the product as an off white solid. The mother liquors were further purified by chromatography on silica, eluting with 10%-100% EtOAc/hexane. The title product was obtained as a pale orange solid;

$^1$H NMR (400 MHz, CDCl$_3$) δ 7.89 (2H, dd), 7.60 (1H, t), 7.48 (2H, t), 3.52 (3H, s), 3.38 (3H, s), 2.26 (3H, s);

LCMS Rt=0.80 min [M+H]+ 259 (Method 2min-LC_v003).

Step 3: 5-Benzoyl-6-(bromomethyl)-1,3-dimethylpyrimidine-2,4(1H,3H)-dione

Bromine (0.497 mL, 9.68 mmol) was added to a solution of 5-benzoyl-1,3,6-trimethyl pyrimidine-2,4(1H,3H)-dione (step 2) (2.5 g, 9.68 mmol) in chloroform (50 mL) with stirring under nitrogen. The mixture was then heated to 55° C. for 2 h. A further portion of bromine (0.25 mL, 0.5 equiv) was then added and heating continued at 55° C. for a further 30 min. The mixture was then cooled to RT, diluted with CHCl$_3$ (50 mL) and poured into saturated sodium thiosulfate solution (150 mL). The layers were separated and the aqueous phase was extracted with CHCl$_3$ (50 mL). The combined organics were washed with water (50 mL), brine (50 mL), dried (Na$_2$SO$_4$) and filtered under reduced pressure. The solvent was then evaporated under reduced pressure to afford a pale yellow solid. This solid was dissolved in hot EtOAc (50 mL) and slowly evaporated until crystallisation was observed. The resulting white solid was collected by reduced pressure filtration and washed with cold EtOAc (10 mL) and dried in air. The compound was further dried under vacuum at 50° C. for 2 h. The title product was isolated as white micro needles.

$^1$H NMR (400 MHz, DMSO-d$_6$) δ 7.90 (2H, d), 7.67 (1H, t), 7.52 (2H, t), 4.40 (2H, s), 3.50 (3H, s), 3.17 (3H, s);

LC-MS Rt=2.75 min [M+H]+ 337/339 (Method 10min-LC_v003).

Intermediate D

2-Tritylsulfanyl-ethylamine

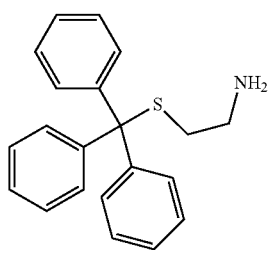 [SMILES: NCCSC(c1ccccc1)(c1ccccc1)c1ccccc1]

Cysteamine (commercial) (900 mg, 11.67 mmol) was added to a stirred solution of triphenylmethanol (commercial) (3.037 g, 11.67 mmol) in TFA (10 ml) and the mixture stirred at RT for 3 hours. The mixture was then concentrated under reduced pressure and the residue partitioned between DCM (20 mL) and water (20 mL). The mixture was basified by the slow addition of solid K$_2$CO$_3$. The aqueous phase was extracted with DCM (2×20 mL), the combined organic phases passed through a hydrophobic frit and the solvent evaporated under reduced pressure. The material was used without further purification.

Intermediate E (S)-6-(2-Mercaptopropyl)-1,3-dimethyl-5-phenyl-1H-pyrrolo[3,4-d]pyrimidine-2,4(3H,6H)-dione

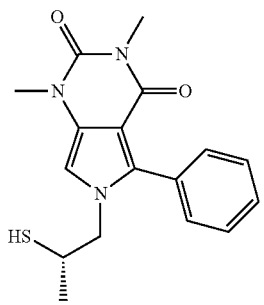 [SMILES: C[C@H](S)Cn1cc2c(c1-c1ccccc1)c(=O)n(C)c(=O)n2C]

Step 1: (R)-6-(2-Hydroxypropyl)-1,3-dimethyl-5-phenyl-1H-pyrrolo[3,4-d]pyrimidine-2,4(3H,6H)-dione 5-Benzoyl-6-(bromomethyl)-1,3-dimethylpyrimidine-2,4(1H,3H)-dione (Intermediate C) (1 g 2.97 mmol) was added to a microwave vial (10-25 mL) equipped with a stirrer bar. To the vial was added ethanol (10 ml) followed by triethylamine (0.41 ml, 2.97 mmol) and (R)-1-aminopropan-2-ol (commercial). (223 mg, 2.97 mmol) The vial was heated to 100° C. in a microwave reactor for 1 h. The ethanol was removed in vacuo to yield a solid. The solid was dissolved in DCM and water added. The DCM water mixture was separated and the aqueous extracted with DCM (×2). The organics were combined, washed with water and passed through a hydrophobic frit. The solvent was removed in vacuo to yield the title compound as a pale yellow solid.

LC-MS: Rt 0.86 mins; MS m/z 314 [M+H]+; Method 2minLowpHv01

Step 2: (R)-1-(1,3-Dimethyl-2,4-dioxo-5-phenyl-3,4-dihydro-1H-pyrrolo[3,4-d]pyrimidin-6(2H)-yl)propan-2-yl methanesulfonate To a solution of (R)-6-(2-hydroxypropyl)-1,3-dimethyl-5-phenyl-1H-pyrrolo[3,4-d]pyrimidine-2,4(3H,6H)-dione (step 1) (925 mg, 2.95 mmol) in DCE (16 ml) was added triethylamine (2.05 ml, 14.8 mmol), DMAP (36 mg, 0.29 mmol) and methanesulfonyl chloride (1.15 ml, 14.8 mmol) at 0° C. and reaction stirred for 30 min. Solid K$_2$CO$_3$ was added to the reaction mixture and the resulting mixture was diluted with water and extracted with DCM (3×20 ml) The organics were passed through a hydrophobic frit and concentrated in vacuo to yield a yellow oil. The material was used without further purification.

LC-MS Rt 1.04 mins; MS m/z 392 [M+H]+; (Method 2minLowpHv01)

Step 3: (S)-1,3-Dimethyl-5-phenyl-6-(2-(tritylthio) propyl)-1H-pyrrolo[3,4-d]pyrimidine-2,4(3H,6H)-dione To a stirred solution of triphenylmethylthiol (0.93 mg, 3.37 mmol) in dry THF (50 ml) was added sodium hydride (225 mg, 5.62 mmol) at 0° C. and the solution stirred for 1 hour at RT. To the resulting yellow solution was added crude (R)-1-(1,3-dimethyl-2,4-dioxo-5-phenyl-3,4-dihydro-1H-pyrrolo[3,4-d]pyrimidin-6(2H)-yl)propan-2-yl methanesulfonate (step 2) (1.1 mg, 2.81 mmol) as a solution in dry DMF (3 ml) at 0° C. The solution was stirred overnight at RT. The reaction was poured into dilute HCl and extracted with EtOAc, The organic layer was successively washed with water and dried over $Na_2SO_4$. The solvent was removed in vacuo to yield a yellow oil/semi-solid. The oil was dissolved in a minimal volume of DCM and purified via ISCO column chromatography, 24 g, liquid load, 20-35% iso-hexane:EtOAc, product eluting at 30% affording 12 fractions. The corresponding fractions were reduced in vacuo to yield an oil of title compound. The material was used without further purification.

LC-MS Rt 1.55 mins; MS m/z 572 [M+H]+ (Method 2min-LowpHv01)

Step 4: (S)-6-(2-Mercaptopropyl)-1,3-dimethyl-5-phenyl-1H-pyrrolo[3,4-d]pyrimidine-2,4(3H,6H)-dione To crude (S)-1,3-dimethyl-5-phenyl-6-(2-(tritylthio)propyl)-1H-pyrrolo[3,4-d]pyrimidine-2,4(3H,6H)-dione (step 3)(1.35 mg, 1.06 mmol) in DCM (30 ml) was added TFA (4.09 ml, 53.1 mmol) and triethylsilane (1.7 ml, 10.6 mmol) giving a yellow solution. The mixture was stirred at RT overnight. The reaction mixture was evaporated under vacuum. The residue was partitioned between DCM/water and the phases separated. The organic phase was passed through a hydrophobic frit and evaporated under vacuum. The solid was dissolved in a minimal volume of DCM and purified via ISCO column chromatography, 40 g silica, liquid load, 0-60% iso-hexane:EtOAc, product eluting at 50% affording 7 pure fractions. Corresponding fractions were reduced in vacuo to yield the title compound as a white solid.

1H NMR (400 MHz, CDCl3) δ 7.52-7.43 (5H, m); 6.44 (1H, s); 4.01 (2H, d); 3.44 (3H, s); 3.36 (3H, s); 3.12 (1H, sextet); 1.43 (1H, d); 1.16 (3H, d).

LCMS Rt 1.00 mins; MS m/z 330 [M+H]+; (Method 2min-LowpHv01)

Intermediate F 1,3-Dimethyl-2,4-dioxo-6-(2-(tritylthio)ethyl)-2,3,4,6-tetrahydro-1H-pyrrolo[3,4-d]pyrimidin-5-ylboronic acid

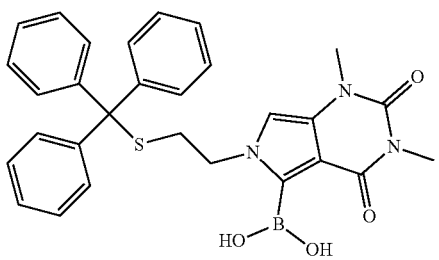 [SMILES: Cn1c(=O)c2c(B(O)O)n(CCSC(c3ccccc3)(c3ccccc3)c3ccccc3)cc2n(C)c1=O]

Step 1 (2-Chloroethyl)(trityl)sulfane

Synthesised by a modified Method of Trujillo, D. A.; McMahon, W. A.; Lyle, R. E. *J. Org. Chem.*, 1987, 52, 2932-2933

(Chloromethanetriyl)tribenzene (100 g, 359 mmol) was dissolved in dichloromethane (500 mL) under nitrogen. Ethylene sulfide (25 mL, 420 mmol) was charged and the reaction aged at room temperature for 22 h. The solvent was then evaporated under reduced pressure to afford a pale yellow solid. The solid was dissolved in hot (60° C.) toluene (150 mL) and hot filtered under gravity, then cooled slowly to room temperature. The resultant white crystalline solid was collected by reduced pressure filtration and washed with toluene (2×100 mL) and iso-hexanes (2×100 mL), dried under vacuum at 50° C. for 16 h. The title compound was isolated as a white crystalline solid;

LCMS Rt 1.57 mins; MS m/z 243.4 [M+H]+; Method 2minLowpHv01;

1H NMR (400 MHz, DMSO-d6) δ 7.38-7.32 (12H, m), 7.30-7.24 (3H, m), 3.21 (2H, t), 2.55 (2H, t).

Step 2: 1,3-Dimethyl-1H-pyrrolo[3,4-d]pyrimidine-2,4(3H,6H)-dione 1,3-Dimethylpyrimidine-2,4(1H,3H)-dione (commercially available, 40 g, 285 mmol) and toluenesulfonylmethyl isocyanide (commercially available, 84 g, 428 mmol) were dissolved in 2-MeTHF (1000 mL) under nitrogen at 30° C. and held for 5 mins. The vessel was cooled to 0° C. (internal). A solution of KOtBu (commercially available, 64.1 g, 571 mmol) in 2-MeTHF (500 mL was then added to the solution via a dropping funnel over 0.5 h, such that the internal temperature remained below 5° C. On addition of the KOtBu solution, an orange precipitate formed. An additional portion of 2-MeTHF (455 mL) was then charged via dropping funnel over 5 mins. After 40 mins, the dark orange suspension was quenched with sat $NH_4Cl$ solution (2×400 mL) charged via dropping funnel over 15 mins. The suspension was diluted with EtOAc (1 L), the layers were separated and the aqueous extracted with EtOAc (3×1 L). The combined organics were dried ($MgSO_4$) and filtered under reduced pressure. The solvent was removed under reduced pressure to afford a brown semi-solid. The solids were suspended in MeOH (300 mL), sonicated and stirred at room temperature for 15 mins, filtered by reduced pressure filtration and washed with MeOH (100 mL). The solid was dried under vacuum at 50° C. for 24 h. The title compound was obtained as a pale brown amorphous solid;

1H NMR (400 MHz, DMSO-d6) δ 11.81 (1H br s), 7.43 (1H, d); 6.74 (1H, d); 3.29 (3H, s); 3.20 (3H, s)

LC-MS: Rt 0.59 mins; not ionised; Method 2minLowpHv01

A second crop of material could be obtained by evaporation of the MeOH to afford a red oil. Trituration with MeOH (50 mL), filtration under reduced pressure and washing with MeOH (20 mL) and drying under vacuum at 50° C. for 16 h afforded the title compound as a pale brown amorphous solid;

1H NMR (400 MHz, DMSO-d6) δ 11.82 (1H, s), 7.43 (1H, dd), 6.74 (1H, t), 3.29 (3H, s), 3.19 (3H, s).

Step 3:1,3-Dimethyl-6-(2-(tritylthio)ethyl)-1H-pyrrolo[3,4-d]pyrimidine-2,4(3H,6H)-dione 1,3-Dimethyl-1H-pyrrolo[3,4-d]pyrimidine-2,4(3H,6H)-dione) (step 2)(10 g, 55.8 mmol), (2-chloroethyl)(trityl)sulfane (step 1) (20.81 g, 61.4 mmol), potassium iodide (1.853 g, 11.16 mmol) and caesium carbonate (36.4 g, 112 mmol) were suspended in anhydrous dimethylacetamide (250 mL), forming a dark orange suspension. The vessel was evacuated and back-filled with $N_2$ (×3) and stirred under nitrogen at 50° C. for 41.7 h. The reaction was cooled to room temperature and decanted slowly into a stirring water (800 mL) and EtAcO (200 mL) mixture. The layers were separated and the aqueous extracted with EtOAc (4×100 mL). The solids present where collected by reduced pressure filtration (solid 1). The combined organics were washed with water (4×100 mL), brine (2×100 mL), dried ($Na_2SO_4$) and filtered under reduced pressure. The organic solvent was evaporated under reduced pressure to afford a pale yellow solid, which was suspended in Et$_2$O (200 mL) and stirred at room temperature for 10 mins; the pale tan solid was then collected by reduced pressure filtration (solid 2). The solid collected from the extraction mixture (solid 1) was washed with water (100 mL), EtOAc (100 mL) and stirred in Et$_2$O (100 mL) for 10 mins at room temperature and collected by reduced pressure filtration. Both solids were dried under vacuum at 50° C. for 16 h. Both crops were then blended to afford the title compound as a tan solid;

1H NMR (400 MHz, CDCl3) δ 7.46-7.39 (6H, m), 7.36-7.29 (6H, m), 7.29-7.22 (3H, m), 7.01 (1H, d), 6.03 (1H d), 3.48 (2H, t), 3.38 (3H, s), 3.33 (3H, s), 2.67 (2H, t).

LC-MS: Rt 1.38 mins; MS m/z 482.2 [M+H]+; Method 2minLowpHv01

Step 4: 1,3-Dimethyl-2,4-dioxo-6-(2-(tritylthio)ethyl)-2,3,4,6-tetrahydro-1H-pyrrolo[3,4-d]pyrimidin-5-ylboronic acid 1,3-Dimethyl-6-(2-(tritylthio)ethyl)-1H-pyrrolo[3,4-d]pyrimidine-2,4(3H,6H)-dione (step 2)(3.6 g, 7.47 mmol) was dissolved in anhydrous THF (67.3 mL) at room temperature in an oven dried flask. The flask was evacuated and backfilled with nitrogen (×3) and cooled to −78° C. LDA (0.719 M, 16.63 mL, 11.96 mmol) was added over 10 mins followed by triisopropyl borate (2.76 mL, 11.96 mmol) and the reaction aged for 2 hr at −78° C. The reaction was quenched with saturated NH$_4$Cl solution (60 mL) added via syringe under nitrogen and the mixture was warmed to room temperature and stirred overnight under nitrogen. The mixture was then diluted DCM (400 mL). The layers were separated and the aqueous extracted with DCM (2×100 mL). The combined organics were passed through a hydrophobic frit and the solvent was reduced to ~20 mL under reduced pressure and EtOAc (100 mL) added to the resulting red oil. Reduction of solvent volume under reduced pressure to ~25 mL afforded precipitation of a white solid. The solid was collected by reduced pressure filtration, washed with EtOAc (10 mL) and dried under vacuum 50° C. for 16 h to afford the title compound;

LC-MS: Rt 1.41 mins; MS m/z 526.4 [M+H]+; Method 2minLowpHv01;

1H NMR (400 MHz, DMSO-d6) δ 9.61 (2H, s), 7.36-7.29 (6H, m), 7.29-7.20 (9H, m), 6.79 (1H, s), 4.27 (2H, t), 3.28 (3H, s), 3.27 (3H, s), 2.54 (2H, t).

Intermediate G 3-(6-(2-Mercaptoethyl)-1,3-dimethyl-2,4-dioxo-2,3,4,6-tetrahydro-1H-pyrrolo[3,4-d]pyrimidin-5-yl)benzonitrile

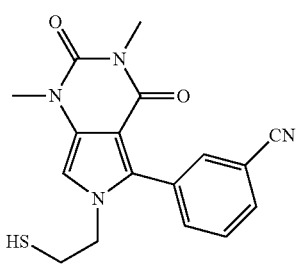 [SMILES: Cn1c(=O)c2c(-c3cccc(C#N)c3)n(CCS)cc2n(C)c1=O]

Step 1: 3-(1,3-Dimethyl-2,4-dioxo-6-(2-(tritylthio)ethyl)-2,3,4,6-tetrahydro-1H-pyrrolo[3,4-d]pyrimidin-5-yl)benzonitrile A suspension comprising 1,3-dimethyl-2,4-dioxo-6-(2-(tritylthio)ethyl)-2,3,4,6-tetrahydro-1H-pyrrolo[3,4-d]pyrimidin-5-ylboronic acid (Intermediate F) (300 mg, 0.571 mmol), 3-bromobenzonitrile (104 mg, 0.571 mmol) and barium hydroxide (196 mg, 1.142 mmol) in n-BuOAc (5710 μL) was treated with Pd-118 (18.61 mg, 0.029 mmol) and the mixture was heated to 80° C. Water (247 μL, 13.70 mmol) was added at 80° C. and the suspension was stirred rapidly for 90 minutes. After cooling to RT, the mixture was allowed to stand at RT overnight. The mixture was diluted with DCM (50 ml) and washed with water (50 ml). The layers were separated and the aqueous portion was extracted with DCM (3×30 ml). The organics were combined and dried over MgSO$_4$, filtered and concentrated. Purification of the crude product by trituration with EtOAc/iso-hexane afforded the title compound;

LCMS: Rt 1.45 min, [M+H]+ 583.6. Method 2minLowpHv01.

Step 2: 3-(6-(2-Mercaptoethyl)-1,3-dimethyl-2,4-dioxo-2,3,4,6-tetrahydro-1H-pyrrolo[3,4-d]pyrimidin-5-yl)benzonitrile 3-(1,3-Dimethyl-2,4-dioxo-6-(2-(tritylthio)ethyl)-2,3,4,6-tetrahydro-1H-pyrrolo[3,4-d]pyrimidin-5-yl)benzonitrile (step 1)(573 mg, 0.983 mmol) was dissolved in DCM (20 ml) to form a clear brown solution and passed through 2×500 mg Isolute® Si-TMT (silica bound equivalent of 2,4,6-trimercatotriazine) cartridges to afford a colourless solution. The solution was placed under a nitrogen atmosphere and whilst stirring rapidly, treated dropwise with triethylsilane (1.571 ml, 9.83 mmol) followed TFA (3.79 ml, 49.2 mmol). After stirring at RT for 1 h, the reaction mixture was concentrated under reduced pressure to yield a white solid. The isolated crude product was triturated with diethyl ether and dried in a vacuum oven at 50° C. to afford the title compound;

LCMS: Rt 0.99 min, [M+H]+ 341.3. Method 2minLowpHv01.

Intermediate GA

3-Chloro-5-(1,3-dimethyl-2,4-dioxo-6-(2-(tritylthio)ethyl)-2,3,4,6-tetrahydro-1H-pyrrolo[3,4-d]pyrimidin-5-yl)benzonitrile

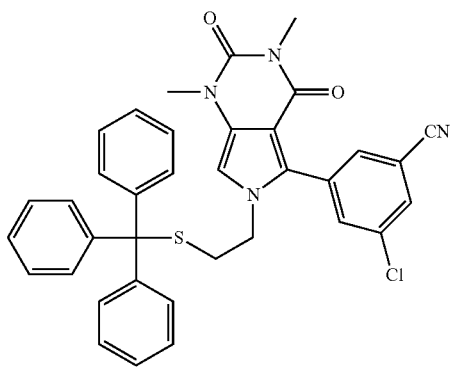 [SMILES: Cn1c(=O)c2c(-c3cc(Cl)cc(C#N)c3)n(CCSC(c3ccccc3)(c3ccccc3)c3ccccc3)cc2n(C)c1=O]

The title compound was prepared analogously to 3-(1,3-dimethyl-2,4-dioxo-6-(2-(tritylthio)ethyl)-2,3,4,6-tetrahydro-1H-pyrrolo[3,4-d]pyrimidin-5-yl)benzonitrile (Intermediate GA step 1) by replacing bromobenzonitrile with 3-bromo-5-chlorobenzonitrile;

LC-MS: Rt 1.53 mins; MS m/z 617.3/619.3 [M+H]+; Method 2minLowpHv01

Intermediate GB

Ethyl 2-(1,3-dimethyl-2,4-dioxo-6-(2-(tritylthio)ethyl)-2,3,4,6-tetrahydro-1H-pyrrolo[3,4-d]pyrimidin-5-yl)thiazole-4-carboxylate

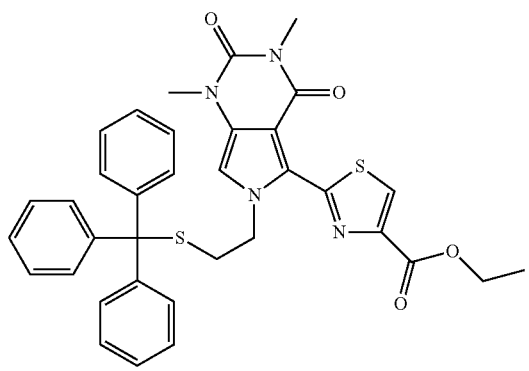 [SMILES: CCOC(=O)c1csc(-c2c3c(=O)n(C)c(=O)n(C)c3cn2CCSC(c2ccccc2)(c2ccccc2)c2ccccc2)n1]

(1,3-dimethyl-2,4-dioxo-6-(2-(tritylthio)ethyl)-2,3,4,6-tetrahydro-1H-pyrrolo[3,4-d]pyrimidin-5-yl)boronic acid (Intermediate F) (1001 mg, 1.906 mmol), ethyl 2-bromothiazole-4-carboxylate (409 mg, 1.732 mmol), sodium hydrogen carbonate (291 mg, 3.46 mmol) and Pd-118 (113 mg, 0.173 mmol) were suspended in n-butyl acetate (12.3 ml) and heated to 80° C. Water (3.08 ml) was then added and the mixture heated at 80° C. for 21 hours. The mixture was then cooled to room temperature and diluted with water (100 ml) and DCM (100 ml). The mixture was extracted with DCM (3×100 ml) and the combined organic extracts were washed with water (50 ml) and brine (50 ml). Silica-TMT (30 g) was added and the mixture stirred at room temperature for 5 mins, then filtered. The residue was rinsed with DCM (20 ml) and the filtrates evaporated under vacuum. The resultant residue was rinsed with diethyl ether and filtered to afford the title compound.

1H NMR (400 MHz, DMSO-d6) δ 8.62 (1H, s), 7.30-7.24 (6H, m), 7.24-7.18 (9H, s), 6.85 (1H, s), 4.36 (2H, t), 4.32 (2H, q), 3.31 (3H, s), 3.23 (3H, s), 2.57 (2H, t), 1.30 (3H, t)

LC-MS Rt 1.76 mins [M+H]+ 637.5 (Method 2minLowpHv03)

Intermediate H 1,3-Diethyl-6-(2-mercaptoethyl)-5-phenyl-1H-pyrrolo[3,4-d]pyrimidine-2,4(3H,6H)-dione

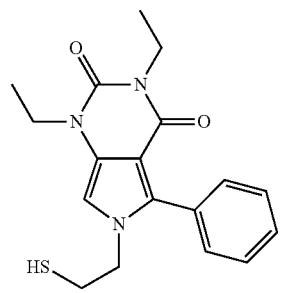 [SMILES: CCn1c(=O)c2c(-c3ccccc3)n(CCS)cc2n(CC)c1=O]

Step 1:
1,3-Diethyl-6-methylpyrimidine-2,4(1H,3H)-dione

6-Methylpyrimidine-2,4(1H,3H)-dione (5.5 g, 43.6 mmol) was suspended in water (80 ml) and cooled to 0° C. NaOH (17.44 g, 436 mmol) was added slowly, forming a solution. Ethyl iodide (14.10 ml, 174 mmol) was added and the mixture heated at 60° C. for 3 days. The reaction mixture was cooled to RT and diluted with water. The mixture was extracted with chloroform (3×). The basic extracts were evaporated under vacuum. The residue was dissolved in DCM and evaporated onto silica. The silica was deposited onto a 25 g silica cartridge and the system eluted progressively with 10% EtOAc/isohexane, 20% EtOAc/isohexane, 40% EtOAc/isohexane, 75% EtOAc/isohexane and EtOAc to yield the title compound as a colourless oil;

1H NMR (400 MHz, CDCl3) δ 5.59 (1H, s), 4.01 (2H, q), 3.92 (2H, q), 2.26 (3H, s), 1.30 (3H, t), 1.24 (3H, t).

LC-MS Rt 0.72 mins; MS 183.5 m/z [M+H] (Method 2minLowpHv01)

Step 2: 5-Benzoyl-1,3-diethyl-6-methylpyrimidine-2,4(1H,3H)-dione 1,3-Diethyl-6-methylpyrimidine-2,4(1H,3H)-dione (step 1)(680 mg, 3.73 mmol), benzoyl chloride (1.299 mL, 11.20 mmol) and tin(IV) chloride (1.314 mL, 11.20 mmol) were combined in chlorobenzene (30 mL, 295 mmol) and the mixture heated at reflux for 16 h. The reaction mixture was cooled to RT and diluted with EtOAc. The mixture was washed with 2M NaOH(aq) until basic. The organic phase was washed with brine, dried over sodium sulphate and evaporated under vacuum. The residue was dissolved in DCM and evaporated onto silica. The silica was deposited onto a 10 g silica cartridge and the system eluted with 10% EtOAc/hexane, 20% EtOAc/hexane, 40% EtOAc/hexane and 50% EtOAc/hexane. Product elutes at 40% EtOAc/hexane. Fractions were concentrated under vacuum to yield the title compound as an off white solid;

1H NMR (, 400 MHz, CDCl3) δ 7.89 (2H, d), 7.60 (1H, t), 7.48 (2H, t), 4.03 (2H, q), 4.02 (2H, q), 2.27 (3H, s), 1.37 (3H, t), 1.24 (3H, t).

LC-MS Rt 1.00 mins; MS 287.5 m/z [M+H] (Method 2minLowpHv01)

Step 3: 5-Benzoyl-6-(bromomethyl)-1,3-diethylpyrimidine-2,4(1H,3H)-dione

5-Benzoyl-1,3-diethyl-6-methylpyrimidine-2,4(1H,3H)-dione (step 2)(800 mg, 2.79 mmol) was dissolved in chloroform (Volume: 60 mL) and bromine (0.288 mL, 5.59 mmol) was added. The mixture was heated at 60° C. for 1 h. A further portion of bromine (0.288 mL, 5.59 mmol) was added. The mixture was heated for 30 mins and further bromine (0.288 mL, 5.59 mmol) was added. The reaction mixture was cooled to RT and washed with aqueous sodium metabisulfite. The organic phase was separated, passed through a hydrophobic frit and evaporated under vacuum. The residue was dissolved in DCM and evaporated onto silica. The silica was deposited onto a 10 g silica cartridge and the system eluted with 20% EtOAc/hexane, 30% EtOAc/hexane, and 40% EtOAc/hexane.

Product containing fractions were concentrated under vacuum. The resultant oily residue was triturated with hexane, which was collected by filtration. The title compound was collected as an off white solid.

1H NMR (400 MHz, CDCl3) δ 7.87 (2H, d), 7.62 (1H, t), 7.49 (2H, t), 4.26 (2H, s), 4.16 (2H, q), 4.02 (2H, q), 1.43 (3H, t), 1.25 (3H, t).

Step 4: 1,3-Diethyl-5-phenyl-6-(2-(tritylthio)ethyl)-1H-pyrrolo[3,4-d]pyrimidine-2,4(3H,6H)-dione 5-Benzoyl-6-(bromomethyl)-1,3-diethylpyrimidine-2,4(1H,3H)-dione (step 3) (850 mg, 2.327 mmol), 2-(tritylthio)ethanamine (commercially available, 1115 mg, 3.49 mmol) and triethylamine (0.973 mL, 6.98 mmol) were combined in EtOH (Volume: 20 mL) and the mixture heated at reflux for 20 mins. The reaction mixture was cooled to RT and evaporated under vacuum. The residue was partitioned between DCM and water and extracted with DCM. The organic phase was passed through a hydrophobic frit and evaporated onto silica. The silica was deposited onto a 10 g silica cartridge and purification by chromatography on silica eluting with 10-50% EtOAc in iso-hexane afforded the title compound as a white solid;

1H NMR (400 MHz, CDCl3) δ 7.45 (4H, mult), 7.40-7.21 (16H, mult), 5.99 (1H, s), 4.01 (2H, mult), 3.88 (2H, mult), 3.66 (2H, mult), 2.49 (2H, t), 1.34 (3H, mult), 1.19 (3H, mult).

LC-MS Rt 1.59 mins; MS 586.3 m/z [M+H] (Method 2minLowpHv02)

Step 5: 1,3-Diethyl-6-(2-mercaptoethyl)-5-phenyl-1H-pyrrolo[3,4-d]pyrimidine-2,4(3H,6H)-dione 1,3-Diethyl-5-phenyl-6-(2-(tritylthio)ethyl)-1H-pyrrolo[3,4-d]pyrimidine-2,4(3H,6H)-dione (step 4) (1.45 g, 2.475 mmol) was dissolved in DCM (50 mL) and treated with TFA (5 mL, 64.9 mmol) followed by triethylsilane (0.791 mL, 4.95 mmol). The mixture was stirred at RT for 16 h. The reaction mixture was basified by slow addition of sat. NaHCO3(aq) and extracted with DCM. The organic phase was passed through a hydrophobic frit and evaporated under vacuum. The residue was dissolved in DCM, evaporated onto silica and the silica deposited onto a 10 g silica cartridge. The system was eluted with 20%-60% EtOA in iso-hexane to yield the title compound as a pale yellow oil.

1H NMR (400 MHz, CDCl3) δ 7.53-7.44 (5H, mult), 6.46 (1H, s), 4.11 (2H, t), 4.03 (2H, q), 3.94 (2H, q), 2.74 (1H, dt), 1.37 (3H, t), 1.21 (3H, t).

LC-MS Rt 1.19 mins; MS 344.6 m/z [M+H] (Method 2minLowpHv01)

Intermediate I 1,3-Dimethyl-5-phenyl-7,8-dihydropyrimido[4,5-a]indolizine-2,4(1H,3H)-dione

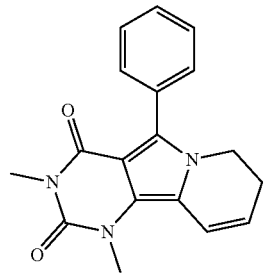 [SMILES: Cn1c(=O)c2c(-c3ccccc3)n3c(c2n(C)c1=O)C=CCC3]

5-Benzoyl-6-(bromomethyl)-1,3-dimethylpyrimidine-2,4(1H,3H)-dione (Intermediate C), (1.169 g, 3.47 mmol) in EtOH (20 mL) was treated with 4,4-diethoxybutan-1-amine (0.659 mL, 3.81 mmol) and TEA (0.966 mL, 6.93 mmol) and the mixture heated at reflux for 50 min. The reaction mixture was cooled to RT and evaporated under reduced pressure. The residue was re-dissolved in THF (20 mL), 1M hydrochloric acid (3.47 mL) was added and the mixture stirred at RT for 1.5 h. The reaction mixture was diluted with EtOAc, washed with water, brine and the organic phase was dried over sodium sulphate and evaporated under reduced pressure. The residue was triturated with DCM/hexane and the precipitate collected by filtration to give the title product as a pale pink solid.

1H NMR (400 MHz, CDCl3) δ 7.53-7.44 (m, 5H), 6.85 (dt, 1H), 5.84 (dt, 1H), 3.97 (t, 2H), 3.66 (s, 3H), 3.37 (s, 3H), 2.47 (m, 2H);

LC-MS Rt=1.11 min [M+H]+ 308 (Method 2min-LC_v003).

Intermediate J

4-Methyl-2-tributylstannanyl-thiazole

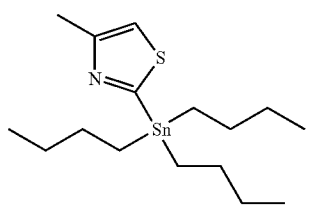 [SMILES: CCC[CH2][Sn]([CH2]CCC)([CH2]CCC)[c]1nc(C)cs1]

4-Methylthiazole (0.5 ml, 5.50 mmol) was dissolved in Et2O (10 ml) and cooled to −78° C. Methyllithium (1.6 M in hexanes, 5.15 ml, 8.24 mmol) was added slowly and the mixture stirred at −78° C. for 1 hour. Tri-n-butyltin chloride (1.640 ml, 6.05 mmol) was then added slowly, the mixture stirred briefly at −78° C. then allowed to warm to RT and stirred overnight. The reaction mixture was quenched with water and extracted with Et2O. The organic phase was washed with brine, dried over sodium sulphate and evaporated under vacuum to afford the title product as a crude pale yellow oil. The material was used without further purification.

Intermediate K

1,3-Dimethyl-2,4-dioxo-5-phenyl-1,2,3,4,7,8-hexahydropyrimido[4,5-a]indolizin-10-yl trifluoromethanesulfonate

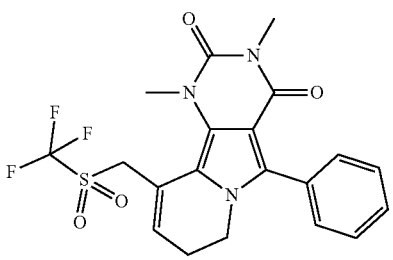 [SMILES: Cn1c(=O)c2c(-c3ccccc3)n3c(c2n(C)c1=O)C(CS(=O)(=O)C(F)(F)F)=CCC3]

Step 1: 4-(1,3-Dimethyl-2,4-dioxo-5-phenyl-1,2,3,4-tetrahydro-pyrrolo[3,4-d]pyrimidin-6-yl)-butyric acid ethyl ester 5-Benzoyl-6-(bromomethyl)-1,3-dimethylpyrimidine-2,4(1H,3H)-dione (Intermediate C) (996 mg, 2.95 mmol), ethyl 4-aminobutanoate hydrochloride (489 mg, 2.95 mmol) and triethylamine (0.823 ml, 5.91 mmol) were combined in EtOH (15 ml) and heated at reflux for 2.5 hours. The reaction mixture was cooled to RT and evaporated under reduced pressure. The residue was dissolved in EtOAc and washed with water (1×) and brine (1×). The organic phase was dried over sodium sulphate and evaporated under reduced pressure to afford the title compound as an off-white solid;

1H NMR (400 MHz, CDCl3) δ 7.51-7.41 (m, 5H), 6.43 (br s, 1H), 4.08 (q, 2H), 3.99 (t, 2H), 3.44 (s, 3H), 3.36 (s, 3H), 2.20 (t, 2H), 2.00 (m, 2H), 1.24 (t, 3H);

LC-MS Rt 1.11 min [M+H]+ 370.5 (Method: 2minLowpH)

Step 2: 4-(1,3-Dimethyl-2,4-dioxo-5-phenyl-1,2,3,4-tetrahydro-pyrrolo[3,4-d]pyrimidin-6-yl)-butyric acid 4-(1,3-Dimethyl-2,4-dioxo-5-phenyl-1,2,3,4-tetrahydropyrrolo[3,4-d]pyrimidin-6-yl)-butyric acid ethyl ester (step 1)(1.01 g, 2.73 mmol) was dissolved in THF (10 ml) and water (10 ml) and lithium hydroxide (0.655 g, 27.3 mmol) were added. The mixture was stirred at 60° C. for 5 hours. Further lithium hydroxide (0.655 g, 27.3 mmol) was added and the mixture stirred at 60° C. for a further 24 hours. The reaction mixture was cooled to RT and concentrated under reduced pressure. The residue was acidified using 1M HCl (aq) and extracted with chloroform (5×). The combined organic phases were passed through a hydrophobic frit and evaporated under reduced pressure. The title product was obtained as a white solid.

1H NMR (400 MHz, CDCl3) δ 7.52-7.41 (m, 5H), 6.42 (s, 1H), 4.00 (t, 2H), 3.43 (s, 3H), 3.35 (s, 3H), 2.25 (t, 2H), 2.00 (m, 2H);

LC-MS Rt 0.82 min [M+H]+ 342.5 (Method: 2minLowpH)

Step 3: 1,3-Dimethyl-5-phenyl-8,9-dihydropyrimido[4,5-a]indolizine-2,4,10(1H,3H,7H)-trione 4-(1,3-Dimethyl-2,4-dioxo-5-phenyl-1,2,3,4-tetrahydropyrrolo[3,4-d]pyrimidin-6-yl)-butyric acid (step 2)(1.3 g, 3.81 mmol) and polyphosphoric acid (10 g, 3.81 mmol) were combined and heated at 80° C. for 1 hour. The reaction mixture was cooled to RT, diluted with water and extracted with chloroform (4×). The combined organic extracts were passed through a hydrophobic frit and evaporated under reduced pressure. The title product was afforded as a pale yellow solid.

1H NMR (400 MHz, CDCl3) δ 7.57-7.50 (m, 3H), 7.50-7.43 (m, 2H), 4.01 (t, 2H), 3.93 (s, 3H), 3.36 (s, 3H), 2.72 (t, 2H), 2.22 (m, 2H).

LC-MS Rt 0.91 min [M+H]+ 324 (Method: 2minLowpH)

Step 4: 1,3-Dimethyl-2,4-dioxo-5-phenyl-1,2,3,4,7,8-hexahydropyrimido[4,5-a]indolizin-10-yl trifluoromethanesulfonate 1,3-dimethyl-5-phenyl-8,9-dihydropyrimido[4,5-a]indolizine-2,4,10(1H,3H,7H)-trione (step 3) (920 mg, 2.85 mmol) and 2,6-lutidine (0.497 ml, 4.27 mmol) were dissolved in DCM (25 ml) at 0° C. Trifluoromethanesulfonic anhydride (0.577 ml, 3.41 mmol) was added slowly and the mixture stirred in an ice bath for 1.5 hours. The reaction mixture was diluted with water and extracted with DCM. The organic phase was passed through a hydrophobic frit and evaporated under reduced pressure. Purification by chromatography on silica eluting with 40% EtOAc/hexane yielded the title compound as a yellow solid.

1H NMR (400 MHz, CDCl3) δ 7.54-7.46 (m, 5H), 6.00 (t, 1H), 3.92 (t, 2H), 3.61 (s, 3H), 3.37 (s, 3H), 2.57 (dt, 2H);

LC-MS Rt 1.14 min [M+H]+ 456 (Method: 2minLowpH).

Intermediate L

5-(3-Fluorophenyl)-10-hydroxy-1,3-dimethyl-7,8,9,10-tetrahydropyrimido[4,5-a]indolizine-2,4(1H,3H)-dione

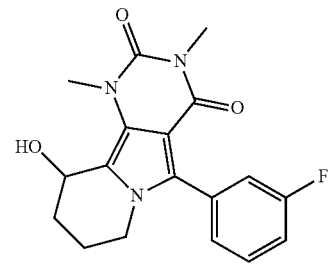 [SMILES: Cn1c(=O)c2c(-c3cccc(F)c3)n3c(c2n(C)c1=O)C(O)CCC3]

Step 1: 5-(3-Fluorophenyl)-1,3-dimethyl-8,9-dihydropyrimido[4,5-a]indolizine-2,4,10(1H,3H,7H)-trione The title compound was prepared analogously to 3-(1,3-dimethyl-2,4,10-trioxo-1,2,3,4,7,8,9,10-octahydropyrimido[4,5-a]indolizin-5-yl)benzonitrile (Example 9 steps 1-7) by replacing 3-bromobenzonitrile (step 3) with 1-bromo-3-fluorobenzene (commercially available).

LC-MS: Rt 1.02 mins; MS m/z 342.5 [M+H]+; Method 2minLowpHv01

Step 2: 5-(3-Fluorophenyl)-10-hydroxy-1,3-dimethyl-7,8,9,10-tetrahydropyrimido[4,5-a]indolizine-2,4(1H,3H)-dione To a stirred solution of 5-(3-fluorophenyl)-1,3-dimethyl-8,9-dihydropyrimido[4,5-a]indolizine-2,4,10(1H,3H,7H)-trione (step 1)(150 mg, 0.439 mmol) in MeOH (2197 µL) at 0° C. was added sodium borohydride (49.9 mg, 1.318 mmol) portionwise. The resulting yellow solution was warmed to room temperature and stirred for 15 minutes. The reaction was concentrated in vacuo. The residue was diluted with water (5 mL) and DCM (10 mL). The aqueous phase was separated and extracted with DCM (3×10 mL). The combined organic fractions were dried ($Na_2SO_4$) and concentrated under reduced pressure to afford the title compound as a pale yellow solid;

1H NMR (400 MHz, DMSO-d6) δ 7.50 (1H, q), 7.33-7.24 (3H, m), 5.34-5.25 (1H, m), 5.22-5.15 (1H, m), 3.93-3.74 (2H, m), 3.70 (3H, s), 3.17 (3H, s), 2.19-2.04 (1H, m), 2.03-1.82 (2H, m), 1.82-1.74 (1H, m).

LCMS: Rt 0.94 mins; MS m/z 344.5 [M+H]+; Method 2minlowpHv01.

Intermediate La 5-(3-Fluorophenyl)-10-hydroxy-1,3,8-trimethyl-7,8,9,10-tetrahydropyrimido[4,5-a]indolizine-2,4(1H,3H)-dione

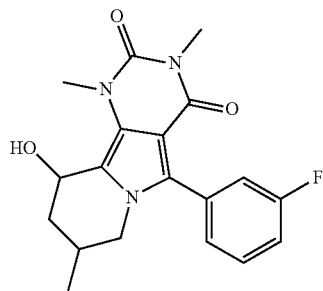 [SMILES: CC1CC(O)c2c3c(c(-c4cccc(F)c4)n2C1)c(=O)n(C)c(=O)n3C]

Step 1: 5-(3-Fluorophenyl)-1,3,8-trimethyl-8,9-dihydropyrimido[4,5-a]indolizine-2,4,10(1H,3H,7H)-trione The title compound was prepared analogously to 3-(1,3-dimethyl-2,4,10-trioxo-1,2,3,4,7,8,9,10-octahydropyrimido[4,5-a]indolizin-5-yl)benzonitrile (Example 9 steps 1-7) by replacing 3-bromobenzonitrile (step 3) with 1-bromo-3-fluorobenzene (commercially available) and methyl 4-bromobutanoate (Step 5) with methyl 4-bromo-3-methylbutanoate (Intermediate T).

LC-MS Rt 1.05 mins; [M+H]+ 356.5 (Method 2minLowpHv01)

Step 2: 5-(3-Fluorophenyl)-10-hydroxy-1,3,8-trimethyl-7,8,9,10-tetrahydropyrimido[4,5-a]indolizine-2,4(1H,3H)-dione The title compound was prepared analogously to Intermediate L using by replacing 5-(3-fluorophenyl)-1,3-dimethyl-8,9-dihydropyrimido[4,5-a]indolizine-2,4,10(1H,3H,7H)-trione in (step 2) with 5-(3-fluorophenyl)-1,3,8-trimethyl-8,9-dihydropyrimido[4,5-a]indolizine-2,4,10(1H,3H,7H)-trione.

LC-MS Rt 1.01 mins [M+H]+ 358.6 (Method 2minLowpHv01)

Intermediate Lb 5-(3-Fluorophenyl)-10-hydroxy-1,3,9-trimethyl-7,8,9,10-tetrahydropyrimido[4,5-a]indolizine-2,4(1H,3H)-dione

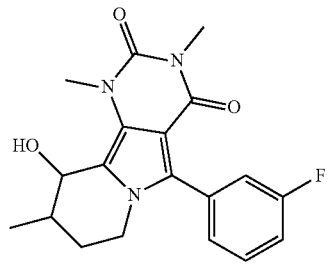 [SMILES: CC1CCn2c(-c3cccc(F)c3)c3c(=O)n(C)c(=O)n(C)c3c2C1O]

The title compound was prepared analogously to 5-(3-fluorophenyl)-10-hydroxy-1,3,8-trimethyl-7,8,9,10-tetrahydropyrimido[4,5-a]indolizine-2,4(1H,3H)-dione (Intermediate La) by replacing Methyl 4-bromo-3-methylbutanoate (Intermediate T) with methyl 4-bromo-2-methylbutanoate (Intermediate S).

LC-MS Rt 1.01 mins [M+H]+ 358.6 (Method 2minLowpHv01)

Intermediate M 1,3-Dimethyl-10-(4-methylthiazol-2-yl)-5-m-tolyl-7,8-di hydropyrimido[4,5-a]indolizine-2,4(1H,3H)-dione

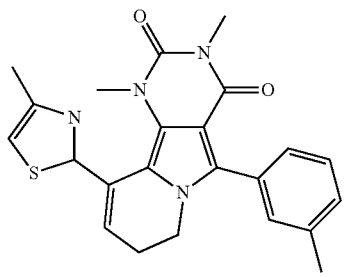 [SMILES: CC1=CSC(C2=CCCn3c(-c4cccc(C)c4)c4c(=O)n(C)c(=O)n(C)c4c32)N1]

Step 1: Ethyl 4-(1,3-dimethyl-2,4-dioxo-5-m-tolyl-3,4-dihydro-1H-pyrrolo[3,4-d]pyrimidin-6(2H)-yl)butanoate The title compound was prepared analogously to Intermediate I, step 1 by replacing 5-benzoyl-6-(bromomethyl)-1,3-dimethylpyrimidine-2,4(1H,3H)-dione (Intermediate C) with 6-bromomethyl-1,3-dimethyl-5-(3-methyl-benzoyl)-1H-pyrimidine-2,4-dione (Intermediate F).

$^1$H NMR (400 MHz, CDCl$_3$) δ 7.37 (1H, t), 7.27-7.20 (3H, mult), 6.40 (1H, s), 4.08 (2H, q), 3.96 (2H, t), 3.42 (3H, s), 3.35 (3H, s), 2.42 (3H, s), 2.19 (2H, t), 1.99 (2H, t), 1.22 (3H, t);

LC-MS Rt=1.16 mins; [M+H]+ 384.3 (Method 2minLowpHv01).

Step 2: 4-(1,3-Dimethyl-2,4-dioxo-5-m-tolyl-3,4-dihydro-1H-pyrrolo[3,4-d]pyrimidin-6(2H)-yl)butanoic acid Lithium hydroxide (2.64 g, 63.0 mmol) was added to a solution of ethyl 4-(1,3-dimethyl-2,4-dioxo-5-m-tolyl-3,4-dihydro-1H-pyrrolo[3,4-d]pyrimidin-6(2H)-yl)butanoate (step 1) (4.83 g, 12.6 mmol) in THF (48 mL)/water (12 mL). The mixture was stirred at room temperature for 24 hours. The organic solvent was largely removed under vacuum, the residue was acidified to pH 1, using 1M. The precipitate was extracted into chloroform (1×100 mL, 4×50 mL). The combined organic extracts were dried with magnesium sulfate and the solvent was removed under vacuum. The resulting solid was dried under vacuum at 50° C. to give the title compound.

$^1$H NMR (400 MHz, CDCl$_3$) δ 7.37 (1H, t), 7.27-7.22 (3H, mult), 6.40 (1H, s), 3.98 (2H, t), 3.42 (3H, s), 3.35 (3H, s), 2.42 (3H, s), 2.25 (2H, t), 1.99 (2H, mult);

LC-MS Rt=0.96 mins; [M+H]$^+$ 356.3 (Method 2minLowpHv01).

Step 3: 1,3-Dimethyl-5-m-tolyl-8,9-dihydropyrimido[4,5-a]indolizine-2,4,10(1H,3H,7H)-trione A solution of T3P® (1-propylphosphonic acid cyclic anhydride 50% solution in DMF) (1.0M, 329 µL, 0.56 mmol) was added to solid 4-(1,3-dimethyl-2,4-dioxo-5-m-tolyl-3,4-dihydro-1H-pyrrolo[3,4-d]pyrimidin-6(2H)-yl)butanoic acid (step 2) (200 mg, 0.56 mmol), giving a paste. DMF (1 mL) was added and a solution formed. The solution was stirred at room temperature for 1 hour and at 100° C. for 1 hour. The reaction mixture was diluted with ethyl acetate (10 mL) and washed with sat. sodium bicarbonate (1×5 mL) and brine (3×5 mL). The organic phase was dried with magnesium sulfate and the solvent was removed under vacuum to give the title compound.

$^1$H NMR (400 MHz, CDCl$_3$) δ 7.42 (1H, t), 7.34 (1H, d), 7.27-7.23 (2H, mult), 4.00 (2H, mult), 3.93 (3H, s), 3.36 (3H, s), 2.71 (2H, t), 2.45 (3H, s), 2.21 (2H, mult);

LC-MS Rt=1.05 mins; [M+H]$^+$ 338.4 (Method 2minLowpHv01).

Step 4: 1,3-Dimethyl-2,4-dioxo-5-m-tolyl-1,2,3,4,7,8-hexahydropyrimido[4,5-a]indolizin-10-yl trifluoromethanesulfonate Trifluoromethanesulfonic anhydride (253 µL, 1.50 mmol) was added to an ice-cooled solution of 1,3-dimethyl-5-m-tolyl-8,9-dihydropyrimido[4,5-a]indolizine-2,4,10(1H,3H,7H)-trione (step 3) (388 mg, 1.15 mmol) and 2,6-lutidine (201 µL, 1.73 mmol) in DCM (7 mL). The solution was allowed to reach room temperature slowly and was stirred for 16 hours. A further portion of trifluoromethanesulfonic anhydride (39 µL, 0.23 mmol) was added and the solution was stirred for a further 30 minutes. The reaction mixture was diluted with dichloromethane (15 mL) and washed with water (2×8 mL) and sat brine (1×8 mL). The organic phase was dried with magnesium sulfate and the solvent was removed under vacuum, keeping the rotary evaporator water bath at 20° C. to give the title compound.

LC-MS Rt=1.31 min; [M+H]$^+$ 470.5 (Method 2minLowpHv01).

Step 5: 1,3-Dimethyl-10-(4,4,5,5-tetramethyl-1,3,2-dioxaborolan-2-yl)-5-m-tolyl-7,8-dihydropyrimido[4,5-a]indolizine-2,4(1H,3H)-dione A mixture of 1,3-dimethyl-2,4-dioxo-5-m-tolyl-1,2,3,4,7,8-hexahydropyrimido[4,5-a]indolizin-10-yl trifluoromethanesulfonate (unpurified material from step 4, assumed 1.15 mmol), bis(pinaolato)diboron (321 mg, 1.27 mmol), bis(triphenylphosphine)palladium(II) chloride (24 mg, 0.035 mmol), triphenylphosphine (18 mg, 0.07 mmol) and potassium phenoxide (J. Am. Chem. Soc., 1959, Vol. 81, pp 2705-2715, 228 mg, 1.73 mmol) in toluene (8 mL) was stirred at 60° C., under nitrogen for 4 hours. The reaction mixture was diluted with water (20 mL) and was extracted with ethyl acetate (3×20 mL). The combined organic extracts were washed with brine (1×20 mL), dried with magnesium sulfate and the solvent was removed under vacuum. Purification by chromatography on silica, eluting with 20-50% EtOAc/hexane gave the product as an oil.

Addition of iso-hexane and subsequent removal under vacuum gave the title compound as an off-white solid.

1H NMR (400 MHz, CDCl3) δ 7.35 (1H, t), 7.28-7.22 (3H, mult), 6.75 (1H, t), 3.79 (2H, t), 3.58 (3H, s), 3.35 (3H, s), 2.41 (3H, s), 2.38 (2H, mult), 1.35 (12H, s);

LC-MS Rt=1.36 min [M+H]$^+$ 448.6 (Method 2minLowpHv01).

Step 6: 1,3-Dimethyl-10-(4-methylthiazol-2-yl)-5-m-tolyl-7,8-dihydropyrimido[4,5-a]indolizine-2,4(1H,3H)-dione A mixture of 1,3-dimethyl-10-(4,4,5,5-tetramethyl-1,3,2-dioxaborolan-2-yl)-5-m-tolyl-7,8-dihydropyrimido[4,5-a]indolizine-2,4(1H,3H)-dione (step 5) (295 mg, 0.66 mmol), 2-iodo-4-methylthiazole (Intermediate O) (135 mg, 0.60 mmol), Pd-118 (19.6 mg, 0.03 mmol) and barium hydroxide (206 mg, 1.20 mmol) in acetonitrile/water (1:1, 3 mL) was stirred at 80° C. for 30 minutes. The reaction mixture was diluted with 1M HCl (5 mL) and extracted with DCM (3×5 mL). The combined organic layers were filtered through a hydrophobic frit and the solvent was removed under vacuum. The residue was purified by chromatography on silica, eluting with 1-2% MeOH/DCM to give the title compound.

LC-MS Rt=1.24 mins; [M+H]$^+$ 419.1 (Method 2minLowpHv01).

Intermediate Na 1,3-Dimethyl-2,4-dioxo-5-phenyl-2,3,4,6-tetrahydro-1H-pyrrolo[3,4-d]pyrimidine-7-carbaldehyde

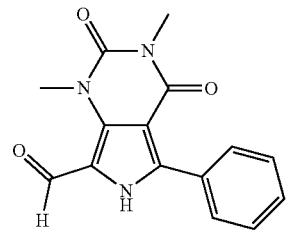 [SMILES: Cn1c(=O)c2c(-c3ccccc3)[nH]c(C=O)c2n(C)c1=O]

Step 1: 1,3-Dimethyl-5-phenyl-1H-pyrrolo[3,4-d]pyrimidine-2,4(3H,6H)-dione

5-Benzoyl-6-(bromomethyl)-1,3-dimethylpyrimidine-2,4 (1H,3H)-dione 13.4a (Intermediate C) (2.33 g, 6.91 mmol), hexamethyldisilazane (2.90 mL, 13.82 mmol) and triethylamine (2.89 mL, 20.73 mmol) were combined in dioxane (20 mL) and the mixture heated at reflux for 22 hours. Further portions of hexamethyldisilazane (2.90 mL, 13.82 mmol) and triethylamine (2.89 mL, 20.73 mmol) were added to allow the reaction to run to completion. The reaction mixture was cooled to room temperature, diluted with EtOAc (150 mL) and washed with 1M HCl (aq) and brine. The organic phases was dried over sodium sulphate and evaporated under vacuum. The residue was triturated with DCM/diethyl ether/hexane to afford the title compound.

LC-MS Rt 0.98 mins; MS 256.1 m/z [M+H] Method 2min-LowpHv03

Step 2: 1,3-Dimethyl-2,4-dioxo-5-phenyl-2,3,4,6-tetrahydro-1H-pyrrolo[3,4-d]pyrimidine-7-carbaldehyde Phosphorous oxychloride (1.081 mL, 11.60 mmol) was added slowly to a solution of 1,3-dimethyl-5-phenyl-1H-pyrrolo[3,4-d]pyrimidine-2,4(3H,6H)-dione (2.96 g, 11.60 mmol) in DMF (40 mL) at 0° C. The mixture was stirred at 0° C. for 15 mins. The reaction was quenched with 2M HCl(aq), diluted with EtOAc, and the mixture stirred overnight. The mixture was then extracted with EtOAc (3×) and the combined organic phases washed with brine, dried over sodium sulphate and evaporated under vacuum. The residue was triturated with diethyl ether/hexane to afford the title compound.

LC-MS Rt 0.97 mins; MS 284.2 m/z [M+H] Method 2min-LowpHv03

Intermediate Nb 3-(7-Formyl-1,3-dimethyl-2,4-dioxo-2,3,4,6-tetrahydro-1H-pyrrolo[3,4-d]pyrimidin-5-yl)benzonitrile

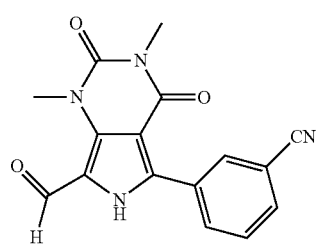 [SMILES: Cn1c(=O)c2c(-c3cccc(C#N)c3)[nH]c(C=O)c2n(C)c1=O]

The title compound was prepared in a similar manner to 1,3-dimethyl-2,4-dioxo-5-phenyl-2,3,4,6-tetrahydro-1H-pyrrolo[3,4-d]pyrimidine-7-carbaldehyde (Intermediate Na), starting from 3-(1,3-dimethyl-2,4-dioxo-2,3,4,6-tetrahydro-1H-pyrrolo[3,4-d]pyrimidin-5-yl)benzonitrile (Example 9.0 Step 4) and omitting step 1.

LC-MS Rt 0.93 mins [M+H]+ 309.2 (Method 2minLowpHv03)

Intermediate Nc 5-(3-Fluorophenyl)-1,3-dimethyl-2,4-dioxo-2,3,4,6-tetrahydro-1H-pyrrolo[3,4-d]pyrimidine-7-carbaldehyde

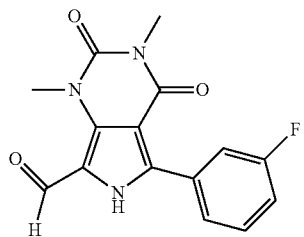 [SMILES: Cn1c(=O)c2c(-c3cccc(F)c3)[nH]c(C=O)c2n(C)c1=O]

The title compound was prepared in a similar manner to 1,3-dimethyl-2,4-dioxo-5-phenyl-2,3,4,6-tetrahydro-1H-pyrrolo[3,4-d]pyrimidine-7-carbaldehyde (Intermediate Na), starting from 5-(3-fluorophenyl)-1,3-dimethyl-1H-pyrrolo[3,4-d]pyrimidine-2,4(3H,6H)-dione (prepared in a similar manner to 3-(1,3-dimethyl-2,4-dioxo-2,3,4,6-tetrahydro-1H-pyrrolo[3,4-d]pyrimidin-5-yl)benzonitrile (Example 9.0 Step 4) using the appropriate halo compound in step 3 and omitting Step 1.

Intermediate Nd 1,3-Dimethyl-5-(4-methylthiazol-2-yl)-1H-pyrrolo[3,4-d]pyrimidine-2,4(3H,6H)-dione

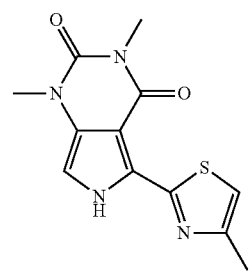

The title compound was prepared analogously to 3-(1,3-dimethyl-2,4-dioxo-2,3,4,6-tetrahydro-1H-pyrrolo[3,4-d]pyrimidin-5-yl)benzonitrile (Example 9.0 Step 4) by replacing 3-bromobenzonitrile by 2-iodo-4-methylthiazole (Intermediate O) in step 3;

LC-MS: Rt 0.95 mins [M+H]+ 277.4 (Method 2minLowpHv03).

Intermediate Ne

5-(3-Fluorophenyl)-1,3-dimethyl-1H-pyrrolo[3,4-d]pyrimidine-2,4(3H,6H)-dione

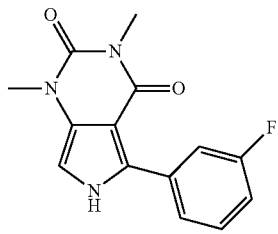 [SMILES: Cn1c(=O)c2c(-c3cccc(F)c3)[nH]cc2n(C)c1=O]

The title compound was prepared analogously to 3-(1,3-Dimethyl-2,4-dioxo-2,3,4,6-tetrahydro-1H-pyrrolo[3,4-d]pyrimidin-5-yl)benzonitrile (Example 9.0 Step 4) by replacing 3-bromobenzonitrile by 3-fluoro-1-bromobenzene in step 3;

LC-MS Rt 1.06 mins [M+H]+ 274.1 (Method 2minLow-pHv03)

Intermediate Nf

5-(3-Fluorophenyl)-1,3-dimethyl-1H-pyrrolo[3,4-d]pyrimidine-2,4(3H,6H)-dione

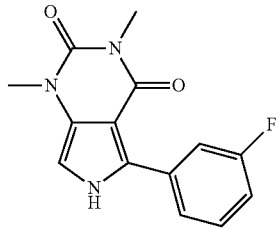 [SMILES: Cn1c(=O)c2c(-c3cccc(F)c3)[nH]cc2n(C)c1=O]

The title compound was prepared by an analogous method to 3-(1,3-dimethyl-2,4-dioxo-2,3,4,6-tetrahydro-1H-pyrrolo[3,4-d]pyrimidin-5-yl)benzonitrile (Ex. 9 step 4) by replacing 3-bromobenzonitrile (step 3) with 1-bromo-3-fluorobenzene (commercially available).

LC-MS Rt 1.04 mins [M+H]+ 274.5 (Method 2minLow-pHv03).

Intermediate O

2-Iodo-4-methylthiazole

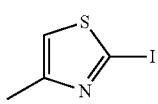

Methyllithium solution (1.6 M in Et$_2$O, 189 ml, 303 mmol) was added dropwise to 4-methylthiazole (22.94 ml, 252 mmol) in diethyl ether (505 ml) at −78° C. The mixture was stirred for 30 mins at −78° C., then iodine (83 g, 328 mmol) was added and the suspension slowly warmed to 0° C. and stirred for 45 mins. The reaction was quenched by the addition of water (150 ml), diluted with diethyl ether (100 ml) and the layers separated. The aqueous phase was extracted with diethyl ether (2×200 ml) and the combined organic phases were washed with saturated aqueous sodium thiosulfate solution (150 ml), 2M Na$_2$CO$_3$(aq) (100 ml), water (100 ml) and brine (100 ml), then dried over magnesium sulfate and evaporated under vacuum. Purification by chromatography on silica, eluting with 0-5% TBME/iso-hexane afforded the title compound.

1H NMR (400 MHz, CDCl3) δ 6.87 (1H, s), 2.48 (3H, s)

LC-MS Rt 1.00 mins [M+H]+ 2.26 (Method 2minLow-pHv03)

Intermediate P

4-Bromo-N-methoxy-N-methylbutanamide

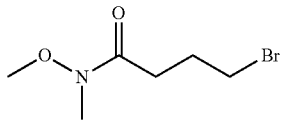

4-Bromobutanoyl chloride (5.62 ml, 48.5 mmol) in DCM (64 ml) was added slowly to a solution of DIPEA (17.80 ml, 102 mmol) and N,O-dimethylhydroxylamine hydrochloride (4.97 g, 51.0 mmol) in DCM (32 ml) at 0° C. The mixture was stirred at room temperature for 16 hours then diluted with DCM (50 ml). The mixture was washed with 1M HCl(aq) (2×50 ml) and saturated NaHCO$_3$(aq) (2×50 ml). The organic phase was passed through a hydrophobic frit and evaporated under vacuum. Purification by chromatography on silica, eluting with 30% EtOAc/hexane afforded the title compound.

1H NMR (400 MHz, CDCl3) δ 3.69 (3H, s), 3.62 (2H, t), 3.49 (3H, s), 3.17 (3H, s), 2.61 (2H, t), 2.17 (2H, quint), 2.09 (2H, quint).

Intermediate Q

4-Chlorothiazole-2-carbaldehyde

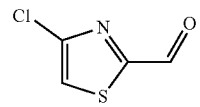

Step 1: 2,5-dibromo-4-chlorothiazole 2,4-Dichlorothiazole (10 g, 64.9 mmol) was dissolved in acetic acid (50.0 ml) and heated to 60° C. Bromine (15.05 ml, 292 mmol) was added dropwise and the reaction mixture stirred at 90° C. for 5.5 hours. The mixture was cooled to room temperature and made basic by slow addition of solid sodium carbonate, then diluted with water (100 mL) and extracted with Et$_2$O (3×150 ml). The combined organic extracts were washed with sat. aq. sodium thiosulfate (50 ml) dried over sodium sulfate evaporated under reduced pressure to afford the title compound as a pale yellow oil.

LC-MS Rt 1.43 min [M+H]+ 275.9/277.9/279.9/281.9 (Method 2minLowpHv03)

Step 2: 2-Bromo-4-chlorothiazole nBuLi (2.5M in hexanes, 7.21 mL, 18.03 mmol) was added dropwise over 20 mins to 2,5-dibromo-4-chlorothiazole (5 g, 18.03 mmol) in THF (100 mL) at −90° C., and the mixture stirred at −90° C. for 30 mins. Water (0.341 mL, 18.93 mmol) in THF (2 mL) was added and the mixture stirred whilst slowly warming to room temperature. The reaction was quenched with 0.1M HCl(aq) (100 mL) and extracted with Et$_2$O (150 ml). The organic phase was washed with saturated NaHCO$_3$(aq) (100 mL) and water (100 mL), dried over magnesium sulphate and evaporated under vacuo to afford the product as a pale yellow oil which slowly crystallised as pale yellow needles.

1H NMR: (400 MHz, CDCl3) δ 7.09 (1H, s).

LC-MS: Rt 1.12 mins [M+H]+ 199.9 (Method 2minLowpHv03)

Step 3: 4-Chlorothiazole-2-carbaldehyde n-Butyllithium (1.732 ml, 2.77 mmol) was added dropwise over 20 mins to a solution of 2-bromo-4-chlorothizaole (500 mg, 2.52 mmol) in diethyl ether (25.2 ml) at −78°. The mixture was stirred at −78° C. for 20, DMF (0.215 ml, 2.77 mmol) was added and the mixture warmed to −35° C. over 40 mins. The reaction was quenched with 6M HCl and the phases separated. The aqueous phase was extracted with diethyl ether (20 ml). The aqueous layer was brought to pH 10 by addition of solid potassium carbonate at 5° C. and extracted with diethyl ether (3×35 ml). The combined organic extracts were dried over magnesium sulfate and evaporated under vacuum. Purification by chromatography on silica, eluting with hexane, afforded the title compound.

1H NMR (400 MHz, CDCl3) δ 9.98 (1H, s), 7.59 (1H, s).

Intermediate R 5-(4-(((4-Methoxybenzyl)oxy)methyl)thiazol-2-yl)-1,3-dimethyl-1H-pyrrolo[3,4-d]pyrimidine-2,4(3H,6H)-dione

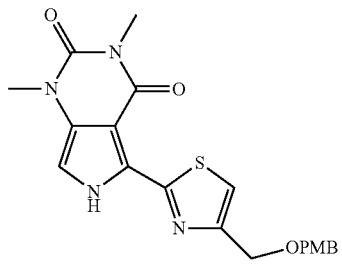

Step 1: Ethyl 2-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)thiazole-4-carboxylate The title compound was prepared by a method analogous to 3-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)benzonitrile (Ex. 9 step 3) using 1,3-dimethyl-2,4-dioxo-6-((2-(trimethylsilyl)ethoxy)methyl)-2,3,4,6-tetrahydro-1H-pyrrolo[3,4-d]pyrimidin-5-ylboronic acid (Example 9 Step 2) and the appropriate commercially available halo compound.

1H NMR (400 MHz, DMSO-d6) δ 8.64 (1H, s), 7.33 (1H, s), 5.94 (2H, s), 4.33 (2H, q), 3.44 (2H, t), 3.34 (3H, s), 3.24 (3H, s), 1.32 (3H, t), 0.75 (2H, t), −0.15 (9H, s)

LC-MS Rt 1.55 mins [M+H]+ 465.3 (Method 2minLowpHv03)

Step 2: 5-(4-(Hydroxymethyl)thiazol-2-yl)-1,3-dimethyl-6-((2-(trimethylsilyl)ethoxy)methyl)-1H-pyrrolo[3,4-d]pyrimidine-2,4(3H,6H)-dione Sodium borohydride (0.856 g, 22.62 mmol) was added to a solution of ethyl 2-(1,3-dimethyl-2,4-dioxo-6-((2-(trimethylsilyl)ethoxy)methyl)-2,3,4,6-tetrahydro-1H-pyrrolo[3,4-d]pyrimidin-5-yl)thiazole-4-carboxylate (step 1) (5.254 g, 11.31 mmol) and lithium chloride (0.959 g, 22.62 mmol) in ethanol (145 ml) and THF (290 ml) at 0° C. The mixture was stirred at room temperature for 16 hours. Further portions of lithium chloride (0.959 g, 22.62 mmol) and sodium borohydride (0.856 g, 22.62 mmol) were added and the mixture stirred for a further 4 hours. The reaction was quenched with saturated NaHCO$_3$ (aq) (250 ml), diluted with water (100 ml) and extracted with chloroform (3×350 ml). The combined organic extracts were washed with water (200 ml) and brine (2×200 ml), dried over sodium sulfate and evaporated under vacuum to afford the title compound.

1H NMR (400 MHz, DMSO-d6) δ 7.60 (1H, s), 7.23 (1H, s), 5.80 (2H, s), 5.38 (1H, t), 4.63 (2H, dd), 3.37 (2H, m), 3.33 (3H, s), 3.22 (3H, s), 0.73 (2H, m), −0.12 (9H, s).

LC-MS Rt 1.28 mins [M+H]+ 423.2 (Method 2minLowpHv03)

Step 3: 5-(4-(((4-Methoxybenzyl)oxy)methyl)thiazol-2-yl)-1,3-dimethyl-6-((2-(trimethylsilyl)ethoxy)methyl)-1H-pyrrolo[3,4-d]pyrimidine-2,4(3H,6H)-dione and 5-(4-(((4-methoxybenzyl)oxy)methyl)thiazol-2-yl)-1,3-dimethyl-1H-pyrrolo[3,4-d]pyrimidine-2,4(3H,6H)-dione Sodium hydride (60% wt, 0.637 g, 15.93 mmol) was added portionwise to a solution of 5-(4-(hydroxymethyl)thiazol-2-yl)-1,3-dimethyl-6-((2-(trimethylsilyl)ethoxy)methyl)-1H-pyrrolo[3,4-d]pyrimidine-2,4(3H,6H)-dione (step 2) (4.43 g, 7.97 mmol) NMP (Volume: 44 ml) at 0° C. and stirred for 1 hour. para-Methoxybenzyl chloride (1.404 ml, 10.36 mmol) was added and the mixture stirred at room temperature for 5 hours. Further portions of para-methoxybenzyl chloride (220 μl) and sodium hydride (60% wt, 64 mg) were added and the mixture stirred for a further 16 hours. The reaction was quenched at 0° C. with saturated NaHCO$_3$(aq) (50 ml), diluted with water (200 ml) and EtOAc (100 ml) and the phases separated. The aqueous phase was extracted with EtOAc (3×100 ml). The combined organic extracts were washed with water (2×100 ml) and brine (100 ml), dried over sodium sulfate and evaporated under vacuum. Purification by chromatography on silica, eluting with 40-60% EtOAc/hexane afforded the title compound and 5-(4-(((4-methoxybenzyl)oxy)methyl)thiazol-2-yl)-1,3-dimethyl-1H-pyrrolo[3,4-d]pyrimidine-2,4(3H,6H)-dione as a mixture which was used without further purification.

LC-MS Rt 1.63 mins [M+H]+ 543.6 (Method 2minLowpHv03)

Step 5: 5-(4-(((4-Methoxybenzyl)oxy)methyl)thiazol-2-yl)-1,3-dimethyl-1H-pyrrolo[3,4-d]pyrimidine-2,4(3H,6H)-dione tetra-n-Butylammonium fluoride solution (1.0 M in THF, 48.3 ml, 48.3 mmol) was added to a solution of 5-(4-(((4-methoxybenzyl)oxy)methyl)thiazol-2-yl)-1,3-dimethyl-6-((2-(trimethylsilyl)ethoxy)methyl)-1H-pyrrolo[3,4-d]pyrimidine-2,4(3H,6H)-dione and 5-(4-(((4-methoxybenzyl)oxy)methyl)thiazol-2-yl)-1,3-dimethyl-1H-pyrrolo[3,4-d]pyrimidine-2,4(3H,6H)-dione (5.24 g) in THF (Volume: 13.91 ml) at 60° C. The mixture was stirred at 60° C. for 6 hours. The mixture was then cooled to room temperature and evaporated under vacuum. The residue partitioned between EtOAc (100 ml) and water (150 ml) and the phases were separated. The organic phase was washed with water (3×200 ml) and both phases were stood for 60 hours. Both phases were filtered and the solids dried under vacuum to afford the title compound.

1H NMR (400 MHz, DMSO-d6) δ 12.79 (1H, s), 7.76 (1H, s), 7.45 (2H, d), 7.12-7.05 (3H, m), 4.77 (2H, s), 4.68 (2H, s), 3.90 (3H, s), 3.48 (3H, s), 3.40 (3H, s)

LC-MS Rt 1.24 mins [M+H]$^+$ 413.5 (Method 2minLow-pHv03)

Intermediate S

Methyl 4-bromo-2-methylbutanoate

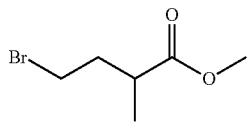

Boron tribromide solution (44.4 mL, 1.0M in DCM, 44.4 mmol) was added dropwise to alpha-methyl-gammabutyrolactone (commercial) (4.23 g, 42.3 mmol) in DCM (47 mL) at 0° C. The mixture was warmed to room temperature and stirred for 19 hours. The reaction was quenched with methanol (10.5 mL) at 0° C. and stirred at room temperature for 30 minutes, then diluted with water (100 mL) and extracted with DCM (1×50 mL). The organic extracts were washed with saturated NaHCO$_3$(aq) (2×50 mL) dried over magnesium sulfate and evaporated under vacuum. Purification by chromatography on silica afforded the title compound.

1H NMR (400 MHz, CDCl3) δ 3.72 (3H, s), 3.44 (2H, br t), 2.74 (1H, mult), 2.29 (1H, mult), 1.94 (1H, mult), 1.22 (3H, mult)

Intermediate Sa (S)-(2,2-Dimethyl-1,3-dioxolan-4-yl)methyl trifluoromethanesulfonate

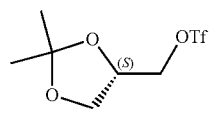

Trifluoromethanesulfonic anyhdride (1.398 ml, 8.32 mmol) was added dropwise to a solution of commercially available R-solketal (1 g, 7.57 mmol) and 2.6-lutidine (1.139 ml, 9.84 mmol) in DCM (25.2 mL) at 0° C. The mixture was warmed to room temperature and stirred for 1 hour. The mixture was then evaporated under vacuum and the residue partitioned between water (10 mL) and DCM (20 mL). The phases were separated and the aqueous phase was extracted with DCM (3×10 mL). The combined organic extracts were dried over magnesium sulfate to afford the title compound as a crude material which was used without further purification.

Intermediate Sb (2,2-Dimethyl-1,3-dioxolan-4-yl)methyl trifluoromethanesulfonate

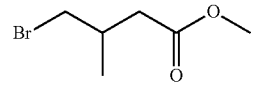

The title compound was prepared by an analogous method to Intermediate Ea from commercially available racemic solketal.

Intermediate T

Methyl 4-bromo-3-methylbutanoate

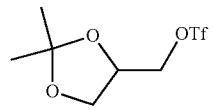 [SMILES: CC1(C)OCC(COS(=O)(=O)C(F)(F)F)O1]

Step 1: 4-Methyldihydrofuran-2(3H)-one

A mixture of 4-methylfuran-2(5H)-one (800 mg, 8.2 mmol) and 10% palladium on carbon (80 mg) in EtOAc (17 mL) was stirred under an atmosphere of hydrogen for 18 hours.

The mixture was filtered and the residue rinsed with EtOAc. The filtrates were evaporated under vacuum to afford the title compound.

1H NMR (400 MHz, CDCl3) δ 4.40 (1H, mult), 3.86 (1H, mult), 2.69-2.59 (2H, mult), 2.13 (1H, mult), 1.15 (3H, d).

Step 2: Methyl 4-bromo-3-methylbutanoate

Boron tribromide solution (9.1 mL, 1.0M in DCM, 9.1 mmol) was added dropwise to a solution of 4-methyldihydrofuran-2(3H)-one (870 mg, 8.7 mmol) in DCM (9 mL) at 0° C. The mixture was stirred at room temperature for 20 hours. The reaction mixture was re-cooled to 0° C. and methanol (2 mL) was added dropwise. The mixture was warmed to room temperature and stirred for a further 30 minutes. The reaction was quenched with water (20 mL) and extracted with DCM (3×10 mL). The combined organic extracts were washed with saturated NaHCO$_3$(aq) (1×10 mL), dried over magnesium sulfate and evaporated under vacuum. Purification by chromatography on silica, eluting with 20-50% DCM/hexane, afforded the title compound.

1H NMR (400 MHz, CDCl3) δ 3.70 (3H, s), 3.44 (2H, mult), 2.54 (1H, mult), 2.38-2.23 (2H, mult), 1.08 (3H, d).

The invention claimed is:

1. A compound of the formula (I) or a pharmaceutically acceptable salt thereof:

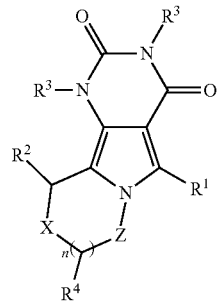

wherein $R^1$ represents phenyl, $(C_4$-$C_7)$cycloalkenyl or $Het^1$, which $R^1$ group may be unsubstituted or substituted on one or two carbon atoms by substituents $R^a$, and may further be substituted on a nitrogen atom with a substituent $R^{a1}$;

each $R^a$ independently represents $(C_1$-$C_4)$alkyl, halo, halo$(C_1$-$C_4)$alkyl, cyano, hydroxy$(C_1$-$C_4)$alkyl, $(C_1$-$C_4)$alkoxy, halo$(C_1$-$C_4)$alkoxy, $(C_1$-$C_4)$alkoxy$(C_1$-$C_4)$alkyl, $R^6OC(O)$—, or $R^6OC(O)(C_1$-$C_4)$alkyl-;

$R^{a1}$ represents $(C_1$-$C_4)$alkyl, hydroxy$(C_1$-$C_4)$alkyl, $(C_1$-$C_4)$alkoxy$(C_1$-$C_4)$alkyl, $(C_1$-$C_4)$alkylamino$(C_1$-$C_4)$alkyl-, di[$(C_1$-$C_4)$alkyl]amino$(C_1$-$C_4)$alkyl-, aryl$(C_1$-$C_4)$alkyl or $R^6OC(O)(C_1$-$C_4)$alkyl-;

$R^2$ represents $(C_1$-$C_6)$alkyl, $(C_3$-$C_7)$cycloalkyl, $(C_4$-$C_7)$cycloalkenyl, phenyl, furanyl, thiazolyl or thienyl, which $R^2$ may be unsubstituted or substituted on from one to three carbon atoms with substituents $R^b$;

each $R^b$ independently represents $(C_1$-$C_4)$alkyl, halo, halo$(C_1$-$C_4)$alkyl, cyano, $(C_1$-$C_4)$alkylamino$(C_1$-$C_4)$alkyl-, di[$(C_1$-$C_4)$alkyl]amino$(C_1$-$C_4)$alkyl-, $(R^6)_2NC(O)(C_1$-$C_4)$alkyl- or $R^6OC(O)(C_1$-$C_4)$alkyl-;

X represents S, Z represents $CHR^{4a}$ and n represents 1; or
X represents $CHR^{4b}$, Z represents $NR^5$ and n represents 1 or 2; or
X represents $CHR^{4b}$, Z represents $CHR^{4a}$ and n represents 0, 1 or 2; or
X represents $C(=CH_2)$, $CF_2$ or $C(CH_3)_2$, Z represents $CHR^{4a}$ and n represents 0 or 1;

each $R^3$ independently represents methyl or ethyl;

when X represents S, $R^4$ represents hydrogen, $(C_1$-$C_4)$alkyl, halo$(C_1$-$C_4)$alkyl, hydroxy$(C_1$-$C_4)$alkyl, $(C_1$-$C_4)$alkoxy$(C_1$-$C_4)$alkyl-, amino$(C_1$-$C_4)$alkyl-, $(C_1$-$C_4)$alkylamino$(C_1$-$C_4)$alkyl-, di[$(C_1$-$C_4)$alkyl]amino$(C_1$-$C_4)$alkyl-, phenyl, $Het^1(C_1$-$C_4)$alkyl-, $Het^2(C_1$-$C_4)$alkyl-, $(C_1$-$C_4)$alkylS$(O)_2NH(C_1$-$C_4)$alkyl-, or $R^7C(O)NH(C_1$-$C_4)$alkyl-;

when X represents $CHR^{4b}$, each $R^4$ independently represents hydrogen, hydroxy, $(C_1$-$C_4)$alkyl, $(C_1$-$C_4)$alkoxy, halo$(C_1$-$C_4)$alkyl, hydroxy$(C_1$-$C_4)$alkyl, $(C_1$-$C_4)$alkoxy$(C_1$-$C_4)$alkyl-, amino$(C_1$-$C_4)$alkyl-, $(C_1$-$C_4)$alkylamino$(C_1$-$C_4)$alkyl-, di[$(C_1$-$C_4)$alkyl]amino$(C_1$-$C_4)$alkyl-, amino, $(C_1$-$C_4)$alkylamino-, di[$(C_1$-$C_4)$alkyl]amino-, phenyl, $Het^1(C_1$-$C_4)$alkyl-, $Het^2(C_1$-$C_4)$alkyl-, $(C_1$-$C_4)$alkylS$(O)_2NH(C_1$-$C_4)$alkyl-, or $R^7C(O)NH(C_1$-$C_4)$alkyl-;

$R^{4a}$ represents hydrogen, $(C_1$-$C_4)$alkyl, hydroxy$(C_1$-$C_4)$alkyl, halo$(C_1$-$C_4)$alkyl, amino$(C_1$-$C_4)$alkyl-, $(C_1$-$C_4)$alkylamino$(C_1$-$C_4)$alkyl-, di[$(C_1$-$C_4)$alkyl]amino$(C_1$-$C_4)$alkyl-, $Het^1(C_1$-$C_4)$alkyl-, $Het^2(C_1$-$C_4)$alkyl-, or $R^6OC(O)$—;

$R^{4b}$ represents hydrogen or methyl;
$R^5$ represents hydrogen or $(C_1$-$C_4)$alkyl;
$R^6$ represents hydrogen or $(C_1$-$C_4)$alkyl;
$R^7$ represents $(C_1$-$C_2)$alkyl, $(C_1$-$C_2)$alkoxy, $(C_1$-$C_2)$alkoxy$(C_1$-$C_2)$alkyl or phenyl;

$Het^1$ represents a 5- or 6-membered heteroaryl ring comprising a) one oxygen or sulphur atom and optionally one or two nitrogen atoms; or b) from one to four nitrogen atoms; and $Het^2$ represents a 4- to 7-membered heterocyclic ring comprising a) 1 or 2 heteroatoms selected from N, O and S; or b) —C(O)— and 1 or 2 heteroatoms selected from N and O.

2. A compound according to claim 1, wherein $R^1$ represents phenyl, cyclohexenyl, thiazolyl, pyrazolyl, thienyl, pyrimidin-2-yl or pyridine-2-yl and wherein $R^1$ may be unsubstituted or substituted on one or two carbon atoms by substituents $R^a$, and may further be substituted on a nitrogen atom with a substituent $R^{a1}$.

3. A compound according to claim 1, wherein $R^2$ represents phenyl, furanyl, thiazolyl, or thieny, which $R^2$ may be unsubstituted or substituted on from one to three carbon atoms with substituents $R^b$.

4. A compound according to claim 1, wherein each $R^b$ independently represents $(C_1$-$C_2)$alkyl, halo, halo$(C_1$-$C_2)$alkyl, or cyano.

5. A compound according to claim 1, wherein each $R^3$ represents methyl.

6. A compound according to claim 1, wherein $R^4$ represents hydrogen, methyl, phenyl or $HOCH_2$—.

7. A compound according to claim 1, wherein X represents S, Z represents $CHR^{4a}$ and n represents 1.

8. A compound according to claim 1, wherein $R^{4a}$ represents hydrogen or methyl.

9. A compound according to claim 1, wherein the compound is of formula (Ia):

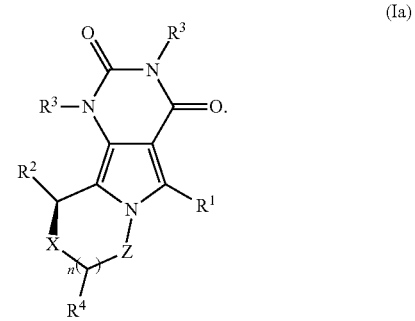

10. A compound according to claim 1 which is selected from:
1,3-Dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione;
1,3-Dimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione;
10-(5-Chlorofuran-2-yl)-1,3-dimethyl-5-phenyl-7,8-dihydro-1H-pyrimido[4',5':3,4]pyrrolo[2,1-c][1,4]thiazine-2,4(3H,10H)-dione;

10-(3-Chlorophenyl)-1,3-dimethyl-5-phenyl-7,8-dihydro-1H-pyrimido[4',5':3,4]pyrrolo[2,1-c][1,4]thiazine-2,4(3H,10H)-dione;

1,3-Dimethyl-5-phenyl-10-(m-tolyl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(m-tolyl)-7,8-dihydro-1H-pyrimido[4',5':3,4]pyrrolo[2,1-c][1,4]thiazine-2,4(3H,10H)-dione;

1,3-Dimethyl-10-(4-methylthiazol-2-yl)-5-(m-tolyl)-7,8-dihydro-1H-pyrimido[4',5':3,4]pyrrolo[2,1-c][1,4]thiazine-2,4(3H,10H)-dione;

1,3-Dimethyl-10-(5-methylthiophen-2-yl)-5-phenyl-7,8-dihydro-1H-pyrimido[4',5':3,4]pyrrolo[2,1-c][1,4]thiazine-2,4(3H,10H)-dione;

1,3-Dimethyl-10-(4-methylthiophen-2-yl)-5-phenyl-7,8-dihydro-1H-pyrimido[4',5':3,4]pyrrolo[2,1-c][1,4]thiazine-2,4(3H,10H)-dione;

7-((dimethylamino)methyl)-1,3-dimethyl-10-(5-methylfuran-2-yl)-5-phenyl-7,8-dihydro-1H-pyrimido[4',5':3,4]pyrrolo[2,1-c][1,4]thiazine-2,4(3H,10H)-dione;

10-(5-chlorofuran-2-yl)-1,3,8-trimethyl-5-phenyl-7,8-dihydro-1H-pyrimido[4',5':3,4]pyrrolo[2,1-c][1,4]thiazine-2,4(3H,10H)-dione;

1,3,8-trimethyl-10-(4-methylthiazol-2-yl)-5-phenyl-7,8-dihydro-1H-pyrimido[4',5':3,4]pyrrolo[2,1-c][1,4]thiazine-2,4(3H,10H)-dione;

3-(10-(5-Chlorofuran-2-yl)-1,3-dimethyl-2,4-dixox-2,3,4,7,8,10-hexahydro-1H-pyrimido[4',5':3,4]pyrrolo[2,1-c][1,4]thiazine-5-yl)benzonitrile;

10-(5-Chlorofuran-2-yl)-1,3-dimethyl-5-(methylthiazol-2-yl)-7,8-dihydro-1H-pyrimido[4',5':3,4]pyrrolo[2,1-c][1,4]thiazine-2,4(3H,10H)-dione;

10-(5-Chlorofuran-2-yl)-5-(cyclohex-1-en-1-yl)-1,3-dimethyl-7,8-dihydro-1H-pyrimido[4',5':3,4]pyrrolo[2,1-c][1,4]thiazine-2,4(3H,10H)-dione;

10-(5-Chlorofuran-2-yl)-5-(3,5-difluorophenyl)-1,3-dimethyl-7,8-dihydro-1H-pyrimido[4',5':3,4]pyrrolo[2,1-c][1,4]thiazine-2,4(3H,10H)-dione;

10-(5-Chlorofuran-2-yl)-1,3-diethyl-5-phenyl-7,8-dihydro-1H-pyrimido[4',5':3,4]pyrrolo[2,1-c][1,4]thiazine-2,4(3H,10H)-dione;

3-Chloro-5-(10-(5-chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

10-(2,3-Difluorophenyl)-1,3-dimethyl-5-phenyl-7,8,9,10-tetrahydropyrimido[4,5-a]indolizine-2,4(1H,3H)-dione;

1,3-Dimethyl-10-(5-methylfuran-2-yl)-5-phenyl-7,8,9,10-tetrahydropyrimido[4,5-a]indolizine-2,4(1H,3H)-dione;

1,3-Dimethyl-10-(4-methylthiazol-2-yl)-5-phenyl-7,8,9,10-tetrahydropyrimido[4,5-a]indolizine-2,4(1H,3H)-dione;

5-(3-Fluorophenyl)-1,3-dimethyl-10-(5-methylfuran-2-yl)-7,8,9,10-tetrahydropyrimido[4,5-a]indolizine-2,4(1H,3H)-dione;

5-(3-fluorophenyl)-1,3,9-trimethyl-10-(5-methylfuran-2-yl)-7,8,9,10-tetrahydropyrimido[4,5-a]indolizine-2,4(1H,3H)-dione;

5-(3-fluorophenyl)-1,3,8-trimethyl-10-(5-methylfuran-2-yl)-7,8,9,10-tetrahydropyrimido[4,5-a]indolizine-2,4(1H,3H)-dione;

5-(3-fluorophenyl)-1,3,9-trimethyl-10-(4-methylthiazol-2-yl)-7,8,9,10-tetrahydropyrimido[4,5-a]indolizine-2,4(1H,3H)-dione;

1,3-Dimethyl-10-(4-methylthiazol-2-yl)-5-m-tolyl-7,8,9,10-tetrahydropyrimido[4,5-a]indolizine-2,4(1H,3H)-dione;

5-(3-Chlorophenyl)-10-(4-chlorothiazol-2-yl)-1,3-dimethyl-7,8,9,10-tetrahydropyrimido[4,5-a]indolizine-2,4(1H,3H)-dione;

3-(1,3-Dimethyl-10-(4-methylthiazol-2-yl)-2,4-dioxo-1,2,3,4,7,8,9,10-octahydropyrimido[4,5-a]indolizin-5-yl)benzonitrile;

3-(1,3-Dimethyl-2,4-dioxo-5-phenyl-1,2,3,4,7,8,9,10-octahydropyrimido[4,5-a]indolizin-10-yl)benzonitrile;

1,3-Dimethyl-10-(4-methylthiazol-2-yl)-5-phenyl-7,8,9,10-tetrahydropyrimido[4',5':3,4]pyrrolo[1,2-b]pyridazine-2,4(1H,3H)-dione;

5-(3-Chlorophenyl)-1,3-dimethyl-10-(4-methylthiazol-2-yl)-7,8,9,10-tetrahydropyrimido[4',5':3,4]pyrrolo[1,2-b]pyridazine-2,4(1H,3H)-dione;

1,3-dimethyl-9-(5-methylfuran-2-yl)-5-phenyl-8,9-dihydro-1H-pyrimido[4,5-a]pyrrolizine-2,4(3H,7H)-dione;

10-(5-chlorofuran-2-yl)-8-(hydroxymethyl)-1,3-dimethyl-5-phenyl-7,8-dihydro-1H-pyrimido[4',5':3,4]pyrrolo[2,1-c][1,4]thiazine-2,4(3H,10H)-dione;

10-(5-chlorofuran-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione;

3-(10-(5-chlorofuran-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

3-(10-(4-chlorothiazol-2-yl)-8-(hydroxymethyl)-1,3-dimethyl-2,4-dioxo-2,3,4,7,8,10-hexahydro-1H-pyrimido[4',5':3,4]pyrrolo[2,1-c][1,4]thiazin-5-yl)benzonitrile;

10-(4-chlorothiazol-2-yl)-5-(3-fluorophenyl)-8-(hydroxymethyl)-1,3-dimethyl-7,8-dihydro-1H-pyrimido[4',5':3,4]pyrrolo[2,1-c][1,4]thiazine-2,4(3H,10H)-dione;

3-(10-(4-Chlorothiazol-2-yl)-1,3-dimethyl-2,4-dioxo-1,2,3,4,7,8,9,10-octahydropyrimido[4,5-a]indolizin-5-yl)benzonitrile;

10-(4-Chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione;

1,3-Dimethyl-5,10-bis(4-methylthiazol-2-yl)-7,8,9,10-tetrahydropyrimido[4,5-a]indolizine-2,4(1H,3H)-dione;

10-(4-Chlorothiazol-2-yl)-1,3-dimethyl-5-(4-methylthiazol-2-yl)-7,8,9,10-tetrahydropyrimido[4,5-a]indolizine-2,4(1H,3H)-dione;

10-(4-Chlorothiazol-2-yl)-1,3-dimethyl-5-(2-methylthiazol-4-yl)-7,8,9,10-tetrahydropyrimido[4,5-a]indolizine-2,4(1H,3H)-dione;

10-(5-chlorofuran-2-yl)-8-((dimethylamino)methyl)-1,3-dimethyl-5-phenyl-7,8-dihydro-1H-pyrimido[4',5':3,4]pyrrolo[2,1-c][1,4]thiazine-2,4(3H,10H)-dione;

10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

10-(4-Chlorothiazol-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

10-(5-Chlorofuran-2-yl)-5-(3-ethoxyphenyl)-1,3-dimethyl-7,8-dihydro-1H-pyrimido[4',5':3,4]pyrrolo[2,1-c][1,4]thiazine-2,4(3H,10H)-dione;

5-(3-Methoxyphenyl)-1,3-dimethyl-10-(4-methylthiazol-2-yl)-7,8-dihydro-1H-pyrimido[4',5':3,4]pyrrolo[2,1-c][1,4]thiazine-2,4(3H,10H)-dione;

10-(5-Chlorofuran-2-yl)-5-(3-methoxyphenyl)-1,3-dimethyl-7,8-dihydro-1H-pyrimido[4',5':3,4]pyrrolo[2,1-c][1,4]thiazine-2,4(3H,10H)-dione;

10-(2-Chlorothiazol-4-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(1-methyl-1H-imidazol-4-yl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(1-methyl-1H-pyrazol-4-yl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(5-methyl-1,3,4-oxadiazol-2-yl)-7,8-dihydro-1H-pyrimido[4',5':3,4]pyrrolo[2,1-c][1,4]thiazine-2,4(3H,10H)-dione;

10-(5-Chlorofuran-2-yl)-1,3-dimethyl-5-(4-methyloxazol-2-yl)-7,8-dihydro-1H-pyrimido[4',5':3,4]pyrrolo[2,1-c][1,4]thiazine-2,4(3H,10H)-dione;

10-(5-chlorofuran-2-yl)-5-(4-(1-hydroxyethyl)thiazol-2-yl)-1,3-dimethyl-7,8-dihydro-1H-pyrimido[4',5':3,4]pyrrolo[2,1-c][1,4]thiazine-2,4(3H,10H)-dione;

9-(4-Chlorothiazol-2-yl)-1,3-dimethyl-5-phenyl-8,9-dihydro-1H-pyrimido[4,5-a]pyrrolizine-2,4(3H,7H)-dione;

1,3-Dimethyl-9-(4-methylthiazol-2-yl)-5-phenyl-8,9-dihydro-1H-pyrimido[4,5-a]pyrrolizine-2,4(3H,7H)-dione;

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

10-(5-chlorofuran-2-yl)-8-(hydroxymethyl)-1,3-dimethyl-5-(1-methyl-1H-pyrazol-3-yl)-7,8-dihydro-1H-pyrimido[4',5':3,4]pyrrolo[2,1-c][1,4]thiazine-2,4(3H,10H)-dione;

10-(5-Chlorofuran-2-yl)-8-(hydroxymethyl)-1,3-dimethyl-5-(2-methylthiazol-4-yl)-7,8-dihydro-1H-pyrimido[4',5':3,4]pyrrolo[2,1-c][1,4]thiazine-2,4(3H,10H)-dione;

9,9-Difluoro-5-(3-fluorophenyl)-1,3-dimethyl-10-(5-methylfuran-2-yl)-7,8,9,10-tetrahydropyrimido[4,5-a]indolizine-2,4(1H,3H)-dione;

8-(aminomethyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

3-(9-(4-Chlorothiazol-2-yl)-1,3-dimethyl-2,4-dioxo-2,3,4,7,8,9-hexahydro-1H-pyrimido[4,5-a]pyrrolizin-5-yl)benzonitrile;

9-(4-Chlorothiazol-2-yl)-1,3-dimethyl-5-(4-methylthiazol-2-yl)-8,9-dihydro-1H-pyrimido[4,5-a]pyrrolizine-2,4(3H,7H)-dione;

9-(4-Chlorothiazol-2-yl)-5-(3-fluorophenyl)-1,3-dimethyl-8,9-dihydro-1H-pyrimido[4,5-a]pyrrolizine-2,4(3H,7H)-dione;

9-(4-Chlorothiazol-2-yl)-1,3,8,8-tetramethyl-5-phenyl-8,9-dihydro-1H-pyrimido[4,5-a]pyrrolizine-2,4(3H,7H)-dione;

9-(4-Chlorothiazol-2-yl)-5-(3-fluorophenyl)-1,3,8,8-tetramethyl-8,9-dihydro-1H-pyrimido[4,5-a]pyrrolizine-2,4(3H,7H)-dione;

3-(1,3,8,8-Tetramethyl-9-(4-methylthiazol-2-yl)-2,4-dioxo-2,3,4,7,8,9-hexahydro-1H-pyrimido[4,5-a]pyrrolizin-5-yl)benzonitrile;

5-(3-Fluorophenyl)-1,3,8,8-tetramethyl-9-(4-methylthiazol-2-yl)-8,9-dihydro-1H-pyrimido[4,5-a]pyrrolizine-2,4(3H,7H)-dione;

1,3,8,8-Tetramethyl-9-(4-methylthiazol-2-yl)-5-phenyl-8,9-dihydro-1H-pyrimido[4,5-a]pyrrolizine-2,4(3H,7H)-dione;

10-(4-Chlorothiazol-2-yl)-1,3-dimethyl-5-(1-methyl-1H-pyrazol-3-yl)-7,8,9,10-tetrahydropyrimido[4,5-a]indolizine-2,4(1H,3H)-dione;

10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione;

3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile;

7-((2H-1,2,3-triazol-2-yl)methyl)-1,3-dimethyl-10-(5-methylfuran-2-yl)-5-phenyl-7,8,9,10-tetrahydropyrimido[4,5-a]indolizine-2,4(1H,3H)-dione;

2-(10-(5-Chlorofuran-2-yl)-1,3-dimethyl-2,4-dioxo-2,3,4,7,8,10-hexahydro-1H-pyrimido[4',5':3,4]pyrrolo[2,1-c][1,4]thiazin-5-yl)thiazole-4-carboxylic acid;

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8)methyl)methanesulfonamide;

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)-2-methoxyacetamide;

Methyl ((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)carbamate;

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)acetamide;

N-((10-(5-chlorofuran-2-yl)-1,3-dimethyl-5-(4-methylthiazol-2-yl)-2,4-dioxo-2,3,4,7,8,10-hexahydro-1H-pyrimido[4',5':3,4]pyrrolo[2,1-c][1,4]thiazin-8-yl)methyl)benzamide;

9-(4-Chlorothiazol-2-yl)-5-(3-fluorophenyl)-7-(hydroxymethyl)-1,3-dimethyl-8,9-dihydro-1H-pyrimido[4,5-a]pyrrolizine-2,4(3H,7H)-dione;

9-(4-chlorothiazol-2-yl)-7-(hydroxymethyl)-1,3-dimethyl-5-phenyl-8,9-dihydro-1H-pyrimido[4,5-a]pyrrolizine-2,4(3H,7H)-dione;

7-(hydroxymethyl)-1,3-dimethyl-9-(4-methylthiazol-2-yl)-5-phenyl-8,9-dihydro-1H-pyrimido[4,5-a]pyrrolizine-2,4(3H,7H)-dione;

3-(9-(4-chlorothiazol-2-yl)-7-(hydroxymethyl)-1,3-dimethyl-2,4-dioxo-2,3,4,7,8,9-hexahydro-1H-pyrimido[4,5-a]pyrrolizin-5-yl)benzonitrile;

8-((1H-imidazol-1-yl)methyl)-10-(5-chlorofuran-2-yl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

9-(4-Chlorothiazol-2-yl)-5-(3-fluorophenyl)-1,3-dimethyl-8-methylene-8,9-dihydro-1H-pyrimido[4,5-a]pyrrolizine-2,4(3H,7H)-dione;

10-(5-chlorofuran-2-yl)-1,3-dimethyl-5-(4-methylthiazol-2-yl)-8-((2-oxooxazolidin-3-yl)methyl)-7,8-dihydro-1H-pyrimido[4',5':3,4]pyrrolo[2,1-c][1,4]thiazine-2,4(3H,10H)-dione;

10-(5-chlorofuran-2-yl)-1,3-dimethyl-5-(4-methylthiazol-2-yl)-8-((2-oxopyrrolidin-1-yl)methyl)-7,8-dihydro-1H-pyrimido[4',5':3,4]pyrrolo[2,1-c][1,4]thiazine-2,4(3H,10H)-dione;

3-(11-(4-Chlorothiazol-2-yl)-1,3-dimethyl-2,4-dioxo-2,3,4,7,8,9,10,11-octahydro-1H-pyrimido[4',5':3,4]pyrrolo[1,2-a]azepin-5-yl)benzonitrile;

11-(4-Chlorothiazol-2-yl)-5-(3-fluorophenyl)-1,3-dimethyl-8,9,10,11-tetrahydro-1H-pyrimido[4',5':3,4]pyrrolo[1,2-a]azepine-2,4(3H,7H)-dione;

1,3-Dimethyl-11-(4-methylthiazol-2-yl)-5-phenyl-8,9,10,11-tetrahydro-1H-pyrimido[4',5':3,4]pyrrolo[1,2-a]azepine-2,4(3H,7H)-dione; and 11-(4-Chlorothiazol-2-yl)-1,3-dimethyl-5-phenyl-8,9,10,11-tetrahydro-1H-pyrimido[4',5':3,4]pyrrolo[1,2-a]azepine-2,4(3H,7H)-dione;

or a pharmaceutically acceptable salt thereof.

11. A pharmaceutical composition comprising a therapeutically effective amount of a compound according to claim 1 or a pharmaceutically acceptable salt thereof and one or more pharmaceutically acceptable carriers.

12. A method of treating a disorder or disease selected from polycystic kidney disease and diarrhea, comprising administering to the subject a therapeutically effective amount of the compound according to claim 1 or a pharmaceutically acceptable salt thereof.

13. A compound according to claim 1 which is selected from:

(R)-3-(10-(4-chlorothiazol-2-yl)-1,3-dimethyl-2,4-dioxo-1,2,3,4,7,8,9,10-octahydropyrimido[4,5-a]indolizin-5-yl)benzonitrile;

10-(4-chlorothiazol-2-yl)-5-(4-(hydroxymethyl)thiazol-2-yl)-1,3-dimethyl-7,8,9,10-tetrahydropyrimido[4,5-a]indolizine-2,4(1H,3H)-dione;

10-(4-chlorothiazol-2-yl)-1,3-dimethyl-5-(4-methylthiazol-2-yl)-7,8,9,10-tetrahydropyrimido[4,5-a]indolizine-2,4(1H,3H)-dione;

10-(4-chlorothiazol-2-yl)-1,3-dimethyl-5-(2-methylthiazol-4-yl)-7,8,9,10-tetrahydropyrimido[4,5-a]indolizine-2,4(1H,3H)-dione;

10-(5-Chlorofuran-2-yl)-5-(4-(hydroxymethyl)thiazol-2-yl)-1,3-dimethyl-7,8-dihydro-1H-pyrimido[4',5':3,4]pyrrolo[2,1-c][1,4]thiazine-2,4(3H,10H)-dione;

10-(5-chlorofuran-2-yl)-8-(hydroxymethyl)-1,3-dimethyl-5-(4-methylthiazol-2-yl)-7,8-dihydro-1H-pyrimido[4',5':3,4]pyrrolo[2,1-c][1,4]thiazine-2,4(3H,10H)-dione;

10-(4-chlorothiazol-2-yl)-5-(3-fluorophenyl)-8-(hydroxymethyl)-1,3-dimethyl-7,8,9,10-tetrahydropyrimido[4,5-a]indolizine-2,4(1H,3H)-dione; and 3-(10-(4-chlorothiazol-2-yl)-8-(hydroxymethyl)-1,3-dimethyl-2,4-dioxo-1,2,3,4,7,8,9,10-octahydropyrimido[4,5-a]indolizin-5-yl)benzonitrile;

or a pharmaceutically acceptable salt thereof.

14. A compound 3-(10-(4-Chlorothiazol-2-yl)-1,3-dimethyl-2,4-dioxo-1,2,3,4,7,8,9,10-octahydropyrimido[4,5-a]indolizin-5-yl)benzonitrile or a pharmaceutically acceptable salt thereof.

15. A pharmaceutical composition comprising a therapeutically effective amount of the compound according to claim 14 or a pharmaceutically acceptable salt thereof and one or more pharmaceutically acceptable carriers.

16. A method of treating a disorder or disease selected from polycystic kidney disease and diarrhea, comprising administering to the subject a therapeutically effective amount of the compound according to claim 14 or a pharmaceutically acceptable salt thereof.

17. A pharmaceutical composition comprising a therapeutically effective amount of the compound according to claim 9 or a pharmaceutically acceptable salt thereof and one or more pharmaceutically acceptable carriers.

18. A method of treating a disorder or disease selected from polycystic kidney disease and diarrhea, comprising administering to the subject a therapeutically effective amount of the compound according to claim 9 or a pharmaceutically acceptable salt thereof.

19. A pharmaceutical composition comprising a therapeutically effective amount of the compound according to claim 13 or a pharmaceutically acceptable salt thereof and one or more pharmaceutically acceptable carriers.

20. A method of treating a disorder or disease selected from polycystic kidney disease and diarrhea, comprising administering to the subject a therapeutically effective amount of the compound according to claim 13 or a pharmaceutically acceptable salt thereof.

21. A pharmaceutical composition comprising a therapeutically effective amount of the compound according to claim 8 or a pharmaceutically acceptable salt thereof and one or more pharmaceutically acceptable carriers.

22. A pharmaceutical composition comprising a therapeutically effective amount of the compound according to claim 10 or a pharmaceutically acceptable salt thereof and one or more pharmaceutically acceptable carriers.

23. A method of treating a disorder or disease selected from polycystic kidney disease and diarrhea, comprising administering to the subject a therapeutically effective amount of the compound according to claim 10 or a pharmaceutically acceptable salt thereof.

* * * * *